US012655437B2

(12) United States Patent
Barrangou et al.

(10) Patent No.: US 12,655,437 B2
(45) Date of Patent: Jun. 16, 2026

(54) COMPOSITIONS AND METHODS FOR MODULATING THE GASTROINTESTINAL TRACT USING BILE SALT HYDROLASES

(71) Applicant: North Carolina State University, Raleigh, NC (US)

(72) Inventors: Rodolphe Barrangou, Raleigh, NC (US); Casey Theriot, Raleigh, NC (US); Sarah O'Flaherty, Raleigh, NC (US); Matthew Foley, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 765 days.

(21) Appl. No.: 17/609,283

(22) PCT Filed: May 7, 2020

(86) PCT No.: PCT/US2020/031777
§ 371 (c)(1),
(2) Date: Nov. 5, 2021

(87) PCT Pub. No.: WO2020/227471
PCT Pub. Date: Nov. 12, 2020

(65) Prior Publication Data
US 2022/0213493 A1 Jul. 7, 2022

Related U.S. Application Data

(60) Provisional application No. 62/844,518, filed on May 7, 2019.

(51) Int. Cl.
| | |
|---|---|
| *A61K 39/02* | (2006.01) |
| *C12N 9/80* | (2006.01) |
| *C12N 15/70* | (2006.01) |
| *C12N 15/74* | (2006.01) |

(52) U.S. Cl.
CPC ............. *C12N 15/746* (2013.01); *C12N 9/80* (2013.01); *C12N 15/70* (2013.01)

(58) Field of Classification Search
None
See application file for complete search history.

(56) References Cited

U.S. PATENT DOCUMENTS

| | | | |
|---|---|---|---|
| 7,939,061 B2* | 5/2011 | Prakash | A61K 9/5021 424/93.4 |
| 10,328,132 B2* | 6/2019 | Bermudez-Humaran | A61P 33/02 |
| 2010/0028945 A1 | 2/2010 | Klaenhammer et al. | |
| 2019/0010506 A1 | 1/2019 | Falb et al. | |

FOREIGN PATENT DOCUMENTS

| | | |
|---|---|---|
| CN | 103992991 A | 8/2014 |
| CN | 105543200 A | 5/2016 |
| CN | 109661236 A | 4/2019 |
| JP | 2010523144 A | 7/2010 |
| JP | 2016537409 A | 12/2016 |
| KR | 20150001330 A | 1/2015 |
| WO | WO-2004076657 A2 | 9/2004 |
| WO | WO-2016020544 A1 | 2/2016 |
| WO | WO-2017091783 A2 | 6/2017 |
| WO | WO-2017123592 A1 | 7/2017 |

OTHER PUBLICATIONS

Devos et al., (Proteins: Structure, Function and Genetics, 2000, vol. 41: 98-107),.*
Whisstock et al., (Quarterly Reviews of Biophysics 2003, vol. 36 (3): 307-340,).*
Witowski et al., (Biochemistry 38:11643-11650, 1999).*
Kisselev L., (Structure, 2002, vol. 10: 8-9).*
Mikayama et al. (Nov. 1993. Proc.Natl.Acad.Sci. USA, vol. 90 : 10056-10060).*
Rudinger et al. (Jun. 1976. Peptide Hormones. Biol. Council. pp. 5-7).*
Jiang, "Diversity of bile salt hydrolase activities in different lactobacilli toward human bile salts" Ann Microbiol (2010), 60:81-88.
Chand et al., "Structure and function of a highly active Bile Salt Hydrolase (BSH) from Enterococcus faecalis and post-translation processing of BSH enzymes" BBA—Proteins and Proteomics (2018), 1866:507-518.
Database Accession No. GSP: AED00451, Jun. 15, 2007, Kleenhammer TR, Lactobacillus acidophilus stress-related protein #184.
International Search Report and Written Opinion for PCT/US20/31777. Mailed Sep. 24, 2020. 22 pages.
Dong et al., Bile salt hydrolases: Structure and function, substrate preference, and inhibitor development. Protein Sci. Oct. 2018;27(10):1742-1754.
Duar et al., Lifestyles in transition: evolution and natural history of the genus *Lactobacillus*. FEMS Microbiol Rev. Aug. 1, 2017;41(Supp_1):S27-S48.
Foley et al., Bile salt hydrolases: gatekeepers of bile acid metabolism and host-microbiome crosstalk in the gastrointestinal tract. PLOS pathogens. 2019. 1-6.
Kumer et al., Structural and functional analysis of a conjugated bile salt hydrolase from Bifidobacterium longum reveals an evolutionary relationship with penicillin V acylase. J Biol Chem. Oct. 27, 2006;281(43):32516-25.

(Continued)

*Primary Examiner* — Jennifer E Graser
(74) *Attorney, Agent, or Firm* — Casimir Jones, S.C.; Peter J. Schlueter

(57) ABSTRACT

The present disclosure provides compositions and methods related to modulating the gastrointestinal tract. In particular, the present disclosure provides a novel therapeutic strategy for selective modulation of the gut microbiota bile acid pool using bile acid hydrolases (BSHs) for the prevention and treatment of diseases such as obesity, diabetes, Inflammatory bowel disease (IBD), liver and colon cancer, and *Clostridioides difficile* infections, among others.

14 Claims, 31 Drawing Sheets
Specification includes a Sequence Listing.

(56)                  References Cited

OTHER PUBLICATIONS

Moser et al., Bile salt hydrolase activity and resistance to toxicity of conjugated bile salts are unrelated properties in lactobacilli. Appl Environ Microbiol. Aug. 2001;67(8):3476-80.

O'Flaherty et al., The Lactobacillus Bile Salt Hydrolase Repertoire Reveals Niche-Specific Adaptation. mSphere. May 30, 2018;3(3):e00140-18.

Xiong et al., Short communication: Improving the activity of bile salt hydrolases in Lactobacillus casei based on in silico molecular docking and heterologous expression. J Dairy Sci. Feb. 2017;100(2):975-980.

Extended European Search Report for European Application No. 20802924.9, mailed Mar. 21, 2023, 13 Pages.

Huang Q., et al., "Molecular Cloning and Expression of the Bile Salt Hydrolase Gene (bsh) From Lactobacillus Plantarum Y1", Journal of Nanjing Normal University (Natural Science Edition), No. 3, Sep. 20, 2010, pp. 1-4.

Partial Supplementary European Search Report for European Application No. 20802924.9, mailed Dec. 21, 2022, 15 Pages.

Zhang H-X., et al., "Research Progress in Physiological Characteristics and Gene Sequencing of Bile Salt Hydrolase from Lactic Acid Bacteria", Food Science, No. 1, Jan. 15, 2011, pp. 1-3.

* cited by examiner

FIGS. 15A-15C

| BSH | SEQ ID NO: |
|---|---|
| Ls963BSH | 103 |
| Lavi | 23 |
| LgBSHa | 41 |
| LjoRB263BSHa | 69 |
| LjoBSH56 | 69 |
| LjoRB271BSHc | 69 |
| Lrog | 97 |
| Lmur | 85 |
| Lcol | 25 |
| LaBSHa | 1 |
| Lcr2487 | 29 |
| Lcr2514 | 27 |
| Lreu | 113 |
| LjoRB271BSHb | 73 |
| LgBSHb | 43 |
| LaBSHb | 3 |
| LjoBSH47 | 71 |
| LjoRB271BSHa | 71 |
| Ling | 61 |
| Lpla | 93 |
| Lgig | 51 |

B

Specific Activity
(µmol amino acid / sec / µmol BSH)

4000  3000  2000  1000  0

TLCA
TDCA
TCDCA
TCA
GUDCA
GDCA
GCDCA
GCA

A (cont'd)
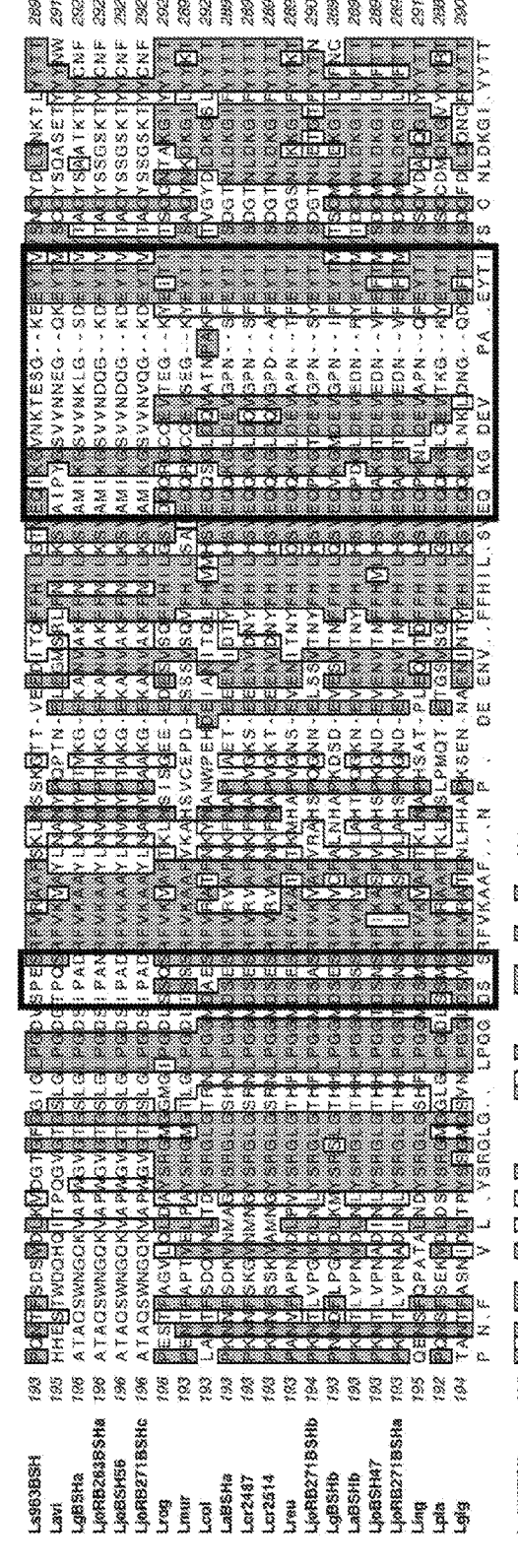
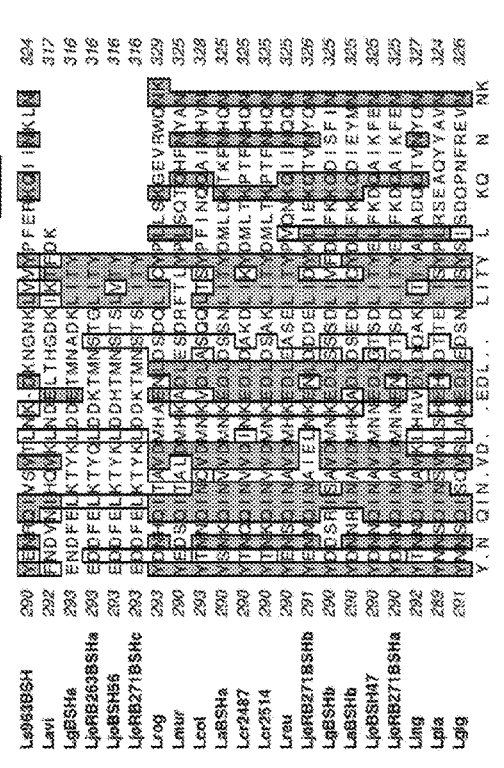
FIGS. 21A-21C

Cefoperazone-treated mouse cecum
*ex vivo C. difficile* growth

SEQUENCE LISTING

<160> NUMBER OF SEQ ID NOS: 114

<210> SEQ ID NO 1
<211> LENGTH: 325
<212> TYPE: PRT
<213> ORGANISM: Lactobacillus acidophilus

<400> SEQUENCE: 1

Met Cys Thr Ser Ile Ile Phe Ser Pro Lys Asp His Tyr Phe Gly Arg
1               5                   10                  15

Asn Leu Asp Leu Glu Ile Thr Phe Gly Gln Gln Val Val Ile Thr Pro
            20                  25                  30

Arg Asn Tyr Thr Phe Lys Phe Arg Lys Met Pro Ser Leu Lys Lys His
        35                  40                  45

Tyr Ala Met Ile Gly Ile Ser Leu Asp Met Asp Asp Tyr Pro Leu Tyr
    50                  55                  60

Phe Asp Ala Thr Asn Glu Lys Gly Leu Gly Met Ala Gly Leu Asn Tyr
65                  70                  75                  80

Pro Gly Asn Ala Thr Tyr Tyr Glu Glu Lys Glu Asn Lys Asp Asn Ile
                85                  90                  95

Ala Ser Phe Glu Phe Ile Pro Trp Ile Leu Gly Gln Cys Ser Thr Ile
            100                 105                 110

Ser Glu Val Lys Asp Leu Leu Ser Arg Ile Asn Ile Ala Asp Leu Asn
            115                 120                 125

Phe Ser Glu Lys Met Gln Ala Ser Ser Leu His Trp Leu Ile Ala Asp
        130                 135                 140

Lys Thr Gly Thr Ser Leu Val Val Glu Thr Asp Lys Asp Gly Met His
145                 150                 155                 160

Ile Tyr Asp Asn Pro Val Gly Cys Leu Thr Asn Asn Pro Gln Phe Pro
                165                 170                 175

Lys Gln Leu Phe Asn Leu Asn Asn Tyr Ala Asp Val Ser Pro Lys Met
            180                 185                 190

Pro Lys Asn Asn Phe Ser Asp Lys Val Asn Met Ala Gly Tyr Ser Arg
            195                 200                 205

Gly Leu Gly Ser His Asn Leu Pro Gly Gly Met Asp Ser Glu Ser Arg
    210                 215                 220

Phe Val Arg Val Ala Phe Asn Lys Phe Asn Ala Pro Ile Ala Glu Thr
225                 230                 235                 240

Glu Glu Glu Asn Ile Asp Thr Tyr Phe His Ile Leu His Ser Val Glu
                245                 250                 255

Gln Gln Lys Gly Leu Asp Glu Val Gly Pro Asn Ser Phe Glu Tyr Thr
            260                 265                 270

Ile Tyr Ser Asp Gly Thr Asn Leu Asp Lys Gly Ile Phe Tyr Tyr Thr
        275                 280                 285

Thr Tyr Ser Asn Lys Gln Ile Asn Val Val Asp Met Asn Lys Glu Asp
    290                 295                 300

Leu Asp Ser Ser Asn Leu Ile Thr Tyr Asp Met Leu Asp Lys Thr Lys
305                 310                 315                 320

Phe Asn His Gln Asn
                325

<210> SEQ ID NO 2
<211> LENGTH: 978
<212> TYPE: DNA
<213> ORGANISM: Lactobacillus acidophilus -continued

```
<400> SEQUENCE: 2
atgtgtacat caattatatt cagtcccaaa gatcattact ttggtcgtaa ccttgattta      60
gaaattactt ttggtcaaca agttgttatt acgccacgca attacacttt taaattccgt     120
aagatgccca gtttaaaaaa gcactatgca atgattggta tctcattaga tatggatgat     180
tatcccctat atttcgacgc tacaaatgaa aaaggtttag gtatggccgg actcaactat     240
ccaggaaatg ctacatatta tgaagaaaaa gaaataaaag ataatattgc ttcctttgaa     300
ttcatccctt ggattttagg acagtgtagc actattagcg aagtaaagga tttacttagc     360
agaatcaaca tcgccgattt aaatttcagc gaaaaaatgc aagcctcctc tcttcactgg     420
cttattgcag ataaaacagg tacatcatta gttgttgaaa cagacaaaga tggaatgcat     480
atttatgata tccagttgg ctgcttaact aataatccac aatttccaaa gcaattattc      540
aatttaaata actatgctga cgtatctcca aaaatgccta aaaataactt ctcagataaa     600
gtaaatatgg ctggctacag ccgtggatta gggtctcaca acttaccagg tggaatggat     660
tctgaatcac gttttgtcag agtagctttc aataaattta atgctccaat tgctgaaacc     720
gaagaagaaa atattgatac ttacttccac attttacatt cggttgaaca acaaaaggga     780
ctggatgaag ttggtccaaa ctcatttgaa tatacaattt attctgatgg aactaactta     840
gacaaaggta ttttctacta caccacttat tcaaacaaac aaattaacgt tgttgatatg     900
aataaagaag atctagatag cagcaatttg atcacttatg atatgcttga taaaactaaa     960
tttaaccatc aaaactaa                                                    978
```

```
<210> SEQ ID NO 3
<211> LENGTH: 325
<212> TYPE: PRT
<213> ORGANISM: Lactobacillus acidophilus

<400> SEQUENCE: 3

Met Cys Thr Ser Ile Cys Tyr Asn Pro Asn Asp His Tyr Phe Gly Arg
1               5                   10                  15

Asn Leu Asp Tyr Glu Ile Ala Tyr Gly Gln Lys Val Val Ile Val Pro
                20                  25                  30

Arg Asn Tyr Glu Phe Lys Tyr Arg Glu Met Pro Ser Gln Lys Met His
            35                  40                  45

Tyr Ala Phe Ile Gly Val Ser Val Val Asn Asp Asp Tyr Pro Leu Leu
        50                  55                  60

Cys Asp Ala Ile Asn Glu Lys Gly Leu Gly Ile Ala Gly Leu Asn Phe
65                  70                  75                  80

Gln Gly Pro Asn His Tyr Phe Pro Lys Ile Glu Gly Lys Lys Asn Ile
                85                  90                  95

Ala Ser Phe Glu Leu Met Pro Tyr Leu Leu Ser Asn Cys Glu Asn Thr
            100                 105                 110

Asp Asp Val Lys Glu Ile Leu Asp Asn Ala Asn Ile Leu Asn Ile Ser
        115                 120                 125

Phe Ser Ala Asn Tyr Pro Ala Ala Asp Leu His Trp Ile Leu Ser Asp
        130                 135                 140

Lys Ala Gly Lys Ser Ile Val Val Glu Ser Thr Asn Ser Gly Leu His
145                 150                 155                 160

Ile Tyr Asp Asn Pro Val Asn Val Leu Thr Asn Asn Pro Glu Phe Pro
                165                 170                 175

Asp Gln Leu Ile Lys Leu Ser Asp Tyr Ala Asp Val Thr Pro His Asn
            180                 185                 190
```

```
Pro Lys Asn Thr Leu Val Pro Asn Val Asp Leu Asn Leu Tyr Ser Arg
        195                 200                 205

Gly Leu Gly Thr His His Leu Pro Gly Gly Met Asp Ser Ser Ser Arg
        210                 215                 220

Phe Val Lys Val Ala Phe Val Leu Ala His Thr Pro Gln Gly Lys Asn
225                 230                 235                 240

Glu Val Glu Asn Val Thr Asn Tyr Phe His Ile Leu His Ser Val Glu
                245                 250                 255

Gln Pro Asp Gly Leu Asp Glu Val Glu Asp Asn Arg Tyr Glu Tyr Thr
                260                 265                 270

Met Tyr Thr Asp Cys Met Asn Leu Asp Lys Gly Ile Leu Tyr Phe Thr
        275                 280                 285

Thr Tyr Asp Asn Asn Arg Ile Asn Ala Val Asp Met His Lys Ala Asp
        290                 295                 300

Leu Asp Ser Glu Asp Leu Ile Cys Tyr Asp Leu Phe Lys Lys Gln Asp
305                 310                 315                 320

Ile Glu Tyr Met Asn
                325
```

```
<210> SEQ ID NO 4
<211> LENGTH: 978
<212> TYPE: DNA
<213> ORGANISM: Lactobacillus acidophilus

<400> SEQUENCE: 4
atgtgtacat caatttgtta taatcctaac gatcattatt ttggtagaaa tcttgactat      60
gaaattgctt atggtcaaaa agtagtcatt gtaccaagaa actacgaatt taagtataga     120
gaaatgccct ctcaaaagat gcattatgct tttatcggag tatctgtagt taatgatgat     180
tatccattat tatgtgatgc aattaatgaa aaggggcttg gtattgcagg attaaatttt     240
caaggtccta atcattactt tcctaaaatc gaaggtaaga agaatattgc ttcttttgaa     300
ttaatgccat acttattaag taattgtgaa aatactgacg atgttaaaga aatcttagat     360
aatgcaaata ttttaaatat tagcttttca gcaaattatc ctgcagctga tttacattgg     420
attttaagtg ataaagctgg taagagtatc gtagttgaat caaccaattc aggtttacat     480
atttatgata tccagtgaa tgtcttaact aacaatcctg aatttccgga tcaattaatt     540
aaattaagtg actacgccga cgttactcca cataatccta agaatacatt ggttcctaat     600
gttgatctta atctatatag tagaggctta ggtactcacc acttacctgg tggaatggat     660
tctagctctc gatttgttaa ggtagctttt gtcttggcac acactccaca aggaaaaaat     720
gaagtggaaa atgttactaa ttatttccat attctgcatt cagtagaaca acctgatggt     780
ttagatgaag tagaagataa tcgctatgaa tatactatgt atacagattg tatgaactta     840
gataaaggta ttttgtactt tactacttat gacaataatc ggattaatgc agtagatatg     900
cataaagcag atttagattc agaagattta atctgctacg atttgtttaa gaaacaagat     960
attgaatata tgaattaa                                                    978
```

```
<210> SEQ ID NO 5
<211> LENGTH: 324
<212> TYPE: PRT
<213> ORGANISM: Lactobacillus agilis

<400> SEQUENCE: 5

Met Cys Thr Ala Ile Thr Phe Thr Gly Thr Ser Asn Tyr Phe Gly Arg
```

```
1                    5                    10                   15

Asn Leu Asp Leu Asn Tyr Ser Tyr Gly Glu Gln Val Val Ile Thr Pro
                20                   25                   30

Gln Asn Tyr Glu Phe Asn Trp Arg Gln Leu Pro Ser Val Lys Thr His
                35                   40                   45

Leu Ala Leu Ile Gly Val Gly Ile Val Val Ala Asp Tyr Pro Leu Tyr
        50                   55                   60

Phe Asp Ala Ile Asn Glu Ala Gly Leu Gly Met Ala Gly Leu Asn Phe
65                   70                   75                   80

Pro Gly Asn Ala Tyr Tyr Gly Lys Val Thr Val Gly Lys Asn Asn Val
                85                   90                   95

Ser Pro Phe Glu Phe Ile Pro Trp Leu Leu Gly Gln Ala His Asn Val
                100                  105                  110

Gly Glu Ala Arg Lys Leu Leu Ala Asp Leu Asn Leu Val Lys Ile Asn
                115                  120                  125

Phe Ser Glu Gln Leu Pro Leu Ala Asp Leu His Trp Leu Ile Ala Asp
        130                  135                  140

Lys Asp Glu Ser Ile Val Val Glu Ala Thr Lys Thr Gly Leu His Ile
145                  150                  155                  160

Tyr Asp Asn Pro Val Gly Val Leu Thr Asn Asn Pro Ala Phe Asn Tyr
                165                  170                  175

Gln Leu Glu Asn Leu Lys Asn Tyr Arg Gln Leu Asn Ala Arg Thr Thr
                180                  185                  190

Pro Asn Thr Phe Ala Ser Ser Leu Asp Leu Pro Val Asp Ala Thr Gly
                195                  200                  205

Phe Gly Ser Ile Gly Leu Pro Gly Asp Leu Ser Pro Lys Gly Arg Phe
        210                  215                  220

Val Arg Ala Ser Phe Ala Lys Leu Asn Ala Leu Lys Gly Thr Asp Pro
225                  230                  235                  240

Leu Ser Asp Val Asn Gln Phe Phe Gln Ile Leu Ala Thr Val Lys Gln
                245                  250                  255

Val Lys Gly Leu Asn Trp Ala Asp Glu His Ser Cys Glu Tyr Thr Val
                260                  265                  270

Tyr Ser Asp Cys Tyr Asp Leu Gln Ala Gly Val Leu Tyr Tyr Leu Thr
        275                  280                  285

Tyr Glu Ser Pro Gln Leu His Ala Ala Lys Leu Gln Gly Gln Gln Leu
        290                  295                  300

Ala Thr Ser Gln Leu Ile Thr Tyr Pro Leu Lys Asn Gln Val Val Val
305                  310                  315                  320

Asp Trp Gln Asn
```

<210> SEQ ID NO 6
<211> LENGTH: 975
<212> TYPE: DNA
<213> ORGANISM: Lactobacillus agilis
<400> SEQUENCE: 6

```
atgtgtacag caattacttt tacaggaacg agcaactatt ttggtcgtaa cttggattta      60
aattactctt atggtgaaca ggtggtaatc acgccccaaa attatgaatt taactggcgg     120
caactcccta gtgtgaagac acacctagcc ttaattgggg tgggaattgt agtagctgat     180
tatccacttt attttgatgc cattaacgag gcgggactag ggatggcagg cttaaatttc     240
ccgggaaatg cttattatgg caagtaaca gttggtaaaa acaatgtcag tcccttgaa     300
```

-continued

```
tttatcccct ggttgttagg gcaagcccat aacgtcggtg aagcccggaa gttattagcc      360
gatttaaacc tagttaagat taactttagc gagcagttac ccttggctga tttacattgg      420
ctgattgctg acaaagatga aagcatcgtg gtagaggcaa ctaaaacggg gttacacatt      480
tatgataacc cagtcggggt cctaaccaat aacccagcct ttaattacca actagaaaac      540
ctaaaaaatt accggcagtt aaatgcgcgg accacccccca acacttttgc ttccagctta      600
gacttaccgg tagatgctac tggctttgga agtattggct taccaggaga tttatcccct      660 aagggcgct ttgttagggc tagttttgct aagctcaacg ctttaaaagg gacagatccc      720
cttagcgatg ttaaccagtt cttccaaatt ttagcaacgg ttaagcaggt aaagggcctt      780
aactgggcag acgaacacag ttgtgaatat acggtctact cagattgcta tgacctgcaa      840 gcggggtat tatattatct tacttacgag agcccacagc ttcatgccgc taaattacag      900
ggacagcaac tagcaacgag ccaactgatt acctacccac taaaaaatca agtggttgtt      960
gactggcaaa actaa                                                       975
```

<210> SEQ ID NO 7
<211> LENGTH: 325
<212> TYPE: PRT
<213> ORGANISM: Lactobacillus amylovorus

<400> SEQUENCE: 7

```
Met Cys Thr Ser Ile Val Phe Ser Pro Lys Asp His Tyr Phe Gly Arg
1               5                   10                  15

Asn Leu Asp Leu Glu Ile Thr Phe Gly Gln Gln Val Val Ile Thr Pro
            20                  25                  30

Arg Asn Tyr Asp Phe Lys Phe Arg Lys Met Pro Glu Leu Lys Gln His
        35                  40                  45

Tyr Ala Met Val Gly Ile Ala Leu Asn Ala Gly Gly Tyr Pro Leu Tyr
    50                  55                  60

Phe Asp Ala Ala Asn Glu Lys Gly Leu Gly Met Ala Gly Leu Asn Tyr
65                  70                  75                  80

Pro Gly Asn Ala Thr Tyr Tyr Asp Val Lys Asp Gly Lys Asp Asn Val
                85                  90                  95

Ala Ser Phe Glu Phe Ile Pro Trp Ile Leu Gly Gln Cys Ala Thr Val
            100                 105                 110

Glu Glu Ala Lys Lys Leu Leu Ala Lys Ile Asn Ile Ala Asp Ile Asn
        115                 120                 125

Phe Ser Glu Lys Met Val Ala Ser Lys Leu His Trp Leu Ile Ala Asp
    130                 135                 140

Lys Thr Gly Thr Ser Ile Val Val Glu Thr Asp Lys Asp Gly Met His
145                 150                 155                 160

Val Tyr Asp Asn Pro Val Gly Cys Leu Thr Asn Asn Pro Gln Phe Pro
                165                 170                 175

Lys Gln Leu Phe Asn Leu Asn Asn Tyr Ala Asp Val Ser Ala Ala Met
            180                 185                 190

Pro Lys Asn Asn Phe Ser Asp Gln Val Lys Met Asp Gly Tyr Ser Arg
        195                 200                 205

Gly Leu Gly Ser Arg Asn Leu Pro Gly Gly Met Asp Ser Glu Ser Arg
    210                 215                 220

Phe Val Arg Val Ala Phe Asn Lys Phe Asn Ala Pro Thr Ser Asp Ser
225                 230                 235                 240

Glu Glu Glu Asn Val Asp Thr Tyr Phe His Ile Leu His Ser Val Glu
                245                 250                 255
```

```
Gln Gln Lys Gly Leu Asp Gln Val Gly Pro Asp Ala Phe Glu Tyr Thr
            260                 265                 270

Ile Tyr Ser Asp Gly Ile Asn Leu Asp Lys Gly Ile Phe Tyr Tyr Thr
            275                 280                 285

Thr Tyr Thr Asn Lys Gln Ile Asn Val Val Asp Ile Asn Lys Glu Asp
        290                 295                 300

Leu Asp Ser Ser Asp Leu Ile Thr Tyr Asp Met Leu Thr Lys Gly Lys
305                 310                 315                 320

Phe Asn His Gln Asn
            325

<210> SEQ ID NO 8
<211> LENGTH: 978
<212> TYPE: DNA
<213> ORGANISM: Lactobacillus amylovorus

<400> SEQUENCE: 8
atgtgtactt caattgtgtt tagtcctaaa gatcactact ttggtcgtaa tcttgaccta      60
gaaataactt tcggtcaaca agtcgtgatt acccctcgca actatgattt taagttccgc     120
aagatgccgg aattaaaaca acattacgct atggtaggaa tcgcccttaa tgctggcggc     180
tatcctttat actttgatgc tgctaatgaa aagggcttgg gaatggccgg actaaattat     240
cctggcaatg ccacttacta tgacgtcaaa gatggcaaag acaatgttgc ttcttttgaa     300
ttcatccctt ggattttggg ccaatgcgct acagtagaag aagctaagaa attgcttgcc     360
aaaatcaaca ttgctgacat caactttagc gaaaaaatgg ttgcttctaa acttcactgg     420
ttaattgccg ataaaaccgg cacttcaatt gttgttgaaa ctgataaaga tggtatgcat     480
gtttacgata accctgttgg ctgcttaact aacaacccac aattccctaa gcaattgttc     540
aacttaaaca actacgcaga tgtttctgcc gcaatgccaa agaacaactt ctcagatcaa     600
gttaaaatgg acggctacag tcgcggctta ggttcacgca atttgccagg tggtatggat     660
tcagaatctc gttttgtcag agtagccttc aacaagttta cgcccctac ttccgattct      720 gaagaagaaa acgtggacac ttacttccat attctgcatt cagtagaaca acaaaaaggc     780
ctggatcaag tcggcccaga tgcttttgag tacactattt actctgatgg tatcaatttg     840
gataaaggta tcttctacta cactacttac actaataagc aaatcaacgt agttgatata     900
aataaagaag atttagacag cagtgattta attacttacg atatgctcac taaaggtaaa     960
tttaatcatc aaaactaa                                                     978

<210> SEQ ID NO 9
<211> LENGTH: 325
<212> TYPE: PRT
<213> ORGANISM: Lactobacillus amylovorus

<400> SEQUENCE: 9

Met Cys Thr Ser Ile Cys Tyr Ser Pro Ser Asp His Tyr Phe Gly Arg
1               5                   10                  15

Asn Leu Asp Tyr Glu Ile Ala Tyr Gly Gln Lys Val Val Ile Val Pro
            20                  25                  30

Arg Asn Tyr Glu Phe Glu Tyr Arg Glu Leu Pro Thr Gln Lys Ser His
        35                  40                  45

Tyr Ala Phe Ile Gly Val Ser Val Val Asn Asp Asp Tyr Pro Leu Leu
    50                  55                  60

Cys Asp Ala Ile Asn Glu Lys Gly Leu Gly Ile Ala Gly Leu Asn Phe
```

```
65                70                75                80

Gln Gly Pro Asn His Tyr Phe Pro Lys Met Glu Gly Lys Lys Asn Ile
                 85                90                95

Thr Ser Phe Glu Leu Thr Pro Tyr Leu Leu Ser Asn Cys Glu Thr Thr
                100               105               110

Asp Asp Val Lys Glu Ile Leu Ala Asp Ala Ser Ile Leu Asn Val Ser
            115               120               125

Phe Ser Asp Asn Leu Pro Val Ala Asp Leu His Trp Ile Leu Ser Asp
    130               135               140

Lys Ser Gly Lys Ser Ile Val Val Glu Ser Thr Lys Ser Gly Leu His
145               150               155               160

Val Tyr Asp Asn Pro Val His Val Leu Thr Asn Asn Pro Glu Phe Pro
                165               170               175

Asp Gln Leu Ile Lys Leu Ser Asp Tyr Ala Asp Val Thr Pro His Asn
                180               185               190

Pro Lys Asn Thr Leu Val Pro Asn Val Asp Leu Asn Leu Tyr Ser Arg
            195               200               205

Gly Leu Gly Thr His His Leu Pro Gly Gly Met Asp Ser Ser Ser Arg
    210               215               220

Phe Val Lys Val Ala Phe Val Leu Ser His Ala Pro Lys Gly Lys Asp
225               230               235               240

Glu Ala Glu Asn Val Thr Asn Tyr Phe His Ile Leu His Ser Val Glu
                245               250               255

Gln Pro Lys Gly Leu Asp Glu Val Glu Asp Asn Arg Tyr Glu Tyr Thr
            260               265               270

Met Tyr Ser Asp Cys Met Asn Leu Asp Lys Gly Ile Leu Tyr Phe Thr
            275               280               285

Thr Tyr Asp Asn Asn Arg Ile Asn Ala Val Asp Met His Lys Ala Asp
    290               295               300

Leu Asp Ser Lys Asp Leu Ile Cys Tyr Asp Leu Phe Lys Lys Gln Asp
305               310               315               320

Ile Glu Tyr Met Asn
                325
```

<210> SEQ ID NO 10
<211> LENGTH: 978
<212> TYPE: DNA
<213> ORGANISM: Lactobacillus amylovorus

<400> SEQUENCE: 10

```
atgtgtacat caatttgtta tagtccaagt gatcactatt ttggtagaaa tcttgattat      60
gaaattgctt atggtcaaaa ggtagttatc gtaccaagaa actatgaatt tgaatacaga     120
gaattgccaa cgcaaaagtc tcactacgct tttatcggtg tttccgtggt taatgatgat     180
tatccacttt tatgtgatgc tattaatgaa aagggctgg gtattgctgg tttaaacttc      240
caaggtccta atcactactt cccaaagatg gaaggtaaga agaatattac ttcttttgaa     300
ttaacgccat atttgttaag caactgcgaa actaccgatg atgttaagga aatcttagct     360
gatgcaagta ttttaaacgt tagcttttca gataatttac ctgtagctga cttgcactgg     420
attttaagtg ataaatctgg caagagcatc gtagttgaat ccactaagtc aggtttgcac     480
gtttacgaca tccagttca tgtttttaact aacaatcctg aatttccaga tcaattgatc     540
aagttgagtg actatgccga tgttactcca cataatccta gaacacttt agttcctaat      600 gtcgatctca acttgtacag tagaggtctt ggtactcacc atttgcctgg tggtatggat     660
```

-continued

```
tcaagttctc gttttgttaa agtcgctttc gttttgtcac atgctcctaa ggggaaggat    720
gaagcagaaa acgtaactaa ctacttccac attttgcatt ctgttgaaca acctaaaggc    780
ttggatgaag tagaagacaa tcgctatgaa tacactatgt attctgattg tatgaacttg    840
gataaaggca ttttgtactt cactacttat gacaataacc ggatcaatgc agtagatatg    900
cataaggcag atttggattc aaaggacttg atttgctacg acttgttcaa gaaacaagat    960
attgaatata tgaattag                                                  978
```

<210> SEQ ID NO 11
<211> LENGTH: 324
<212> TYPE: PRT
<213> ORGANISM: Lactobacillus animalis

<400> SEQUENCE: 11

```
Met Cys Thr Ala Val Ser Phe Lys Thr Asn Ser His Tyr Phe Gly Arg
1               5                   10                  15

Asn Leu Asp Leu Glu Leu Ser Tyr Gly Glu Lys Ala Val Ile Val Pro
            20                  25                  30

Arg Asn Phe Val Phe Asn Leu Arg Lys Leu Pro Ala Leu Ser Glu His
        35                  40                  45

Tyr Ala Met Ile Gly Val Ala Ala Val Phe Ala Asp Thr Pro Leu Tyr
    50                  55                  60

Tyr Asp Ala Val Asn Glu Tyr Gly Leu Gly Met Ala Gly Leu Asn Phe
65                  70                  75                  80

Glu Gly Asn Ala Val Phe Arg Glu Phe Glu Pro Glu Met Asp Asn Val
                85                  90                  95

Thr Pro Phe Glu Phe Ile Pro Tyr Ile Leu Gly Gln Cys Lys Thr Val
            100                 105                 110

Ala Glu Ala Arg Glu Met Leu Ala Asn Ile Asn Leu Val Asn Glu Ala
        115                 120                 125

Phe Ser Pro Glu Leu Pro Leu Ser Pro Leu His Trp Ile Ile Ser Asp
        130                 135                 140

Lys Lys Glu Ser Ile Val Val Glu Pro Met Ala Asp Gly Leu Lys Val
145                 150                 155                 160

Tyr Asp Asp Pro Val Gly Val Leu Thr Asn Asn Pro Thr Phe Asp Lys
                165                 170                 175

Gln Leu Phe Thr Leu Asn Asn Tyr Arg Thr Leu Ser Pro Lys Thr Pro
            180                 185                 190

Glu Asn Thr Phe Tyr Pro Gly Val Glu Leu Asp Thr Tyr Ser Arg Gly
            195                 200                 205

Met Gly Thr Leu Gly Leu Pro Gly Asp Leu Thr Ser Ser Ser Arg Phe
    210                 215                 220

Val Lys Ala Val Phe Thr Lys Ala His Ser Val Cys Gln Pro Asp Glu
225                 230                 235                 240

Asn Ser Ser Val Gly Gln Tyr Phe His Ile Leu Gly Ser Val Glu Gln
                245                 250                 255

Gln Lys Gly Cys Cys Asp Val Gly Asn Gly Lys Tyr Glu Tyr Thr Ile
            260                 265                 270

Tyr Ser Asp Cys Tyr Asn Thr Asp Lys Gly Ile Phe Tyr Tyr Lys Thr
            275                 280                 285

Tyr Glu Asn Ser Gln Ile Thr Ala Leu Asp Met His Lys Val Asp Leu
    290                 295                 300

Asp Gly His Thr Phe Thr Ser Tyr Asp Leu Leu Glu Thr Gln Gln Ile
```

-continued

| 305 | 310 | 315 | 320 |
|-----|-----|-----|-----|

Asn Tyr Ala Asn

<210> SEQ ID NO 12
<211> LENGTH: 975
<212> TYPE: DNA
<213> ORGANISM: Lactobacillus animalis

<400> SEQUENCE: 12

```
atgtgtactg cagtatcgtt taagactaat tcacattatt ttgggagaaa tttggatcta      60
gaactttctt atggtgagaa agcagttatt gttccacgga attttgtttt taatttaaga     120
aaattgcctg ctttaagcga gcactatgca atgatcgggg tggctgcggt ttttgctgac     180 acccccattgt attatgatgc agtcaatgaa tatggcttag gaatggcagg gctcaacttt     240
gaaggtaatg cagtctttcg tgaatttgaa ccagaaatgg ataatgtgac accatttgaa     300
tttattccat atattttggg tcaatgcaag actgtagcgg aagcccgtga aatgttagct     360
aatatcaatt tggtaaatga agcctttagt cctgaattgc cattatcgcc tttgcattgg     420
atcatctcag ataaaaaaga gtcgatcgtg gtcgaaccga tggctgatgg cttgaaggtt     480
tatgatgatc cagtgggtgt gttaacgaat aatccaactt ttgataagca attatttact     540
ttgaataact atcggacatt atcgcctaag acaccagaaa atacttttta tcctggggtc     600
gaattggata cttatagccg tggcatgggg actctaggtt taccaggaga tctaacttca     660
agttctcgct ttgtcaaagc agtctttacg aaagctcatt cggtctgcca accagatgaa     720
aattccagtg ttggtcaata tttccacatc ttaggttctg ttaacaaca aaagggttgc     780 tgtgatgttg gtaatggcaa atatgaatat acgatctatt ctgattgcta taacaccgac     840
aaagggatct tttattacaa gacatatgaa aacagtcaga tcacagcctt agacatgcac     900
aaagtcgatc ttgatggtca tacctttact agctatgact tattggagac gcaacagatc     960
aattacgcta attaa                                                       975
```

<210> SEQ ID NO 13
<211> LENGTH: 325
<212> TYPE: PRT
<213> ORGANISM: Lactobacillus antri

<400> SEQUENCE: 13

```
Met Cys Thr Ser Ile Leu Tyr Thr Ala Gly Asp Cys Tyr Phe Gly Arg
1               5                   10                  15

Asn Leu Asp Leu Glu Val Ser Phe Gly Gln Glu Val Val Ile Thr Pro
            20                  25                  30

Arg Asp Tyr Arg Phe Asn Phe Arg Gln Met Pro Ala Leu Asp His His
        35                  40                  45

Tyr Ala Ile Ile Gly Met Ala Leu Val Gln Asp Asn Tyr Pro Leu Tyr
    50                  55                  60

Phe Asp Gly Ala Asn Glu Glu Gly Leu Gly Met Ala Gly Leu Asn Phe
65                  70                  75                  80

Ala Gly Pro Ala His Tyr Phe Pro Val Asp Asp His Lys Asp Asn Val
                85                  90                  95

Ser Pro Phe Glu Phe Ile Pro Tyr Ile Leu Gly Gln Cys Lys Asn Val
            100                 105                 110

Val Glu Ala Lys Gln Leu Leu Lys Lys Leu Asn Leu Val Lys Ile Asn
        115                 120                 125

Phe Ser Asp His Leu Gln Leu Ser Pro Leu His Trp Leu Ile Ala Asp
```

-continued

```
        130                135                140
Arg Ser Gly Lys Ser Ile Val Val Glu Ser Thr Val Ser Gly Leu His
145                150                155                160

Val Tyr Asp Asn Ser Val Asn Val Leu Thr Asn Asn Pro Glu Phe Pro
                    165                170                175

Gly Gln Leu Thr Asn Leu Ala Asn Tyr Gln Ser Ile Ser Pro Glu Gln
                180                185                190

Pro Thr Asn Gly Leu Ala Pro Asn Ile Lys Ile Gly Phe Tyr Ser Arg
            195                200                205

Gly Leu Gly Ser Arg Met Leu Pro Gly Gly Met Asp Ser Gln Ser Arg
        210                215                220

Phe Val Lys Glu Val Phe Thr Leu Gln His Ala Pro Ala Gly Ala Ser
225                230                235                240

Glu Val Glu Asn Val Thr Asn Tyr Phe His Cys Leu His Ala Val Glu
                245                250                255

Gln Gln Lys Gly Leu Asp Glu Val Ala Pro Asn Thr Phe Glu His Thr
            260                265                270

Ile Tyr Ser Asp Gly Ile Asn Leu Ser Thr Gly Thr Phe Tyr Tyr Thr
        275                280                285

Thr Tyr Ala Asn His Gln Ile Asn Ala Val Ser Leu Gln His Ala Asp
    290                295                300

Leu Asn Asn Asn Thr Leu Ala Pro Phe Pro Leu Arg Glu Gln Gln Ser
305                310                315                320

Ile Asn Met Gln Asn
                325
```

<210> SEQ ID NO 14
<211> LENGTH: 978
<212> TYPE: DNA
<213> ORGANISM: Lactobacillus antri

<400> SEQUENCE: 14

```
atgtgtacat caattttata taccgcgggt gactgctatt ttggtcggaa cctggacttg      60
gaagtttcat ttgggcagga agtagtaatt acgccacgcg attaccgctt taatttccgc     120
caaatgcctg cactggacca ccattatgcc attattggga tggccttagt ccaggataac     180
tatcctttat actttgacgg ggctaatgaa gaggggctcg ggatggctgg cctgaacttc     240
gccgggcctg cccactattt cccggtcgat gaccacaagg ataatgtttc accatttgaa     300
tttattccgt atattttggg gcaatgcaag aatgttgtcg aagccaaaca attattgaag     360
aaacttaacc tggtcaaaat caattttcc gaccacctgc agctgtcgcc attgcactgg      420
ttgattgccg accggtctgg taaatcgatc gtggttgaat cgacggtgag tggcctgcac     480
gtttacgaca actcggtcaa cgttttgact aataatccgg aatttccggg tcagttgact     540
aacctggcca actaccagag tatctcacca gagcaaccaa ctaatgggct ggcgccaaat     600
atcaagatag ttttttatag ccggggatta ggctcccgca tgttgccagg ggggatggat     660
tcccagagcc gttttgtaaa agaagtcttt accctgcagc acgccccagc tggtgccagt     720
gaggtagaaa acgttactaa ctatttccac tgcctgcacg cggtggagca gcaaaagggt     780
ctcgatgagg tggccccgaa cacttttgaa cacaccattt attctgacgg gatcaattta     840
tcgacgggaa ccttctacta tactacttat gctaatcatc aaattaatgc ggtcagcttg     900
caacatgcag atttgaataa caacactttg gcaccattcc cattgcggga gcaacagtca     960
attaatatgc aaaattaa                                                    978
```

<210> SEQ ID NO 15
<211> LENGTH: 323
<212> TYPE: PRT
<213> ORGANISM: Lactobacillus antri

<400> SEQUENCE: 15

```
Met Glu Val Val Asn Met Cys Thr Gly Leu Arg Phe Thr Asp Pro Glu
1               5                   10                  15

Gly Asn Leu Tyr Phe Gly Arg Asn Leu Asp Val Gly Ile Asp Tyr Gly
            20                  25                  30

Lys Lys Leu Ile Ile Thr Pro Arg Asn Tyr Pro Leu Pro Tyr Lys Phe
        35                  40                  45

Leu Asn Asp Arg Thr Thr Lys Lys Ala Thr Ile Gly Met Gly Ile Val
        50                  55                  60

Met Asp Asp Tyr Pro Leu Tyr Phe Asp Cys Cys Asn Glu Asp Gly Leu
65                  70                  75                  80

Cys Ile Ala Gly Leu Asn Phe Pro His Tyr Ala His Phe Ser Ala Gly
                85                  90                  95

Pro Val Asp Asp Lys Thr Asn Leu Ala Pro Tyr Glu Leu Met Met Trp
            100                 105                 110

Val Thr Gln Glu Phe Thr Ser Val Ala Glu Val Lys Thr Ala Leu Gln
            115                 120                 125

Asp Val Asn Leu Val Asn Gln Ala Leu Val Asp Ser Leu Pro Val Ala
        130                 135                 140

Pro Leu His Trp Leu Ile Ser Asp Gln His Glu Ala Ile Val Leu Glu
145                 150                 155                 160

Gln Ser Gln Gln Tyr Gly Leu Arg Val Phe Asp Asn Arg Leu Gly Val
                165                 170                 175

Leu Thr Asn Ser Pro Asp Phe Ala Trp Gln Met Thr Asn Leu Cys Asn
            180                 185                 190

Tyr Thr Gly Leu Thr Pro His Asp Ala Gln Pro Gln Thr Trp Thr Lys
        195                 200                 205

Gln Asp Leu Ile Pro Leu Gly Val Gly Thr Gly Ser Leu Gly Leu Pro
    210                 215                 220

Gly Asp Ser Ile Pro Ala Ser Arg Phe Val Lys Ala Ala Tyr Leu Asn
225                 230                 235                 240

Ala Asn Tyr Pro Ala Val Glu Gly Glu Thr Ala Asn Val Ala Lys Phe
                245                 250                 255

Phe Asn Ile Leu Lys Ala Val Ala Met Val Lys Gly Ser Val Val Asn
            260                 265                 270

Val Lys Gly Lys Tyr Glu Tyr Thr Val Tyr Thr Ala Cys Tyr Ser Ala
        275                 280                 285

Lys Ser Lys Thr Tyr Tyr Tyr Asn Leu Tyr Asn Asp Phe Asn Leu His
    290                 295                 300

Arg Cys Gln Leu Thr Ala Asp Asn Val Asn Gly Lys Gln Leu Ile Val
305                 310                 315                 320

Lys Glu Ala
```

<210> SEQ ID NO 16
<211> LENGTH: 972
<212> TYPE: DNA
<213> ORGANISM: Lactobacillus antri

<400> SEQUENCE: 16

```
atggaggttg ttaatatgtg tacaggttta agattcactg atccagaagg aaacttatat       60
ttcggtcgga acctcgacgt gggaatcgat tacggcaaga aactgattat tacaccgcgc      120
aactacccgc ttccttacaa attcttaaat gatcgaacaa ctaagaaggc aacaatcggc      180
atgggaatcg taatggacga ttacccgctc tacttcgatt gctgcaacga agacggcctg      240
tgtattgccg gcttaaactt cccccactac gcccacttca gcgctggtcc cgttgatgat      300
aagaccaacc tggcccccta tgaattaatg atgtgggtta ctcaagaatt cacttcagtg      360
gcggaagtca aaacagccct gcaggacgtc aacctggtca atcaggccct cgtcgactcc      420
ctcccggtag cgccactcca ctggctcatc agcgaccagc atgaggcaat cgtactcgag      480
cagtcacagc aatatggctt gcgcgtattt gacaaccggc tgggggtatt gaccaacagt      540
ccggattttg cttggcagat gaccaacctg tgtaactaca ccggcttaac cccgcacgac      600
gcgcaaccgc aaacctggac gaagcaggac ctgatcccgc ttggcgttgg caccggcagc      660
ctgggcctgc tggcgacag tatcccggca tcacgctttg tcaaagcagc gtacctcaac      720
gccaactacc cggccgtcga gggtgaaacc gccaacgtag caaagttctt caacattctc      780
aaggcggtcg caatggtcaa gggcagcgta gttaacgtta agggcaagta tgaatatacc      840
gtttataccg cctgctactc tgctaagagc aagacttact actacaacct ttacaatgac      900
ttcaacctgc accgttgtca gctgactgcg gacaacgtca atggcaagca gttgattgtt      960
aaagaggcct aa                                                          972
```

```
<210> SEQ ID NO 17
<211> LENGTH: 324
<212> TYPE: PRT
<213> ORGANISM: Lactobacillus apodemi

<400> SEQUENCE: 17

Met Cys Thr Ala Val Ser Phe Lys Thr Lys Asp His Tyr Phe Gly Arg
1               5                   10                  15

Asn Phe Asp Phe Asp Phe Ser Tyr Ser Glu Gln Ala Val Ile Thr Pro
            20                  25                  30

Arg Glu Phe Glu Phe Lys Leu Arg Glu Leu Ser Ala Leu Lys Lys His
        35                  40                  45

Tyr Ala Leu Val Gly Ile Ala Ala Ile Phe Asp Asp Val Pro Leu Tyr
    50                  55                  60

Tyr Asp Ala Val Asn Glu Tyr Gly Leu Gly Met Ala Gly Leu Asn Phe
65                  70                  75                  80

Glu Gly Asn Ala Val Phe Asn Glu Ile Asp Pro Asn Met Asp Asn Val
                85                  90                  95

Ala Pro Tyr Glu Phe Ile Pro Tyr Ile Leu Gly Gln Cys Lys Thr Val
            100                 105                 110

Ala Glu Ala Arg Val Leu Leu Glu Lys Val Asn Leu Val Asn Leu Ala
        115                 120                 125

Phe Ser Asp Asn Leu Pro Val Ala Ser Leu His Trp Ile Ile Ala Asp
    130                 135                 140

Lys Asp Glu Ser Ile Val Val Glu Pro Leu Ala Asp Gly Leu Lys Ile
145                 150                 155                 160

Tyr Asp Asp Pro Val Gly Val Leu Thr Asn Asn Pro Thr Phe Asp Arg
                165                 170                 175

Gln Leu Phe Asn Leu Asn Asn Tyr Arg Gly Leu Ser Ala Lys Thr Pro
            180                 185                 190

Glu Asn Thr Phe Asp Pro Asn Ala Asp Leu Asp Val Tyr Ser Arg Gly
```

```
        195                 200                 205
Met Gly Thr Leu Gly Leu Pro Gly Asp Leu Thr Ser Ser Ser Arg Phe
    210                 215                 220
Val Lys Ala Thr Phe Thr Arg Ala His Ser Val Cys Asp Asp Asp Glu
225                 230                 235                 240
Asn Ser Ser Val Ser Gln Phe Phe His Ile Leu Gly Ser Val Ala Gln
                245                 250                 255
Gln Lys Gly Cys Cys Asp Val Gly Asn Asp Glu Tyr Glu Tyr Thr Ile
            260                 265                 270
Tyr Ser Asn Cys Tyr Asn Thr Glu Thr Gly Val Met Tyr Tyr Arg Thr
            275                 280                 285
Tyr Tyr Asn Ser Gln Leu Thr Ala Leu Asp Leu Arg Lys Ala Asp Leu
        290                 295                 300
Asp Ser Asp Lys Tyr Val Ala Phe Pro Leu Ile Glu Thr Gln Gln Ile
305                 310                 315                 320
Asn His Leu Asn
```

```
<210> SEQ ID NO 18
<211> LENGTH: 975
<212> TYPE: DNA
<213> ORGANISM: Lactobacillus apodemi

<400> SEQUENCE: 18
atgtgtacag cagtttcgtt caagaccaaa gatcactact ttggacgcaa ttttgatttt      60 gattttcat atagcgaaca ggccgtaata acaccacgtg aattcgaatt taaattacgt     120
gaactctcag ctttgaaaaa gcattatgct ttagttggga ttgccgctat tttcgatgat     180
gtaccactat attatgatgc cgtgaatgaa tatggcttag catggctgg tttaaacttc     240 gaaggtaatg ctgtatttaa cgaaattgat cctaacatgg ataacgtagc accatacgaa     300
tttatcccat atattttagg acaatgtaag actgtagcag aagcgcgtgt cttgttagaa     360
aaagtcaatt tagttaatct tgcttttagt gataatttgc cagttgcatc cctacattgg     420
atcattgctg ataaagacga atcgatcgta gttgaacctt tagctgatgg tttaaagatt     480
tatgatgatc cagtgggagt tttgaccaat aatccaacct ttgatcgtca attgttcaac     540
ttgaacaact accgtgggtt atccgctaag acgccagaaa atacttttga ccctaatgct     600
gatctagatg tctatagccg tgggatgggg acattaggtc ttcctggtga cttaacatca     660
agttcacgtt ttgtcaaagc aacctttacg cgcgcacatt ctgtgtgtga tgacgatgaa     720
aactctagtg tgagccaatt tttccatatt ttaggttcag tagcacaaca aaaaggttgc     780
tgtgatgtcg gtaatgatga atatgaatac acgatctata gcaactgcta caataccgaa     840
actggtgtaa tgtattaccg cacatactat aacagtcaat taacagcatt agatcttcgg     900
aaagctgatt tagattcaga taaatatgtc gcatttccat tgatcgaaac acaacagatc     960
aatcatttaa actaa                                                       975
```

```
<210> SEQ ID NO 19
<211> LENGTH: 325
<212> TYPE: PRT
<213> ORGANISM: Lactobacillus apodemi

<400> SEQUENCE: 19

Met Cys Thr Ala Val Ser Phe Lys Thr Lys Asp His Tyr Phe Gly Arg
1               5                   10                  15
Asn Phe Asp Tyr Glu Leu Ser Tyr Gly Glu Lys Ala Ile Ile Ile Pro
```

```
                20                    25                    30

Arg Asn Tyr Val Phe Glu Leu Arg Lys Leu Pro Ala Leu Ser Lys His
            35                    40                    45

Tyr Ala Met Val Gly Leu Thr Ser Val Phe Asp Asn Thr Pro Leu Ile
        50                    55                    60

Tyr Asp Ala Val Asn Glu His Gly Leu Ala Met Ala Gly Leu Asn Phe
65                    70                    75                    80

Glu Gly Asn Ala Val Phe Tyr Asp Phe Asp His Ala Met Asp Asn Val
                85                    90                    95

Thr Pro Phe Glu Phe Ile Pro Tyr Ile Leu Gly Gln Cys Lys Asn Val
            100                   105                   110

Ala Glu Ala Lys Glu Met Leu Thr Lys Ile Asn Leu Val Asn Glu Ala
        115                   120                   125

Phe Ser Ala Asp Leu Pro Leu Ala Pro Leu His Trp Ile Ile Ser Asp
        130                   135                   140

Ser Glu Asp Asn Thr Ile Val Val Glu Thr Leu Ala Asp Gly Met Lys
145                   150                   155                   160

Val Tyr Asp Asp Pro Val Gly Val Met Thr Asn Asn Pro Thr Phe Asp
                165                   170                   175

Lys Gln Leu Phe Asn Leu Asn Asn Tyr Arg Gly Leu Ser Ala Lys Thr
            180                   185                   190

Pro Glu Asn Thr Phe Asp Pro Thr Val Asp Leu Pro Ala Tyr Ser Arg
            195                   200                   205

Gly Met Gly Thr Leu Gly Leu Pro Gly Asp Leu Thr Ser Ser Ser Arg
        210                   215                   220

Phe Val Lys Ala Ala Phe Val Lys Ala His Ser Val Cys Glu Thr Asp
225                   230                   235                   240

Glu Ser Ser Ser Val Ser Gln Gly Phe His Ile Leu Ser Ala Ile Glu
                245                   250                   255

Gln Gln Arg Gly Cys Cys Glu Val Ser Glu Gly Lys Tyr Glu Tyr Thr
            260                   265                   270

Ile Tyr Ser Ala Cys Tyr Asn Lys Asp Lys Gly Ile Leu Tyr Tyr Lys
        275                   280                   285

Thr Tyr Glu Asp Ser Gln Ile Thr Ala Leu Asn Met His Lys Ala Asp
    290                   295                   300

Leu Glu Ser Glu Gln Phe Thr Leu Tyr Pro Leu Ser Gln Thr Gln His
305                   310                   315                   320

Phe Asn Tyr Ala Asn
            325

<210> SEQ ID NO 20
<211> LENGTH: 978
<212> TYPE: DNA
<213> ORGANISM: Lactobacillus apodemi

<400> SEQUENCE: 20
atgtgtactg cagtatcatt taaaacaaag gatcactatt ttgggagaaa ttttgattat        60
gagctctctt atggtgaaaa agcgatcatc atcccacgta attatgtttt tgaattgcga       120
aaattaccgg ctttgagcaa acactatgca atggtcggtt tgacttccgt ttttgacaat       180
acgccactta tttatgatgc cgtcaacgag catggcttag ctatggctgg tttgaacttt       240
gaaggcaatg ccgtctttta tgactttgat catgcgatgg ataatgtgac tccatttgaa       300
tttattccat acattttagg acaatgtaaa aacgtggctg aagctaagga aatgttgact       360
```

```
aagatcaact tagtcaatga agcatttagt gctgatctac cgttagctcc attgcactgg      420
atcatcagtg acagtgaaga taatacgatc gtggtcgaga ctttggctga tggcatgaaa      480
gtctatgatg atcccgtggg tgtgatgacc aataatccaa cgtttgataa gcaactattt      540
aatttgaaca attatcgagg cctatcggct aaaacgcctg aaaatacttt tgatccgacg      600
gttgatctac cagcatacag tcgtgggatg ggaactttag gtcttccagg cgatttgact      660
tcgagctcac gttttgtcaa agcagctttt gttaaagcac attcagtttg tgaaacagat      720
gaaagttcta gtgtcagtca aggtttccat attttaagtg cgatcgaaca caacgaggc      780 tgttgtgaag tgagcgaagg aaagtatgaa tatacgatct attctgcttg ttataacaaa      840
gataaaggga tcttatatta taagacgtat gaagatagtc agatcacagc tttaaatatg      900
cataaagccg atctagaaag tgaacagttc acccttatc ccttgagtca aacacaacat       960
ttcaattacg ctaattaa                                                    978
```

```
<210> SEQ ID NO 21
<211> LENGTH: 321
<212> TYPE: PRT
<213> ORGANISM: Lactobacillus aviarius subsp. araffinosus

<400> SEQUENCE: 21

Met Lys Gly Val Phe Ile Met Cys Thr Gly Leu Arg Phe Asn Asp Ser
1               5                   10                  15

Glu Gly Asn Leu Tyr Phe Gly Arg Asn Leu Asp Val Glu Ser Thr Tyr
            20                  25                  30

Gly Glu Lys Val Ile Val Thr Pro Arg Asn Tyr Glu Leu Pro Tyr Lys
        35                  40                  45

Phe Leu Glu Asn Gly Lys Thr Thr Lys Ala Ile Ile Gly Met Gly Ile
    50                  55                  60

Met Ala Gly Asp Tyr Pro Met Tyr Phe Asp Cys Ile Asn Glu Asn Gly
65                  70                  75                  80

Leu Gly Ile Ala Gly Leu Asn Phe Pro Arg Tyr Ala Tyr Phe Thr Glu
                85                  90                  95

Gly Pro Val Asp Gly Lys Thr Asn Met Ala Pro Tyr Glu Phe Met Leu
            100                 105                 110

Trp Leu Met Glu Glu Phe Asp Thr Val Glu Glu Ala Lys Lys Gly Leu
        115                 120                 125

Ala Asn Leu Asn Leu Val Asp Ala Pro Phe Ala Pro Gln Met Pro Val
    130                 135                 140

Ala Pro Leu His Trp Ile Ile Ser Asp Lys Lys Glu Ser Val Val Val
145                 150                 155                 160

Glu Gln Thr Lys Asp Gly Leu Lys Val Tyr Asp Asn His Val Gly Val
                165                 170                 175

Leu Thr Asn Asn Pro Asp Tyr Pro Trp His Met Thr Asn Leu Asn Asn
            180                 185                 190

Tyr Ala Gly Leu Thr Pro Asn Asp Ala Thr Thr His Asp Trp Asn Gly
        195                 200                 205

Gln Glu Ile Arg Pro Leu Gly Val Gly Thr Gly Ser Leu Gly Leu Pro
    210                 215                 220

Gly Asp Ser Ile Pro Ala Ser Arg Phe Val Lys Val Ala Tyr Leu Asn
225                 230                 235                 240

Ala Asn Tyr Pro Thr Val Asp Gly Glu Lys Ala Asn Val Ala Lys Phe
                245                 250                 255

Phe Asn Ile Leu Lys Ser Val Ala Met Val Asp Gly Ser Val Ile Asn
```

```
             260             265             270
Glu Gln Gly Lys Asp Glu Tyr Thr Val Tyr Thr Gly Cys Phe Ser Thr
        275             280             285

Lys Thr Asn Thr Tyr Tyr Tyr Asn Arg Phe Asp Asp Phe Glu Met Lys
        290             295             300

Ser Val Gln Phe Thr Glu Glu Asn Met Asn Ala Asp Lys Val Thr Ile
305             310             315             320

Tyr

<210> SEQ ID NO 22
<211> LENGTH: 966
<212> TYPE: DNA
<213> ORGANISM: Lactobacillus aviarius subsp. araffinosus

<400> SEQUENCE: 22
gtgaaagggg tttttattat gtgtacaggt ttacgtttta atgattcaga aggcaattta      60
tattttggtc gtaacttaga tgttgaatca acatatggcg aaaaagtgat cgtaacacca     120
agaaattacg aattaccata taagttttta gaaaatggta agacaacaaa agcaattatc     180
ggaatgggaa tcatggctgg tgattaccca atgtactttg actgcatcaa cgaaaatggt     240
cttggaattg ccggattaaa cttcccacgc tatgcttatt ttacagaagg tccagttgac     300
ggtaagacaa acatggcacc atatgaattc atgttatggt tgatggaaga attcgataca     360
gttgaagaag ctaagaaggg cttagcaaac ttgaacttag ttgatgctcc atttgcaccg     420
caaatgccgg ttgctccatt acactggatc atcagcgaca agaaggaatc agttgttgtt     480
gaacaaacaa aggatggcct taaggtttat gataaccacg ttggcgtttt gacaaataat     540
cctgattacc catggcacat gacaaatctt aacaattatg ctgggttaac accaaatgat     600
gcgacaactc atgactggaa cggtcaagaa attcgtccat taggtgtcgg aacaggtagt     660
ttaggtttgc caggcgacag cattcctgct tcacggtttg taaaggttgc ttacttaaat     720
gcaaactacc caaccgttga cggtgaaaag gcaaatgttg ctaagttctt taacattttg     780
aagtccgttg caatggttga tggaagtgtc atcaatgaac aaggtaaaga tgaatatact     840
gtttacacag gctgcttctc aaccaagaca aacacatact actataaccg ttttgatgac     900
ttcgaaatga gagcgttca atttacagaa gaaaatatga atgcagataa ggttacaatc     960
tactaa                                                              966

<210> SEQ ID NO 23
<211> LENGTH: 317
<212> TYPE: PRT
<213> ORGANISM: Lactobacillus aviarius subsp. araffinosus

<400> SEQUENCE: 23

Met Cys Thr Gly Ile Lys Phe Thr Asp Thr Asn Gln Asn Met Tyr Phe
1               5                   10                  15

Gly Arg Asn Leu Asp Tyr Gly Ile Asn Phe Gly Glu Lys Pro Ile Val
            20                  25                  30

Ala Pro Ile Gly Tyr Glu Met Asn Tyr Arg His Leu Pro Lys Gln Thr
        35                  40                  45

Phe Ser Lys Pro Ile Val Gly Met Gly Leu Asp Val Asn Asn Tyr Pro
    50                  55                  60

Leu Leu Phe Glu Gly Asn Thr Lys Ser Leu Cys Met Ala Gly Leu Met
65                  70                  75                  80

Phe Pro Asn Asn Ala Tyr Tyr Asn Pro Glu Val Val Asp Gly Lys Tyr
```

```
                       85              90              95

Asn Ile Thr Ser Phe Glu Phe Ile Pro Trp Val Leu Glu Asn Phe Asp
             100             105             110

Thr Val Lys Glu Val Arg Asp Val Ile Ala Glu Lys Val Asn Ile Val
             115             120             125

Ala Asp Ala Phe Ser Glu Gln Leu Gln Pro Ser Pro Leu His Trp Leu
         130             135             140

Ile Ser Asp Lys Asn Asp Ser Ile Val Val Glu Gln Thr Lys Asp Gly
145             150             155             160

Met His Val Tyr Asp Asn Asp Val Asp Val Leu Thr Asn Asn Pro Glu
                 165             170             175

Phe Pro Trp His Met Gln Asn Leu Asn Asn Tyr Val Asn Leu Thr Pro
             180             185             190

Asn Asp His His Glu Ser Thr Trp Asp Gln His Gln Ile Thr Pro Gln
             195             200             205

Gly Val Gly Thr Gly Ser Leu Gly Leu Pro Gly Asp Gly Thr Pro Gln
         210             215             220

Ser Arg Phe Val Lys Val Ala Tyr Leu Asn Ala Asn Tyr Pro Gln Pro
225             230             235             240

Thr Asn Glu Leu Glu Gly Met Ser Arg Leu Phe Asn Ile Leu Lys Ser
                 245             250             255

Val Ala Ile Pro Tyr Gly Ser Val Val Asn Asn Glu Gly Gln Lys Glu
             260             265             270

Tyr Thr Met Tyr Ser Cys Cys Tyr Ser Gln Ala Ser Glu Thr Tyr Tyr
             275             280             285

Tyr Asn Trp Phe Asn Asp Val Asn Ile His Gln Val Lys Leu Asn Asp
         290             295             300

Glu Leu Thr His Gly Asp Lys Ile Lys Thr Phe Asp Lys
305             310             315
```

<210> SEQ ID NO 24
<211> LENGTH: 954
<212> TYPE: DNA
<213> ORGANISM: Lactobacillus aviarius subsp. araffinosus

<400> SEQUENCE: 24

```
atgtgtacag gtattaaatt tacagatacg aatcaaaata tgtatttcgg tcgtaattta      60
gattatggga ttaattttgg agaaaaaccg attgttgctc caatcggata tgaaatgaat     120
taccgtcatt tgccaaaaca aactttttca aaaccaatcg taggaatggg attagacgta     180
aataactatc cgcttctttt tgaagggaat acaaaaagtt tatgtatggc agggttaatg     240
tttcctaata tgcatatta taatcctgag gttgtcgatg gtaagtacaa tatcacatcg     300
tttgaattta ttccatgggt tttagaaaat tttgatactg ttaaagaagt tagagatgta     360
attgcggaaa aagttaatat tgtagctgat gcatttagtg agcaacttca accatctcca     420
ctccattggt tgatttcaga taaaaacgac tcaattgttg ttgaacaaac caaggatgga     480
atgcatgttt acgataacga tgttgatgtt ttgactaaca atccagaatt tccatggcat     540
atgcaaaact aaataatta tgttaacttg actcctaatg atcatcatga atcaacgtgg     600
gatcagcatc aaattactcc tcaagggggtt ggaacaggtt cattgggtct tccgggagat     660
ggaacaccgc aatcacggtt tgtaaaagtg gcatatttaa atgctaatta tccgcaacca     720
acaaatgaat tagaaggaat gtcacgttta tttaatattt taaagagtgt tgccatccct     780
tatggaagtg ttgtaaataa tgagggacaa aaggaatata caatgtatag ttgttgttat     840
```

```
tcacaagcaa gtgaaactta ctattacaat tggtttaatg atgtaaatat tcatcaggtt        900
aaactaaatg acgaattaac gcacggcgat aaaattaaga cttttgacaa ataa            954
```

<210> SEQ ID NO 25
<211> LENGTH: 328
<212> TYPE: PRT
<213> ORGANISM: Lactobacillus coleohominis

<400> SEQUENCE: 25

```
Met Cys Thr Ala Met Ser Phe Thr Val Ala Asn His His Tyr Phe Gly
1               5                   10                  15

Arg Asn Leu Asp Leu Glu Ile Ser Tyr Gly Gln Gln Val Val Ile Thr
            20                  25                  30

Pro Arg Asn Lys Pro Phe Asn Phe His Glu Val Asp Asp Leu Asn Gln
        35                  40                  45

His Tyr Ala Leu Ile Gly Val Ala Ala Val Met Asn Asp Tyr Pro Leu
    50                  55                  60

Tyr Phe Asp Ala Ala Asn Glu His Gly Leu Ala Met Gly Gly Leu Asn
65                  70                  75                  80

Tyr Pro Asp Asn Ala Phe Tyr Ala Asp Ser Lys Ala Gly Tyr Lys Asn
                85                  90                  95

Val Ala Ser Phe Glu Leu Ile Pro Trp Val Leu Gly Gln Cys Ala Thr
            100                 105                 110

Val Asp Glu Ala Lys Lys Leu Leu Thr Asn Val Asn Val Thr Asn Arg
        115                 120                 125

Gln Phe Ser Pro Asn Leu Pro Ala Ser Pro Leu His Trp Leu Ile Ala
    130                 135                 140

Asp Gln Thr Ser Ala Ile Val Val Glu Ser Asp Arg Asp Gly Val His
145                 150                 155                 160

Val Tyr Asp Asp Pro Val Gly Val Leu Thr Asn Asn Pro Ser Phe Pro
                165                 170                 175

Lys Gln Leu Phe Asn Leu Asn Asn Tyr Arg Thr Leu Ser Ala Asn Thr
            180                 185                 190

Leu Ala Asn Thr Phe Ser Asp Gln Val Asn Leu Thr Asp Tyr Ser Arg
        195                 200                 205

Gly Leu Gly Thr Arg Asn Leu Pro Gly Gly Met Asp Ala Glu Ser Arg
    210                 215                 220

Phe Val Arg Ala Thr Phe Asn Lys Tyr Asn Ala Asn Trp Pro Glu His
225                 230                 235                 240

Asp Glu Ile Ala Asn Ile Thr Gln Leu Phe His Val Met His Ser Val
                245                 250                 255

Glu Gln Gln Ser Gly Leu Asp Gln Val Ala Thr Asn Pro Ala Lys Phe
            260                 265                 270

Glu Tyr Thr Ile Tyr Thr Val Gly Tyr Asp Leu Asp Lys Gly Ser Leu
        275                 280                 285

Tyr Tyr Thr Thr Tyr Thr Asn Asn Gln Ile Asn Cys Val Asp Met Asn
    290                 295                 300

Lys Val Asp Leu Ala Ser Gln Gln Leu Thr Ser Tyr Pro Phe Ile Asn
305                 310                 315                 320

Gln Gln Ala Ile Asn His Val Asn
                325
```

<210> SEQ ID NO 26
<211> LENGTH: 987

<212> TYPE: DNA
<213> ORGANISM: Lactobacillus coleohominis

<400> SEQUENCE: 26

```
atgtgtactg caatgagttt tactgtggct aatcatcatt attttggccg caatctggat        60
ttagaaatat catacggcca acaggtggtg attacaccac gtaacaagcc gttcaatttt       120
cacgaagttg atgatcttaa tcaacattat gccttgatag gggttgctgc tgtgatgaat       180
gactatccct tatacttcga cgctgccaat gagcacggac tagcaatggg tggccttaat       240
tatcctgaca atgctttcta cgctgacagc aaagctggat acaaaaatgt tgcctccttt       300
gaattaatac catgggtttt aggtcaatgt gcaactgttg atgaagctaa aaaattatta       360
acgaatgtca acgttactaa ccggcaattc agtcctaact tgcctgcttc tccattacac       420
tggttaatcg ctgatcaaac atccgccatc gtcgttgaaa gcgatcgcga tggtgtccat       480
gtttatgacg atcccgttgg tgtattaact aataacccct cattccccaa acaactcttc       540
aacctcaata attaccgtac tttatcagct aacacccttg ccaacacatt ttctgaccaa       600
gtcaacttaa ctgattacag ccgtggatta ggtactcgta acctccctgg cggaatggac       660
gctgaaagtc gttttgttcg ggccaccttt aataaataca atgccaactg gccagagcat       720
gatgaaattg ccaacattac tcaattattc cacgtgatgc actcggtcga acagcaaagc       780
ggtcttgacc aagttgcaac taaccccgct aagtttgaat acacaattta cacggtcggc       840
tatgatctag ataagggaag cctttactac acaacctaca ccaacaatca aatcaactgt       900
gtggatatga ataaggtcga cttagctagc cagcaattaa cttcttaccc atttattaac       960
caacaagcaa tcaatcatgt gaactaa                                           987
```

<210> SEQ ID NO 27
<211> LENGTH: 325
<212> TYPE: PRT
<213> ORGANISM: Lactobacillus crispatus

<400> SEQUENCE: 27

```
Met Cys Thr Ser Ile Ile Phe Ser Pro Gln Asp His Tyr Phe Gly Arg
1               5                   10                  15

Asn Leu Asp Leu Glu Val Thr Phe Gly Gln Gln Val Val Val Thr Pro
            20                  25                  30

Arg Asn Tyr Val Phe Asn Phe Arg Lys Met Pro Glu Met Lys Gln His
        35                  40                  45

Tyr Ala Met Val Gly Ile Ala Leu Asp Ala Gly Asp Tyr Pro Leu Tyr
    50                  55                  60

Phe Asp Ala Ala Asn Glu Lys Gly Leu Gly Met Ala Gly Leu Asn Tyr
65                  70                  75                  80

Pro Asp Asn Ala Thr Tyr Tyr Asp Val Val Asp Gly Lys Asp Asn Ile
                85                  90                  95

Ala Ser Phe Glu Phe Ile Pro Trp Ile Leu Gly Gln Cys Glu Thr Val
            100                 105                 110

Ala Asp Ala Lys Lys Leu Leu Glu Lys Ile Asn Ile Val Asp Ile Asn
        115                 120                 125

Phe Ser Asp Lys Met Gln Ala Ser Pro Leu His Trp Leu Ile Ala Asp
    130                 135                 140

Lys Thr Gly Val Ser Ile Val Val Glu Thr Asp Lys Asp Gly Met His
145                 150                 155                 160

Val Tyr Asp Asn Pro Val Gly Cys Leu Thr Asn Asn Pro Gln Phe Ser
                165                 170                 175
```

-continued

```
Ser Gln Leu Phe Asn Leu Asn Asn Tyr Ala Asp Val Ser Pro Ala Met
            180                 185                 190

Pro Lys Asn Asn Phe Ser Ser Lys Val Ala Met Asn Gly Tyr Ser Arg
            195                 200                 205

Gly Leu Gly Ser Arg Asn Leu Pro Gly Gly Met Asp Ser Glu Ser Arg
            210                 215                 220

Phe Val Arg Val Ala Phe Asn Lys Phe Asn Ala Pro Val Gly Lys Thr
225                 230                 235                 240

Glu Glu Glu Asn Val Asp Asn Tyr Phe His Ile Leu His Ser Val Glu
            245                 250                 255

Gln Gln Lys Gly Leu Asp Gln Val Gly Pro Asp Ala Phe Glu Tyr Thr
            260                 265                 270

Ile Tyr Ser Asp Gly Thr Asn Leu Asp Lys Gly Ile Phe Tyr Tyr Thr
            275                 280                 285

Thr Tyr Thr Asn Lys Gln Ile Asn Val Val Asp Met Asn Lys Glu Asp
            290                 295                 300

Leu Asp Ser Ala Lys Leu Ile Thr Tyr Asp Met Leu Thr Lys Pro Thr
305                 310                 315                 320

Phe Asn His Gln Asn
                325
```

<210> SEQ ID NO 28
<211> LENGTH: 978
<212> TYPE: DNA
<213> ORGANISM: Lactobacillus crispatus

<400> SEQUENCE: 28

```
atgtgtactt ctattatttt tagtccacaa gatcactatt tcggccgtaa cctcgacctt      60
gaagttacct ttggccaaca agtagttgtt actccacgca attacgtctt caacttccgc     120
aagatgccag agatgaagca acactacgct atggtcggaa ttgcgcttga cgctggcgat     180
tacccacttt actttgacgc agctaatgaa aaaggtttag gcatggccgg gcttaactac     240
cctgacaatg ctacttacta cgatgtagtt gacggtaagg acaacattgc ttcatttgaa     300
ttcatccctt ggattttggg gcaatgtgaa actgttgctg atgctaaaaa gttgcttgaa     360
aagatcaaca tcgttgacat caacttctcc gacaagatgc aagcatcccc acttcactgg     420
ttaatcgctg ataagaccgg tgtttcaatc gtggttgaaa ctgacaaaga cgggatgcat     480
gtttacgaca acccagtcgg ctgtttgact aacaacccac aattctcaag tcaattattc     540
aacttaaaca actacgccga cgtttcacca gcaatgccta agaacaactt ctcttctaag     600
gtagcaatga acggctacag ccgcggcctt ggttcacgca acttgccagg gggtatggac     660
tcagaatcac gctttgttcg tgtagccttc aacaagttca acgctcctgt tggcaagact     720
gaagaagaaa acgttgataa ttacttccac attttgcatt cagttgaaca acaaaaaggc     780
cttgaccaag ttggtcctga cgcattcgaa tacaccatct attctgatgg taccaacctc     840
gacaagggta tcttctacta caccacttac accaacaagc aaattaacgt tgtcgacatg     900
aacaaggaag acttagattc tgctaagtta atcacctacg acatgttgac taagccaact     960
tttaaccacc aaaactaa                                                    978
```

<210> SEQ ID NO 29
<211> LENGTH: 325
<212> TYPE: PRT
<213> ORGANISM: Lactobacillus crispatus

<400> SEQUENCE: 29

```
Met Cys Thr Ser Ile Ile Phe Ser Pro Gln Asp His Tyr Phe Gly Arg
1               5                   10                  15

Asn Leu Asp Leu Glu Ile Thr Phe Gly Gln Gln Val Val Val Thr Pro
            20                  25                  30

Arg Asn Tyr Val Phe Asn Phe Arg Lys Met Pro Glu Met Lys Gln His
        35                  40                  45

Tyr Ala Met Val Gly Ile Ala Leu Asp Ala Gly Asp Tyr Pro Leu Tyr
    50                  55                  60

Phe Asp Ala Ala Asn Glu Lys Gly Leu Gly Met Ala Gly Leu Asn Tyr
65                  70                  75                  80

Pro Asp Asn Ala Thr Tyr Tyr Asp Glu Val Ala Asn Lys Asp Asn Ile
                85                  90                  95

Ala Ser Phe Glu Phe Ile Pro Trp Ile Leu Gly Gln Cys Ala Thr Val
            100                 105                 110

Ala Asp Ala Lys Val Leu Leu Lys Lys Ile Asn Ile Val Asn Leu Asn
            115                 120                 125

Phe Ser Asp Lys Met Gln Ala Ser Pro Leu His Trp Leu Ile Ala Asp
    130                 135                 140

Lys Thr Gly Val Ser Ile Val Val Glu Thr Asp Lys Asp Gly Met His
145                 150                 155                 160

Val Tyr Asp Asn Pro Val Gly Cys Leu Thr Asn Asn Pro Gln Phe Ser
                165                 170                 175

Cys Gln Leu Phe Asn Leu Asn Asn Tyr Ala Asp Val Ser Pro Ala Met
            180                 185                 190

Pro Lys Asn Asn Phe Ser Lys Glu Val Asn Met Asn Gly Tyr Ser Arg
            195                 200                 205

Gly Leu Gly Ser Arg Asn Leu Pro Gly Gly Met Asp Ser Glu Ser Arg
    210                 215                 220

Phe Val Arg Val Ala Phe Asn Lys Phe Asn Ala Pro Val Gly Lys Ser
225                 230                 235                 240

Glu Glu Glu Asn Val Asp Asn Tyr Phe His Ile Leu His Ser Val Glu
                245                 250                 255

Gln Gln Lys Gly Leu Asp Gln Val Gly Pro Asn Ser Phe Glu Tyr Thr
            260                 265                 270

Ile Tyr Ser Asp Gly Thr Asn Leu Asp Lys Gly Ile Phe Tyr Tyr Thr
            275                 280                 285

Thr Tyr Thr Asn Gln Gln Ile Asn Val Val Asp Ile Asn Lys Glu Asp
    290                 295                 300

Leu Asp Ala Lys Asp Leu Ile Lys Tyr Asp Met Leu Thr Lys Pro Thr
305                 310                 315                 320

Phe Asn His Gln Asn
                325
```

<210> SEQ ID NO 30
<211> LENGTH: 978
<212> TYPE: DNA
<213> ORGANISM: Lactobacillus crispatus

<400> SEQUENCE: 30

```
atgtgtactt caattatttt cagtccacaa gatcactatt ttggacgtaa cctcgatctt      60
gagattactt tcggccaaca agtagttgtt actccacgca attacgtctt caacttccgc     120
aagatgccag agatgaagca acactacgct atggtcggaa ttgcgcttga cgctggcgat     180
```

-continued

```
tacccacttt actttgacgc agctaatgaa aaaggtttag gcatggcagg acttaactac      240
cctgacaatg ctacctacta tgatgaagtt gccaataaag acaacattgc ttcatttgaa      300
tttattccct ggattctggg tcaatgcgca actgtagcgg atgctaaggt attacttaaa      360
aagatcaaca ttgttaacct taatttctct gacaagatgc aggcatcccc acttcattgg      420
ttaattgccg ataagacagg tgtttcaatt gtcgttgaaa ccgataaaga tggaatgcac      480
gtttatgata tcctgtcgg ttgcctgact aacaatcctc agttttcatg tcaattattt      540
aatttaaata attatgctga tgtttcacct gcaatgccta agaacaactt ttcaaaagag      600
gtcaatatga atggctacag ccgtgggctt ggttcacgca atttgccagg tgggatggat      660
tcagaatcgc gctttgttcg tgtagctttt aacaagttca acgctcctgt tggtaaaagt      720
gaggaagaaa acgtagacaa ttacttccat attttgcatt ctgttgaaca acaaaaagga      780
cttgatcaag ttggtcctaa ttcatttgaa tacactattt actctgatgg taccaacctt      840
gacaagggga ttttctatta cactacttat actaatcagc aaattaatgt cgttgacata      900
aacaaagaag acctcgatgc taaggattta atcaagtatg atatgttaac taagccaaca      960
tttaatcacc aaaactaa                                                    978
```

```
<210> SEQ ID NO 31
<211> LENGTH: 316
<212> TYPE: PRT
<213> ORGANISM: Lactobacillus crispatus

<400> SEQUENCE: 31

Met Cys Thr Gly Leu Arg Phe Thr Asp Asp Lys Gly Asn Leu Tyr Phe
1               5                   10                  15

Gly Arg Asn Leu Asp Val Gly Gln Asp Tyr Gly Glu Gly Val Ile Ile
            20                  25                  30

Thr Pro Arg Asn Tyr Pro Leu Pro Tyr Lys Phe Leu Asp Asp Thr Lys
        35                  40                  45

Thr Thr Lys Ala Val Ile Gly Met Gly Ile Val Val Asp Gly Tyr Pro
    50                  55                  60

Ser Tyr Phe Asp Cys Phe Asn Glu Asp Gly Leu Gly Ile Ala Gly Leu
65                  70                  75                  80

Asn Phe Pro His Tyr Ala Lys Phe Ser Asp Gly Pro Ile Asp Gly Lys
                85                  90                  95

Ile Asn Leu Ala Ser Tyr Glu Ile Met Leu Trp Val Thr Gln Asn Phe
            100                 105                 110

Thr Lys Val Ser Glu Val Lys Glu Ala Leu Lys Asn Val Asn Leu Val
        115                 120                 125

Asn Glu Ala Ile Asn Ser Ser Phe Ala Val Ala Pro Leu His Trp Ile
    130                 135                 140

Ile Ser Asp Asn Lys Glu Ala Ile Ile Val Glu Met Ser Lys Gln Tyr
145                 150                 155                 160

Gly Phe Lys Val Phe Glu Asp Lys Leu Gly Val Leu Thr Asn Ser Pro
                165                 170                 175

Asp Phe Asn Trp Gln Val Thr Asn Leu Gly Asn Tyr Thr Gly Leu Asn
            180                 185                 190

Pro His Asp Ala Thr Asn Glu Asn Trp Asn Gly Glu Asn Val Ala Pro
        195                 200                 205

Trp Gly Val Gly Thr Gly Ser Val Gly Leu Pro Gly Asp Ser Ile Pro
    210                 215                 220

Ala Asp Arg Phe Val Lys Ala Ala Tyr Leu Asn Ala Asn Tyr Pro Val
```

```
225                 230                 235                 240

Ala Lys Gly Glu Lys Ala Asn Val Ala Lys Phe Phe Asn Ile Leu Lys
                245                 250                 255

Ser Val Ala Met Ile Lys Gly Ser Val Val Asn Thr His Asn Ser Asp
                260                 265                 270

Glu Tyr Thr Val Tyr Thr Ala Cys Tyr Ser Ala Asn Thr Lys Thr Tyr
                275                 280                 285

Tyr Cys Asn Phe Glu Asn Asp Phe Glu Leu Lys Glu Tyr Gln Leu Asn
                290                 295                 300

Asp Glu Thr Met Asn Glu Lys Lys Val Ile Thr Phe
305                 310                 315
```

```
<210> SEQ ID NO 32
<211> LENGTH: 951
<212> TYPE: DNA
<213> ORGANISM: Lactobacillus crispatus

<400> SEQUENCE: 32
atgtgtacag gattaagatt tacagatgac aaaggtaatt tatatttcgg tcgtaatttg      60
gatgtaggtc aagattatgg tgaaggcgta attattaccc cacgtaatta tccattacca     120
tataagttct ggatgatac  taaaaccact aaagcagtaa tcggaatggg gattgtagtt     180
gatggttatc cttcatattt tgattgcttt aatgaagatg gtttggggat tgccggttta     240
aactttccac actatgctaa gttcagtgat ggtccgattg atggcaagat taatttggct     300
tcttatgaaa taatgctctg ggtaacgcaa aactttacaa aagtgagtga agtaaaagaa     360
gccttaaaga atgttaattt ggttaatgag gctattaact catcctttgc tgtagctcca     420
cttcactgga ttattagcga caacaaggaa gctattattg tagaaatgtc taagcaatat     480
gggtttaagg tatttgaaga caagcttggc gtcttgacta atagccctga ctttaactgg     540
caagtaacta acttgggtaa ttatactggt ttgaatccac atgatgcgac aaacgaaaac     600
tggaatggtg aaaatgttgc tccatggggt gtaggtacag gtagtgtagg ccttccaggc     660
gatagtattc cagctgatcg ctttgttaaa gcagcatatt tgaatgctaa ttatccagtt     720
gctaagggcg aaaaagcaaa tgtagccaaa ttctttaata ttcttaagtc agtagcaatg     780
attaaaggca gcgtagttaa cacgcataat agtgatgaat atacggtata tactgcttgt     840
tactctgcta atactaagac ttactactgc aactttgaaa atgactttga gcttaaagag     900
tatcaactta tgatgagac  aatgaatgaa aagaaagtaa ttacatttta a             951
```

```
<210> SEQ ID NO 33
<211> LENGTH: 324
<212> TYPE: PRT
<213> ORGANISM: Lactobacillus delbrueckii

<400> SEQUENCE: 33

Met Cys Thr Ala Ile Thr Phe Ala Thr Asn Asp His Tyr Ile Gly Arg
1               5                   10                  15

Asn Leu Asp Leu Asp Phe Ser Tyr Asn Glu Thr Val Thr Ile Thr Pro
                20                  25                  30

Arg Asn Tyr Val Phe Pro Met Arg Lys Val Pro Asp Leu Asn Ser His
                35                  40                  45

Tyr Ala Ile Ile Gly Met Ala Thr Val Val Gly Asp Tyr Pro Leu Tyr
                50                  55                  60

Tyr Asp Ala Val Asn Glu Lys Gly Leu Gly Met Ala Gly Leu Asn Phe
65                  70                  75                  80
```

-continued

```
Pro Gly Asn Ala His Tyr Phe Pro Asp Gln Glu Gly Lys Asp Asn Ile
                85              90              95

Ala Ser Phe Glu Phe Ile Pro Tyr Ile Leu Gly Thr Cys Lys Ser Val
                100             105             110

Ala Glu Ala Lys Glu Ala Leu Lys Lys Ile Ser Ile Ser Ala Glu Asp
            115             120             125

Phe Ser Lys Asp Phe Pro Thr Ser Thr Leu His Trp Ile Ile Ala Asp
    130             135             140

Lys Asp Ser Ser Ile Val Val Glu Ser Met Glu Asp Gly Leu His Val
145             150             155             160

Tyr Asp Asn Pro Val Gly Val Met Thr Asn Asn Pro Pro Phe Pro Ile
                165             170             175

Met Lys Phe Ala Leu Asn Asp Tyr Tyr Ala Leu Ser Ala His Cys Leu
                180             185             190

Asp His Lys Phe Ala Asp Gly Val Glu Leu Thr Glu Tyr Ser Arg Gly
            195             200             205

Met Ser Ser Ile Gly Leu Pro Gly Asp Leu Ser Ser Lys Ser Arg Phe
    210             215             220

Val Arg Cys Val Phe Thr Lys Tyr Asn Ser Leu Cys Asp Lys Asp Glu
225             230             235             240

Ala Ser Ser Val Asn Gln Phe Phe Lys Ile Leu Gly Ser Val Glu Gln
            245             250             255

Val Lys Gly Leu Cys Glu Val Thr Pro Gly Glu Tyr Glu Tyr Thr Ile
            260             265             270

Tyr Ser Ser Cys Met Asn Gln Glu Lys Gly Ile Tyr Tyr Tyr Thr Thr
    275             280             285

Tyr Gly Asn Pro Glu Val His Ala Val Asp Met His Lys Thr Asp Leu
    290             295             300

Asp Gly Lys Glu Leu Thr Ser Tyr Lys Leu Gln Lys Asp Leu Gln Phe
305             310             315             320

His Phe Asp Asn
```

```
<210> SEQ ID NO 34
<211> LENGTH: 975
<212> TYPE: DNA
<213> ORGANISM: Lactobacillus delbrueckii

<400> SEQUENCE: 34
atgtgtacag ctattacttt tgcaactaac gaccactaca ttggccgtaa tttggacctg     60
gacttttctt acaatgaaac agtcactatc actccaagaa actatgtttt cccaatgcgg    120
aaagtgccgg acttaaacag ccactacgcc atcatcggga tggcaacggt tgtcggcgac    180
tatccgcttt actatgatgc cgttaatgaa aagggcctgg gtatggccgg cttgaacttc    240
ccgggcaatg cccactactt cccggaccag gaaggcaagg acaacatcgc ttcctttgaa    300
tttatcccat acatcctggg aacttgcaag agcgtggctg aagccaagga agccttgaag    360
aagattagca tctcagctga agacttttca aaggacttcc caaccagcac cctgcactgg    420
atcatcgccg acaaggactc cagcatcgtg gttgaatcaa tggaagacgg cctgcacgtt    480
tacgacaacc cagtcggcgt catgaccaac aacccgccat cccaatcat gaagtttgcc    540 ttgaacgact actacgccct gtcagcccac tgcttggacc acaagtttgc tgacggcgtt    600
gaattgactg aatactcccg cggtatgagc agcataggcc tgccaggcga cctgtccagc    660
aagtcccgct tcgtccgctg cgtcttcacc aagtacaaca gcctctgcga caaggatgaa    720
```

-continued

```
gccagctcag tcaaccagtt cttcaagatc ctgggctcag ttgaacaagt caagggactg      780
tgtgaagtta ccccgggtga atacgagtac actatctact catcctgcat gaaccaggaa      840
aaggggatct actactacac cacctacggc aacccggaag ttcacgccgt tgacatgcac      900
aagactgacc tggatggcaa ggaactgacc agctacaagc tgcaaaagga cctgcaattc      960
cacttcgaca actag                                                       975
```

```
<210> SEQ ID NO 35
<211> LENGTH: 324
<212> TYPE: PRT
<213> ORGANISM: Lactobacillus equicursoris

<400> SEQUENCE: 35

Met Cys Thr Ala Ile Thr Tyr His Thr Ala Asp His Tyr Phe Gly Arg
1               5                   10                  15

Asn Leu Asp Leu Asp Phe Ser Tyr Asn Glu Thr Val Thr Val Thr Pro
                20                  25                  30

Arg Asn Tyr Val Phe Pro Met Arg Lys Val Asp Asp Leu Ser Thr His
            35                  40                  45

Tyr Ala Ile Ile Gly Met Ser Thr Val Ala Gly Asn Tyr Pro Leu Tyr
        50                  55                  60

Tyr Asp Ala Val Asn Glu Lys Gly Leu Ala Met Ala Gly Leu Asn Phe
65                  70                  75                  80

Glu Gly Asn Ala Tyr Tyr Phe Asp Asp Gln Glu Gly Lys Lys Asn Ile
                85                  90                  95

Thr Ser Phe Glu Leu Ile Pro Tyr Ile Leu Gly Thr Cys Gln Asp Leu
                100                 105                 110

Ala Glu Ala Lys Lys Glu Leu Ser Glu Ile Ser Ile Ser Asn Glu Ala
            115                 120                 125

Phe Ser Lys Asp Phe Pro Leu Ser Thr Leu His Trp Met Ile Ala Asp
        130                 135                 140

Lys Thr Gly Ala Ile Val Val Glu Ser Met Lys Asp Gly Leu His Val
145                 150                 155                 160

Tyr Asp Asn Pro Val Gly Val Met Thr Asn Asn Pro Pro Phe Pro Ile
                165                 170                 175

Met Lys Phe Ala Leu Asn Asp Tyr Phe Ala Leu Ser Ala His His Lys
                180                 185                 190

Glu His Thr Phe Gly Pro Gly Val Glu Leu Asp Glu Tyr Ser Arg Gly
            195                 200                 205

Met Gly Gly Leu Gly Leu Pro Gly Asp Leu Ser Ser Lys Ser Arg Phe
        210                 215                 220

Ile Arg Cys Val Phe Thr Lys Phe Asn Ser Gln Gly Glu Ser Asp Glu
225                 230                 235                 240

Val Ser Ser Val Asn Gln Phe Leu Lys Ile Leu Tyr Ser Val Glu Gln
                245                 250                 255

Val Lys Gly Leu Cys Glu Val Thr Pro Gly Lys Tyr Glu Tyr Thr Ile
            260                 265                 270

Tyr Ser Ser Cys Met Asn Gln Glu Lys Gly Ile Tyr Tyr Tyr Thr Thr
            275                 280                 285

Tyr Glu Asn Ser Asp Ile His Ala Ile Asp Met His Lys Thr Asp Leu
        290                 295                 300

Asp Ser Ser Glu Leu Ser Val Tyr Pro Leu Gln Arg Gln Leu Gln Ile
305                 310                 315                 320
```

His Leu Asp Asn

<210> SEQ ID NO 36
<211> LENGTH: 975
<212> TYPE: DNA
<213> ORGANISM: Lactobacillus equicursoris

<400> SEQUENCE: 36
atgtgtacag caattaccta tcacactgcg gaccactact ttggccgcaa cttagactta      60
gatttttctt acaatgaaac cgtgacggtt acgccgcgca attacgtttt cccaatgcgg     120
aaggtcgatg acttgtccac ccactacgct atcatcggca tgtccacggt cgcgggcaac     180 tatcccctt actatgatgc cgtcaacgaa aagggcttgg cgatggcagg cctcaacttt     240
gaaggcaacg cctactactt tgacgaccaa gaagggaaaa agaacatcac ctctttgag      300 ctgatccctt acattctggg cacttgccaa gacctagctg aggctaaaaa ggaattaagc     360
gagatctcta tttcaaacga ggcttttct aaagacttcc cgctctcaac cctgcactgg     420
atgatcgccg acaagaccgg cgctatcgtc gttgaatcca tgaaagacgg cttgcatgtt     480
tatgacaacc cggttggggt catgactaac aacccgccat tcccaatcat gaagtttgcc     540
ctaaacgact actttgccct ctctgcccac cacaaggaac acaccttcgg tccaggtgta     600
gaattagatg aatattcccg cggcatgggc ggcctgggtc tgccaggcga cttgtctagc     660
aagtcccgct tcatccgctg cgtctttacc aaatttaaca gccaaggtga gagcgacgaa     720
gtcagctcag tcaaccaatt tttgaagatc ctctactcag ttgagcaggt caagggcctg     780
tgtgaagtaa ccccaggcaa gtacgaatac accatttatt cctcttgcat gaaccaagaa     840
aagggaatct actactacac cacctacgaa aattccgaca tccacgccat cgacatgcac     900
aagacggatt tggatagtag tgaattgtcc gtttatccgc ttcaaagaca gctgcagatc     960
cacttggata attaa                                                     975

<210> SEQ ID NO 37
<211> LENGTH: 325
<212> TYPE: PRT
<213> ORGANISM: Lactobacillus frumenti

<400> SEQUENCE: 37

Met Cys Thr Ser Val Ile Tyr Thr Val Gly Asp Ala Tyr Phe Gly Arg
1               5                   10                  15

Asn Leu Asp Leu Glu Val Ser Phe Gly Gln Gln Val Val Ile Met Pro
            20                  25                  30

Arg Asp Phe Ala Leu His Phe Arg Lys Leu Pro Thr Ile Ala His His
        35                  40                  45

Tyr Ala Ile Thr Gly Met Ala Leu Val Gln Asp Asn Tyr Pro Leu Tyr
    50                  55                  60

Phe Asp Gly Ala Asn Glu Lys Gly Leu Gly Met Ala Gly Leu Asn Phe
65                  70                  75                  80

Asp Gly Pro Ala His Tyr Phe Pro Glu Gln Thr Asp Lys Gln Asn Val
                85                  90                  95

Thr Pro Phe Glu Phe Val Pro Tyr Val Leu Gly Gln Cys Ala Thr Val
            100                 105                 110

Ala Glu Ala Lys Lys Leu Leu Lys Asn Val Ser Leu Ile Asn Ile Asn
        115                 120                 125

Phe Ser Asp Lys Leu Ala Leu Ser Pro Leu His Trp Leu Ile Ala Asp
    130                 135                 140

-continued

```
Lys Ser Gly Ala Ser Ile Val Val Glu Ser Thr Thr Ala Gly Leu Asn
145             150                 155                 160

Val Tyr Asp Asn Pro Val Gly Val Leu Thr Asn Asn Pro Glu Phe Pro
                165                 170                 175

Gln Gln Leu Gln Asn Leu Ala Asn Tyr Gln Ser Val Ser Pro Ala Asn
            180                 185                 190

Pro Glu Asn Thr Leu Ala Val Asn Leu Ser Leu Pro Val Tyr Ser Arg
            195                 200                 205

Gly Leu Gly Ser His Phe Leu Pro Gly Gly Met Asp Ser Glu Ser Arg
        210                 215                 220

Phe Val Lys Val Ala Phe Thr Lys Glu Asn Ala Pro Val Gly Lys Thr
225             230                 235                 240

Glu Asp Glu Asn Val Ile Asn Tyr Phe His Ile Leu His Ser Val Glu
            245                 250                 255

Gln Gln Lys Gly Leu Asp Glu Val Ala Pro Asn Thr Phe Glu Tyr Thr
            260                 265                 270

Ile Tyr Ser Asp Gly Met Asp Leu Thr Thr Gly Thr Phe Tyr Tyr Thr
        275                 280                 285

Thr Tyr Thr Asn Asn Gln Ile Asn Ala Val Lys Met Pro Lys Asp His
    290                 295                 300

Leu Asp Gln Asp Gln Leu Met Thr Phe Asp Leu Gln Asp Lys Pro Thr
305             310                 315                 320

Ile Asn Tyr Gln Asn
                325
```

```
<210> SEQ ID NO 38
<211> LENGTH: 978
<212> TYPE: DNA
<213> ORGANISM: Lactobacillus frumenti

<400> SEQUENCE: 38
atgtgcactt cagttattta tacggtaggc gatgcatatt ttggtcgcaa cctggatcta        60
gaagtatctt tcggtcaaca agtagtaatt atgccgcgtg attttgccct acattttcgt       120
aaactgccaa ccatcgctca tcactatgca atcaccggga tggcactcgt ccaggataac       180
tacccgctat attttgatgg tgccaatgag aagggcttag ggatggctgg attaaacttt       240
gatggtccgg cacattactt cccagaacag actgataaac agaatgtgac tccatttgaa       300
tttgtgcctt acgttcttgg tcagtgtgca acggttgctg aagcaaagaa actattaaag       360
aatgttagtt tgattaatat taacttctct gataagttag cgctgtcgcc attgcattgg       420
ttaattgctg ataaaagtgg ggcatcgatt gttgttgaat caaccactgc gggattaaac       480
gtttacgata tccagtgggg agttttaacc aataatccgg aattccccca acaattgcaa       540
aatttggcta attaccagag tgtttcgcca gctaatccag aaaacacatt agcggttaac       600
ttatcgttac cagtgtacag tcgcggactg gggtcgcatt ttcttccagg cgggatggac       660
tctgaaagtc ggtttgtcaa agtcgctttt acgaaagaaa atgcccctgt tggtaaaaca       720
gaggatgaga acgttatcaa ctactttcac attcttcatt ctgtggaaca acaaaaggga       780
ctggatgaag tcgcaccaaa tacatttgaa tacacgatct attctgatgg aatggattta       840
acgaccggaa ccttttatta caccacctac actaataacc aaattaatgc tgttaagatg       900
ccaaaagatc atttagatca agatcaacta atgacgtttg acttgcaaga caagccgacc       960
attaattacc aaaactaa                                                    978
```

-continued

<210> SEQ ID NO 39
<211> LENGTH: 325
<212> TYPE: PRT
<213> ORGANISM: Lactobacillus gallinarum

<400> SEQUENCE: 39

```
Met Cys Thr Ser Ile Ile Phe Ser Pro Lys Asp His Tyr Phe Gly Arg
1               5                   10                  15

Asn Leu Asp Leu Asp Ile Thr Phe Gly Gln Gln Val Val Ile Thr Pro
            20                  25                  30

Arg Asn Tyr Pro Phe Lys Phe Arg Lys Met Pro Ser Ile Asp His His
        35                  40                  45

Tyr Ala Ile Ile Gly Ile Ala Leu Asp Asn Asn Asn Tyr Pro Leu Tyr
    50                  55                  60

Phe Asp Ala Ala Asn Glu Met Gly Leu Gly Met Ala Gly Leu Asn Tyr
65                  70                  75                  80

Pro Gly Asn Ala Thr Tyr Tyr Lys Glu Lys Glu Gly Lys Asp Asn Ile
                85                  90                  95

Ala Ser Phe Glu Phe Ile Pro Trp Leu Leu Gly Gln Ala Ala Asn Ile
            100                 105                 110

Lys Glu Ala Lys Lys Ile Leu Ser Thr Ile Asn Ile Thr Asp Ile Asn
        115                 120                 125

Phe Ser Glu Lys Met Ile Ala Ser Pro Leu His Trp Leu Ile Ala Asp
        130                 135                 140

Lys Thr Gly Lys Ser Ile Val Val Glu Thr Asp Lys Asp Gly Met His
145                 150                 155                 160

Ile Tyr Asp Asn Pro Ile Gly Cys Leu Thr Asn Asn Pro Gln Phe Pro
                165                 170                 175

Lys Gln Leu Phe Asn Leu Asn Asn Tyr Ala Asp Val Ser Ala Ala Thr
            180                 185                 190

Pro Lys Asn Asn Phe Ser Ser Gln Ile Glu Leu Ser Asp Tyr Ser Arg
        195                 200                 205

Gly Leu Gly Ser Arg Asn Leu Pro Gly Gly Met Asp Ser Glu Ser Arg
    210                 215                 220

Phe Val Arg Ala Thr Phe Asn Lys Phe Asn Ala Pro Ile Ser Asp Asn
225                 230                 235                 240

Glu Val Glu Asn Val Asp Thr Tyr Phe His Ile Leu His Ser Val Glu
                245                 250                 255

Gln Gln Lys Gly Leu Asp Gln Thr Asp Pro Asp Thr Phe Glu Tyr Thr
            260                 265                 270

Ile Tyr Ser Asp Gly Thr Asn Leu Asp Lys Gly Ile Phe Tyr Tyr Thr
        275                 280                 285

Thr Tyr Thr Asp Lys Gln Ile Lys Val Val Asp Met His Lys Glu Asn
    290                 295                 300

Leu Asp Ala Asn Asp Leu Ile Val Phe Asp Met Ile Asn Lys Pro Thr
305                 310                 315                 320

Phe Lys Tyr Gln Asn
                325
```

<210> SEQ ID NO 40
<211> LENGTH: 978
<212> TYPE: DNA
<213> ORGANISM: Lactobacillus gallinarum

<400> SEQUENCE: 40

```
atgtgtactt caatcatttt tagtccaaaa gatcattatt ttggccgcaa ccttgattta      60
```

-continued

```
gatataactt ttggacaaca agtcgtaatc actccgcgta attatccttt caaatttcgc      120
aagatgccat caattgatca tcattatgca attattggta ttgctctaga taacaataac      180
tatcccttat actttgacgc agctaatgaa atgggtttag gcatggccgg gttgaattat      240
cctggtaatg caacttacta taaagaaaaa gaaggcaaag ataatattgc ttcatttgaa      300
tttattcctt ggcttttagg acaggctgct aatattaagg aagctaaaaa aatattgtct      360
accattaaca tcactgatat caacttttct gaaaaaatga tagcatcccc actccactgg      420
ttaatcgctg ataaaactgg caagagcatt gtagttgaaa ctgataaaga tgggatgcac      480
atttatgaca atccaattgg ctgtttaacc aataatccgc aatttcctaa acaattattc      540
aacttgaata actacgctga tgtatctgcc gccacaccta aaaataactt ttcaagtcaa      600
attgaactaa gcgactatag ccggggcgtt ggctcacgta acttacctgg cggaatggat      660
tctgaatcac gctttgtcag agccactttt aataaattta atgcgccaat aagtgataat      720
gaagttgaaa atgtcgacac atatttccat attttgcatt ctgttgaaca acaaaaaggc      780
ttagatcaaa cagaccctga tacctttgaa tataccattt attctgacgg cactaaccta      840
gataagggaa tctttttacta cacaacatat accgacaagc agatcaaggt ggttgatatg      900
cataaagaaa atcttgatgc taatgatcta attgtttttg atatgatcaa taagcctact      960
tttaaatatc aaaattaa                                                     978
```

<210> SEQ ID NO 41
<211> LENGTH: 316
<212> TYPE: PRT
<213> ORGANISM: Lactobacillus gasseri

<400> SEQUENCE: 41

```
Met Cys Thr Gly Leu Arg Phe Thr Asp Asp Gln Gly Asn Leu Tyr Phe
1               5                   10                  15

Gly Arg Asn Leu Asp Val Gly Gln Asp Tyr Gly Glu Gly Val Ile Ile
            20                  25                  30

Thr Pro Arg Asn Tyr Pro Leu Pro Tyr Lys Phe Leu Asp Asn Thr Thr
        35                  40                  45

Thr Lys Lys Ala Val Ile Gly Met Gly Ile Val Val Asp Gly Tyr Pro
    50                  55                  60

Ser Tyr Phe Asp Cys Phe Asn Glu Asp Gly Leu Gly Ile Ala Gly Leu
65                  70                  75                  80

Asn Phe Pro His Phe Ala Lys Phe Ser Asp Gly Pro Ile Asp Gly Lys
                85                  90                  95

Ile Asn Leu Ala Ser Tyr Glu Ile Met Leu Trp Val Thr Gln Asn Phe
            100                 105                 110

Thr Lys Val Ser Asp Val Lys Glu Ala Leu Lys Asn Val Asn Leu Val
        115                 120                 125

Asn Glu Ala Ile Asn Ser Ser Phe Ala Val Ala Pro Leu His Trp Ile
    130                 135                 140

Ile Ser Asp Lys Asp Glu Ala Ile Ile Val Glu Val Ser Lys Gln Tyr
145                 150                 155                 160

Gly Met Lys Val Phe Asp Asp Lys Leu Gly Val Leu Thr Asn Ser Pro
                165                 170                 175

Asp Phe Asn Trp His Leu Thr Asn Leu Gly Asn Tyr Thr Gly Leu Asp
            180                 185                 190

Pro His Asp Ala Thr Ala Gln Ser Trp Asn Gly Gln Lys Val Ala Pro
        195                 200                 205
```

-continued

```
Trp Gly Val Gly Thr Gly Ser Leu Gly Leu Pro Gly Asp Ser Ile Pro
    210             215             220
```

```
Ala Asp Arg Phe Val Lys Ala Ala Tyr Leu Asn Val Asn Tyr Pro Thr
225             230             235             240
```

```
Val Lys Gly Glu Lys Ala Asn Val Ala Lys Phe Phe Asn Ile Leu Lys
                245             250             255
```

```
Ser Val Ala Met Ile Lys Gly Ser Val Val Asn Lys Leu Gly Ser Asp
            260             265             270
```

```
Glu Tyr Thr Val Tyr Thr Ala Cys Tyr Ser Ala Ala Thr Lys Thr Tyr
        275             280             285
```

```
Tyr Cys Asn Phe Glu Asn Asp Phe Glu Leu Lys Thr Tyr Lys Leu Asp
    290             295             300
```

```
Asp Glu Thr Met Asn Ala Asp Lys Leu Ile Thr Tyr
305             310             315
```

```
<210> SEQ ID NO 42
<211> LENGTH: 951
<212> TYPE: DNA
<213> ORGANISM: Lactobacillus gasseri

<400> SEQUENCE: 42
atgtgtactg gtttaagatt tacagatgat caaggaaatc tctactttgg acgtaactta      60
gatgttggac aagattatgg tgaaggtgta attatcacac cacgcaacta tcctcttcca     120
tataagtttt tagataatac gactactaaa aaagccgtta tcggtatggg aattgtagtt     180
gatggctatc cttcttactt tgactgtttc aatgaagatg tttaggaat tgctggtcta     240 aacttcccac attttgccaa atttagcgat ggaccaattg atggaaaaat caatttagct     300
tcttacgaaa ttatgctctg ggttactcaa aacttcacta agttagcga tgtgaaagaa     360 gctttaaaga acgttaactt agttaatgaa gctattaatt catcatttgc agttgctcct     420
cttcactgga ttattagtga caaggatgaa gctatcattg ttgaagtttc aaagcaatac     480
ggaatgaaag tctttgatga taagcttggc gttttaacta acagtccaga ctttaactgg     540
catcttacta accttggcaa ctatactggt ttagatccac atgatgctac agctcaaagc     600
tggaacggtc aaaaagttgc tccatggggc gttggcactg gcagcttagg tttaccaggt     660
gatagcattc cagcagatcg ctttgttaaa gcagcttact aaatgttaa ttacccaact     720 gttaagggtg aaaaagctaa cgtggctaag ttctttaaca tcttaaagtc tgttgcgatg     780
attaagggta gcgtagttaa caaactgggt agcgatgaat acactgtcta caccgcttgc     840
tactctgctg ctactaagac ttattactgc aactttgaaa atgattttga attaaagact     900
tataagttag acgatgaaac gatgaacgct gacaagctaa tcacctatta a             951

<210> SEQ ID NO 43
<211> LENGTH: 325
<212> TYPE: PRT
<213> ORGANISM: Lactobacillus gasseri

<400> SEQUENCE: 43

Met Cys Thr Ser Ile Leu Tyr Ser Pro Lys Asp His Tyr Phe Gly Arg
1               5               10              15

Asn Leu Asp Tyr Glu Ile Ala Tyr Gly Gln Lys Val Val Ile Thr Pro
            20              25              30

Arg Asn Tyr Glu Phe Lys Phe Ala Asn Leu Pro Ala Glu Lys Ser His
        35              40              45
```

-continued

```
Tyr Ala Met Ile Gly Ile Ala Ala Val Ala Asn Asn Thr Pro Leu Tyr
    50              55                  60

Cys Asp Ala Ile Asn Glu Lys Gly Leu Gly Val Ala Gly Leu Ser Phe
65              70                  75                  80

Ala Gly Gln Gly Lys Tyr Phe Pro Val Val Glu Asp Lys Lys Asn Ile
                85                  90                  95

Ala Ser Phe Glu Phe Ile Ser Tyr Ile Leu Ala Thr Tyr Glu Thr Val
            100                 105                 110

Asp Gln Val Lys Glu Asn Leu Thr Asp Val Asn Ile Ser Asp Val Ser
            115                 120                 125

Phe Ser Lys Asn Thr Pro Ala Ser Glu Leu His Trp Leu Val Gly Asp
    130                 135                 140

Lys Thr Gly Lys Ser Ile Val Val Glu Ser Asp Glu Lys Gly Leu His
145                 150                 155                 160

Val Tyr Asp Asn Pro Val Asn Ala Leu Thr Asn Ala Pro Leu Phe Pro
                165                 170                 175

Gln Gln Leu Thr Asn Leu Ala Asn Tyr Ala Ala Val Val Pro Gly Gln
            180                 185                 190

Pro Asn Asn Asp Phe Leu Pro Gly Val Asp Leu Lys Met Tyr Ser Arg
            195                 200                 205

Ser Leu Gly Thr His His Leu Pro Gly Gly Met Asp Ser Glu Ser Arg
    210                 215                 220

Phe Val Lys Val Cys Phe Ala Leu Asn His Ala Pro Lys Asp Ser Asp
225                 230                 235                 240

Glu Val Glu Ser Val Thr Asn Phe Phe His Ile Leu Gln Ser Val Glu
                245                 250                 255

Gln Val Lys Gly Met Asp Glu Val Gly Pro Asn Ile Phe Glu Tyr Thr
            260                 265                 270

Met Tyr Thr Ser Cys Met Asn Leu Glu Lys Gly Ile Leu Tyr Phe Asn
            275                 280                 285

Cys Tyr Asp Asp Ser Arg Ile Ser Ala Val Asp Met Asn Lys Glu Asp
    290                 295                 300

Leu Ser Ser Ser Asp Leu Ile Val Phe Asp Leu Phe Lys Lys Gln Asp
305                 310                 315                 320

Ile Ser Phe Ile Asn
                325
```

```
<210> SEQ ID NO 44
<211> LENGTH: 978
<212> TYPE: DNA
<213> ORGANISM: Lactobacillus gasseri

<400> SEQUENCE: 44
atgtgtacat caattttata tagtcccaaa gaccactatt ttggtagaaa cttagattat        60
gaaattgctt atggtcaaaa agtggttatt acaccaagaa attatgaatt taagtttgcc       120
aatttaccag ctgaaaaatc acattatgca atgattggca tagctgctgt agcaaataat       180
accccactat attgcgatgc gattaatgaa aagggtttgg gagtagctgg tttaagtttt       240
gctggacaag aaagtatttt tccagtagta gaagataaga aaaacattgc ttcatttgaa       300
tttatttctt atatattagc tacttatgaa actgttgatc aggttaaaga aaatttgact       360
gatgttaata tttctgatgt gagtttttct aaaaatacac cagcttcaga acttcattgg       420
ctagtaggag ataagaccgg taagagtatc gttgttgagt cagatgaaaa aggtttacat       480
gtttatgata atccagttaa tgctttgacg aacgcaccgt tattcccgca gcagttaact       540
```

-continued

```
aatttggcaa attatgctgc agttgttccc ggccaaccta ataatgattt tttacctgga    600
gttgatctta agatgtatag ccgcagctta ggaactcatc atttacctgg tggaatggat    660
tcagaatcac gttttgttaa agtatgtttt gctttgaatc atgcaccaaa agatagtgat    720
gaggtagaaa gtgttactaa tttttttccat attttgcagt ctgttgaaca ggtaaaaggg    780
atggatgaag ttggtcctaa tattttttgaa tacaccatgt atactagttg tatgaatctt    840
gaaaagggta ttttgtactt caattgttat gatgacagta gaattagtgc tgtagacatg    900
aacaaggaag atttgagttc atcagacttg atcgtgtttg acttgttcaa gaaacaggat    960
attagtttta taaattaa                                                  978
```

```
<210> SEQ ID NO 45
<211> LENGTH: 326
<212> TYPE: PRT
<213> ORGANISM: Lactobacillus paragasseri

<400> SEQUENCE: 45

Met Cys Thr Ser Ile Ile Tyr Thr Ala Asn Gly Gln His Tyr Phe Gly
1               5                   10                  15

Arg Asn Leu Asp Leu Glu Ile Ser Phe Gly Glu His Pro Val Ile Thr
            20                  25                  30

Pro Arg Asn Tyr Val Phe Lys Tyr Arg Lys Leu Pro Asn Arg Lys Ala
        35                  40                  45

Thr Tyr Ala Met Ile Gly Met Ala Ile Val Lys Asp Asn Tyr Pro Leu
    50                  55                  60

Tyr Phe Asp Ala Ala Asn Glu Lys Gly Leu Gly Ile Ala Gly Leu Asn
65                  70                  75                  80

Phe Asp Gly Pro Cys His Tyr Phe Ser Glu Ser Ala Glu Lys Asp Asn
                85                  90                  95

Val Ala Ser Phe Glu Leu Ile Pro Tyr Leu Leu Ser Gln Tyr Thr Ser
            100                 105                 110

Val Glu Glu Val Lys Asn Ala Leu Lys Asn Ile Asn Leu Val Asp Ile
        115                 120                 125

Asn Phe Ser Glu Lys Leu Gln Val Ser Pro Leu His Trp Leu Ile Ala
    130                 135                 140

Asp Lys Thr Gly Lys Ser Ile Val Val Glu Ser Thr Val Ser Gly Leu
145                 150                 155                 160

His Val Tyr Asp Asn Pro Val Ser Val Leu Thr Asn Asn Pro Glu Phe
                165                 170                 175

Pro Glu Gln Phe Ala Asn Leu Ala Asn Tyr Ile Asn Ile Ser Pro Ala
            180                 185                 190

Gln Pro Glu Asn Thr Leu Ile Pro Asp Ala Asn Ile Asn Leu Tyr Ser
        195                 200                 205

Arg Gly Leu Gly Thr His His Leu Pro Gly Gly Met Asp Ser Ala Ser
    210                 215                 220

Arg Phe Val Lys Val Ala Phe Val Leu Ala His Ala Pro Lys Gly Gln
225                 230                 235                 240

Asn Glu Ala Lys Ser Ile Thr Asn Tyr Phe His Ile Leu His Ser Val
                245                 250                 255

Glu Gln Pro Lys Gly Thr Asp Glu Val Arg Pro Asn Ser Tyr Glu Tyr
            260                 265                 270

Thr Ile Tyr Ser Asp Gly Thr Asn Leu Glu Thr Gly Thr Phe Tyr Tyr
        275                 280                 285
```

```
Thr Asn Tyr Glu Asn Asn Gln Ile Asn Ala Ile Lys Leu Glu His Glu
    290             295             300
```

```
Asn Val Asp Gly Glu Lys Ile Ile Asn Tyr Asp Leu Leu Glu Lys Gln
305             310             315             320
```

```
Glu Ile His Tyr Gln Asn
            325
```

<210> SEQ ID NO 46
<211> LENGTH: 981
<212> TYPE: DNA
<213> ORGANISM: Lactobacillus paragasseri

<400> SEQUENCE: 46

```
atgtgtacct caattattta tactgcgaat ggtcagcatt attttgggcg taatttagat        60
ttagaaattt cttttggtga acacccagta attacaccga gaaattatgt gttcaaatat       120
cgtaagttac ctaatagaaa ggcaacctat gctatgattg ggatggcaat cgttaaagat       180
aactatcctt tatattttga tgcagcgaat gaaaaagggc taggaattgc tggacttaat       240
tttgatgggc catgtcacta tttctctgaa tcagcagaaa aagacaatgt agcctcgttt       300
gaattgattc catatttatt gagtcaatat acttcagttg aagaagtaaa aaatgccttg       360
aaaaatatta atttggtaga tattaatttt tctgaaaaat tacaagtatc accactacac       420
tggttaatag ccgataagac aggcaaatca attgtggtag aatcgactgt aagtggttta       480
catgtctatg acaatccagt aagtgtttta accataatc ctgaatttcc agaacaattt       540
gctaatttag caattatat taatatttct ccagcacaac ctgaaaacac tttgattcct       600
gatgcaaata ttaatcttta gtaggggga ttaggcacac atcacttacc aggtggaatg       660
gattccgcaa gtcgctttgt aaagttgct tttgtgcttg cgcatgctcc gaaaggtcaa       720
aatgaagcta atctataac taattatttc catatttac attccgttga acaacccaaa       780
gggacggacg aggtaagacc aaattcttat gaatatacta tttattctga tggaactaac       840
ttagaaactg gaactttcta ctacacaaat tatgaaaata atcaaattaa tgctatcaag       900
cttgaacatg aaaatgtgga tggcgaaaaa ataattaatt atgatttact cgaaaagcaa       960
gagattcatt atcagaatta a                                                981
```

<210> SEQ ID NO 47
<211> LENGTH: 326
<212> TYPE: PRT
<213> ORGANISM: Lactobacillus gasseri

<400> SEQUENCE: 47

```
Met Cys Thr Ser Ile Ile Tyr Asp Ser Asn Gly Gln His Tyr Phe Gly
1               5               10              15
```

```
Arg Asn Leu Asp Leu Glu Ile Ser Phe Gly Glu His Pro Val Ile Thr
            20              25              30
```

```
Pro Arg Asn Tyr Val Phe Lys Tyr Arg Asn Leu Pro Asn Arg Lys Ala
        35              40              45
```

```
Thr Tyr Ala Met Ile Gly Met Ala Ile Val Lys Asp Asn Tyr Pro Leu
    50              55              60
```

```
Tyr Phe Asp Ala Ala Asn Glu Lys Gly Leu Gly Ile Ala Gly Leu Asn
65              70              75              80
```

```
Phe Asp Gly Pro Cys His Tyr Phe Ser Glu Ser Ala Glu Lys Asp Asn
                85              90              95
```

```
Val Ala Pro Phe Glu Leu Ile Pro Tyr Leu Leu Ser Gln Tyr Thr Ser
            100             105             110
```

-continued

```
Val Glu Glu Val Lys Asn Ala Leu Lys Asn Ile Asn Leu Val Asp Ile
        115                 120                 125

Asn Phe Ser Glu Lys Leu Gln Val Ser Pro Leu His Trp Leu Ile Ala
        130                 135                 140

Asp Lys Thr Gly Lys Ser Ile Val Val Glu Ser Thr Val Ser Gly Leu
145                 150                 155                 160

His Val Tyr Asp Asn Pro Val Ser Val Leu Thr Asn Asn Pro Glu Phe
                165                 170                 175

Pro Glu Gln Phe Ala Asn Leu Ala Asn Tyr Ile Asn Val Ser Pro Ala
                180                 185                 190

Gln Pro Glu Asn Thr Leu Ile Pro Asp Ala Asn Ile Asn Leu Tyr Ser
        195                 200                 205

Arg Gly Leu Gly Thr His His Leu Pro Gly Gly Met Asp Ser Ala Ser
        210                 215                 220

Arg Phe Val Lys Val Ala Phe Val Arg Ala His Ala Pro Glu Gly Lys
225                 230                 235                 240

Asp Glu Ala Ser Ser Ile Thr Asn Tyr Phe His Ile Leu His Ser Val
                245                 250                 255

Glu Gln Pro Lys Gly Thr Asp Glu Val Gly Pro Asn Ser Tyr Glu Tyr
        260                 265                 270

Thr Ile Tyr Ser Asp Gly Thr Asn Leu Glu Thr Gly Thr Phe Tyr Tyr
        275                 280                 285

Thr Asn Tyr Glu Asn Asn Gln Ile Asn Ala Ile Lys Leu Ser Asn Glu
        290                 295                 300

Asn Leu Asp Ser Asp Lys Leu Ile Asp Tyr Glu Leu Leu Glu Lys Gln
305                 310                 315                 320

His Ile Asn Tyr Gln Asn
                325
```

```
<210> SEQ ID NO 48
<211> LENGTH: 981
<212> TYPE: DNA
<213> ORGANISM: Lactobacillus gasseri

<400> SEQUENCE: 48
atgtgtacct caattattta tgattcaaac ggccaacatt attttgggcg taatttagat        60
ttagaaattt cttttggtga acacccagta attacaccga gaaattatgt gttcaaatat       120
cggaatttac ctaatagaaa ggcaacctat gctatgattg ggatggcaat cgttaaagat       180
aactatcctt tatattttga tgcagcgaat gaaaaagggc taggaattgc tggacttaat       240
tttgatgggc cgtgtcacta tttctctgaa tcagcagaaa aagacaatgt agccccgttt       300
gaattgattc catatttatt gagtcaatat acttcagttg aagaagtaaa aaatgccttg       360
aaaaatatta atttggtaga tattaatttt tctgaaaaat acaagtatc accactacac        420 tggttaatag ctgataagac aggcaaatca attgtggtag aatcgactgt aagtggttta       480
catgtctatg acaatccagt aagtgtttta accaataatc ctgaatttcc agaacaattt       540
gctaatttag caaattatat taatgtttct ccagcacaac ctgaaaacac tttgattcct       600
gatgcaaata ttaatcttta tagtagggga ttaggcacac atcacttacc aggtggaatg       660
gattccgcca gtcgatttgt aaagttgcc tttgttcgag ctcatgcacc tgaaggcaag        720
gatgaggcaa gtagtataac aaattatttc catattcttc attctgtcga acaaccaaaa       780
ggaacagatg aagtaggtcc aaattcatat gaatatacta tttactctga tggaactaat       840
```

-continued ttggagactg gaactttcta ctataccaac tatgaaaata atcaaattaa tgctattaaa      900
ttaagcaatg aaaatttaga tagtgacaag ttaattgatt atgaattgct tgaaaagcaa      960
catattaact atcaaaatta a                                                981

<210> SEQ ID NO 49
<211> LENGTH: 326
<212> TYPE: PRT
<213> ORGANISM: Lactobacillus gasseri

<400> SEQUENCE: 49

Met Cys Thr Ser Ile Ile Tyr Asp Ser Asn Gly Gln His Tyr Phe Gly
1               5                   10                  15

Arg Asn Leu Asp Leu Glu Ile Ser Phe Gly Glu His Pro Val Ile Thr
            20                  25                  30

Pro Arg Asn Tyr Val Phe Lys Tyr Arg Lys Leu Pro Asn Arg Lys Ala
        35                  40                  45

Thr Tyr Ala Met Ile Gly Met Ala Ile Val Lys Asp Asn Tyr Pro Leu
    50                  55                  60

Tyr Phe Asp Ala Ala Asn Glu Lys Gly Leu Gly Ile Ala Gly Leu Asn
65                  70                  75                  80

Phe Asp Gly Pro Cys His Tyr Phe Pro Glu Ser Ala Glu Lys Glu Asn
                85                  90                  95

Val Thr Pro Phe Glu Leu Ile Pro Tyr Leu Leu Ser Gln Tyr Ala Ser
            100                 105                 110

Val Asp Glu Val Lys Asp Ala Leu Glu Asn Val Asn Leu Val Asp Ile
            115                 120                 125

Asn Phe Ser Lys Lys Leu Gln Leu Ser Pro Leu His Trp Leu Ile Ala
        130                 135                 140

Asp Lys Thr Gly Lys Ser Ile Val Val Glu Ser Thr Val Ser Gly Leu
145                 150                 155                 160

His Val Tyr Asp Asn Pro Val His Val Leu Thr Asn Asn Pro Glu Phe
                165                 170                 175

Pro Gly Gln Leu Thr Asn Leu Ala Asn Tyr Ala Asn Ile Ser Pro Ala
            180                 185                 190

Gln Pro Lys Asn Thr Val Val Pro Asp Ala Asp Ile Asn Leu Tyr Ser
        195                 200                 205

Arg Gly Leu Gly Thr His His Leu Pro Gly Gly Met Asp Ser Ala Ser
    210                 215                 220

Arg Phe Val Lys Val Ala Phe Val Arg Ala His Ala Pro Glu Gly Lys
225                 230                 235                 240

Asp Glu Ala Ser Ser Ile Thr Asn Tyr Phe His Ile Leu His Ser Val
                245                 250                 255

Glu Gln Pro Lys Gly Thr Asp Glu Val Gly Pro Asn Ser Tyr Glu Tyr
            260                 265                 270

Thr Ile Tyr Ser Asp Gly Thr Asn Leu Glu Thr Gly Thr Phe Tyr Tyr
        275                 280                 285

Thr Asn Tyr Glu Asn Asn Gln Ile Asn Ala Ile Lys Leu Ser Asn Glu
    290                 295                 300

Asn Leu Asp Ser Asp Lys Leu Ile Asp Tyr Glu Leu Leu Glu Lys Gln
305                 310                 315                 320

His Ile Asn Tyr Gln Asn
                325

<210> SEQ ID NO 50

<211> LENGTH: 981
<212> TYPE: DNA
<213> ORGANISM: Lactobacillus gasseri

<400> SEQUENCE: 50
atgtgtacct caattatta tgattcaaac ggccaacatt attttgggcg taatttagat        60
ttagaaattt cttttggtga acacccagta attacaccga gaaattatgt gttcaaatat       120
cggaagttac ctaatagaaa ggcaacctat gctatgattg ggatggcaat cgttaaagat       180
aactatcctt tatattttga tgcagctaat gagaaagggt taggaattgc tggacttaat       240
tttgatggtc catgtcacta tttccccgaa tcagcagaaa aagaaaatgt gactccattt       300
gaattaatcc catatttatt gagtcaatat gcttcagttg atgaggtaaa agatgcatta       360
gaaaatgtta atttggttga tattaatttt tctaaaaaat acaattatc accgctacat        420 tggttaattg ctgataagac tggtaagtca attgttgtag aatcaactgt aagtggctta       480
catgtctatg acaatccagt tcatgttttg actaataacc cggaatttcc aggtcaatta       540
accaatttag caaattacgc taatatttct cctgcacaac ctaaaaatac tgtggttcct       600
gatgctgata ttaatctta tagtagaggt ttaggtacac atcacttacc tggaggaatg        660
gattcagcca gtcgatttgt taaagttgcc tttgttcgag ctcatgcacc tgaaggcaag       720
gatgaggcaa gtagtataac aaattatttc catattcttc attctgtcga acaaccaaaa       780
ggaacagatg aagtaggtcc aaattcatat gaatatacta tttactctga tggaactaat       840
ttggagactg gaactttcta ctataccaac tatgaaaata atcaaattaa tgctattaaa       900
ttaagcaatg aaaatttaga tagtgacaag ttaattgatt atgaattgct tgaaaagcaa       960
catattaact atcaaaatta a                                                 981

<210> SEQ ID NO 51
<211> LENGTH: 326
<212> TYPE: PRT
<213> ORGANISM: Lactobacillus gigeriorum

<400> SEQUENCE: 51

Met Cys Thr Ser Ile Ile Phe Ser Pro Lys Asn His Tyr Phe Gly Arg
1               5                   10                  15

Asn Leu Asp Leu Asp Ile Ser Tyr Gly Gln Lys Val Val Ile Thr Pro
            20                  25                  30

Arg Asn Tyr Gln Phe Asp Phe Arg Lys Glu Asn Ser Ile Ser His His
        35                  40                  45

Phe Ala Ile Ile Gly Ile Ala Leu Val Ala Asn Asp Tyr Pro Leu Tyr
    50                  55                  60

Phe Asp Ala Ala Asn Glu Ala Gly Leu Gly Met Ala Gly Leu Asn Tyr
65                  70                  75                  80

Pro Gly Asn Ala Tyr Tyr Gln Glu Thr Leu Ser Leu Thr Lys Ala Asn
                85                  90                  95

Ile Ser Pro Phe Glu Phe Ile Pro Trp Val Leu Ser Gln Cys Ser Asn
            100                 105                 110

Leu Thr Glu Ala Glu Ala Leu Ile Val Lys Thr Asn Leu Val Ala Ile
        115                 120                 125

Asn Phe Ser Glu Lys Met Pro Leu Ala Ser Leu His Trp Leu Leu Ala
    130                 135                 140

Asp Lys Thr Gly Gln Ala Leu Val Val Glu Ala Asp Arg Asp Gly Leu
145                 150                 155                 160

His Leu Tyr His Asn Glu Val Gly Val Leu Thr Asn Asn Pro Gln Phe

```
              165                170                175
Pro Lys Gln Arg Phe Ala Leu Asn Ile Tyr Arg Asn Leu Ser Val Gln
              180                185                190

Pro Thr Ala Asn Thr Phe Ala Ser Asn Ile Asp Leu Thr Pro Tyr Ser
              195                200                205

Ser Gly Met Gly Ser Val Asn Leu Pro Gly Gly Leu Asp Ser Val Ser
              210                215                220

Arg Phe Val Arg Ala Thr Phe Asn Leu His His Ala Pro Lys Ser Glu
225                230                235                240

Asn Asn Ala Glu Asn Ile Asn Thr Tyr Phe His Ile Leu Lys Ser Val
              245                250                255

Glu Gln Gln Lys Gly Leu Asn Lys Leu Asp Asn Gly Gln Asp Glu Phe
              260                265                270

Thr Ile Tyr Ser Asp Cys Phe Asp Leu Asp Gln Asn Cys Phe Tyr Tyr
              275                280                285

Thr Thr Tyr Asn Asn Ser Gln Ile Ser Gln Val Ser Leu Ala His Glu
              290                295                300

Asp Leu Glu Asp Ser Asn Leu Ile Ser Tyr Ser Ile Ser Asp Gln Pro
305                310                315                320

Asn Phe Arg Glu Val Asn
              325
```

<210> SEQ ID NO 52
<211> LENGTH: 981
<212> TYPE: DNA
<213> ORGANISM: Lactobacillus gigeriorum

<400> SEQUENCE: 52

```
atgtgtactt cgattatctt cagtcctaaa aatcactact ttggacgaaa tcttgattta      60
gatatttctt atggtcaaaa agttgtcatt actcctcgca actatcaatt tgattttcgc     120
aaagaaaatt ctatatctca tcacttcgct atcatcggaa ttgcccttgt agccaacgat     180
tatccccttt attttgatgc tgctaatgaa gccggtcttg gaatggcagg actaaattat     240
cccggcaacg cttactatca ggagactctt tcattaacca aagcaaacat cagtcccttt     300
gaattcattc cttgggtact aagtcaatgc tcaaacttaa cagaagcaga agcactaatt     360
gtcaaaacca atttagtagc aatcaacttt agtgaaaaaa tgccactcgc atcccttcac     420 tggctttag ccgacaaaac cggtcaagct ttagttgtag aagctgatcg tgatgggctt     480
cacctttatc ataatgaagt tggcgttctt accaataatc cgcaatttcc taagcaacga     540
tttgcactaa atatttatcg taatcttagt gttcaaccaa ccgctaatac ttttgcttcg     600
aatattgacc ttaccccata tagcagtggc atgggatccg tcaacttacc tggtggactt     660
gattcggttt ctcgttttgt cagagcaact ttcaatttac atcatgcacc taagagcgaa     720
aacaacgctg aaaatattaa tacctacttt cacattctga aatcagttga caacaaaaa     780 gggcttaata aattagataa tggccaagat gaattcacaa tttattctga ttgtttcgat     840
ctcgatcaaa attgtttta ctacactact tacaataact cacagatttc acaagtaagc     900
ttagcacatg aagatttaga agattcaaac ttgattagtt attccattag tgatcaacct     960
aacttcagag aggtaaatta a                                              981
```

<210> SEQ ID NO 53
<211> LENGTH: 326
<212> TYPE: PRT
<213> ORGANISM: Lactobacillus gorillae

<400> SEQUENCE: 53

Met Cys Thr Ala Val Thr Tyr Thr Ala Gly Asp His Tyr Phe Gly Arg
1               5                   10                  15

Asn Leu Asp Leu Glu Ile Ser Tyr Gly Glu Lys Val Thr Ile Thr Pro
                20                  25                  30

Arg Asn Phe Pro Leu Thr Phe Arg Lys Met Pro Thr Leu Glu His His
                35                  40                  45

Tyr Ala Met Ile Gly Met Ala Thr Thr Val Asp Asn Tyr Pro Leu Tyr
        50                  55                  60

Phe Asp Ala Thr Asn Glu Lys Gly Leu Ser Met Ala Gly Leu Asn Tyr
65                  70                  75                  80

Pro Gly Asn Ala Asp Tyr Lys Pro Leu Ala Glu Asp Lys Asp Asn Val
                85                  90                  95

Thr Pro Phe Glu Phe Ile Pro Trp Ile Leu Gly Gln Cys Ala Thr Leu
                100                 105                 110

Asp Glu Ala Lys Val Leu Leu Asn Lys Ile Asn Leu Val Lys Ile Asn
        115                 120                 125

Phe Asn Asp Gln Phe Pro Leu Ser Pro Leu His Trp Met Met Gly Glu
        130                 135                 140

Thr Ala Ser Glu Lys Thr Leu Thr Ile Glu Cys Asp Arg Asp Gly Leu
145                 150                 155                 160

His Val Tyr Asp Asn Pro Val Gly Val Leu Thr Asn Asn Pro Gln Phe
                165                 170                 175

Asp Lys Gln Leu Phe Asn Leu Asn Asn Tyr Gln Phe Leu Ser Pro Gln
        180                 185                 190

Gln Pro Glu Asn Lys Phe Ser Gln Asn Val Asp Leu Asp Asn Tyr Ser
        195                 200                 205

Arg Gly Leu Gly Thr Arg Gly Leu Pro Gly Gly Met Asp Ser Met Ser
        210                 215                 220

Arg Phe Val Lys Val Ala Phe Thr Lys Leu Asn Ala Pro Lys Gly Glu
225                 230                 235                 240

Ser Glu Ser Glu Asn Val Gly Asn Phe Phe His Ile Ser His Ser Val
                245                 250                 255

Glu Gln Gln Lys Asn Leu Asp Gly Val Glu Asn Asn Gln Phe Glu Phe
        260                 265                 270

Thr Ile Tyr Ser Ser Cys Val Asn Ala Asp Arg Gly Ile Tyr Tyr Tyr
        275                 280                 285

Thr Thr Tyr Asn Asn Asn Gln Ile Asn Ala Val Asp Met His Lys Thr
        290                 295                 300

Asp Leu Asp Gly Gln Glu Leu Val Asp Tyr Ala Leu Ala Asp Asp Gln
305                 310                 315                 320

Asn Ile Asn Trp Gln Asn
                325

<210> SEQ ID NO 54
<211> LENGTH: 981
<212> TYPE: DNA
<213> ORGANISM: Lactobacillus gorillae

<400> SEQUENCE: 54
atgtgtactg cagtaaccta taccgctgga gaccactact ttggtcggaa tttggatttg      60
gaaatttctt atggtgaaaa agttacgatt acgccgcgta attttccact gactttccgc     120
aagatgccaa cgcttgaaca ccactatgcc atgattggta tggccacaac agttgacaac     180

-continued

```
tatccactct actttgatgc cacgaacgaa aagggcttga gcatggccgg cttgaactac        240
ccgggcaacg ctgattacaa gccgctggca gaagataagg ataacgtaac gccttttgaa        300
ttcatcccgt ggattttggg ccaatgcgca accttggatg aagcaaaggt tctattaaac        360
aagattaacc tggttaagat caactttaat gaccagttcc cgctttcccc actgcactgg        420
atgatgggtg aaacggcttc tgaaaagacc ttgacgattg aatgcgatcg cgacgggctg        480
catgtttatg acaacccggt tggtgtgttg accaacaacc cgcaattcga caagcagctg        540
tttaacttaa acaactacca attcttgagc ccacagcagc ctgaaaacaa gttcagtcaa        600
aacgtggacc ttgataacta cagccgtggc ctcggaacgc ggggtctgcc aggcgggatg        660
gactcaatgt cacgctttgt taaggttgcc tttaccaagc tcaacgcacc taagggcgaa        720
agcgagagtg aaaacgtggg taacttcttc cacatttcac actctgttga gcaacaaaag        780
aacctggatg gcgtcgaaaa caaccaattc gagtttacga tctactcatc ctgtgtcaac        840
gccgatcgtg gtatctacta ctacacgacc tacaacaaca accagatcaa tgccgttgat        900
atgcacaaga ctgacctgga cggccaagag ttagttgact acgctttggc agacgaccaa        960
aacatcaact ggcaaaatta a                                                  981
```

```
<210> SEQ ID NO 55
<211> LENGTH: 325
<212> TYPE: PRT
<213> ORGANISM: Lactobacillus hamsteri

<400> SEQUENCE: 55

Met Cys Thr Ser Ile Ile Phe Ser Pro Lys Asp His Tyr Phe Gly Arg
1               5                   10                  15

Asn Leu Asp Leu Glu Val Ser Phe Gly Gln Gln Val Val Val Thr Pro
            20                  25                  30

Arg Asn Tyr Asn Phe Lys Phe Arg Lys Met Pro Asp Met Lys Lys His
        35                  40                  45

Phe Ala Met Val Gly Ile Ala Leu Val Ala Asp Glu Tyr Pro Leu Tyr
    50                  55                  60

Phe Asp Ala Ala Asn Glu Lys Gly Leu Gly Met Ala Gly Leu Asn Tyr
65                  70                  75                  80

Pro Asp Asn Phe His Ala Phe Glu Val Glu Asp Gly Lys Asp Asn Ile
                85                  90                  95

Ser Pro Phe Glu Phe Ile Pro Trp Val Leu Gly Gln Cys Ala Thr Val
            100                 105                 110

Asp Glu Ala Lys Lys Leu Leu Glu Lys Ile Asn Leu Val Asn Ile Asn
        115                 120                 125

Phe Ser Glu Lys Met Gln Leu Ser Pro Leu His Trp Leu Ile Ala Asp
    130                 135                 140

Lys Thr Gly Lys Ser Ile Thr Val Glu Ser Asp Ile Asp Gly Leu His
145                 150                 155                 160

Val Tyr Asp Asn Pro Ile Gly Cys Leu Thr Asn Asn Pro Gln Phe Pro
                165                 170                 175

Lys Gln Leu Thr Asn Leu Asp Asn Tyr Ala Asn Leu Ser Pro Ala Met
            180                 185                 190

Pro Glu Asn Thr Phe Ser Lys Glu Ile Asn Phe Asn Gly Tyr Ser Arg
        195                 200                 205

Gly Leu Gly Ser His Asn Leu Pro Gly Gly Met Asp Ser Glu Ser Arg
    210                 215                 220
```

```
Phe Val Arg Val Ala Phe Asn Lys Phe Asn Ala Pro Lys Phe Asp Thr
225             230             235             240

Glu Glu Glu Asn Val Asp Thr Tyr Phe His Ile Leu His Ser Val Glu
            245             250             255

Gln Gln Lys Gly Leu Asp Glu Val Ala Pro Gly Gln Phe Glu Tyr Thr
        260             265             270

Ile Tyr Ser Asp Gly Thr Asn Leu Asp Thr Gly Val Phe Tyr Tyr Thr
        275             280             285

Thr Tyr Thr Asn Lys Arg Ile Thr Lys Val Asp Met Asn Lys Leu Asp
    290             295             300

Leu Asp Ser Asp Gln Met Thr Val Tyr Pro Ile Asn Asp Lys Ile Thr
305             310             315             320

Phe Asp Glu Glu Asn
            325
```

```
<210> SEQ ID NO 56
<211> LENGTH: 978
<212> TYPE: DNA
<213> ORGANISM: Lactobacillus hamsteri

<400> SEQUENCE: 56
atgtgtacat ctattatttt tagtccaaaa gatcactatt tcggccgtaa tcttgacctt        60
gaagtttcat ttggtcaaca agttgttgtc acccctagaa actacaactt caaattccgt       120
aaaatgccag atatgaagaa gcactttgct atggtaggaa ttgctttagt agccgatgaa       180
tatcctcttt acttcgatgc agcaaacgaa aaaggcttgg ggatggctgg tcttaattat       240
cctgacaact tccatgcttt tgaagtagaa gatggaaaag acaatattag tcccttcgaa       300
tttattcctt gggtttttagg acaatgcgca actgttgacg aagctaaaaa acttttagaa       360
aagatcaact tagtaaacat caatttcagc gaaaagatgc aattatctcc tcttcactgg       420
ttaattgctg ataaaactgg caaatcaatt accgttgaat cagatattga tggcttgcac       480
gtttacgaca atcctattgg ttgccttact aacaatccac aatttccaaa gcaattaacc       540
aacttggaca actatgctaa tctttcacca gctatgccag aaaatacttt ttctaaagaa       600
atcaatttca atggctacag ccgtggtctt ggttctcaca acttgccagg tggcatggat       660
tcagaatcac gttttgttag agtagctttc aacaaattta acgcaccaaa atttgatact       720
gaagaagaaa atgttgatac ttacttccat attttgcatt cagtagaaca acaaaagggc       780
ttagatgaag tcgctcctgg tcaatttgaa tataccattt actcagacgg cactaacctt       840
gatacaggcg tattctacta caccacttat actaacaagc gtatcaccaa agttgatatg       900
aacaagcttg atcttgatag tgatcaaatg actgtttacc caatcaacga caagatcact       960
tttgatgaag aaaattaa                                                     978
```

```
<210> SEQ ID NO 57
<211> LENGTH: 325
<212> TYPE: PRT
<213> ORGANISM: Lactobacillus helveticus

<400> SEQUENCE: 57

Met Cys Ser Ser Ile Ile Phe Ser Pro Lys Asp His Tyr Phe Gly Arg
1               5               10              15

Asn Leu Asp Leu Glu Ile Thr Phe Gly Gln Gln Val Ile Ile Thr Pro
            20              25              30

Arg Asp Tyr Val Phe Lys Phe Arg Asp Met Pro Glu Ile Asp His His
        35              40              45
```

```
Tyr Ala Met Val Gly Ile Ala Leu Asn Ala Gly Gly Tyr Pro Leu Tyr
    50              55              60

Phe Asp Ala Ala Asn Glu Lys Gly Leu Gly Met Gly Gly Leu Asn Tyr
65              70              75              80

Pro Asp Asn Ala Val Tyr Tyr Asp Val Lys Glu Gly Lys Asp Asn Ile
                85              90              95

Ala Ser Phe Glu Phe Ile Pro Trp Ile Leu Ser Gln Ala Ala Thr Val
            100             105             110

Glu Glu Ala Lys Lys Leu Leu Ala Lys Ile Asn Ile Thr Lys Lys Asn
        115             120             125

Phe Ser Asp Lys Met His Val Ser Pro Leu His Trp Ile Ile Ala Asp
    130             135             140

Lys Thr Gly Ala Ser Ile Val Val Glu Thr Asp Ala Asp Ser Met His
145             150             155             160

Val Tyr Asp Asn Pro Val Gly Cys Leu Thr Asn Asn Pro Gln Phe Pro
                165             170             175

Lys Gln Leu Phe Ser Leu Asn Asn Tyr Gln Asp Val Ser Pro Ala Met
            180             185             190

Pro Lys Asn Asn Phe Ser Ser Lys Ile Asn Met Asp Gly Tyr Ser Arg
        195             200             205

Gly Leu Gly Ser Arg Asn Leu Pro Gly Gly Met Asp Ala Glu Ser Arg
    210             215             220

Phe Val Arg Val Ala Phe Asn Lys Phe Asn Ala Pro Val Ala Asp Thr
225             230             235             240

Glu Glu Glu Asn Ile Asp Thr Tyr Leu His Ile Leu His Ser Ala Glu
                245             250             255

Gln Gln Lys Gly Leu Asp Gln Val Gly Pro Asp Ser Phe Glu Tyr Thr
            260             265             270

Ile Tyr Ser Asp Gly Thr Asn Leu Asp Lys Gly Ile Phe Tyr Tyr Thr
        275             280             285

Thr Tyr Thr Asp Lys Gln Ile Lys Val Val Asp Met Asn Lys Glu Asp
    290             295             300

Leu Asp Ser Lys Asp Leu Ile Thr Phe Asp Met Leu Thr Lys Thr Cys
305             310             315             320

Phe Asn Tyr Gln Asn
                325
```

<210> SEQ ID NO 58
<211> LENGTH: 978
<212> TYPE: DNA
<213> ORGANISM: Lactobacillus helveticus

<400> SEQUENCE: 58

```
atgtgttcat ctattatatt tagtcctaaa gatcattact ttggtcgtaa ccttgacctt      60
gaaatcactt ttggacaaca agttattatt accccacgtg actacgtatt caaattccgt     120
gatatgcctg aaatcgatca tcactatgca atggttggta ttgcattaaa tgctggtggt     180
tatcctttat actttgacgc agctaatgaa aaaggtctag gaatgggcgg ccttaattat     240
cctgataatg ccgtttacta cgatgtaaaa gaaggcaagg acaacatcgc ctcattcgaa     300
ttcatcccat ggatcttaag ccaagcagct actgttgaag aagctaagaa gttattagcc     360
aagatcaaca tcactaagaa gaacttcagc gacaagatgc atgtatcccc acttcactgg     420
atcatcgcag ataaaactgg tgcttctatt gttgttgaaa ctgacgcaga cagtatgcac     480
```

```
gtttacgaca accctgtcgg ctgcttaact aacaacccac aattccctaa gcaattgttc      540
agcttgaaca actaccaaga cgtttcacct gccatgccta agaacaactt ctcaagcaaa      600
attaacatgg atggctacag ccgcggtctt ggttcacgta acttgccagg tggtatggac      660
gctgaatcac gttttgtcag agtagcattc aacaagttca atgctccagt tgctgatacc      720
gaagaagaaa acatcgatac ttacctccac atcttgcatt cagctgaaca acaaaagggc      780
ttggatcaag taggtccaga ttccttcgaa tatactattt actcagacgg taccaactta      840
gataagggta ttttctacta cacaacttat acagacaagc aaatcaaagt tgttgatatg      900
aacaaagaag atcttgattc taaagacttg attacttttg atatgctcac taagacctgc      960
ttcaattacc aaaattaa                                                    978
```

```
<210> SEQ ID NO 59
<211> LENGTH: 325
<212> TYPE: PRT
<213> ORGANISM: Lactobacillus hominis

<400> SEQUENCE: 59

Met Cys Thr Ser Ile Leu Tyr Ser Pro Lys Asp His Tyr Phe Gly Arg
1               5                   10                  15

Asn Leu Asp Tyr Glu Ile Ala Tyr Gly Gln Lys Val Val Ile Thr Pro
                20                  25                  30

Arg Asn Tyr Glu Phe Glu Phe Thr Asp Leu Pro Ala Glu Lys Ser His
            35                  40                  45

Tyr Ala Met Ile Gly Val Ala Ala Val Ala Asp Asn Thr Pro Leu Tyr
        50                  55                  60

Cys Asp Ala Ile Asn Glu Lys Gly Leu Gly Val Ala Gly Leu Ser Phe
65                  70                  75                  80

Ala Gly Gln Gly Lys Tyr Phe Pro Asn Ala Ala Asp Lys Lys Asn Ile
                85                  90                  95

Ala Ser Phe Glu Phe Ile Ser Tyr Leu Leu Ala Thr Tyr Glu Thr Val
            100                 105                 110

Asp Gln Val Lys Glu Ser Leu Thr Asn Ala Asn Ile Ser Asn Val Ser
            115                 120                 125

Phe Ala Lys Asn Thr Pro Ala Ser Glu Leu His Trp Leu Val Gly Asp
        130                 135                 140

Lys Thr Gly Lys Ser Ile Val Val Glu Ser Asp Glu Lys Gly Leu His
145                 150                 155                 160

Val Tyr Asp Asn Pro Val Asn Ala Leu Thr Asn Ala Pro Leu Phe Pro
                165                 170                 175

Glu Gln Leu Thr Asn Leu Ala Asn Tyr Ala Ser Val Val Pro Gly Glu
            180                 185                 190

Pro Asp Asn Asn Phe Leu Pro Gly Val Asn Leu Lys Leu Tyr Ser Arg
            195                 200                 205

Ser Leu Gly Thr His His Leu Pro Gly Gly Met Asp Ser Glu Ser Arg
        210                 215                 220

Phe Val Lys Val Cys Phe Ala Leu Asn His Ala Pro Lys Asp Ser Asn
225                 230                 235                 240

Glu Val Glu Asn Val Thr Asn Phe Phe His Ile Leu Glu Ser Val Glu
                245                 250                 255

Gln Ala Lys Gly Met Asp Gln Val Gly Pro Asn Ser Phe Glu Tyr Thr
            260                 265                 270

Met Tyr Thr Ser Cys Met Asn Leu Glu Lys Gly Ile Leu Tyr Phe Asn
        275                 280                 285
```

```
Cys Tyr Asp Asp Ser Arg Ile Ser Ala Val Asp Met Asn Lys Glu Asp
    290             295             300

Leu Asp Ser Ser Asp Leu Val Val Tyr Asp Leu Phe Lys Lys Gln Asp
305             310             315             320

Ile Asn Phe Val Asn
            325
```

<210> SEQ ID NO 60
<211> LENGTH: 978
<212> TYPE: DNA
<213> ORGANISM: Lactobacillus hominis

<400> SEQUENCE: 60

```
atgtgtacat caattttata cagtcctaaa gaccactatt ttggcagaaa tcttgattat      60
gaaattgctt atggtcaaaa agtggttatt acaccaagaa attatgaatt cgagtttacc     120
gatttaccag ctgaaaaatc acattatgca atgattggtg tagccgctgt agcagataac     180
actccgttat attgcgacgc aattaatgaa aaaggattgg gagttgctgg tttaagcttt     240
gctggacaag ggaagtactt tccaaatgca gcagataaaa agaatattgc ttcatttgaa     300
tttatttcat atttattagc tacttatgaa actgttgatc aagtaaaaga aagcctaact     360
aatgcaaata tttctaatgt gagttttgct aaaaataccc cagcttcaga acttcactgg     420
ctagtaggag ataaaactgg taagagtatt gttgttgagt cagatgaaaa aggcctgcat     480
gtttatgaca tcctgtcaa tgctctgact aacgcacctt tattcccaga gcagttaact     540
aatttggcaa actatgcttc ggttgttcca ggcgaacctg ataataattt tttacctggt     600
gttaatctta agttatatag tcgcagttta ggtacgcatc acttaccagg cgggatggat     660
tcagaatcac gttttgttaa ggtatgtttt gccttgaatc acgcaccaaa agatagtaat     720
gaggtagaaa atgttaccaa tttcttccat attttagagt ctgttgaaca agcaaaaggg     780
atggatcaag ttggtcctaa tagttttgaa tatacgatgt atactagctg tatgaatctg     840
gaaaaaggaa ttttgtactt taattgctat gatgacagta gaattagtgc tgttgatatg     900
aacaaagaag atttggattc atcagactta gttgtatatg atttgtttaa gaaacaagat     960
attaattttg taaattaa                                                     978
```

<210> SEQ ID NO 61
<211> LENGTH: 327
<212> TYPE: PRT
<213> ORGANISM: Lactobacillus ingluviei

<400> SEQUENCE: 61

```
Met Cys Thr Ala Val Asn Phe Gln Thr Gly Ser His His Phe Phe Gly
1               5               10              15

Arg Asn Leu Asp Leu Glu Ile Ser Tyr Gly Glu Gln Val Val Val Thr
            20              25              30

Pro Arg Asn Tyr Pro Phe His Phe Arg Gln Val Ala Pro Leu Thr His
        35              40              45

His Tyr Ala Leu Ile Gly Met Gly Ile Val Val Asp Asp Tyr Pro Leu
    50              55              60

Tyr Phe Asp Ala Thr Asn Glu Lys Gly Leu Ser Met Ala Gly Leu Asn
65              70              75              80

Tyr Pro Asp Asn Ala Asp Tyr Lys Ala Leu Ala Thr Asp Lys Ala Asn
                85              90              95

Val Thr Pro Phe Glu Phe Ile Pro Trp Val Leu Gly Gln Ala Ala Ser
```

-continued

```
                   100                105                110

Ile Ala Glu Ala Lys Gln Leu Leu Thr Lys Leu Asn Leu Val Lys Ile
             115                120                125

Asn Phe Ser Asp Asp Leu Pro Leu Ser Pro Leu His Trp Leu Ile Gly
     130                135                140

Asp Thr His Ser Ala Thr Ser Leu Val Val Glu Cys Asp Lys Asp Gly
145                150                155                160

Leu His Val Tyr Asp Asn Pro Val Gly Val Leu Thr Asn Asn Pro Ser
                 165                170                175

Phe Asp Lys Gln Leu Phe Asn Leu Asn Asn Tyr Arg Ser Val Ser Pro
                 180                185                190

Arg Val Gln Glu Asn Ser Phe Gln Pro Ala Thr Ala Leu Asn Asp Tyr
             195                200                205

Ser Arg Gly Leu Gly Ser His Phe Leu Pro Gly Gly Met Asp Ser Met
     210                215                220

Ser Arg Phe Val Lys Val Ala Phe Thr Lys Leu Asn Ala Pro His Ser
225                230                235                240

Ala Thr Pro Leu Glu Gln Val Thr Asp Phe Phe His Ile Leu His Ser
                 245                250                255

Val Glu Gln Pro Lys Asn Leu Asp Glu Val Ala Pro Asn Gln Phe Glu
             260                265                270

Tyr Thr Ile Tyr Ser Ser Cys Val Asp Ala Asp Gln Gly Ile Tyr Tyr
             275                280                285

Tyr Thr Thr Tyr Thr Asn Asn Gln Ile Asn Ala Val Lys Leu His Asn
     290                295                300

Val Asp Leu Asp Gln Ala Lys Leu Thr Thr Tyr Ala Leu Ala Asp Gln
305                310                315                320

Gln Thr Val Asn Tyr Gln Asn
                 325
```

<210> SEQ ID NO 62
<211> LENGTH: 984
<212> TYPE: DNA
<213> ORGANISM: Lactobacillus ingluviei

<400> SEQUENCE: 62

```
atgtgtacag cagttaattt ccaaaccggt tcccaccact tctttggccg caacctggac      60
ctagaaattt cgtatggtga acaagttgtt gtcacccccc ggaactaccc gtttcatttt     120
cggcaagttg ctccgttgac gcaccactac gctcttattg gcatgggat  tgttgtcgat     180 gattacccccc tttactttga tgccaccaat gaaaaggggc tgtctatggc tggtctgaac     240
tatcctgaca tgccgatta  caaggctttg gccacggata aggctaacgt gactcccttt     300
gagtttatcc cgtgggtatt aggacaagct gcttccattg ccgaagccaa acaattgttg     360
accaagctta atttagtcaa aattaatttc agtgatgatt taccattgtc accccctccac    420 tggttgattg gtgacaccca cagcgctacc agtttagtag ttgaatgtga caaagatggt     480
ctccacgttt atgacaaccc ggtcggagta ttgactaaca acccttcctt tgataaacag     540
ctgtttaacc tgaacaacta ccggtcagtt agcccgcggg tgcaagaaaa cagcttccaa     600
cctgcgacag ccttaaatga ttacagtcgg ggactaggtt cgcatttcct tcctggcggg     660
atggattcga tgtcacggtt tgttaaggtg gctttttacca agctcaacgc ccgcacagc     720 gctactcctt tggaacaggt aacggacttc ttccacatcc tccattcggt ggaacagccc     780
aagaatctgg atgaagtggc ccccaaccag tttgaataca ccatttattc ttcctgcgtt     840
```

-continued

```
gatgctgacc aaggtattta ttattacacg acctacacta acaaccaaat caatgccgtt      900
aagctgcata acgttgattt agaccaagct aagctgacga cctacgcctt ggcggatcag      960
caaacggtta actaccaaaa ttaa                                            984
```

```
<210> SEQ ID NO 63
<211> LENGTH: 325
<212> TYPE: PRT
<213> ORGANISM: Lactobacillus intestinalis

<400> SEQUENCE: 63

Met Cys Thr Ser Ile Leu Tyr Asn Ser Asn Glu His Tyr Phe Gly Arg
1               5                   10                  15

Asn Leu Asp Tyr Glu Ile Ala Tyr Gly Gln Lys Ile Val Ile Thr Pro
                20                  25                  30

Arg Asn Tyr Glu Phe Asp Phe His Asp Leu Pro Ser Gln Lys Ser His
            35                  40                  45

Tyr Ala Met Ile Gly Val Ser Val Val Asp Asp Asn Tyr Pro Leu Tyr
        50                  55                  60

Cys Asp Ala Ile Asn Glu Lys Gly Leu Gly Val Ala Gly Leu Asn Phe
65                  70                  75                  80

Glu Gly Pro Gly Gln Tyr Phe Pro Val Glu Lys Gly Lys Lys Asn Ile
                85                  90                  95

Thr Ser Tyr Glu Leu Ile Ala Tyr Leu Leu Ser Asn Tyr Glu Thr Val
            100                 105                 110

Glu Asp Val Lys Gln Gly Leu Ala Asp Ala Asn Ile Ser Asp Ile Ser
            115                 120                 125

Phe Ser Glu Asn Leu Pro Ala Ala Val Leu His Trp Met Val Ala Asp
        130                 135                 140

Lys Thr Gly Lys Ser Ile Val Ile Glu Ser Ser His Lys Gly Leu Asn
145                 150                 155                 160

Ile Tyr Glu Asn Pro Val Asn Val Met Thr Asn Asn Pro Val Phe Pro
                165                 170                 175

Val His Leu Ile Asn Leu Ser Asn Tyr Ala Asp Val Ser Pro Ile Gln
            180                 185                 190

Pro Thr Asn Phe Leu Ala Pro Lys Val Glu Leu Asn Met Tyr Ser Arg
        195                 200                 205

Gly Leu Gly Thr His His Leu Pro Gly Gly Met Asp Ser Ala Ser Arg
    210                 215                 220

Phe Val Lys Ala Thr Phe Ala Leu Ala His Ala Pro Gln Gly Lys Ser
225                 230                 235                 240

Glu Ile Glu Asn Val Thr Asn His Leu His Val Leu Lys Ser Val Glu
                245                 250                 255

Gln Ala Lys Gly Leu Asp Glu Val Gly Pro Asp Ser Tyr Glu Tyr Thr
            260                 265                 270

Met Tyr Ser Asp Cys Met Asn Leu Glu Lys Gly Ile Leu Tyr Cys Thr
            275                 280                 285

Thr Tyr Asn Asp Ser Arg Ile Arg Ala Val Asp Met His Lys Glu Asp
        290                 295                 300

Leu Asp Ser Glu Lys Leu Ile Cys Tyr Asn Leu Phe Lys Asp Gln Asp
305                 310                 315                 320

Ile Glu Tyr Glu Asn
                325
```

<210> SEQ ID NO 64
<211> LENGTH: 978
<212> TYPE: DNA
<213> ORGANISM: Lactobacillus intestinalis

<400> SEQUENCE: 64
atgtgtacat caatacttta caattctaac gaacattatt ttggtagaaa cttagattat        60
gaaattgctt atggtcaaaa gattgtaatt acacccgta attatgaatt tgattttcat       120
gatcttccaa gtcagaagag tcactatgca atgattggtg tctcagtagt agatgataat       180
tatcctttat actgtgatgc cattaatgaa aaaggtttag gtgttgcagg acttaatttt       240
gaaggtccag gtcaatattt cccagtagaa aagggtaaga aaaacattac ttcctatgaa       300
ttgattgcct atttgttgag taattatgaa acggtagaag atgtaaaaca aggcttagct       360
gatgctaata tttctgatat tagctttca gaaaatttgc ctgctgctgt tcttcactgg       420
atggttgctg ataaaactgg caagagcatt gtaattgaat ctagccacaa gggattaaat       480
atttacgaaa tcctgtcaa tgtcatgact aataatcctg tcttccctgt gcacttaatt       540
aacttgagta attacgcaga tgtctcacca attcaaccaa ctaatttctt agctcctaag       600
gtagaattga atatgtatag tcggggctta ggaacgcatc atttacctgg tggaatggat       660
tctgcttcac gttttgttaa ggctacattt gcattagccc atgctcctca aggcaagagt       720
gaaattgaga atgtaactaa ccatcttcac gttttaaagt ctgttgaaca agctaaaggt       780
ttagatgaag taggacctga ttcttatgaa tacactatgt attccgattg tatgaattta       840
gagaaaggaa ttctttactg cactacttat aatgatagta gaattcgtgc ggttgatatg       900
cataaggaag atttagatag tgaaaagttg atttgttaca atttatttaa ggatcaagat       960
attgaatatg aaaactaa                                                     978

<210> SEQ ID NO 65
<211> LENGTH: 326
<212> TYPE: PRT
<213> ORGANISM: Lactobacillus intestinalis

<400> SEQUENCE: 65

Met Cys Thr Ser Ile Ile Phe Ser Pro Asn Asp His Tyr Phe Gly Arg
1               5                   10                  15

Asn Phe Asp Tyr Glu Met Ser Phe Gly Gln Gln Val Val Val Thr Pro
            20                  25                  30

Arg Asn Tyr Glu Phe Lys Phe Arg Lys Met Pro Thr Ile Thr Thr His
        35                  40                  45

Tyr Ala Met Val Gly Ile Ser Ala Val Arg Asp Asp Tyr Pro Leu Tyr
    50                  55                  60

Phe Asp Ala Ala Asn Glu Lys Gly Leu Gly Met Ala Gly Leu Asn Tyr
65                  70                  75                  80

Ala Gly Asn Ala Tyr Tyr Pro Glu Lys Glu Glu Glu Gly Lys Asp Asn
                85                  90                  95

Ile Ser Pro Phe Glu Phe Ile Pro Trp Ile Leu Gly Gln Cys Ala Asn
            100                 105                 110

Leu Asp Glu Ala Lys Lys Leu Ile Asp Arg Ile His Leu Val His Ile
        115                 120                 125

Asn Phe Ser Glu Lys Leu Pro Leu Ser Pro Leu His Trp Leu Ile Ala
    130                 135                 140

Asp Lys Ser Gly Lys Ser Ile Val Ile Glu Ser Asp Lys Asp Gly Leu
145                 150                 155                 160

```
His Val Tyr Asp Asn Pro Val Gly Thr Leu Thr Asn Asn Pro Pro Phe
                165                 170                 175

Pro Lys Gln Leu Phe Asn Leu Asn Asn Tyr Ala Asp Val Ser Pro Lys
            180                 185                 190

Met Pro Thr Asn Arg Phe Ser Asp Lys Val Asn Phe Asp Leu Tyr Ser
            195                 200                 205

Arg Gly Leu Gly Ser His Asn Leu Pro Gly Gly Met Asp Ser Glu Ser
        210                 215                 220

Arg Phe Val Arg Ala Leu Phe Thr Lys Ser Asn Ala Pro Ala Ala Asp
225                 230                 235                 240

Asn Glu Ala Asp Asn Val Asn Asn Tyr Phe His Ile Leu His Ala Val
                245                 250                 255

Glu Gln Pro Lys Gly Leu Asp Glu Val Gly Pro Asn Ser Phe Glu Tyr
            260                 265                 270

Thr Ile Tyr Ser Asp Cys Thr Asn Leu Glu Lys Gly Leu Phe Tyr Tyr
            275                 280                 285

Thr Thr Tyr Asn Gln Arg Gln Ile Thr Glu Val Asn Met Asn Lys Glu
        290                 295                 300

Asp Leu Glu Lys Asp Asp Leu Ile Ile Tyr Pro Ile Glu Asp Lys Val
305                 310                 315                 320

Glu Phe Asn Arg Glu Asn
                325
```

```
<210> SEQ ID NO 66
<211> LENGTH: 981
<212> TYPE: DNA
<213> ORGANISM: Lactobacillus intestinalis

<400> SEQUENCE: 66
atgtgtactt caattatttt cagtcccaat gaccattatt tcggccgtaa ttttgactac      60
gaaatgtcat ttggccaaca agtagtagtt accccaagaa attatgaatt taagtttcgt     120
aaaatgccaa ctattactac acactatgct atggtaggaa tttcggcagt cagagatgat     180
tatcctcttt actttgatgc cgctaatgaa aaaggcctag gaatggccgg tcttaactat     240
gctggcaatg cttactatcc tgaaaaagaa gaagagggca aagacaatat ttcaccattt     300
gaatttattc cttggatttt aggtcaatgc gctaatttag atgaagctaa aaagctaatt     360
gatcgtattc atcttgtaca tattaacttt agtgaaaaat tacctctttc tcctcttcac     420
tggctcatag ccgacaagag tggtaaatca atcgttattg aatctgataa agacggtctg     480
catgtttatg acaacccagt tggaacttta actaataatc cacctttccc taagcaatta     540
ttcaacttaa acaattatgc tgatgtttca cctaagatgc caactaacag attctcagat     600
aaagttaact ttgatttata cagtcgtgga ctcggttctc acaatttacc aggtgggatg     660
gattctgaat ctcgttttgt cagagctctt ttcactaaat ctaatgctcc cgcagccgat     720
aacgaagccg acaacgtcaa taattacttc cacatccttc atgctgttga caacctaaa     780
ggcttagatg aagttggccc taacagtttt gaatatacta tttattctga ctgcactaac     840
cttgaaaaag gactcttcta ctacaccacc tataatcaaa gacaaattac agaagtcaat     900
atgaacaaag aagaccttga aaaagatgat ttaattattt atccaatcga agacaaagtt     960
gaatttaatc gtgaaaacta a                                              981
```

```
<210> SEQ ID NO 67
<211> LENGTH: 316
<212> TYPE: PRT
```

<213> ORGANISM: Lactobacillus intestinalis

<400> SEQUENCE: 67

```
Met Cys Thr Gly Leu Arg Phe Thr Asp Asp Gln Gly Asn Leu Tyr Phe
1               5                   10                  15

Gly Arg Asn Leu Asp Val Gly Gln Asp Tyr Gly Glu Lys Val Ile Val
            20                  25                  30

Thr Pro Arg Asn Tyr Pro Leu Pro Tyr Lys Phe Leu Ala Asp Thr Lys
        35                  40                  45

Thr Ser Lys Ala Val Ile Gly Met Gly Ile Val Val Asp Gly Tyr Pro
    50                  55                  60

Ser Tyr Phe Asp Cys Phe Asn Glu Asp Gly Leu Gly Ile Ala Gly Leu
65                  70                  75                  80

Asn Phe Pro His Tyr Ala Gln Phe Ser Lys Glu Pro Val Asn Gly Lys
                85                  90                  95

Ile Asn Leu Ala Ser Tyr Glu Ile Met Leu Trp Val Thr Gln Asn Phe
            100                 105                 110

Thr Thr Val Lys Glu Val Lys Glu Ala Leu Lys Asn Val Asn Leu Val
        115                 120                 125

Ser Glu Ala Ile Asn Ser Asp Phe Ala Val Ala Pro Leu His Trp Ile
    130                 135                 140

Ile Ser Asp Asn Glu Glu Ala Ile Val Val Glu Val Ser Lys Gln Tyr
145                 150                 155                 160

Gly Met Lys Val Phe Glu Asp Lys Leu Gly Val Leu Thr Asn Ser Pro
                165                 170                 175

Asp Phe Asn Trp Gln Val Thr Asn Leu Gly Asn Tyr Thr Gly Leu Ser
            180                 185                 190

Pro His Asp Ala Thr Leu Gln Asn Trp Asn Gly Gln Glu Val Met Pro
        195                 200                 205

Trp Gly Val Gly Thr Gly Ser Leu Gly Leu Pro Gly Asp Ser Ile Pro
    210                 215                 220

Ala Ser Arg Phe Ala Lys Val Ala Tyr Leu Asn Ala Asn Tyr Pro Thr
225                 230                 235                 240

Gln Lys Gly Glu Thr Ala Asn Val Ala Lys Phe Phe Asn Ile Leu Lys
                245                 250                 255

Ser Val Ala Met Val Lys Gly Ser Val Ile Asn Asn Gln Gly Lys Asp
                260                 265                 270

Glu Tyr Thr Val Tyr Thr Ala Cys Tyr Ser Ser Lys Thr Lys Thr Tyr
        275                 280                 285

Tyr Cys Asn Tyr Ala Thr Asp Phe Glu Leu Lys Lys Tyr Thr Ile Thr
    290                 295                 300

Asp Glu Asn Leu Ser Leu Asn Lys Leu Thr Ile Tyr
305                 310                 315
```

<210> SEQ ID NO 68
<211> LENGTH: 951
<212> TYPE: DNA
<213> ORGANISM: Lactobacillus intestinalis

<400> SEQUENCE: 68

```
atgtgtacag gtttaagatt tacagatgat caaggaaatt tgtattttgg tagaaatctt      60
gatgtgggcc aagattatgg tgaaaaagta atcgttacgc cacgtaatta tcctttacca     120
tataaatttc tagctgatac caagactagc aaagctgtta ttgggatggg tatcgtagta     180
gatggttatc cttcttattt tgattgcttt aatgaagatg gcttgggaat agctggttta     240
```

```
aacttccctc attatgccca atttagtaaa gaaccagtga atggaaaaat taatttagcc      300
tcttatgaga ttatgctttg ggtaacgcaa aactttacta cagttaaaga agtaaaggaa      360
gctttgaaaa atgtaaactt agtcagtgaa gctattaatt cagattttgc agttgctcct      420
cttcactgga ttatcagtga taatgaagaa gcaatagttg tagaagtttc taaacaatat      480
gggatgaaag tttttgaaga taagttaggc gttttaacta atagtccaga ttttaattgg      540
caagtaacta atttaggaaa ttatactggc ttgagtcctc atgatgctac gcttcaaaat      600
tggaatggcc aagaggttat gccatggggc gttggtactg gtagcttggg tttaccgggc      660
gatagtattc ctgcttctcg atttgccaaa gtagcatatt tgaatgcaaa ttatcctact      720
caaaaaggtg aaactgcgaa tgtggcaaaa ttctttaata ttttgaagtc agtcgctatg      780
gtaaaaggaa gcgtcattaa taatcaagga aaagatgaat atacggttta cacagcttgc      840
tattcatcaa aaacgaagac atattattgt aattatgcta ctgattttga gttgaaaaaa      900
tatactatta ctgatgaaaa tttaagctta aataaactta caatttatta g              951
```

```
<210> SEQ ID NO 69
<211> LENGTH: 316
<212> TYPE: PRT
<213> ORGANISM: Lactobacillus johnsonii

<400> SEQUENCE: 69

Met Cys Thr Gly Leu Arg Phe Thr Asp Asp Gln Gly Asn Leu Tyr Phe
1               5                   10                  15

Gly Arg Asn Leu Asp Val Gly Gln Asp Tyr Gly Glu Gly Val Ile Ile
            20                  25                  30

Thr Pro Arg Asn Tyr Pro Leu Pro Tyr Lys Phe Leu Asp Asn Thr Thr
        35                  40                  45

Thr Lys Lys Ala Val Ile Gly Met Gly Ile Val Val Asp Gly Tyr Pro
    50                  55                  60

Ser Tyr Phe Asp Cys Tyr Asn Glu Asp Gly Leu Gly Ile Ala Gly Leu
65                  70                  75                  80

Asn Phe Pro His Phe Ala Lys Phe Ser Asp Gly Pro Ile Asp Gly Lys
                85                  90                  95

Ile Asn Leu Ala Ser Tyr Glu Ile Met Leu Trp Val Thr Gln Asn Phe
            100                 105                 110

Thr His Val Ser Glu Val Lys Glu Ala Leu Lys Asn Val Asn Leu Val
        115                 120                 125

Asn Glu Ala Ile Asn Thr Ser Phe Ala Val Ala Pro Leu His Trp Ile
    130                 135                 140

Ile Ser Asp Ser Asp Glu Ala Ile Ile Val Glu Val Ser Lys Gln Tyr
145                 150                 155                 160

Gly Met Lys Val Phe Asp Asp Lys Val Gly Val Leu Thr Asn Ser Pro
                165                 170                 175

Asp Phe Asn Trp His Leu Thr Asn Leu Gly Asn Tyr Thr Gly Leu Asn
            180                 185                 190

Pro His Asp Ala Thr Ala Gln Ser Trp Asn Gly Gln Lys Val Ala Pro
        195                 200                 205

Trp Gly Val Gly Thr Gly Ser Leu Gly Leu Pro Gly Asp Ser Ile Pro
    210                 215                 220

Ala Asp Arg Phe Val Lys Ala Ala Tyr Leu Asn Val Asn Tyr Pro Thr
225                 230                 235                 240

Ala Lys Gly Glu Lys Ala Asn Val Ala Lys Phe Phe Asn Ile Leu Lys
```

```
                    245                 250                 255
Ser Val Ala Met Ile Lys Gly Ser Val Val Asn Asp Gln Gly Lys Asp
            260                 265                 270

Glu Tyr Thr Val Tyr Thr Ala Cys Tyr Ser Ser Gly Ser Lys Thr Tyr
        275                 280                 285

Tyr Cys Asn Phe Glu Asp Asp Phe Glu Leu Lys Thr Tyr Lys Leu Asp
    290                 295                 300

Asp His Thr Met Asn Ser Thr Ser Leu Val Thr Tyr
305                 310                 315
```

```
<210> SEQ ID NO 70
<211> LENGTH: 951
<212> TYPE: DNA
<213> ORGANISM: Lactobacillus johnsonii

<400> SEQUENCE: 70
atgtgtactg gtttaagatt cacagatgat caaggaaatt tatactttgg ccgtaatcta      60
gatgttggac aggattatgg cgaaggcgtt attattacgc cgcgtaatta tcctcttcca     120
tataagttct tagataacac cactactaaa aaggctgtta ttggaatggg aattgtggtt     180
gatggctatc catcatactt tgactgctat aacgaagatg gattaggtat tgcaggttta     240
aacttcccac attttgctaa atttagtgat ggtcctattg acggtaaaat caacttagct     300
tcttacgaaa ttatgctctg ggttactcaa aactttactc atgttagtga agtaaaggaa     360
gctttaaaga tgttaactt agtgaatgaa gctattaaca catcatttgc ggttgcccct     420
cttcactgga tcattagtga tagtgacgaa gccattattg ttgaggtttc aaaacaatat     480
ggaatgaaag tctttgatga caaagttggc gttttaacta atagccctga ctttaactgg     540
caccttacta accttggtaa ctacaccggt ttaaacccac atgacgctac agcccaaagc     600
tggaacgggc aaaaagttgc tccttgggc gtaggaactg gtagcttagg tctgccggt      660 gacagtattc cagccgatcg tttttgttaaa gctgcttact taaacgtaaa ctatccaact     720
gctaaaggtg aaaaagcaaa cgtcgctaaa ttctttaaca tcttaaagtc tgttgccatg     780
atcaaaggca gtgtagtcaa cgatcaaggc aaggacgaat atactgttta tactgcatgc     840
tactcttctg gaagcaagac ttactactgt aattttgaag atgattttga attaaagacc     900
tataaactag atgatcacac gatgaattca accagtcttg tgacttacta g            951
```

```
<210> SEQ ID NO 71
<211> LENGTH: 325
<212> TYPE: PRT
<213> ORGANISM: Lactobacillus johnsonii

<400> SEQUENCE: 71

Met Cys Thr Ser Ile Leu Tyr Ser Pro Lys Asp Asn Tyr Phe Gly Arg
1               5                   10                  15

Asn Leu Asp Tyr Glu Ile Ala Tyr Gly Gln Lys Val Val Ile Thr Pro
            20                  25                  30

Arg Asn Tyr Gln Leu Asn Tyr Arg His Leu Pro Thr Gln Asp Thr His
        35                  40                  45

Tyr Ala Met Ile Gly Val Ser Val Val Ala Asn Asp Tyr Pro Leu Tyr
    50                  55                  60

Cys Asp Ala Ile Asn Glu Lys Gly Leu Gly Ile Ala Gly Leu Asn Phe
65                  70                  75                  80

Thr Gly Pro Gly Lys Tyr Phe Ser Val Asp Glu Ser Lys Lys Asn Val
                85                  90                  95
```

-continued

```
Thr Ser Phe Glu Leu Ile Pro Tyr Leu Leu Ser Asn Cys Glu Thr Ile
            100                 105                 110

Glu Asp Val Lys Lys Leu Leu Ser Glu Thr Asn Ile Thr Asp Glu Ser
            115                 120                 125

Phe Ser Lys Asp Leu Pro Val Thr Thr Leu His Trp Leu Met Gly Asp
            130                 135                 140

Lys Ser Gly Lys Ser Ile Val Ile Glu Ser Thr Glu Thr Gly Leu His
145                 150                 155                 160

Val Tyr Asp Asn Pro Val Asn Thr Leu Thr Asn Asn Pro Val Phe Pro
                165                 170                 175

Ala Gln Val Glu Thr Leu Ala Asn Phe Ala Ser Val Ser Pro Ala Gln
            180                 185                 190

Pro Lys Asn Thr Leu Val Pro Asn Ala Asp Ile Asn Leu Tyr Ser Arg
            195                 200                 205

Gly Leu Gly Thr His His Leu Pro Gly Gly Thr Asp Ser Asn Ser Arg
            210                 215                 220

Phe Ile Lys Ala Ser Phe Val Leu Ala His Ser Pro Lys Gly Asn Asp
225                 230                 235                 240

Glu Val Glu Asn Val Thr Asn Phe Phe His Val Leu His Ser Val Glu
                245                 250                 255

Gln Ala Lys Gly Thr Asp Glu Val Glu Asp Asn Val Phe Glu Phe Thr
            260                 265                 270

Met Tyr Ser Asp Cys Met Asn Leu Asp Lys Gly Ile Leu Tyr Phe Thr
            275                 280                 285

Thr Tyr Asp Asn Asn Gln Ile Asn Ala Val Asp Met Asn Asn Glu Asp
            290                 295                 300

Leu Gly Thr Ser Asp Leu Ile Thr Tyr Glu Leu Phe Lys Asp Gln Ala
305                 310                 315                 320

Ile Lys Phe Glu Asn
                325
```

```
<210> SEQ ID NO 72
<211> LENGTH: 978
<212> TYPE: DNA
<213> ORGANISM: Lactobacillus johnsonii

<400> SEQUENCE: 72
atgtgtacat caattttata tagtccaaaa gataattatt ttggtagaaa tttagattat        60
gaaattgcct atggtcagaa agtggtaatt actcctagaa attatcaact taattaccga       120
catttaccaa cacaagatac tcattatgca atgatcggtg tttcagtagt cgccaatgac       180
tatccattat attgtgatgc tatcaatgaa aagggactag ggatagccgg attaaatttc       240
actggtcctg gtaaatattt ttctgtagat gaaagtaaaa agaatgttac ttcttttgaa       300
ctgatcccat atttactaag taattgcgaa actatcgaag atgtaaagaa attattatct       360
gaaactaata ttactgatga agtttctct  aaagatttac cagttactac tcttcattgg       420
ttaatgggtg ataaaagtgg taagagtata gtcattgaat caacagaaac tggcttacac       480
gtttatgaca acccagttaa tactttaaca aataatcctg tctttccagc tcaagttgaa       540
accttggcta actttgcttc agtttctcca gctcaaccta agaataccct tgtacctaat       600
gcagatatta atctgtatag ccgtggatta gggacccatc atttaccagg cggaacagat       660
tcaaattctc gctttattaa ggcatctttt gtattagctc attctccaaa aggtaatgat       720
gaagtcgaaa atgtaactaa tttcttccat gtcttacatt cagttgaaca agcaaagggt       780
```

-continued

```
acagatgaag ttgaagataa tgtatttgaa tttaccatgt attcagactg tatgaatttg    840
gataaaggaa ttttatactt tactacttac gataataacc aaattaatgc tgtggatatg    900
aataatgaag atttaggtac ttctgacttg atcacttatg aattatttaa ggatcaagcc    960
attaaatttg aaaattaa                                                  978
```

```
<210> SEQ ID NO 73
<211> LENGTH: 326
<212> TYPE: PRT
<213> ORGANISM: Lactobacillus johnsonii

<400> SEQUENCE: 73

Met Cys Thr Ser Ile Val Tyr Ser Ser Asn Asn His His Tyr Phe Gly
1               5                   10                  15

Arg Asn Leu Asp Leu Glu Ile Ser Phe Gly Glu His Pro Val Ile Thr
            20                  25                  30

Pro Arg Asn Tyr Glu Phe Gln Tyr Arg Lys Leu Pro Ser Lys Lys Ala
        35                  40                  45

Lys Tyr Ala Met Val Gly Met Ala Ile Val Glu Asn Asn Tyr Pro Leu
    50                  55                  60

Tyr Phe Asp Ala Ala Asn Glu Glu Gly Leu Gly Ile Ala Gly Leu Asn
65                  70                  75                  80

Phe Asp Gly Pro Cys His Tyr Phe Pro Glu Asn Ala Glu Lys Asn Asn
                85                  90                  95

Val Thr Pro Phe Glu Leu Ile Pro Tyr Leu Leu Ser Gln Cys Thr Thr
            100                 105                 110

Val Ala Glu Val Lys Asp Ala Leu Lys Asp Val Ser Leu Val Asn Ile
        115                 120                 125

Asn Phe Ser Glu Lys Leu Pro Leu Ser Pro Leu His Trp Leu Met Ala
        130                 135                 140

Asp Lys Thr Gly Glu Ser Ile Val Val Glu Ser Thr Leu Ser Gly Leu
145                 150                 155                 160

His Val Tyr Asp Asn Pro Val His Val Leu Thr Asn Asn Pro Glu Phe
                165                 170                 175

Pro Gly Gln Leu Arg Asn Leu Ala Asn Tyr Ser Asn Ile Ala Pro Ala
            180                 185                 190

Gln Pro Lys Asn Thr Leu Val Pro Gly Val Asp Leu Asn Leu Tyr Ser
        195                 200                 205

Arg Gly Leu Gly Thr His Phe Leu Pro Gly Gly Met Asp Ser Ala Ser
    210                 215                 220

Arg Phe Val Lys Ile Ala Phe Val Arg Ala His Ser Pro Gln Gly Asn
225                 230                 235                 240

Asn Glu Leu Ser Ser Val Thr Asn Tyr Phe His Ile Leu His Ser Val
                245                 250                 255

Glu Gln Pro Lys Gly Thr Asp Glu Val Gly Pro Asn Ser Tyr Glu Tyr
            260                 265                 270

Thr Ile Tyr Ser Asp Gly Thr Asn Leu Glu Thr Gly Thr Phe Tyr Tyr
        275                 280                 285

Thr Asn Tyr Glu Asn Asn Gln Ile Asn Ala Ile Glu Leu Asn Lys Glu
        290                 295                 300

Asn Leu Asn Gly Asp Glu Leu Thr Asp Tyr Lys Leu Ile Glu Lys Gln
305                 310                 315                 320

Thr Ile Asn Tyr Gln Asn
                325
```

<210> SEQ ID NO 74
<211> LENGTH: 981
<212> TYPE: DNA
<213> ORGANISM: Lactobacillus johnsonii

<400> SEQUENCE: 74
atgtgtacct caattgttta tagttcaaat aatcatcatt attttggccg aaatctagac      60
ttggaaattt cttttggtga acatcctgta attacaccaa ggaattatga gtttcaatat     120
cgtaaattac caagtaaaaa ggcaaaatat gccatggttg ggatggcgat tgtagaaaat     180
aattatccac tatattttga tgcagcaaat gaagaagggc taggaattgc tggccttaat     240
tttgatggtc cgtgtcatta ttttccagaa aatgcggaga aaaataatgt tacaccattt     300
gaattaattc cttatttgct aagtcaatgt actacggttg ctgaagtaaa agatgcattg     360
aaagatgtta gcttagtaaa tataaacttt tcagaaaaac taccactttc tccacttcac     420
tggttaatgg ctgataagac tggtgagtcg atcgttgtag aatcgacttt aagtggatta     480
cacgtttatg ataatccagt tcatgtttta accaataatc ctgaatttcc aggccagtta     540
cgtaacttag ctaattatag taatatagca cctgcacagc taaaaatac tcttgttcca      600 ggtgttgacc ttaatttata tagtcgcggg ttagggactc attttttgcc aggaggaatg     660
gattcggcca gtcgttttgt gaaaatagct tttgttcggg cacattcccc tcaaggaaat     720
aatgaattaa gtagtgtaac aaattatttc catattttac attcggttga acagccaaag     780
ggaacagatg aagtcggacc aaattcttat gagtacacaa tttactctga tggaactaac     840
ttggagacag gcacgtttta ttataccaat tatgaaaata atcaaattaa cgccattgaa     900
ttaaataaag aaaacttaaa tggtgatgag ttaacagatt acaagttgat tgaaaagcaa     960
acaattaatt atcaaaatta g                                              981

<210> SEQ ID NO 75
<211> LENGTH: 326
<212> TYPE: PRT
<213> ORGANISM: Lactobacillus johnsonii

<400> SEQUENCE: 75

Met Cys Thr Ser Ile Val Tyr Ser Ser Asn Asn His His Tyr Phe Gly
1               5                   10                  15

Arg Asn Leu Asp Leu Glu Ile Ser Phe Gly Glu His Pro Val Ile Thr
            20                  25                  30

Pro Arg Asn Tyr Glu Phe Gln Tyr Arg Lys Leu Pro Asn Lys Lys Ala
        35                  40                  45

Lys Tyr Ala Met Val Gly Met Ala Ile Val Glu Asp Asn Tyr Pro Leu
    50                  55                  60

Tyr Phe Asp Ala Ser Asn Glu Glu Gly Leu Gly Ile Ala Gly Leu Asn
65                  70                  75                  80

Phe Asp Gly Pro Cys His Tyr Phe Pro Glu Val Ser Gly Lys Asn Asn
                85                  90                  95

Val Thr Pro Phe Glu Leu Ile Pro Tyr Leu Leu Ser Gln Tyr Thr Thr
            100                 105                 110

Val Ala Glu Val Lys Glu Ala Leu Lys Ser Val Asn Leu Val Lys Ile
        115                 120                 125

Asn Phe Ser Glu Lys Leu Gln Leu Ser Pro Leu His Trp Leu Met Ala
    130                 135                 140

Asp Lys Thr Gly Glu Ser Ile Val Val Glu Ser Thr Leu Ser Gly Leu

```
             145                 150                 155                 160
His Val Tyr Asp Asn Pro Val His Val Leu Thr Asn Asn Pro Glu Phe
                165                 170                 175

Pro Gly Gln Leu Ser Asn Leu Ala Asn Tyr Ser Asn Ile Ala Pro Ser
            180                 185                 190

Gln Pro Lys Asn Thr Leu Val Pro Gly Val Asp Leu Asn Leu Tyr Ser
            195                 200                 205

Arg Gly Leu Gly Thr His Phe Leu Pro Gly Gly Met Asp Ser Ala Ser
        210                 215                 220

Arg Phe Val Lys Val Ala Phe Val Arg Ala His Ser Pro Gln Gly Asn
225                 230                 235                 240

Asn Glu Leu Ser Ser Val Thr Asn Tyr Phe His Ile Leu His Ser Val
                245                 250                 255

Glu Gln Pro Lys Gly Thr Asp Glu Val Gly Pro Asn Ser Tyr Glu Tyr
            260                 265                 270

Thr Ile Tyr Ser Asp Gly Thr Asn Leu Glu Thr Gly Thr Phe Tyr Tyr
            275                 280                 285

Thr Asn Tyr Glu Asn Asn Gln Ile Asn Ala Ile Glu Leu Asn Lys Glu
        290                 295                 300

Asn Leu Asn Gly Asp Glu Leu Ile Asp Tyr Lys Leu Ile Glu Lys Gln
305                 310                 315                 320

Thr Ile Asn Tyr Gln Asn
                325
```

<210> SEQ ID NO 76
<211> LENGTH: 981
<212> TYPE: DNA
<213> ORGANISM: Lactobacillus johnsonii

<400> SEQUENCE: 76

```
atgtgtacct caattgttta tagttcaaat aatcatcatt attttggccg aaatctagac      60
ttggaaattt catttggtga acatcctgta attacaccaa gaaattatga gtttcaatat     120
cgtaaattac caaataaaaa ggcaaaatat gccatggttg ggatggcgat tgtagaagat     180
aattatccat tatattttga tgcatcaaat gaagaagggc taggaattgc tggtcttaat     240
tttgatggac catgtcatta tttcccagaa gtgtctggaa aaaataatgt tacaccattt     300
gaattaattc cttatttgtt aagtcaatat actacagtgg ctgaagtaaa agaagcattg     360
aaaagtgtta acttagtaaa gataaacttt tcagaaaaac tccaactttc tccactgcat     420
tggttaatgg ctgataagac tggagagtca attgttgtag aatctacttt aagtggatta     480
cacgtttatg ataatccagt tcatgtttta accaataatc ctgaatttcc aggccagtta     540
agtaatttag ctaattatag caatatagca ccttcacagc ctaaaaatac tcttgttcca     600
ggtgttgacc ttaatttata tagtcgcggg ttagggactc attttttgcc aggaggaatg     660
gattcagcca gtcgttttgt gaaagtagct tttgttcgtg cacattctcc tcaagggaat     720
aatgaactaa gtagtgtaac aaattacttc catattctac attcagtcga acagccaaaa     780
ggaacagatg aagtaggacc aaattcttat gagtacacaa tttactctga tggaactaat     840
ttagagacag gaacatttta ttatacaaat tatgaaaata atcaaattaa cgccattgaa     900
ttaaataaag aaaacttaaa tggtgatgag ttaatagatt acaagttgat tgaaaagcaa     960
acaattaatt atcaaaatta g                                                981
```

<210> SEQ ID NO 77

<211> LENGTH: 325
<212> TYPE: PRT
<213> ORGANISM: Lactobacillus kalixensis

<400> SEQUENCE: 77

```
Met Cys Thr Ser Ile Ile Phe Ser Pro Lys Asp His Tyr Phe Gly Arg
1               5                   10                  15

Asn Leu Asp Leu Glu Leu Ser Phe Gly Gln Gln Val Val Ile Thr Pro
            20                  25                  30

Arg Asn Tyr Asp Phe Lys Phe Arg Lys Met Pro Glu Ile Lys Ser His
        35                  40                  45

Tyr Ala Met Val Gly Val Ser Leu Val Ala Glu Asn Tyr Pro Leu Tyr
    50                  55                  60

Phe Asp Ala Ala Asn Glu Lys Gly Leu Gly Met Ala Gly Leu Asn Tyr
65                  70                  75                  80

Pro Gly Asn Ala Asp Tyr Lys Asp Phe Asn Pro Glu Lys Asn Asn Val
            85                  90                  95

Ser Pro Phe Glu Phe Ile Pro Trp Val Leu Cys Gln Cys Ala Thr Val
        100                 105                 110

Ala Glu Ala Lys Asp Leu Leu Ala Asn Ile Asn Leu Val Asp Ile Asn
        115                 120                 125

Phe Ser Glu Gln Met Thr Leu Ser Thr Leu His Trp Leu Leu Ala Asp
    130                 135                 140

Lys Thr Gly Ser Ser Ile Val Val Glu Ser Asp Lys Asp Gly Leu His
145                 150                 155                 160

Ile Tyr Asp Asn Pro Val Gly Val Leu Thr Asn Asn Pro Gln Phe Pro
                165                 170                 175

Lys Gln Leu Phe Asn Leu Asn Asn Tyr Ser Asp Val Ser Ala Lys Met
            180                 185                 190

Pro Glu Asn Leu Phe Ser Ser Glu Val Ser Phe Asp Gly Tyr Ser Arg
            195                 200                 205

Gly Leu Gly Ser Arg Asn Leu Pro Gly Gly Ala Asp Ser Glu Ser Arg
    210                 215                 220

Phe Val Arg Ala Thr Phe Asn Lys Phe Asn Ala Pro Lys Thr Asp Asn
225                 230                 235                 240

Glu Gln Glu Asn Val Asp Thr Tyr Phe His Ile Leu His Ser Val Glu
                245                 250                 255

Gln Gln Arg Gly Val Asp Gln Val Gly Pro Asp Lys Phe Glu Tyr Thr
            260                 265                 270

Ile Tyr Ser Asp Gly Thr Asn Leu Glu Thr Gly Val Phe Tyr Tyr Thr
            275                 280                 285

Thr Tyr Thr Asn Lys Arg Ile Asn Lys Val Asp Met Asn His Glu Asp
    290                 295                 300

Leu Asp Ser Glu Lys Leu Ile Cys Tyr Pro Met Leu Asp Gln Ile Thr
305                 310                 315                 320

Phe Asn Glu Gln Asn
                325
```

<210> SEQ ID NO 78
<211> LENGTH: 978
<212> TYPE: DNA
<213> ORGANISM: Lactobacillus kalixensis

<400> SEQUENCE: 78
atgtgtactt caataatttt tagccctaaa gaccactatt ttggtcgaaa tcttgatctt          60

-continued

```
gagctttcct ttggtcagca agttgtaatt actccgcgta attatgattt taagttcaga    120
aagatgcctg aaatcaaaag tcactatgca atggtaggtg tttctttggt tgcagaaaac    180
tatccattat atttcgatgc cgctaatgaa aagggccttg gtatggcagg actcaactat    240
cctggaaatg cggattataa agacttcaac cctgaaaaaa acaacgtttc tccatttgag    300
tttattccat gggttctgtg tcaatgtgca acggttgccg aagctaaaga tttgcttgct    360
aatatcaatt tagttgatat taatttcagt gaacaaatga ctctttcgac ccttcactgg    420
ttacttgctg ataaaactgg tagttcaatt gtcgtcgagt cagataaaga cggtttacat    480
atttacgata tccagttgg tgtcttaacc aacaatccac aatttccaaa gcagttattc    540
aatttgaata actactcaga tgtttcagca aaaatgcctg aaaatttatt ttctagcgaa    600
gtttcctttg atggatatag tcgcggttta ggttcaagaa acttgcctgg tggtgctgat    660
tcagaatccc gctttgttag agcgactttt aacaagttta atgcgccaaa aactgataat    720
gaacaagaaa acgttgatac ttactttcat attttacact cagttgaaca gcaaaggggt    780
gtagaccaag tagggccaga taaatttgaa tacactatct attcagacgg taccaatctc    840
gaaactggtg ttttctacta cacaacttac actaataagc gcattaataa ggtcgatatg    900
aaccatgaag atttagattc ggaaaaatta atttgttatc caatgcttga tcaaattaca    960
tttaatgaac aaaactaa                                                  978
```

<210> SEQ ID NO 79
<211> LENGTH: 325
<212> TYPE: PRT
<213> ORGANISM: Lactobacillus kalixensis

<400> SEQUENCE: 79

```
Met Cys Thr Ser Ile Cys Tyr Thr Ser Thr Asp His Tyr Phe Gly Arg
1               5                   10                  15

Asn Leu Asp Tyr Glu Ile Asp Tyr Gly Gln Lys Val Ile Ile Val Pro
            20                  25                  30

Arg Asn Tyr Val Phe Asn Tyr Arg Asp Met Pro Ala Gln Lys Ser His
        35                  40                  45

Tyr Ala Phe Ile Gly Val Ser Val Val Asn Asp Asn Tyr Pro Leu Leu
    50                  55                  60

Cys Asp Ala Ile Asn Glu Lys Gly Leu Gly Ile Ala Gly Leu Asn Phe
65                  70                  75                  80

Gln Gly Pro Gly Tyr Tyr Phe Pro Gln Ile Lys Gly Lys Lys Asn Ile
                85                  90                  95

Ala Ser Phe Glu Leu Ile Pro Tyr Leu Leu Ser Asn Cys Glu Ser Thr
            100                 105                 110

Ala Glu Val Lys Glu Ile Leu Ala Asp Ala Ser Ile Ser Asn Val Ser
        115                 120                 125

Phe Ser Ser Asn Tyr Pro Ala Ala Asp Leu His Trp Ile Leu Ser Asp
    130                 135                 140

Lys Thr Gly Lys Ser Ile Val Val Glu Ser Thr Lys Ser Gly Leu His
145                 150                 155                 160

Val Tyr Asp Asn Pro Val Asn Val Leu Thr Asn Asn Pro Glu Phe Pro
                165                 170                 175

Ser Gln Leu Thr Lys Leu Ser Asp Tyr Val Asp Val Thr Pro Ser Asn
            180                 185                 190

Pro Lys Asn Thr Leu Val Pro Asn Val Asp Val Asn Ile Tyr Ser Arg
        195                 200                 205
```

-continued

```
Gly Leu Gly Thr His His Leu Pro Gly Gly Met Asp Ser Ser Ser Arg
    210             215                 220

Phe Val Lys Ala Ala Phe Val Leu Ser His Ala Pro Lys Gly Lys Asp
225             230                 235                 240

Glu Val Glu Asn Val Thr Asn Tyr Phe His Ile Leu His Ser Val Glu
            245                 250                 255

Gln Ala Lys Gly Leu Asp Glu Val Glu Asn Asn Arg Tyr Glu Tyr Thr
            260                 265                 270

Met Tyr Thr Asp Cys Met Asn Leu Asp Lys Gly Ile Leu Tyr Phe Thr
            275                 280                 285

Thr Tyr Asp Asn Asn Arg Ile Asn Ala Val Asp Met Tyr Lys Glu Asn
    290                 295                 300

Leu Asp Ala Glu Asp Leu Ile Cys Tyr Asp Leu Phe Lys Lys Gln Asp
305                 310                 315                 320

Ile Asn Tyr Ile Ser
            325
```

```
<210> SEQ ID NO 80
<211> LENGTH: 978
<212> TYPE: DNA
<213> ORGANISM: Lactobacillus kalixensis

<400> SEQUENCE: 80
atgtgtacat cgatttgtta tacttctacc gatcattatt ttggtcgcaa tcttgattat        60
gaaatcgatt atggtcaaaa ggtgattatc gtaccaagaa attacgtatt taactataga       120
gatatgcctg ctcaaaagtc tcattacgct ttcattggtg tttcagtagt taatgataat       180
tatccattat tgtgtgatgc aattaatgaa aagggattag gcatagcagg tttgaacttc       240
caaggaccgg gttactattt cccacaaatt aaaggtaaga agaacatagc ttctttttgaa       300 ttaataccat atttgttaag caattgtgaa agcactgcag aggttaaaga aattttttagct       360 gacgcaagta tttcaaatgt tagttttttct agcaactatc ctgctgcaga tttgcactgg       420
attcttagtg ataaaactgg taagagtatc gtagtagaat caactaaatc tggtttacat       480
gtttacgata tccagttaa tgtttttaacc aacaatccag aatttccaag tcaattaaca       540
aagttgagtg attacgttga tgtcactccg tctaatccta aaaatacatt agttccgaat       600
gttgatgtta atatttacag tagggggattg ggaactcatc acttaccagg tgggatggac       660
tcaagttcac gtttttgttaa agctgccttc gttttatcac atgcaccaaa ggggaaagac       720
gaagttgaaa atgttactaa ttacttccat atcttacatt ctgtagaaca agccaaaggc       780
ttagatgaag ttgaaaacaa tcgttatgaa tatacaatgt atactgactg catgaatttg       840 gacaaggggga ttttgtactt tactacttat gataataatc gtattaatgc ggtagacatg       900
tataaagaaa atctggatgc agaagatctg atttgttatg acttgttcaa aaagcaagac       960
atcaactata tttcttaa                                                     978
```

```
<210> SEQ ID NO 81
<211> LENGTH: 316
<212> TYPE: PRT
<213> ORGANISM: Lactobacillus kefiranofaciens

<400> SEQUENCE: 81

Met Cys Thr Gly Leu Arg Phe Thr Asp Asp Gln Gly Asn Leu Tyr Phe
1               5                   10                  15

Gly Arg Asn Leu Asp Val Ala Gln Asp Tyr Gly Glu Lys Val Ile Ile
            20                  25                  30
```

```
Thr Pro Arg Asn Tyr Pro Leu Pro Tyr Lys Phe Leu Gln Asp Thr Lys
        35                  40                  45

Thr Lys Lys Ala Val Ile Gly Met Gly Ile Val Val Asp Gly Tyr Pro
    50                  55                  60

Ser Tyr Phe Asp Cys Tyr Asn Glu Asp Gly Leu Gly Ile Ala Gly Leu
65                  70                  75                  80

Asn Phe Pro His Phe Ala Gln Phe Ser Ser Gly Pro Val Glu Gly Lys
                85                  90                  95

Thr Asn Leu Ala Ser Tyr Glu Ile Met Leu Trp Val Thr Glu Asn Phe
                100                 105                 110

Ser Thr Val Glu Glu Val Lys Lys Ala Leu Lys Asn Leu Asn Leu Val
                115                 120                 125

Asn Glu Ala Ile Asn Ser Ser Phe Pro Val Ala Pro Leu His Trp Ile
        130                 135                 140

Ile Ser Asp Gln Asn Glu Ala Ile Val Val Glu Asp Ser Lys Gln Tyr
145                 150                 155                 160

Gly Leu Lys Val Phe Glu Asp Lys Leu Gly Val Leu Thr Asn Ser Pro
                165                 170                 175

Asp Phe Asn Trp His Leu Thr Asn Leu Gly Asn Tyr Thr Gly Leu Asn
                180                 185                 190

Val His Asp Ala Ser Val Glu Asn Leu Asn Gly Gln Thr Val Thr Pro
        195                 200                 205

Leu Gly Val Gly Thr Gly Ser Leu Gly Leu Pro Gly Asp Ser Ile Pro
    210                 215                 220

Ala Asp Arg Phe Val Lys Ala Ala Tyr Leu Asn Ala Asn Tyr Pro Val
225                 230                 235                 240

Val Thr Gly Glu Lys Ala Asn Val Ala Lys Phe Phe Asn Ile Leu Lys
                245                 250                 255

Ser Ile Ala Met Ile Lys Gly Ser Ile Glu Asn Thr Asn Asp Gln Ala
                260                 265                 270

Glu Tyr Thr Val Tyr Thr Gly Cys Tyr Ser Ala Lys Thr Lys Thr Tyr
        275                 280                 285

Tyr Cys Asn Tyr Glu Asn Asp Phe Glu Leu Lys Lys Tyr Gln Leu Asp
        290                 295                 300

Glu Pro Lys Met Thr Ser Ser Asn Leu Thr Ile Gly
305                 310                 315
```

<210> SEQ ID NO 82
<211> LENGTH: 951
<212> TYPE: DNA
<213> ORGANISM: Lactobacillus kefiranofaciens

<400> SEQUENCE: 82

```
atgtgtacag gattaagatt tacagatgat caaggtaatc tatactttgg tcgcaactta        60
gatgtagcac aggattatgg tgaaaaagtt attattaccc ctagaaacta tcctttgccg       120
tataagtttt tgcaggatac gaagactaaa aaagctgtta ttgggatggg aatcgttgtt       180
gacggctatc catcatattt tgactgctat aacgaagacg gtttaggaat tgccggtttg       240
aatttccctc actttgcgca atttagctca ggcccagttg aagggaagac caacctggct       300
tcttatgaaa tcatgctctg ggtaaccgaa aacttttcaa ccgttgagga agttaaaaaa       360
gctttgaaga atttaaactt agtcaacgaa gcaattaatt cttcatttcc agttgctccg       420
cttcattgga tcattagtga ccaaaatgaa gcaattgtgg tagaagactc aaaacaatat       480
```

-continued

```
ggtttgaaag tctttgaaga taagttaggt gttttaacta atagtcctga tttcaattgg      540
catttgacca atttaggcaa ttacactggc ttaaatgttc atgatgccag tgttgaaaat      600
ttaaatggtc aaactgtgac acctttgggc gttggcactg gcagcttagg tctacctggt      660
gatagtattc ctgccgaccg tttttgttaag gcagcatacc tcaatgctaa ctatccagta     720
gtaactggtg aaaaagctaa tgtcgctaag ttttttaata ttttaaaatc catagcaatg      780
atcaaaggca gcattgaaaa caccaatgat caagctgaat acactgttta taccggctgc      840
tattcagcta agacaaagac ctattactgc aattatgaaa atgattttga actcaaaaag      900
tatcaacttg atgagccaaa aatgacttct tcaaatttaa ctatcggtta a               951
```

```
<210> SEQ ID NO 83
<211> LENGTH: 326
<212> TYPE: PRT
<213> ORGANISM: Lactobacillus mucosae

<400> SEQUENCE: 83

Met Cys Thr Ala Ala Thr Tyr Thr Ala Gly Asp His Tyr Phe Gly Arg
1               5                   10                  15

Asn Leu Asp Leu Glu Leu Ser Tyr Gly Glu Lys Val Thr Ile Thr Pro
                20                  25                  30

Arg Asn Phe Pro Leu Thr Phe Arg Lys Met Pro Thr Leu Glu His His
            35                  40                  45

Tyr Ala Leu Ile Gly Met Ala Thr Thr Val Asp Asn Tyr Pro Leu Tyr
        50                  55                  60

Phe Asp Ala Thr Asn Glu Lys Gly Leu Ser Met Ala Gly Leu Asn Tyr
65                  70                  75                  80

Pro Gly Asn Ala Asp Tyr Lys Pro Tyr Ala Glu Gly Lys Asp Asn Val
                85                  90                  95

Ser Pro Phe Glu Phe Val Ser Trp Ile Leu Gly Gln Cys Ala Thr Leu
            100                 105                 110

Ala Glu Ala Lys Val Leu Leu Asp Lys Ile Asn Leu Val Lys Ile Asp
        115                 120                 125

Phe Ser Glu Gln Leu Pro Leu Ser Pro Leu His Trp Leu Met Ala Glu
    130                 135                 140

Thr Ala Ser Glu Lys Thr Leu Thr Ile Glu Cys Asp Arg Asp Gly Leu
145                 150                 155                 160

His Val Tyr Asp Asn Pro Val Gly Val Leu Thr Asn Asn Pro Gln Phe
                165                 170                 175

Asp Lys Gln Leu Phe Asn Leu Asn Asn Tyr Gln Phe Leu Ser Pro Gln
            180                 185                 190

Gln Pro Glu Asn Lys Phe Ser Gln Asp Leu Glu Leu Asp Asn Tyr Ser
        195                 200                 205

Arg Gly Leu Gly Thr Arg Gly Leu Pro Gly Gly Met Asp Ser Met Ser
        210                 215                 220

Arg Phe Val Lys Val Ala Phe Thr Lys Leu Asn Ala Pro Lys Gly Glu
225                 230                 235                 240

Thr Glu Asn Glu Asn Val Gly Asn Phe Phe His Ile Leu His Ser Val
                245                 250                 255

Glu Gln Gln Lys Asn Leu Asp Gly Val Glu Asn Asn Gln Phe Glu Phe
            260                 265                 270

Thr Ile Tyr Ser Ser Cys Val Asn Ala Asp Arg Gly Ile Tyr Tyr Tyr
        275                 280                 285

Thr Thr Tyr Asp Asn Asn Gln Ile Asn Ala Val Asp Met His Lys Val
```

-continued

```
                290                 295                 300
Asp Leu Asp Gly Arg Glu Leu Ile Asp Tyr Asp Leu Ala Asn Glu Gln
305                 310                 315                 320

Asn Ile Asn Trp Gln Asn
                325

<210> SEQ ID NO 84
<211> LENGTH: 981
<212> TYPE: DNA
<213> ORGANISM: Lactobacillus mucosae

<400> SEQUENCE: 84
atgtgtactg cagcaaccta tactgctggt gaccactatt ttggtcggaa tttggatttg      60
gaactgtctt atggtgaaaa ggttacgatc acgccacgca attttccgct gaccttccgc     120
aagatgccaa ctcttgaaca tcactatgct ttgatcggta tggcaacgac ggtcgacaat     180
tatccgcttt attttgacgc taccaatgaa aaagggttaa gcatggctgg cttgaactac     240
ccaggcaacg ccgactacaa gccatacgca gaaggcaagg acaacgtatc gccatttgag     300
ttcgtatcat ggattctggg ccaatgcgca acactggccg aagctaaggt tttgttagac     360
aagatcaacc tggttaagat cgactttagc gaacagctgc cgctttcacc gctgcactgg     420
ctgatggctg aaacggcatc tgaaaagact ttaacgattg aatgtgatcg tgatggtctg     480
cacgtttatg acaatccagt tggcgtcttg accaacaatc ctcaatttga taagcagctg     540
ttcaacttga acaactacca gttcttaagt cctcagcagc cagaaaacaa gttcagccaa     600
gaccttgagc tcgacaacta cagccgtggt ctgggaacgc ggggcctgcc tggcgggatg     660
gattcaatgt cgcgctttgt caaggttgcc tttaccaagc ttaacgcgcc taagggagaa     720
accgaaaatg aaaacgtcgg taacttcttc cacattctgc actcggttga acagcaaaag     780
aacctggatg gcgtcgagaa taatcaattt gaatttacga tctattcatc atgtgtcaac     840
gccgaccgcg gtatctacta ctacaccacc tacgacaaca atcagatcaa tgccgttgac     900
atgcacaagg ttgacttgga tggccgggaa ttgattgatt atgatctggc aaacgaacaa     960
aacatcaact ggcaaaacta a                                             981

<210> SEQ ID NO 85
<211> LENGTH: 325
<212> TYPE: PRT
<213> ORGANISM: Lactobacillus murinus

<400> SEQUENCE: 85

Met Cys Thr Ala Val Ser Phe Lys Thr Lys Asp His Tyr Leu Gly Arg
1                 5                  10                  15

Asn Phe Asp Tyr Glu Phe Ser Tyr Gly Glu Lys Ala Val Ile Ile Pro
                20                  25                  30

Arg Asn Tyr Val Phe Glu Leu Arg Lys Leu Pro Ala Leu Ser Lys His
            35                  40                  45

Tyr Ala Met Val Gly Leu Thr Ser Val Phe Asp Asp Thr Pro Leu Leu
        50                  55                  60

Tyr Asp Ala Val Asn Glu His Gly Leu Ala Met Ala Gly Leu Asn Phe
65                  70                  75                  80

Glu Gly Asn Ala Val Phe Tyr Asp Phe Asp Pro Glu Met Asp Asn Val
                85                  90                  95

Thr Pro Phe Glu Phe Ile Pro Tyr Ile Leu Gly Gln Cys Lys Asn Val
                100                 105                 110
```

-continued

```
Ala Glu Ala Lys Gln Met Leu Thr Lys Ile Asn Leu Val Asn Glu Ala
        115                 120                 125

Phe Arg Ala Asp Leu Pro Leu Ser Pro Leu His Trp Ile Ile Ser Asp
        130                 135                 140

Ser Glu Asp Asn Thr Ile Val Val Glu Asn Leu Ala Asp Gly Met Lys
145                 150                 155                 160

Val Tyr Asp Asp Pro Val Gly Val Met Thr Asn Asn Pro Thr Phe Asp
                165                 170                 175

Lys Gln Leu Phe Asn Leu Asn Asn Tyr Arg Gly Leu Ser Ala Lys Thr
                180                 185                 190

Pro Glu Asn Thr Phe Ala Pro Thr Val Glu Leu Pro Ala Tyr Ser Arg
                195                 200                 205

Gly Met Gly Thr Leu Gly Leu Pro Gly Asp Leu Thr Ser Ser Ser Arg
        210                 215                 220

Phe Val Lys Ala Ala Phe Val Lys Ala His Ser Val Cys Glu Pro Asp
225                 230                 235                 240

Glu Ser Ser Ser Val Ser Gln Val Phe His Ile Leu Ser Ala Ile Glu
                245                 250                 255

Gln Gln Arg Gly Cys Cys Glu Val Ser Glu Gly Lys Tyr Glu Tyr Thr
                260                 265                 270

Ile Tyr Ser Ala Cys Tyr Asn Lys Asp Lys Gly Ile Leu Tyr Tyr Lys
                275                 280                 285

Thr Tyr Glu Asp Ser Gln Ile Thr Ala Leu Asp Met His Lys Ala Asp
        290                 295                 300

Leu Glu Ser Asp Arg Phe Thr Leu Tyr Pro Leu Ser Gln Thr Gln His
305                 310                 315                 320

Phe Asn Tyr Ala Asn
                325
```

<210> SEQ ID NO 86
<211> LENGTH: 978
<212> TYPE: DNA
<213> ORGANISM: Lactobacillus murinus

<400> SEQUENCE: 86

```
atgtgtactg cagtatcatt taaaacaaag gatcactatt tggggagaaa ttttgactat      60
gagttctctt atggtgaaaa agctgttatt atcccacgga attatgtttt tgaattgcga     120
aaattaccgg ctttgagcaa acactatgcc atggtcggct tgacgtctgt ttttgacgac     180
acgcctcttc tttatgatgc tgtcaacgag catggcttag cgatggcggg cttgaacttt     240
gaaggcaatg ccgttttta tgactttgat cctgagatgg ataatgtgac accatttgaa     300
tttatcccat atattttagg tcaatgtaaa aatgtggctg aagctaagca aatgttgact     360
aagatcaact tggtcaatga agcatttagg gctgatctac ctttatctcc attgcactgg     420
atcatcagtg acagtgaaga taatacgatc gtggtcgaaa atttggctga tgggatgaaa     480
gtatacgatg atcccgttgg tgtgatgacc aataatccaa catttgataa gcaactcttt     540
aatttgaaca attaccgagg cttatcggct aaaacacctg aaaatacttt tgctccgacg     600
gtcgagctac cagcatacag tcggggatg ggaactttag tcttccagg cgacctgact     660 tcgagctcac gttttgtcaa agcagctttt gttaaagcac attcggtttg tgaaccagat     720
gaaagttcca cgtcagcca gttttccat atcttaagtg cgatcgaaca caacgaggc     780 tgttgtgaag tgagcgaagg aaagtatgaa tatacgatct attctgcttg ttataacaaa     840
gataaaggga tcttatatta taagacgtat gaagatagtc agatcacagc tttagatatg     900
```

-continued cacaaagctg atttagaaag tgatcgtttc acccttttatc ctttgagtca aacacaacat        960
ttcaattacg ctaactaa                                                       978

<210> SEQ ID NO 87
<211> LENGTH: 325
<212> TYPE: PRT
<213> ORGANISM: Lactobacillus oris

<400> SEQUENCE: 87

Met Cys Thr Ser Ile Leu Tyr Asn Ala Gly Asp His Tyr Phe Gly Arg
1               5                   10                  15

Asn Leu Asp Leu Glu Ile Ser Phe Gly Gln Glu Val Val Val Thr Pro
            20                  25                  30

Arg Asp Tyr Gln Phe Asp Phe Arg Gln Ile Pro Ala Leu Ser His His
        35                  40                  45

Tyr Ala Ile Ile Gly Met Ala Leu Val Lys Asp Asn Tyr Pro Leu Tyr
    50                  55                  60

Phe Asp Gly Ala Asn Glu Glu Gly Leu Gly Met Ala Gly Leu Asn Phe
65                  70                  75                  80

Asp Gly Pro Ala His Tyr Phe Pro Val Glu Glu Gly Lys Asp Asn Val
                85                  90                  95

Ser Pro Phe Glu Phe Ile Pro Tyr Val Leu Gly Gln Cys Lys Asn Val
            100                 105                 110

Asn Glu Ala Lys Glu Leu Met Lys Asn Met Ser Leu Val Asn Ile Asn
        115                 120                 125

Phe Ser Asp Gln Leu Gln Leu Ser Pro Leu His Trp Leu Ile Ala Asp
    130                 135                 140

Arg Ser Gly Lys Ser Ile Val Val Glu Ser Thr Glu Ser Gly Leu His
145                 150                 155                 160

Val Tyr Asp Asn Pro Val Asn Val Leu Thr Asn Asn Pro Glu Phe Pro
                165                 170                 175

Glu His Met Thr Asn Leu Ala Asn Tyr Gln Ser Val Ser Pro Ala Glu
            180                 185                 190

Pro Ala Asn Gln Leu Ala Pro Asn Val Asp Leu Gly Thr Tyr Ser Arg
        195                 200                 205

Gly Leu Gly Ser His Met Leu Pro Gly Gly Met Asp Ser Glu Ser Arg
    210                 215                 220

Phe Val Lys Glu Val Phe Thr Leu Gln His Ala Pro Ser Gly Lys Ser
225                 230                 235                 240

Glu Leu Glu Asn Val Thr Asn Tyr Phe His Cys Leu His Ala Val Glu
                245                 250                 255

Gln Gln Asp Gly Leu Asp Glu Val Ala Pro Gly Gln Phe Glu Tyr Thr
            260                 265                 270

Ile Tyr Ser Asp Gly Ile Asn Leu Ser Thr Gly Ser Tyr Tyr Tyr Thr
        275                 280                 285

Thr Tyr Gln Asn Asn Gln Ile Asn Ala Val Gln Met Arg His Val Asn
    290                 295                 300

Leu Asn Ser Gln Asp Leu Ala Leu Phe Pro Leu Gln Thr Glu Gln Val
305                 310                 315                 320

Leu His Phe Gln Asn
                325

<210> SEQ ID NO 88
<211> LENGTH: 978

<212> TYPE: DNA
<213> ORGANISM: Lactobacillus oris

<400> SEQUENCE: 88

```
atgtgtactt caattttata taacgctggg gatcattatt tcggtcgaaa ccttgatcta      60
gaaatttcgt ttggtcaaga ggtggtggta acgccacggg actaccaatt tgactttcgg     120
cagataccag cactgagcca ccactacgca attatcggga tggccctagt gaaggataac     180
tatccattat attttgatgg ggccaacgaa gagggactgg ggatggccgg cctgaacttt     240
gatggtcctg cccactactt cccggttgag gaaggaaaag ataacgtttc accatttgag     300
tttattccgt acgtgctggg gcaatgcaag aacgttaatg aagccaagga acttatgaag     360
aacatgagcc ttgtcaacat caatttctct gaccaattgc agttatcacc gctgcactgg     420
ctgattgctg accggtcagg gaagtcaatc gtggtcgaat caactgaaag cggcctgcac     480
gtttatgaca acccggttaa cgttttgacc aataatccgg aattcccaga acacatgacg     540
aacctggcta attaccaaag tgtttcgcca gccgaaccag ctaatcagct agcaccgaac     600
gtcgatctag gcacgtacag ccggggcctt ggttctcaca tgctgcctgg ggggatggac     660
tccgagagtc gctttgttaa ggaagtcttt actttgcagc acgctccatc aggaaagagt     720
gagctggaaa acgttactaa ctacttccac tgtctccacg ccgtcgaaca acaggatggt     780
ttggacgagg ttgctccggg acaatttgaa tacaccattt actcagatgg tatcaacctg     840
tcgacgggga gctactacta cacaacctac caaaacaacc aaattaacgc ggttcaaatg     900
cgccatgtta acttgaatag ccaggatctt gcgctgttcc cattgcaaac ggagcaagtg     960
ctgcatttcc aaaactaa                                                    978
```

<210> SEQ ID NO 89
<211> LENGTH: 325
<212> TYPE: PRT
<213> ORGANISM: Lactobacillus oris

<400> SEQUENCE: 89

```
Met Cys Thr Ser Ile Leu Tyr Asn Ala Gly Asp His Tyr Phe Gly Arg
1               5                   10                  15

Asn Leu Asp Leu Glu Val Ser Phe Gly Gln Glu Val Val Val Thr Pro
                20                  25                  30

Arg Asn Tyr Gln Phe Asn Phe Arg Arg Val Pro Ser Met Gly His His
            35                  40                  45

Tyr Ala Ile Ile Gly Met Ala Leu Val Lys Asp Asn Tyr Pro Leu Tyr
        50                  55                  60

Phe Asp Gly Ala Asn Glu Glu Gly Leu Gly Met Ala Gly Leu Asn Phe
65                  70                  75                  80

Asp Gly Pro Ala His Tyr Phe Pro Leu Glu Glu Gly Lys Asp Asn Val
                85                  90                  95

Ser Pro Phe Glu Leu Ile Pro Tyr Ile Leu Gly Gln Cys Lys Asn Val
                100                 105                 110

Ala Glu Ala Arg Glu Leu Leu Lys Lys Leu Asn Leu Val Asn Ile Asn
            115                 120                 125

Phe Ser Asp Gln Leu Gln Leu Ser Pro Leu His Trp Leu Ile Ala Asp
        130                 135                 140

Arg Ser Gly Lys Ser Ile Val Val Glu Ser Thr Val Thr Gly Leu His
145                 150                 155                 160

Val Tyr Asp Asn Pro Val Asn Val Leu Thr Asn Asn Pro Glu Phe Pro
                165                 170                 175
```

-continued

```
Gly Gln Leu Thr Asn Leu Ala Asn Tyr Gln Gly Ile Ser Pro Thr Thr
            180                 185                 190

Pro Pro Asn Gln Leu Ala Pro Asp Val Asn Leu Ala Ala Tyr Ser Arg
            195                 200                 205

Gly Leu Gly Ser His Met Leu Pro Gly Gly Met Asp Ser Ala Ser Arg
            210                 215                 220

Phe Val Lys Glu Val Phe Thr Leu His His Ala Pro Thr Gly Lys Asn
225                 230                 235                 240

Glu Leu Glu Asn Val Thr Asn Tyr Phe His Cys Leu His Ala Val Glu
                245                 250                 255

Gln Gln Glu Gly Leu Asp Glu Val Val Pro Gly Lys Phe Glu Ala Thr
            260                 265                 270

Ile Tyr Ser Asp Gly Ile Asn Leu Ser Thr Gly Thr Phe Tyr Tyr Thr
            275                 280                 285

Thr Tyr Gln Asn Asn Gln Ile Asn Ala Val Gln Leu His His Thr Asp
            290                 295                 300

Leu Asn Arg Gln Glu Leu Ala Leu Phe Pro Leu Gln Thr Glu Gln Val
305                 310                 315                 320

Leu His Phe Gln Asn
                325
```

```
<210> SEQ ID NO 90
<211> LENGTH: 978
<212> TYPE: DNA
<213> ORGANISM: Lactobacillus oris

<400> SEQUENCE: 90
atgtgcactt caattttata caatgcgggt gaccactact ttgggcgaaa tctggactta      60
gaagtttcgt ttggtcagga agtagtggtg acgccgcgga actaccaatt caactttcgg     120
cgggtgccgt caatgggtca ccactatgcg atcattggga tggccctggt gaaggataac     180
tatccattat actttgatgg ggccaacgaa gagggactgg ggatggccgg cctgaacttc     240
gacggaccgg cccactactt cccgttggaa gagggcaagg acaacgtttc accctttgaa     300
cttatcccgt acatcctggg acagtgtaag aatgttgccg aagccaggga gctcttaaag     360
aagctcaacc tcgtcaacat caacttctct gaccagttgc aactgtcacc actgcactgg     420
ctgattgctg atcggtctgg aaagtccatt gtggttgaat caacggttac cggcctgcac     480
gtctatgata atccggtcaa tgttttgact aataatccag aatttcctgg ccagctgact     540
aacctggcta attatcaggg aatatcccca acaactccac ccaaccagct ggcaccggac     600
gtgaacctgg cggcatatag tcggggcctt ggctcccata tgctgccagg cgggatggac     660
tccgcgagcc ggttcgttaa ggaagttttt accctgcacc acgctccaac aggcaaaaac     720
gagctggaga acgttactaa ctatttccat tgcctgcacg ccgttgagca gcaggaaggg     780
ttagacgaag tggtacccgg aaagtttgaa gccaccatct actcggatgg gattaattta     840
tcaaccggga ctttctatta cacaacctac cagaataacc aaattaatgc ggttcagttg     900
caccacacag atctgaatcg ccaggagtta gcgctgttcc cattgcaaac ggagcaagtg     960
ctgcatttcc aaaactaa                                                    978
```

```
<210> SEQ ID NO 91
<211> LENGTH: 325
<212> TYPE: PRT
<213> ORGANISM: Lactobacillus panis
```

```
<400> SEQUENCE: 91

Met Cys Thr Ser Ile Leu Tyr Thr Ala Gly Asp His Tyr Phe Gly Arg
1               5                   10                  15

Asn Leu Asp Leu Glu Val Ser Phe Gly Gln Glu Val Val Val Thr Pro
            20                  25                  30

Arg Asp Tyr Pro Phe Asp Phe Arg Lys Met Pro Thr Leu Asn His His
        35                  40                  45

Tyr Ala Ile Ile Gly Met Ala Leu Val Lys Asp Asn Tyr Pro Leu Tyr
    50                  55                  60

Phe Asp Gly Ala Asn Glu Glu Gly Leu Gly Met Ala Gly Leu Asn Phe
65                  70                  75                  80

Ala Gly Leu Ala His Phe Ser Pro Val Glu Asp Gly Lys Asp Asn Val
                85                  90                  95

Ser Pro Phe Glu Phe Ile Pro Tyr Val Leu Gly Gln Cys Lys Asp Val
            100                 105                 110

Ala Glu Ala Lys Lys Leu Leu Thr Asn Leu Asn Leu Val Asn Ile Asn
            115                 120                 125

Phe Ser Asp Gln Leu Gln Leu Ser Pro Leu His Trp Leu Ile Ala Asp
    130                 135                 140

Arg Gln Gly Ala Ser Ile Val Val Glu Ser Thr Gln Ser Gly Leu His
145                 150                 155                 160

Val Tyr Asp Asn Pro Val Gly Val Leu Thr Asn Asn Pro Glu Phe Pro
                165                 170                 175

Ser Gln Met Thr Asn Leu Ala Asn Tyr Gln Ser Val Ser Pro Ala Asp
            180                 185                 190

Pro Val Asn Thr Leu Met Pro Lys Lys Glu Leu Lys Thr Tyr Ser Arg
            195                 200                 205

Gly Leu Gly Ser His Met Leu Pro Gly Gly Met Asp Ser Glu Ser Arg
    210                 215                 220

Phe Val Lys Glu Cys Phe Thr Leu His Asn Ala Pro Ala Gly Gly Ser
225                 230                 235                 240

Glu Leu Glu Asn Val Thr Asn Tyr Phe His Cys Leu His Ala Val Glu
                245                 250                 255

Gln Gln Lys Gly Leu Asp Glu Val Ala Pro Asp Thr Phe Glu Tyr Thr
            260                 265                 270

Ile Tyr Ser Asp Gly Ile Asn Leu Ala Thr Gly Thr Phe Tyr Tyr Thr
        275                 280                 285

Thr Tyr Glu Asn Asn Gln Ile Asn Ala Val Gln Met His Asn Val Asp
    290                 295                 300

Leu Asp Ala Lys Lys Leu Ala Gln Phe Pro Leu Val Lys Glu Gln Val
305                 310                 315                 320

Ile Asn Asn Gln Asn
                325

<210> SEQ ID NO 92
<211> LENGTH: 978
<212> TYPE: DNA
<213> ORGANISM: Lactobacillus panis

<400> SEQUENCE: 92
atgtgtacat cgattctcta tactgctggc gaccattact ttggccgtaa cctagatttg      60
gaagtctcat ttggtcaaga ggtggttgtc accccgcgcg actacccgtt tgattttcgc     120
aagatgccaa ccttaaacca ccactacgcc attatcggga tggccctcgt caaggataac     180
```

```
tacccattgt actttgacgg tgccaatgaa gaagggcttg ggatggccgg actaaacttt      240
gctgggctgg cccacttctc cccagttgaa gatggcaagg ataatgtttc accattcgaa      300
tttattccct atgttttggg tcaatgtaaa gacgttgccg aggcgaagaa actacttacc      360
aacctcaacc tggtaaacat caacttctct gaccaactcc agctttcccc acttcattgg      420
ttgattgctg accgacaggg agcatcgatt gttgttgaat ctactcagag cggtctccac      480
gtttacgata tccagtgggg tgtcttgacc aataaccccg agttcccatc ccagatgacg      540
aacctggcaa attaccagag tgtttcaccc gctgacccgg ttaacacctt gatgccaaag      600
aaggaactca agacatacag ccgggggcctg ggctcccaca tgctgccagg agggatggat      660
tccgaaagtc gttttgtaaa ggaatgcttt accctgcaca atgcaccagc gggtggtagc      720
gagctggaga atgttaccaa ctacttccac tgcctacatg cagttgaaca gcagaaggga      780
ctcgatgagg ttgcaccgga tacttttgaa tacacaatct actccgatgg aatcaacctg      840
gctacgggga ccttctatta cacaacctac gaaaataacc agatcaatgc tgttcagatg      900
cacaatgttg atttagacgc caagaaactt gcccagttcc cattagttaa ggaacaagtc      960
atcaataacc aaaactaa                                                    978
```

```
<210> SEQ ID NO 93
<211> LENGTH: 324
<212> TYPE: PRT
<213> ORGANISM: Lactobacillus plantarum

<400> SEQUENCE: 93

Met Cys Thr Ala Ile Thr Tyr Gln Ser Tyr Asn Asn Tyr Phe Gly Arg
1               5                   10                  15

Asn Phe Asp Tyr Glu Ile Ser Tyr Asn Glu Met Val Thr Ile Thr Pro
                20                  25                  30

Arg Lys Tyr Pro Leu Val Phe Arg Lys Val Glu Asn Leu Asp His His
            35                  40                  45

Tyr Ala Ile Ile Gly Ile Thr Ala Asp Val Glu Ser Tyr Pro Leu Tyr
        50                  55                  60

Tyr Asp Ala Met Asn Glu Lys Gly Leu Cys Ile Ala Gly Leu Asn Phe
65                  70                  75                  80

Ala Gly Tyr Ala Asp Tyr Lys Lys Tyr Asp Ala Asp Lys Val Asn Ile
                85                  90                  95

Thr Pro Phe Glu Leu Ile Pro Trp Leu Leu Gly Gln Phe Ser Ser Val
            100                 105                 110

Arg Glu Val Lys Lys Asn Ile Gln Lys Leu Asn Leu Ile Asn Ile Asn
        115                 120                 125

Phe Ser Glu Gln Leu Pro Leu Ser Pro Leu His Trp Leu Val Ala Asp
    130                 135                 140

Lys Gln Glu Ser Ile Val Ile Glu Ser Val Lys Glu Gly Leu Lys Ile
145                 150                 155                 160

Tyr Asp Asn Pro Val Gly Val Leu Thr Asn Asn Pro Asn Phe Asp Tyr
                165                 170                 175

Gln Leu Phe Asn Leu Asn Asn Tyr Arg Ala Leu Ser Asn Ser Thr Pro
            180                 185                 190

Gln Asn Ser Phe Ser Glu Lys Val Asp Leu Asp Ser Tyr Ser Arg Gly
        195                 200                 205

Met Gly Gly Leu Gly Leu Pro Gly Asp Leu Ser Ser Met Ser Arg Phe
    210                 215                 220

Val Arg Ala Ala Phe Thr Lys Leu Asn Ser Leu Pro Met Gln Thr Glu
```

```
225                 230                 235                 240

Thr Gly Ser Val Ser Gln Phe Phe His Ile Leu Gly Ser Val Glu Gln
                245                 250                 255

Gln Lys Gly Leu Cys Glu Val Thr Lys Gly Lys Tyr Glu Tyr Thr Ile
            260                 265                 270

Tyr Ser Ser Cys Cys Asp Met Asp Lys Gly Val Tyr Tyr Tyr Arg Thr
            275                 280                 285

Tyr Asn Asn Ser Gln Ile Asn Ser Val Asn Leu Ser His Glu His Leu
    290                 295                 300

Asp Thr Thr Glu Leu Ile Ser Tyr Pro Leu Arg Ser Glu Ala Gln Tyr
305                 310                 315                 320

Tyr Ala Val Asn
```

```
<210> SEQ ID NO 94
<211> LENGTH: 975
<212> TYPE: DNA
<213> ORGANISM: Lactobacillus plantarum

<400> SEQUENCE: 94
atgtgtactg ccataactta tcaatcttat aataattact tcggtagaaa tttcgattat      60
gaaatttcat acaatgaaat ggttacgatt acgcctagaa aatatccact agtatttcgt     120
aaggtggaga acttagatca ccattatgca ataattggaa ttactgctga tgtagaaagc     180
tacccacttt actacgatgc gatgaatgaa aaaggattgt gtattgcggg attgaatttt     240
gcaggttatg ctgattataa aaaatatgat gctgataaag ttaatatcac accatttgaa     300
ttaattcctt ggttattggg acaattttca agtgttagag aagtgaaaaa gaacatacaa     360
aaactaaact tgattaatat taattttagt gaacaattac cattatcacc gctacattgg     420
ttggttgctg ataaacagga atcgatagtt attgaaagtg ttaagaagg actaaaaatt     480 tacgacaatc cagtaggtgt gttaacaaac aatcctaatt ttgactacca attatttaat     540
ttgaacaact atcgtgcgtt atcaaatagc acgccccaaa atagtttttc agaaaaagtg     600
gatttagata gttatagtag aggaatgggc ggactaggat tacctggaga cttgtcctca     660
atgtctagat ttgttagagc cgcttttact aaattaaact cgttgccgat gcagacagag     720
actggcagtg ttagtcagtt tttccatata ctagggtctg tagaacaaca aaaagggctt     780
tgtgaagtca ctaaaggaaa gtacgaatat acaatctatt cttcttgttg tgatatggac     840
aagggagttt attactatag aacttataac aatagtcaaa ttaacagtgt caatttaagc     900
catgagcact ggatacgac tgaattaatt tcttatccat tacgatcaga agcacagtac     960
tatgcagtta actaa                                                     975
```

```
<210> SEQ ID NO 95
<211> LENGTH: 325
<212> TYPE: PRT
<213> ORGANISM: Lactobacillus rogosae

<400> SEQUENCE: 95

Met Cys Thr Ala Val Thr Tyr Lys Thr Lys Asp Phe Tyr Phe Gly Arg
1               5                   10                  15

Thr Leu Asp Tyr Glu Phe Ser Tyr Gly Glu Glu Ile Thr Val Thr Pro
                20                  25                  30

Arg Asn Tyr Ile Phe Asp Phe Arg His Ile Gly Gln Leu Lys Ser His
            35                  40                  45

Tyr Ala Ile Ile Gly Met Ala Phe Val Ser Glu Gly Tyr Pro Leu Tyr
```

```
      50              55              60
Tyr Asp Ala Val Asn Glu Lys Gly Leu Gly Met Ala Gly Leu Asn Phe
65              70              75              80

Val Gly Asn Ala Ala Tyr Lys Ala Ser Val Cys Gly Glu Lys Asp Ile
            85              90              95

Ala Gln Phe Glu Phe Ile Pro Trp Ile Leu Ser Gln Cys Ala Thr Val
            100             105             110

Ser Glu Ala Arg Ala Lys Leu Asp Gly Ile Asn Leu Thr Gly Thr Pro
        115             120             125

Phe Ser Ser Gln Leu Pro Ala Ala Gln Leu His Trp Ile Ile Ala Asp
        130             135             140

Lys Asp Glu Ala Ile Thr Val Glu Ser Met Lys Asp Gly Leu His Ile
145             150             155             160

Tyr Asp Asn Pro Val Gly Val Leu Thr Asn Asn Pro Pro Phe Asp Met
            165             170             175

Gln Met Phe Ala Leu Asn Asn Tyr Ala Gly Leu Ser Ser Arg Gln Pro
            180             185             190

Asp Asn Thr Phe Ala Asp Lys Leu Lys Leu Asn Ala Tyr Ser Arg Gly
        195             200             205

Met Gly Ala Met Gly Leu Pro Gly Asp Leu Ser Ser Gln Ser Arg Phe
        210             215             220

Ile Arg Ala Ala Phe Thr Arg Leu Asn Ala Ile Ser Ser Asp Thr Glu
225             230             235             240

Glu Glu Ser Val Ser Gln Phe Phe His Ile Leu Gly Ser Val Glu Gln
            245             250             255

Gln Arg Gly Cys Cys Glu Val Thr Asp Gly Lys Tyr Glu Ile Thr Ile
            260             265             270

Tyr Thr Ser Cys Cys Asn Ala Ala Lys Gly Ile Tyr Tyr Tyr Thr Thr
            275             280             285

Tyr Asp Asn His Gln Ile Thr Ala Val Asp Met His Lys Glu Asn Leu
        290             295             300

Asp Gly Thr Glu Leu Ile Arg Tyr Pro Ile Ile Thr Lys Gly Glu Val
305             310             315             320

Arg Trp Gln Asn Arg
            325
```

<210> SEQ ID NO 96
<211> LENGTH: 978
<212> TYPE: DNA
<213> ORGANISM: Lactobacillus rogosae

<400> SEQUENCE: 96

```
atgtgtacag cagttactta taagactaaa gatttctatt ttggaagaac tcttgattat      60
gagttctcat atggtgaaga gataacagtt acaccaagga attatatatt tgatttcagg     120
catataggac agcttaaaag ccattatgca ataattggta tggcatttgt gtcagaagga     180
tacccacttt attatgatgc ggttaacgaa aaaggtcttg gaatggctgg acttaacttt     240
gttggcaatg cggcatataa agcatcagta tgtggtgaga aggatatagc acagtttgag     300
ttcatacctt ggatattaag ccagtgtgcg acagtcagcg aagcaagagc taagcttgat     360
ggaattaatc ttacaggaac accattcagc agccagcttc cagcggcaca gcttcactgg     420
ataattgcag ataaagatga agcaatcaca gttgagtcta tgaaagacgg acttcatata     480
tatgacaatc cggtcggagt gcttactaac aatccgccat ttgatatgca gatgtttgca     540
```

```
cttaataatt atgcagggct tcaagcaga cagccagata atacatttgc agacaagctt      600
aagttaaatg cttacagccg tggaatggga gctatgggac ttccgggaga tttatcaagc      660
cagtcacgtt ttataagagc agcatttaca agacttaacg caatttcaag cgatacagag      720
gaagaaagtg taagccagtt ctttcatata ctaggttcgg tagaacagca gagaggttgt      780
tgtgaggtaa ctgacggaaa gtatgagatt actatttata catcctgctg caatgcggca      840
aagggaatat attattacac aacatatgat aatcatcaga taacagcagt agatatgcac      900
aaggaaaatc tggacggaac agagcttata agatatccaa ttattactaa gggtgaagta      960
agatggcaga atagatag                                                    978
```

```
<210> SEQ ID NO 97
<211> LENGTH: 329
<212> TYPE: PRT
<213> ORGANISM: Lactobacillus rogosae

<400> SEQUENCE: 97

Met Cys Thr Ala Ala Thr Tyr Lys Thr Lys Asp Phe Tyr Met Gly Arg
1               5                   10                  15

Thr Leu Asp Tyr Glu Phe Ser Tyr Gly Glu Gln Ile Thr Ile Thr Pro
                20                  25                  30

Arg Asn Tyr Glu Phe Asp Phe Arg Phe Ala Gly Lys Ile Lys Ser His
            35                  40                  45

Tyr Ala Leu Ile Gly Met Ala Phe Val Ala Glu Gly Tyr Pro Leu Tyr
        50                  55                  60

Tyr Asp Ala Val Asn Glu Lys Gly Leu Gly Met Ala Gly Leu Asn Phe
65                  70                  75                  80

Val Gly Asn Ala Ala Tyr Glu Glu Ala Leu Pro Glu Asp Glu Thr Glu
                85                  90                  95

Val Ser Gln Val Ala Gln Phe Glu Phe Ile Pro Trp Ile Leu Thr Gln
                100                 105                 110

Cys Ala Thr Val Ala Glu Ala Arg Glu Lys Leu Ala Ala Met Arg Leu
            115                 120                 125

Thr Gly Thr Ala Phe Ser Glu Gln Leu Pro Thr Ala Gln Leu His Trp
        130                 135                 140

Ile Ile Ala Asp Lys Asp Ser Cys Ile Val Val Glu Ser Met Lys Asp
145                 150                 155                 160

Gly Leu His Val Tyr Asp Asn Gln Val Gly Val Leu Thr Asn Asn Pro
                165                 170                 175

Pro Phe Pro Gly Gln Met Phe Ala Leu Asn Asn Tyr Ala Gly Val Ser
            180                 185                 190

Arg Lys Gln Pro Glu Ser Thr Phe Ala Gly Val Leu Gln Leu Asp Ala
            195                 200                 205

Tyr Ser Arg Gly Met Gly Gly Met Gly Ile Pro Gly Asp Leu Ser Ser
        210                 215                 220

Gln Ser Arg Phe Val Lys Val Ala Phe Thr Lys Leu Asn Ser Ile Ser
225                 230                 235                 240

Gly Glu Glu Glu Asp Glu Ser Val Ser Gln Phe Phe His Ile Leu Gly
                245                 250                 255

Ser Val Asp Gln Gln Arg Gly Cys Cys Glu Val Thr Glu Gly Lys Tyr
            260                 265                 270

Glu Ile Thr Ile Tyr Thr Ser Cys Cys Asn Thr Ala Lys Gly Ile Tyr
        275                 280                 285

Tyr Tyr Thr Thr Tyr Asp Asn His Gln Ile Thr Ala Val Asp Met His
```

-continued

```
              290              295              300
Ala Glu Asn Leu Asp Ser Asp Gln Leu Ile Cys Tyr Pro Leu Leu Ser
305              310              315              320

Lys Gly Glu Val Arg Trp Gln Asn Lys
                325

<210> SEQ ID NO 98
<211> LENGTH: 990
<212> TYPE: DNA
<213> ORGANISM: Lactobacillus rogosae

<400> SEQUENCE: 98
atgtgtacag cagcaactta caaaacaaaa gatttttata tgggcagaac gcttgattat        60
gaattttcct atggggaaca gatcacgata acgccaagaa attacgaatt tgatttccgg       120
tttgccggga agataaaaag ccattatgct ttgatcggaa tggcatttgt tgcagaaggt       180
tatccgcttt attatgatgc tgttaatgaa aaaggccttg aatggcagg tcttaatttt        240 gtcggaaatg cggcatatga agaggctttg ccggaagatg aaacagaagt cagccaggtg       300
gcacagttcg agttcatccc atggatcctt acacagtgtg ctactgtagc agaggcgaga       360
gagaagctgg cagcaatgag actgacaggt acagcattca gtaacagct gccgacagca        420 cagcttcact ggatcattgc agacaaagac tcttgtatcg ttgttgagtc tatgaaagat       480
gggctgcatg tatatgataa tcaggtagga gtgcttacca ataatccacc attcccgggt       540
cagatgtttg cactgaataa ttatgccgga gtatccagaa aacagccgga gagtactttt       600
gcaggagtat tacagcttga tgcatatagc agaggaatgg gtggaatggg aatacctgga       660
gatctttcca gccagtcaag atttgtgaaa gttgcctta caaaattaaa ttcgatctcc         720
ggtgaagaag aggatgagag tgtaagccag ttcttccata tcttaggatc cgtagatcag       780
cagcgtggat gctgtgaggt gacagaaggc aaatatgaga tcacgatata cacgtcctgt       840
tgtaatacag caaaaggtat ttattattat acgacttatg ataatcatca gatcacagcg       900
gttgacatgc atgcggaaaa tctggattca gatcagctga tctgttatcc gcttctgtcc       960
aagggcgaag tcagatggca gaataaataa                                        990

<210> SEQ ID NO 99
<211> LENGTH: 324
<212> TYPE: PRT
<213> ORGANISM: Lactobacillus ruminis

<400> SEQUENCE: 99

Met Cys Thr Ala Ala Thr Tyr Thr Gly Lys Asp His Tyr Phe Gly Arg
1               5                10               15

Asn Leu Asp Leu Glu Leu Ser Tyr Asn Glu Ser Val Thr Val Thr Pro
                20               25               30

Arg Lys Phe Pro Leu Lys Phe His Gln Val His Asp Met Asn Glu His
            35               40               45

Phe Ala Ile Ile Gly Met Ala Thr Val Val Ala Asp Tyr Pro Leu Tyr
        50               55               60

Tyr Asp Ala Thr Asn Glu Lys Gly Leu Ser Met Ala Gly Leu Asn Phe
65               70               75               80

Pro Gly Asn Ala Asp Tyr Lys Glu Pro Ala Glu Asp Val Asp Asn Val
                85               90               95

Ala Ser Phe Glu Phe Ile Pro Trp Ile Leu Gly Gln Cys Glu Thr Val
            100              105              110
```

```
Ala Asp Val Arg Lys Leu Leu Ala Lys Ile Asn Ile Thr Asn Val Glu
        115                 120                 125

Phe Ser Glu Gln Phe Pro Pro Ser Pro Leu His Trp Met Ile Ser Asp
        130                 135                 140

Lys Asn Glu Ser Ile Thr Val Glu Gln Thr Lys Ala Gly Leu Asn Val
145                 150                 155                 160

Tyr Asp Asn Pro Val Gly Ile Met Thr Asn Asn Pro Glu Phe Pro Phe
                165                 170                 175

Gln Met Phe Thr Leu Asn Asn Tyr Arg Arg Val Ser Pro Lys Pro Val
                180                 185                 190

Ala Ser Thr Phe Ala Asp Gly Leu Glu Leu Asp Glu Tyr Thr Arg Gly
        195                 200                 205

Met Gly Ser Met Gly Leu Pro Gly Asp Leu Ser Ser Asn Ser Arg Phe
        210                 215                 220

Val Lys Ala Thr Phe Thr Lys Leu Asn Ala Pro Lys Met Ala Asp Glu
225                 230                 235                 240

Asn Thr Ser Val Ser Gln Phe Phe His Ile Leu Gly Ser Val Glu Gln
                245                 250                 255

Gln Lys Gly Cys Cys Asp Val Gly Asn Gly Lys Phe Glu Phe Thr Ile
                260                 265                 270

Tyr Ser Ser Cys Cys Asn Val Asp Arg Gly Ile Tyr Tyr Tyr Lys Thr
        275                 280                 285

Tyr Asp Asn Ser Gln Ile Thr Ala Val Asp Met His Lys Glu Asp Leu
        290                 295                 300

Asp Ser Ala Ala Leu Lys Ser Tyr Lys Leu Ile Glu Glu Gln Gln Ile
305                 310                 315                 320

Phe Ala Gln Asn
```

<210> SEQ ID NO 100
<211> LENGTH: 975
<212> TYPE: DNA
<213> ORGANISM: Lactobacillus ruminis

<400> SEQUENCE: 100

```
atgtgtacag cagcaacgta tactggcaaa gatcactatt ttggtcgcaa tcttgatttg      60
gaactctcct acaatgagtc cgtgacggtt acgccacgca aatttccgtt aaagtttcat     120
caggtacatg atatgaacga acattttgcc atcatcggga tggcaacggt tgtcgctgat     180
tatccgcttt attatgatgc aacgaacgaa aaaggattaa gtatggcagg gttgaatttc     240
ccgggaaatg cagattacaa agaacctgca gaagatgtcg acaatgtcgc atcctttgaa     300
ttcattcctt ggattctcgg acaatgcgag actgttgctg acgtccgtaa attgcttgca     360
aaaatcaata ttacgaacgt tgaattcagt gaacaattcc cgccgagtcc attgcactgg     420
atgatttccg ataagaatga gtcgattacg gttgaacaga cgaaggcggg acttaatgtc     480
tatgacaacc cggtcggcat aatgacgaac aaccctgaat ttccattcca gatgtttacg     540
ttgaacaact atcgccgcgt ttctccaaaa ccggtcgcat caacgtttgc agatggcctt     600
gaacttgatg aatatactcg cggaatgggc agcatgggac tgccgggaga tctttcatcc     660
aactcgcgtt tcgttaaagc aacgttcacg aagctcaacg cgccgaagat ggctgatgaa     720
aacacgagcg tcagtcaatt cttccacatt ctcggttccg ttgaacaaca gaagggatgc     780
tgcgacgttg gcaacggcaa atttgaattc acgatttatt cttcatgctg caacgtcgat     840
cgcggaatct actactataa gacttatgac aacagccaaa tcacggcagt agacatgcac     900
```

-continued

```
aaggaagatc ttgattcagc agctttgaaa tcatataagc tgattgaaga acaacaaatc      960
tttgcgcaaa actaa                                                       975
```

```
<210> SEQ ID NO 101
<211> LENGTH: 325
<212> TYPE: PRT
<213> ORGANISM: Lactobacillus salivarius

<400> SEQUENCE: 101

Met Cys Thr Ser Ile Leu Tyr Thr Ala Gly Asp His Tyr Phe Gly Arg
1               5                   10                  15

Asn Leu Asp Leu Glu Ile Ser Phe Gly Gln Gln Val Val Ile Thr Pro
            20                  25                  30

Arg Asp Tyr Pro Leu Asn Phe Arg Lys Met Pro Arg Leu Asp His His
        35                  40                  45

Tyr Ala Ile Thr Gly Met Ala Leu Val Gln Asp Asn Tyr Pro Leu Tyr
    50                  55                  60

Phe Asp Gly Ala Asn Glu Glu Gly Leu Gly Met Ala Gly Leu Asn Phe
65                  70                  75                  80

Asp Gly Pro Ala His Phe Phe Pro Val Glu Glu Gly Lys Asp Asn Val
                85                  90                  95

Ser Pro Phe Glu Phe Ile Pro Tyr Ile Leu Gly Gln Cys Lys Asn Val
            100                 105                 110

Ala Glu Ala Lys Glu Leu Leu Lys Ser Leu Asn Leu Val Asn Ile Asn
        115                 120                 125

Phe Ser Asp Gln Leu Gln Leu Ser Pro Leu His Trp Leu Ile Ala Asp
    130                 135                 140

Lys Ser Gly Ala Ala Ile Thr Val Glu Ser Thr Ala Ser Gly Leu His
145                 150                 155                 160

Val Tyr Asp Asn Pro Val Asn Val Leu Thr Asn Asn Pro Glu Phe Pro
                165                 170                 175

Asp Gln Leu Thr Asn Leu Ala Asn Tyr Gln Ser Val Ser Pro Ala Asn
            180                 185                 190

Pro Ala Asn Thr Leu Ala Pro Gln Thr Ala Leu Ala Ser Tyr Ser Arg
        195                 200                 205

Gly Ala Gly Ser His Phe Leu Pro Gly Gly Met Asp Ser Glu Ser Arg
    210                 215                 220

Phe Val Lys Glu Val Phe Thr Leu Gln His Ala Pro Ala Gly Glu Thr
225                 230                 235                 240

Glu Val Ala Asn Val Thr Asn Tyr Phe His Cys Leu His Ala Val Glu
                245                 250                 255

Gln Gln Lys Gly Leu Asp Glu Val Gly Lys Asp Gln Phe Glu Tyr Thr
            260                 265                 270

Ile Tyr Ser Asp Gly Val Asn Leu Thr Thr Gly Thr Phe Tyr Tyr Thr
        275                 280                 285

Thr Tyr Asp Asn Asn Gln Ile Asn Ala Val Lys Met His Ala Glu Asp
    290                 295                 300

Met Glu Gly Gln Gln Leu His Arg Phe Pro Ile Ala Ser His Gln Ser
305                 310                 315                 320

Ile Asn Met Gln Asn
                325
```

```
<210> SEQ ID NO 102
<211> LENGTH: 978
<212> TYPE: DNA
```

<213> ORGANISM: Lactobacillus salivarius

<400> SEQUENCE: 102

```
atgtgtacat cgattttata tactgctggc gaccattact ttggccgtaa ccttgattta      60
gagatttcgt ttggtcaaca ggtggtcatt acaccacgtg actatccgct aaactttcgt     120
aagatgccac gcttagacca ccactatgcc attactggga tggcgctagt gcaggataac     180
tatccactat attttgacgg tgccaatgaa gaaggcctag ggatggctgg cctaaacttt     240
gatggcccgg cccacttttt ccccgtggaa gaagggaagg ataatgtatc accatttgaa     300
ttcatcccct atatcttggg ccaatgcaag aacgttgccg aagctaagga actgcttaaa     360
agccttaatt tagtcaacat taacttctct gaccagttgc agttatcccc cttacactgg     420
cttatcgctg ataagagcgg tgcagcaatc acggtggagt caactgcttc tggactacat     480
gtttatgata tcccgttaa tgttttaacg aataatccag aattccctga ccaattgacc     540
aatttggcta actaccagag tgtttcaccg gcaaacccgg ctaatacttt ggcgccccaa     600
acggcacttg ctagttatag tcggggtgcc ggttcacatt tcctgccagg gggaatggat     660
tctgaaagcc ggttcgtcaa agaagtcttc acactccaac atgcacctgc tggcgaaact     720
gaggtagcaa acgttacaaa ttacttccac tgcctacacg cggtggaaca acaaaagggc     780
ctcgatgagg tgggcaagga ccagtttgaa tatactattt attcagatgg ggttaacctg     840
acgacgggga ccttctatta caccacctat gataataacc agattaacgc ggttaaaatg     900
cacgcggaag atatggaagg gcaacagcta caccgcttcc cgattgctag ccaccaatca     960
attaatatgc aaaattaa                                                    978
```

<210> SEQ ID NO 103
<211> LENGTH: 324
<212> TYPE: PRT
<213> ORGANISM: Lactobacillus salivarius

<400> SEQUENCE: 103

```
Met Cys Thr Ala Ile Thr Leu Asn Gly Asn Ser Asn Tyr Phe Gly Arg
1               5                   10                  15

Asn Leu Asp Leu Asp Phe Ser Tyr Gly Glu Glu Val Ile Ile Thr Pro
            20                  25                  30

Ala Glu Tyr Glu Phe Lys Phe Arg Lys Glu Lys Ala Ile Lys Asn His
        35                  40                  45

Lys Ser Leu Ile Gly Val Gly Ile Val Ala Asn Asp Tyr Pro Leu Tyr
    50                  55                  60

Phe Asp Ala Ile Asn Glu Asp Gly Leu Gly Met Ala Gly Leu Asn Phe
65                  70                  75                  80

Pro Gly Asn Ala Tyr Tyr Ser Asp Ala Leu Glu Asn Asp Lys Asp Asn
                85                  90                  95

Ile Thr Pro Phe Glu Phe Ile Pro Trp Ile Leu Gly Gln Cys Ser Asp
            100                 105                 110

Val Asn Glu Ala Arg Asn Leu Val Glu Arg Ile Asn Leu Ile Asn Leu
        115                 120                 125

Ser Phe Ser Glu Gln Leu Pro Leu Ala Gly Leu His Trp Leu Ile Ala
    130                 135                 140

Asp Arg Glu Lys Ser Ile Val Val Glu Val Thr Lys Ser Gly Val His
145                 150                 155                 160

Ile Tyr Asp Asn Pro Ile Gly Val Leu Thr Asn Asn Pro Glu Phe Asn
                165                 170                 175
```

```
Tyr Gln Met Tyr Asn Leu Asn Lys Tyr Arg Asn Leu Ser Ile Ser Thr
            180                 185                 190

Pro Gln Asn Thr Phe Ser Asp Ser Val Asp Leu Lys Val Asp Gly Thr
            195                 200                 205

Gly Phe Gly Gly Ile Gly Leu Pro Gly Asp Ala Ser Pro Glu Ser Arg
    210                 215                 220

Phe Val Arg Ala Ala Phe Ser Lys Leu Asn Ser Ser Lys Gly Thr Thr
225                 230                 235                 240

Val Glu Glu Asp Ile Thr Gln Phe Phe His Ile Leu Gly Thr Val Lys
                245                 250                 255

Gln Ile Lys Gly Val Asn Lys Thr Glu Ser Gly Lys Glu Glu Tyr Thr
            260                 265                 270

Val Tyr Ser Asn Cys Tyr Asp Leu Asp Asn Lys Thr Leu Tyr Tyr Thr
            275                 280                 285

Thr Tyr Glu Asn Arg Gln Ile Val Ser Val Thr Leu Asn Lys Asp Lys
    290                 295                 300

Asn Gly Asn Lys Leu Val Val Tyr Pro Phe Glu Arg Lys Gln Ile Ile
305                 310                 315                 320

Asn Lys Leu Asn
```

```
<210> SEQ ID NO 104
<211> LENGTH: 975
<212> TYPE: DNA
<213> ORGANISM: Lactobacillus salivarius

<400> SEQUENCE: 104
atgtgtacag caattacttt aaatggtaat agtaattatt ttggaagaaa cttagattta       60
gatttttcat atggtgagga ggtaatcatt actccggctg aatatgagtt taaatttaga      120
aaggaaaaag ctataaagaa tcataaatca ttaataggtg ttggaattgt cgctaatgat      180
tatccactgt attttgatgc tattaatgag gatggactag gaatggcagg attgaatttt      240
cctggaaatg catattatag cgatgcttta gagaatgata aagataatat tacgccgttc      300
gagtttattc catggattct gggacagtgt agcgatgtta atgaagcaag aaatttagtt      360
gaaagaataa atctcattaa tcttagtttt agcgaacaat tacctttagc agggttacat      420
tggttaattg cagatagaga aaaatccatt gtagtagaag taactaaatc tggcgtacat      480
atttatgata atccaattgg agtattgact aataatccgg aatttaatta tcagatgtac      540
aatctgaata atatcgcaa cttatctatc agtacaccac aaaatacatt ctcagatagc      600
gtggatttaa aggtagacgg taccggtttt ggtggtattg gcttaccagg cgatgcatct      660
cccgaatctc gttttgtgag agctgctttt agcaagttaa attcaagtaa agggacgacc      720
gtagaagaag atattactca gttttttccat atactaggga cagtaaaaca gataaagggc      780
gttaataaga cagaatcagg aaaagaagaa tatactgtat attcgaattg ctatgattta      840
gacaacaaaa cgttatatta tacaacctat gaaaatagac aaatagtgtc tgttacttta      900
aataaagata agaatggtaa taagttagtc gtatatccat ttgaaagaaa acaaataata      960
aataagttga attaa                                                       975
```

```
<210> SEQ ID NO 105
<211> LENGTH: 324
<212> TYPE: PRT
<213> ORGANISM: Lactobacillus secaliphilus

<400> SEQUENCE: 105
```

-continued

```
Met Cys Thr Ala Leu Thr Phe Asn Ala His Asp His Tyr Phe Gly Arg
1               5                   10                  15

Asn Leu Asp Leu Glu Val Ser Tyr Gly Gln Gln Val Val Val Thr Pro
            20                  25                  30

Arg Asn Tyr Asn Phe Lys Phe Arg Lys Val Ala Asp Leu Ser Asn His
        35                  40                  45

Tyr Ala Met Ile Gly Val Ala Ala Val Ile Asp Asn Tyr Pro Leu Tyr
    50                  55                  60

Phe Asp Ala Thr Asn Glu Lys Gly Leu Ser Met Ala Gly Leu Asn Tyr
65                  70                  75                  80

Pro Asp Asn Ala Phe Tyr Pro Asp Met Ala Ala Asp Lys Asp Asn Ile
                85                  90                  95

Thr Pro Phe Glu Phe Ile Pro Trp Ile Leu Gly Gln Cys Asp Ser Val
            100                 105                 110

Ala Ser Ala Arg Gln Leu Leu Pro Lys Ile Asn Leu Val Asn Ile Asn
        115                 120                 125

Phe Ser Asp Gln Leu Pro Leu Ser Pro Leu His Trp Leu Leu Ala Asp
    130                 135                 140

Gln His Glu Ala Val Val Ile Glu Ser Asp Arg Asp Gly Leu His Val
145                 150                 155                 160

Tyr Asp Asn Pro Val Gly Val Leu Thr Asn Asn Pro Thr Phe Asp Lys
                165                 170                 175

Gln Leu Phe Asn Leu Asn Asn Tyr Arg Asp Leu Ser Ser Ala Asn Pro
            180                 185                 190

Gln Asp Thr Phe Gly Lys Gly Met Pro Leu Thr Asp Tyr Ser Arg Gly
            195                 200                 205

Leu Gly Thr Arg Asn Leu Pro Gly Gly Leu Asp Ser Glu Ser Arg Phe
    210                 215                 220

Val Arg Ala Ala Phe Asn Lys Ala Asn Ala Val Cys Ala Asp Asn Glu
225                 230                 235                 240

Glu Ala Ser Ile Thr Gln Leu Phe His Ile Met His Ser Val Glu Gln
                245                 250                 255

Gln Asn Gly Leu Asp Glu Val Ala Pro Gly Lys Phe Glu Phe Thr Ile
            260                 265                 270

Tyr Thr Val Gly Tyr Asn Gln Asp Gln Gly Leu Leu Tyr Tyr Thr Thr
    275                 280                 285

Tyr His Asn Asn Gln Ile Asn Leu Val Asp Met Asn Lys Cys Asp Leu
    290                 295                 300

Glu Ser Thr Asp Leu Cys Ala Tyr Pro Phe Ile Asp Ser Gln Ala Phe
305                 310                 315                 320

Asn Lys Val Asn
```

```
<210> SEQ ID NO 106
<211> LENGTH: 975
<212> TYPE: DNA
<213> ORGANISM: Lactobacillus secaliphilus

<400> SEQUENCE: 106
atgtgtactg ccttaacatt taacgcgcac gatcattact ttggccggaa cctggacctg      60
gaagtctcat acggtcaaca ggtggttgtg acgccgcgga attacaactt taaattccgt     120
aaagtggcgg acctgtctaa ccactacgca atgatcgggg tcgccgccgt gatcgataac     180
tatccactct actttgacgc gaccaacgaa aaggggctga gcatggccgg cctcaattat     240
ccggacaacg ccttctatcc tgacatggcc gcagacaagg acaacatcac cccatttgaa     300
```

```
ttcattcctt ggattctggg gcagtgtgac agcgtcgcca gcgcacgcca gctgttaccc      360
aaaatcaacc tagtcaatat caacttctcc gaccaactgc cattatcacc cttacattgg      420
ctgttggctg accagcatga agcagtggtg atcgaaagtg accgcgacgg cctgcatgtt      480
tacgacaatc cggtcggcgt tttgaccaac aacccgactt ttgacaagca attgtttaat      540
ctgaacaact accgcgacct gtccagcgcc aacccgcagg atacgttcgg taagggcatg      600
ccgttgacgg attacagtcg cggcttaggg acacgtaatc tgcctggtgg tttggattca      660
gaaagtcgtt tcgtgagagc cgccttcaac aaggccaacg cagtgtgcgc tgataatgag      720
gaagcatcaa tcacccagct gttccacatc atgcactccg ttgagcagca aaacggcttg      780
gatgaagtgg ctcccggcaa attcgaattt accatctaca cggtgggata caaccaagac      840
caaggcctgc tttactacac cacctaccac aacaatcaga tcaacctggt cgacatgaac      900
aagtgcgatc ttgagagtac agacctctgt gcttatccat tcatcgattc gcaggccttc      960
aacaaggtta actaa                                                       975
```

<210> SEQ ID NO 107
<211> LENGTH: 325
<212> TYPE: PRT
<213> ORGANISM: Lactobacillus ultunensis

<400> SEQUENCE: 107

```
Met Cys Thr Ser Ile Ile Phe Ser Pro Lys Asp His Tyr Phe Gly Arg
1               5                   10                  15

Asn Leu Asp Leu Glu Val Ser Phe Gly Gln Gln Val Ile Val Thr Pro
            20                  25                  30

Arg Asn Tyr Asn Phe Lys Phe Arg Lys Met Pro Asp Met Lys Lys His
        35                  40                  45

Phe Ala Met Val Gly Ile Ala Leu Asn Ala Gly Asn Tyr Pro Leu Tyr
    50                  55                  60

Phe Asp Ala Ala Asn Glu Lys Gly Leu Gly Met Ala Gly Leu Asn Tyr
65                  70                  75                  80

Pro Gly Asn Ala Thr Tyr Tyr Lys Glu Lys Glu Gly Lys Asp Asn Ile
                85                  90                  95

Ala Ser Phe Glu Phe Val Pro Trp Val Leu Gly Gln Cys Ser Asn Ile
            100                 105                 110

Ser Glu Val Lys Glu Leu Leu Lys Asn Phe Asn Ile Ile Asp Leu Asn
        115                 120                 125

Phe Ser Asp Lys Met Glu Ala Ser Pro Leu His Trp Leu Ile Ala Asp
    130                 135                 140

Lys Ser Gly Thr Ser Ile Val Val Glu Thr Asp Lys Asp Gly Met His
145                 150                 155                 160

Ile Tyr Asp Asn Pro Val Gly Cys Leu Thr Asn Asn Pro Gln Phe Ser
                165                 170                 175

Lys Gln Leu Phe Asn Leu Asn Asn Tyr Ala Asp Ile Ser Pro Ala Met
            180                 185                 190

Pro Lys Asn Asn Phe Ser Asp Lys Val Asn Met Asp Gly Tyr Ser Arg
        195                 200                 205

Gly Leu Gly Ser Arg Asn Leu Pro Gly Gly Met Asp Ser Glu Ser Arg
    210                 215                 220

Phe Val Arg Val Ala Phe Asn Lys Phe Asn Ala Pro His Cys Glu Thr
225                 230                 235                 240

Glu Glu Glu Asn Val Asp Asn Tyr Phe His Ile Leu His Ser Val Glu
```

```
                245               250               255
Gln Gln Arg Gly Leu Asp Gln Val Gly Pro Asp Ala Phe Glu Tyr Thr
            260               265               270

Ile Tyr Ser Asp Gly Thr Asn Leu Asp Lys Gly Ile Phe Tyr Tyr Thr
            275               280               285

Thr Tyr Thr Asn Lys Gln Ile Asn Val Val Asp Met Asn Lys Glu Asp
    290               295               300

Leu Asp Ser Asp Lys Leu Ile Thr Tyr Glu Leu Leu Thr Lys Pro Asn
305               310               315               320

Phe Asn His Gln Asn
                325
```

```
<210> SEQ ID NO 108
<211> LENGTH: 978
<212> TYPE: DNA
<213> ORGANISM: Lactobacillus ultunensis

<400> SEQUENCE: 108
atgtgtacat caattatatt tagccctaaa gatcactact ttggtcgtaa cctcgacctc      60
gaagttagtt ttggtcaaca agttatagtt acacctcgca actataattt taaattccgc     120
aagatgccag atatgaaaaa gcattttgcc atggtaggta ttgctcttaa tgccggaaat     180
tatcccctat actttgatgc agctaacgaa aagggattag gcatggctgg tttgaattac     240
cctggcaatg ctacatatta caaggaaaaa gaaggcaaag acaatattgc ttcttttgaa     300
tttgttcctt gggtttttagg acaatgcagc aatattagtg aagtaaaaga attgcttaaa     360
aacttcaaca ttatagattt aaacttcagt gataagatgg aagcttcacc acttcactgg     420
ttaattgctg ataaatcagg tacttctatt gtggtagaaa ctgacaaaga tgggatgcat     480
atttatgata tcccgttgg ttgcttgact aataatcctc aattttcaaa acaattgttc     540
aatctcaaca attacgctga catttcccct gcaatgccta agaataattt ctcagacaag     600
gtaaatatgg atggctacag tcgtgggctt ggttcacgca atctccctgg cggcatggat     660
tcagaatcac gttttgttag agttgctttc aacaaattca atgctcctca ttgcgaaact     720
gaggaagaaa acgtggataa ttacttccac atcttgcact ctgtagagca acaaggggga     780
ctcgatcaag taggtcctga cgctttttgaa tatacaattt attcagatgg aaccaacttg     840
gataaaggta tcttttacta tactacttac actaacaagc aaattaatgt agtagatatg     900
aataaagaag atctagacag tgataaatta attacgtatg aattattaac taaaccgaac     960
tttaatcatc aaaactaa                                                    978
```

```
<210> SEQ ID NO 109
<211> LENGTH: 325
<212> TYPE: PRT
<213> ORGANISM: Lactobacillus sp. Marseille-P3519

<400> SEQUENCE: 109

Met Cys Thr Ser Val Ile Tyr Asn Ala Gly Asp Lys Tyr Phe Gly Arg
1               5               10               15

Asn Leu Asp Leu Glu Ile Asp Phe Gly Glu Glu Val Val Ile Ser Pro
            20               25               30

Arg Asp Phe Ala Phe Asn Phe Arg Gln Met Pro Thr Ile Asp His His
            35               40               45

Tyr Ala Ile Ile Gly Met Ala Leu Val Gln Asp Gly Tyr Pro Leu Tyr
    50               55               60
```

```
Phe Asp Gly Val Asn Glu Ala Gly Leu Gly Met Ala Gly Leu Asn Phe
65                  70                  75                  80

Asp Gly Pro Ala His Tyr Phe Pro Val Val Glu Gly Lys Asp Asn Val
                85                  90                  95

Ser Pro Phe Glu Phe Ile Pro Tyr Leu Leu Gly Gln Cys Lys Asp Val
            100                 105                 110

Lys Glu Ala Lys Lys Leu Leu Ala Asn Leu Asn Leu Val Asn Ile Asn
        115                 120                 125

Phe Ser Asp Lys Phe Gln Leu Ser Pro Leu His Trp Leu Ile Ala Asp
    130                 135                 140

Lys Ser Gly Ala Ala Ile Val Val Glu Ser Thr Arg Thr Gly Leu His
145                 150                 155                 160

Val Tyr Asp Asn Pro Val Gly Val Leu Thr Asn Asn Pro Glu Phe Pro
                165                 170                 175

Lys Gln Leu Leu Asn Leu Ser Asn Tyr Gln Ser Val Ser Pro Ala Asp
            180                 185                 190

Pro Gln Asn Thr Leu Thr Pro Gly Val Lys Leu Asp Thr Tyr Ser Arg
            195                 200                 205

Gly Phe Gly Thr His Phe Leu Pro Gly Gly Met Asp Ser Ala Ser Arg
    210                 215                 220

Phe Val Lys Glu Thr Phe Thr Lys Met His Ala Pro Ala Gly Lys Ser
225                 230                 235                 240

Glu Gly Glu Asn Ile Thr Asn Tyr Phe His Ile Leu His Ala Val Glu
                245                 250                 255

Gln Gln Lys Gly Leu Asp Glu Val Ala Pro Asn Thr Phe Glu Tyr Thr
            260                 265                 270

Ile Tyr Ser Asp Gly Thr Asn Leu Thr Lys Gly Ile Phe Tyr Tyr Thr
            275                 280                 285

Ser Tyr Asp Asn Asn Gln Ile Asn Ala Val Asp Met His Lys Glu Asp
    290                 295                 300

Leu Asp Ser Ser Ala Leu Ile Thr Tyr Ala Leu Lys Thr Asp Gln Ala
305                 310                 315                 320

Ile Asn Tyr Gln Asn
                325
```

<210> SEQ ID NO 110
<211> LENGTH: 978
<212> TYPE: DNA
<213> ORGANISM: Lactobacillus sp. Marseille-P3519

<400> SEQUENCE: 110

```
atgtgtacat cagttattta taatgcaggg gacaaatatt ttggtcgaaa tcttgacctg      60
gagattgact ttggggagga agtcgtgatc agtccccgcg actttgcgtt taactttcgg     120
cagatgccaa cgattgacca ccactatgcg attattggga tggccctcgt ccaggatggt     180
tacccattat actttgatgg ggttaacgaa gcaggcctgg ggatggctgg cttgaatttt     240
gatggccctg ctcactactt cccggttgtt gaaggaaagg ataatgtttc gccatttgag     300
tttattccgt acctattagg gcagtgtaag gatgttaagg aggccaaaaa actcttagct     360
aaccttaacc tggttaacat taacttttct gataaattcc aactctcacc gttgcactgg     420
ttgattgctg ataagagtgg ggccgcaatt gtcgttgaat cgacgaggac tggcctgcac     480
gtttacgata accctgttgg tgttttgaca aacaatccgg aatttcctaa gcaattgctt     540
aacctgagca attaccaaag tgtttcacca gcagacccc aaaataccct taccccgggg     600
```

-continued

```
gtaaagcttg atacttatag tcggggattt ggaacccact ttttaccagg ggggatggat        660
tcagcaagtc gcttcgtaaa ggagacattt accaagatgc atgcaccagc ggggaagagc        720
gaaggggaaa acatcaccaa ttacttccat attctgcatg cagttgagca gcaaaagggc        780
cttgatgagg ttgccccgaa tacctttgaa tacacgattt attcagatgg aactaacttg        840
acgaagggaa tcttctatta tactagctat gataataacc aaataaatgc agttgatatg        900
cataaagaag atttggacag cagtgcatta atcacctatg cccttaaaac tgaccaggca        960
attaactacc aaaactaa                                                       978
```

```
<210> SEQ ID NO 111
<211> LENGTH: 325
<212> TYPE: PRT
<213> ORGANISM: Lactobacillus vaginalis

<400> SEQUENCE: 111

Met Cys Thr Ser Ile Ile Tyr Thr Ala Gly Asp Ser Tyr Phe Gly Arg
1               5                   10                  15

Asn Leu Asp Leu Glu Val Ser Phe Gly Gln Glu Val Val Val Thr Pro
                20                  25                  30

Arg Asn Tyr Pro Phe Lys Phe Arg Lys Gly Pro Ser Leu Asp His His
            35                  40                  45

Tyr Ala Ile Thr Gly Met Ala Leu Val Glu Asp Gly Tyr Pro Leu Tyr
        50                  55                  60

Phe Asp Gly Ala Asn Glu Glu Gly Leu Gly Met Ala Gly Leu Asn Phe
65                  70                  75                  80

Asp Gly Pro Cys His Tyr Phe Pro Glu Asp Pro Gly Lys Asp Asn Val
                85                  90                  95

Thr Pro Phe Glu Phe Ile Pro Tyr Ile Leu Gly Gln Cys Lys Asn Val
            100                 105                 110

Thr Glu Ala Arg Lys Leu Leu Ser Asn Leu Asn Leu Val Lys Ile Asp
        115                 120                 125

Phe Ser Ala Lys Leu His Leu Ser Pro Leu His Trp Leu Ile Ala Asp
    130                 135                 140

Lys Ser Gly Glu Ala Ile Val Val Glu Ser Thr Ala Glu Gly Leu Asn
145                 150                 155                 160

Val Tyr Asp Asn Pro Val Gly Val Leu Thr Asn Asn Pro Glu Phe Pro
                165                 170                 175

Lys Gln Leu Leu Asn Leu Ser Asn Tyr Gln Ser Ile Ser Pro Ala Tyr
            180                 185                 190

Pro Glu Asn Thr Leu Ile Pro Glu Val Lys Leu Ser Thr Tyr Ser Arg
        195                 200                 205

Gly Phe Gly Ser Arg Phe Leu Pro Gly Gly Met Asp Ser Glu Ser Arg
    210                 215                 220

Phe Val Lys Glu Val Phe Thr Lys Ala His Ala Pro Lys Gly Lys Ser
225                 230                 235                 240

Glu Ile Glu Asn Ile Thr Asp Tyr Phe His Asn Leu His Ala Val Glu
                245                 250                 255

Gln Gln Lys Gly Leu Asp Gln Val Ala Pro Gly Gln Phe Glu Tyr Thr
            260                 265                 270

Ile Tyr Ser Asp Gly Ile Asn Leu Thr Thr Gly Thr Phe Tyr Tyr Ser
        275                 280                 285

Thr Tyr Asp Asn Asn Gln Ile Asn Ala Val Lys Leu Glu Glu Asp Lys
    290                 295                 300
```

```
Leu Asp Gln Thr Glu Leu Leu Gln Tyr Pro Leu Gln Ser Lys Gln Thr
305                 310                 315                 320

Ile Asn Phe Gln Asn
                325
```

<210> SEQ ID NO 112
<211> LENGTH: 978
<212> TYPE: DNA
<213> ORGANISM: Lactobacillus vaginalis

<400> SEQUENCE: 112

```
atgtgtacat cgattattta tacggctggt gacagctatt tcggtcggaa ccttgatttg      60
gaagtttctt ttggtcaaga agtggttgtg acaccacgaa attatccatt taaatttcgt     120
aaagggccat cattagatca ccactatgcc attacgggga tggcattagt tgaggatggc     180
tatcccttgt attttgatgg agcaaatgaa gaaggcttgg gaatggctgg tttaaacttt     240
gatgggcctt gccattattt cccggaagat ccaggaaagg ataacgtgac accattcgag     300
tttatccctt cattttagg acaatgtaaa aatgttaccg aagcacgcaa gctacttagt     360
aatttgaact tagttaagat tgatttctcc gcaaagctcc acttgtcacc gcttcactgg     420
cttattgccg ataaatccgg tgaggcaatt gtggttgagt caacggcaga ggggctaaat     480
gtttatgata tcctgttgg cgttttgact aataatcccg aatttcctaa gcaattgcta     540
aatttgagta actatcagag tatttcgccg gcctatccag agaacacttt gatccctgaa     600
gttaagctca gtacttatag ccgtggattt ggttcccgct tcttaccggg tgggatggat     660
tcagaaagtc ggtttgttaa agaagtcttc accaaagcac atgcacccaa gggaaaatca     720
gaaattgaaa atattactga ttattttcat aatctgcatg cggttgaaca acaaaagggc     780
cttgatcaag tggctcctgg acaatttgaa tatacaattt attctgacgg gattaactta     840
actacgggaa ctttctacta ttcaacgtac gataataatc aaattaatgc agttaagtta     900
gaagaggata agttggatca aactgagtta cttcaatacc cgcttcagag caaacaaacc     960
attaatttcc aaaactaa                                                    978
```

<210> SEQ ID NO 113
<211> LENGTH: 325
<212> TYPE: PRT
<213> ORGANISM: Lactobacillus reuteri

<400> SEQUENCE: 113

```
Met Cys Thr Ser Val Ile Tyr Thr Ala Gly Asp Tyr Tyr Phe Gly Arg
1               5                   10                  15

Asn Leu Asp Leu Glu Val Asn Leu Gly Gln Glu Val Val Ile Thr Pro
            20                  25                  30

Arg Asn Lys Thr Leu Glu Phe Arg Glu Met Pro Asn Leu Glu His His
        35                  40                  45

Tyr Ala Ile Ile Gly Met Ser Ile Val Arg Asp Asp Tyr Pro Leu Tyr
    50                  55                  60

Phe Asp Gly Val Asn Glu Lys Gly Val Gly Met Ala Gly Leu Asn Phe
65                  70                  75                  80

Asp Gly Pro Ala His Tyr Phe Pro Val Gln Glu Gly Lys Asp Asn Ile
                85                  90                  95

Ala Ser Phe Glu Leu Val Pro Tyr Ile Leu Ala Ala Ala Ser Ser Val
            100                 105                 110

Ala Glu Ala Lys Lys Leu Leu Ser Asn Ala Asn Ile Ala Asn Ile Asn
        115                 120                 125
```

```
Phe Ser Asp Lys Leu Gln Ala Ala Pro Leu His Trp Ile Ile Ala Asp
    130                 135                 140

Lys Thr Gly Ala Ser Val Thr Val Glu Ser Thr Ala Lys Gly Leu Asn
145                 150                 155                 160

Val Tyr Asp Asn Pro Val Gly Val Leu Thr Asn Asn Pro Glu Phe Pro
                165                 170                 175

Arg Gln Leu Leu Asn Leu Ser Asn Tyr Arg Ser Val Ala Pro Ala Asn
                180                 185                 190

Pro Ala Asn Val Phe Ala Pro Asn Val Asp Leu Pro Val Tyr Ser Arg
                195                 200                 205

Gly Leu Gly Thr His Phe Leu Pro Gly Gly Met Asp Ser Glu Ser Arg
    210                 215                 220

Phe Val Lys Ala Thr Phe Thr Lys Met His Ala Pro Val Gly Asn Ser
225                 230                 235                 240

Glu Val Glu Asn Ile Thr Asn Tyr Phe His Ile Leu Gln Ser Val Glu
                245                 250                 255

Gln Gln Lys Gly Leu Asp Glu Val Ala Pro Asn Thr Phe Glu Tyr Thr
                260                 265                 270

Ile Tyr Ser Asp Gly Ser Asn Leu Lys Lys Gly Ile Phe Tyr Tyr Lys
                275                 280                 285

Thr Tyr Glu Asn Ser Gln Ile Asn Ala Val Asp Met His Lys Glu Asp
    290                 295                 300

Leu Glu Ala Ser Glu Leu Ile Thr Tyr Pro Val Gln Asn Lys Gln Ile
305                 310                 315                 320

Ile Asn Gln Gln Asn
                325

<210> SEQ ID NO 114
<211> LENGTH: 978
<212> TYPE: DNA
<213> ORGANISM: Lactobacillus reuteri

<400> SEQUENCE: 114
atgtgcacat cagtaattta tacagcaggt gattattact ttggtcgtaa tcttgatttg      60
gaagtcaacc ttggtcaaga agtagtgatt accccgcgta ataagacttt agaattccgg     120
gaaatgccca atcttgaaca ccattatgca attattggaa tgtcaattgt tcgtgatgat     180
tatccattat actttgatgg ggtaaatgaa aaagggttg ggatggcagg ccttaatttt      240
gatggtccag ctcattattt cccagtccaa gaggggaagg ataatattgc atcctttgaa     300
ttagttcctt atattcttgc ggcagcttcc tcggttgctg aagcgaagaa gttactttca     360
aatgcaaaca ttgctaatat taattttct gataaactcc aagctgcacc gctacactgg      420
attattgctg ataaaacggg tgcttctgtg actgttgaat ccaccgcaaa aggattgaat     480
gtttatgata acccagttgg tgttttgaca ataatccgg agtttcctcg tcaattatta      540
aatcttagta actatcgtag tgttgcacct gctaatccgg ctaacgtatt tgcacctaat     600
gtcgacctac cagtttatag ccgggctta gggacccatt ttctcccggg aggaatggat      660
tctgaaagtc gttttgttaa ggctactttc actaagatgc atgccccagt tggtaattct     720
gaggttgaga atattaccaa ctatttccac attcttcaat ctgtcgaaca acaaaagggt     780
ttggatgaag tagcaccgaa tacttttgaa tatacgattt attctgatgg ttcgaaccta     840
```

-continued

```
aagaaaggga ttttttacta caagacttac gaaaacagtc aaattaatgc agttgatatg    900
cataaggaag atcttgaagc atcagaatta attacctatc cagttcaaaa taaacaaata    960
attaaccaac aaaattaa                                                  978
```

1

COMPOSITIONS AND METHODS FOR
MODULATING THE GASTROINTESTINAL
TRACT USING BILE SALT HYDROLASES

CROSS REFERENCE TO RELATED
APPLICATIONS

This application claims priority to and the benefit of U.S.
Provisional Patent Application No. 62/844,518 filed May 7,
2019, which is incorporated herein by reference in its
entirety for all purposes.

INCORPORATION-BY-REFERENCE OF
MATERIAL SUBMITTED ELECTRONICALLY

Incorporated by reference in its entirety herein is a com-
puter-readable nucleotide/amino acid sequence listing sub-
mitted concurrently herewith and identified as follows: One
237 Kilobyte ASCII (Text) file named "37733-601 ST25"
created on May 7, 2020.

FIELD

The present disclosure provides compositions and meth-
ods related to modulating the gastrointestinal tract. In par-
ticular, the present disclosure provides a novel therapeutic
strategy for selective modulation of the gut microbiota bile
acid pool using bile salt hydrolases (BSHs) for the preven-
tion and treatment of diseases such as obesity, diabetes,
Inflammatory bowel disease (IBD), liver and colon cancer,
and *Clostridioides difficile* infections, among others.

BACKGROUND

Bile salts, also referred to as bile acids, play critical roles
in the human gastrointestinal tract, as influencers and modu-
lators of the microbial composition throughout the gut. In
some cases, various types of bile salts (conjugated, or not)
comprise the bile salt intestinal pool and this mixed com-
position influences the genera, species and strains content of
the large intestine microbiome. Consequently, several gut
health attributes are directly and indirectly impacted by the
bile salt composition in the human gut. For example, certain
bile salts can foster the development of disease (e.g.,
*Clostridium difficile* infection) and others can prevent the
onset or persistence of pathogens. Thus, there is a need to
define functionally important and impactful bile salt hydro-
lases (BSHs) that directly alter and modulate the bile acid
pool in vivo and shift the composition of the gut microbiome
positively to direct and further promote human health.

SUMMARY

Embodiments of the present disclosure include an engi-
neered bacterial cell comprising a heterologous gene encod-
ing a functional bile salt hydrolase derived from *Lactoba-
cillus*. In accordance with these embodiments, the
heterologous gene encoding the bile salt hydrolase com-
prises at least one mutation resulting in at least one amino
acid substitution.

In some embodiments, the at least one mutation resulting
in the at least one amino acid substitution alters bile acid
substrate specificity of the functional bile salt hydrolase. In
some embodiments, the bile salt substrate is selected from
the group consisting of GCDCA, GCA, TCA, TCDCA,
TLCA, TDCA, TUDCA, GLCA, GDCA, GUDCA, FCA,
FCDCA, FLCA, FDCA, FUDCA, LCA, LCDCA, LLCA,

2

LDCA, LUDCA, YCA, YCDCA, YLCA, YDCA, YUDCA,
and combinations thereof. In some embodiments, the bile
acid substrate is GCA, TCA, or TCDCA. In some embodi-
ments, the at least one amino acid substitution comprises at
least one substitution present in the following peptide
motifs: GQD, IPA, and/or AMI.

In some embodiments, a polypeptide encoded by the
heterologous bile salt hydrolase gene comprises at least 90%
identity to a wild type bile salt hydrolase polypeptide
selected from the group consisting of SEQ ID NOs: 1, 3, 5,
7, 9, 11, 13, 15, 17, 19, 21, 23, 25, 27, 29, 31, 33, 35, 37, 39,
41, 43, 45, 47, 49, 51, 53, 55, 57, 59, 61, 63, 65, 67, 69, 71,
73, 75, 77, 79, 81, 83, 85, 87, 89, 91, 93, 95, 97, 99, 101, 103,
105, 107, 109, 111, and 113. In some embodiments, a
polypeptide encoded by the heterologous bile salt hydrolase
gene comprises at least 95% identity to a wild type bile salt
hydrolase polypeptide selected from the group consisting of
SEQ ID NOs: 1, 3, 5, 7, 9, 11, 13, 15, 17, 19, 21, 23, 25, 27,
29, 31, 33, 35, 37, 39, 41, 43, 45, 47, 49, 51, 53, 55, 57, 59,
61, 63, 65, 67, 69, 71, 73, 75, 77, 79, 81, 83, 85, 87, 89, 91,
93, 95, 97, 99, 101, 103, 105, 107, 109, 111, and 113.

In some embodiments, a polypeptide encoded by the
heterologous bile salt hydrolase gene comprises at least 90%
identity to a wild type bile salt hydrolase polypeptide
selected from the group consisting of SEQ ID NOs: 1, 3, 23,
25, 27, 29, 41, 43, 51, 61, 69, 71, 73, 85, 93, 97, 103, and
113. In some embodiments, a polypeptide encoded by the
heterologous bile salt hydrolase gene comprises at least 95%
identity to a wild type bile salt hydrolase polypeptide
selected from the group consisting of SEQ ID NOs: 1, 3, 23,
25, 27, 29, 41, 43, 51, 61, 69, 71, 73, 85, 93, 97, 103, and
113.

In some embodiments, the cell is selected from one of the
following genera: *Bacillus, Bacteroides, Bifidobacterium,
Brevibacteria, Clostridium, Enterococcus, Escherichia coli,
Lactobacillus, Lactococcus, Saccharomyces, Staphylococ-
cus* and *Streptococcus*. In some embodiments, the cell is
selected from one of the following species: *Bacillus coagu-
lans, Bacillus subtilis, Bacteroides fragilis, Bacteroides sub-
tilis, Bacteroides thetaiotaomicron, Bifidobacterium bifi-
dum, Bifidobacterium infantis, Bifidobacterium lactis,
Bifidobacterium longum, Clostridium butyricum, Enterococ-
cus faecium, Escherichia coli, Escherichia coli* Nissle, *Lac-
tobacillus acidophilus, Lactobacillus bulgaricus, Lactoba-
cillus casei, Lactobacillus crispatus, Lactobacillus gasseri,
Lactobacillus johnsonii, Lactobacillus paracasei, Lactoba-
cillus plantarum, Lactobacillus reuteri, Lactobacillus rham-
nosus, Lactobacillus salivarius Lactobacillus fermentum,
Lactobacillus delbrueckii, Lactococcus lactis*, and *Saccha-
romyces boulardii*.

In some embodiments, the cell is selected from one of the
following strains: *L. acidophilus* NCFM, *L. acidophilus*
La-14, *L. casei* Lc11, *L. crispatus* NCK 1350, *L. crispatus*
NCK 1351, *L. crispatus* DNH-429, *L. gasseri* ATCC 33323,
*L. gasseri* NCK 1338, *L. gasseri* NCK 1340, *L. gasseri* NCK
1341, *L. gasseri* NCK 1342, *L. gasseri* NCK 1343, *L.
gasseri* Lg-36, *L. gasseri* NCK2140, *L. gasseri* NCK2141,
*L. gasseri* JV V03, *L. plantarum* Lp-115, *L. johnsonii*
NCK948, *L. johnsonii* NCK957, *L. johnsonii* NCK964, *L.
johnsonii* NCK979, *L. johnsonii* NCK1370, *L. johnsonii*
NCK2677, *L. johnsonii* NCC 533 *L. plantarum* Lpc-37, *L.
plantarum* Lp115, *L. rhamnosus* HN001, *L. rhamnosus* GG,
*L. rhamnosus* Lr-32, *L. reuteri* 1E1, *L. salivarius* Ls-33, *L.
salivarius* NCK1352, *L. salivarius* NCK1355, *B. lactis*
BL-04, *B. lactis* Bb-02, *B. lactis* Bl-04, *B. lactis* Bi-07, *B.
breve* Bb-03, *B. bifidum* Bb-06, *B. longum* Bl-05, *B. longum
sp infantis* Bi-26, or any combination thereof.

In some embodiments, the cell improves at least one physiological parameter associated with a disease or condition when administered to a subject in need thereof as part of a therapeutic composition. In some embodiments, the disease or condition is associated with bile acid dysregulation. In some embodiments, the disease or condition is selected from the group consisting of cardiovascular disease, metabolic disease, liver disease, cirrhosis, cancer, obesity, diabetes, Inflammatory Bowel Disease (IBD), antibiotic associated diarrhea, Nonalcoholic fatty liver disease (NAFLD), Nonalcoholic steatohepatitis (NASH), and *Clostridioides difficile* infections. In some embodiments, the disease or condition is associated with a *Clostridioides difficile* infection, and wherein administering the therapeutic composition treats the *Clostridioides difficile* infection.

Embodiments of the present disclosure also include a pharmaceutical composition comprising an engineered bacterial cell comprising a heterologous gene encoding a functional bile salt hydrolase derived from *Lactobacillus*, wherein the heterologous gene encoding the bile salt hydrolase comprises at least one mutation resulting in at least one amino acid substitution, and a pharmaceutically acceptable carrier or excipient. In accordance with these embodiments, administration of the composition improves at least one physiological parameter in a subject.

In some embodiments, the at least one mutation resulting in the at least one amino acid substitution alters bile acid substrate specificity of the functional bile salt hydrolase. In some embodiments, the bile acid substrate is selected from the group consisting of GCDCA, GCA, TCA, TCDCA, TLCA, TDCA, TUDCA, GLCA, GDCA, GUDCA, FCA, FCDCA, FLCA, FDCA, FUDCA, LCA, LCDCA, LLCA, LDCA, LUDCA, YCA, YCDCA, YLCA, YDCA, YUDCA, and combinations thereof. In some embodiments, a polypeptide encoded by the heterologous bile salt hydrolase gene comprises at least 90% identity to a wild type bile salt hydrolase polypeptide selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, and 113. In some embodiments, the cell is selected from one of the following species: *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Escherichia coli Nissle, Lactobacillus acidophilus, Lactobacillus bulgaricus, Lactobacillus casei, Lactobacillus crispatus, Lactobacillus gasseri, Lactobacillus johnsonii, Lactobacillus paracasei, Lactobacillus plantarum, Lactobacillus reuteri, Lactobacillus rhamnosus, Lactobacillus salivarius Lactobacillus fermentum, Lactobacillus delbrueckii, Lactococcus lactis*, and *Saccharomyces boulardii*.

In some embodiments, the administration of the composition to the subject improves at least one physiological parameter associated with a disease or condition. In some embodiments, the disease or condition is associated with bile acid dysregulation. In some embodiments, the disease or condition is selected from the group consisting of cardiovascular disease, metabolic disease, liver disease, cirrhosis, cancer, obesity, diabetes, Inflammatory Bowel Disease (IBD), antibiotic associated diarrhea, Nonalcoholic fatty liver disease (NAFLD), Nonalcoholic steatohepatitis (NASH), and *Clostridioides difficile* infections. In some embodiments, the disease or condition is associated with a

*Clostridioides difficile* infection, and wherein administering the composition treats the *Clostridioides difficile* infection.

Embodiments of the present disclosure also include a method of modulating at least one bile acid in a subject in need thereof. In accordance with these embodiments, the method includes administering a therapeutic composition comprising an engineered bacterial cell comprising a heterologous gene encoding a functional bile salt hydrolase derived from *Lactobacillus*, wherein the heterologous gene encoding the bile salt hydrolase comprises at least one mutation resulting in at least one amino acid substitution that alters bile acid substrate specificity of the functional bile salt hydrolase, and a pharmaceutically acceptable carrier or excipient. In some embodiments, the composition improves at least one physiological parameter in a subject by modulating the at least one bile acid.

BRIEF DESCRIPTION OF THE DRAWINGS

FIG. 3: Mapping BSH proteins to a phylogenetic tree of 170 *Lactobacillus* species (O'Flaherty et al. 2018). The colors of the groups follow those previously described: *Lactobacillus animalis* group is indicated in purple, *Lactobacillus vaginalis* group in green, *Lactobacillus buchneri* group in red, *Lactobacillus rhamnosus* group in yellow, *Lactobacillus acidophilus* group in maroon, and *Lactobacillus* gasseri group in blue. The inner metadata layer maps lifestyle designations as described by Duar et al. (2017). The outer metadata layer maps the presence or absence of BSH and PVA proteins with respect to each of the 170 *Lactobacillus* species.

Figure 4:
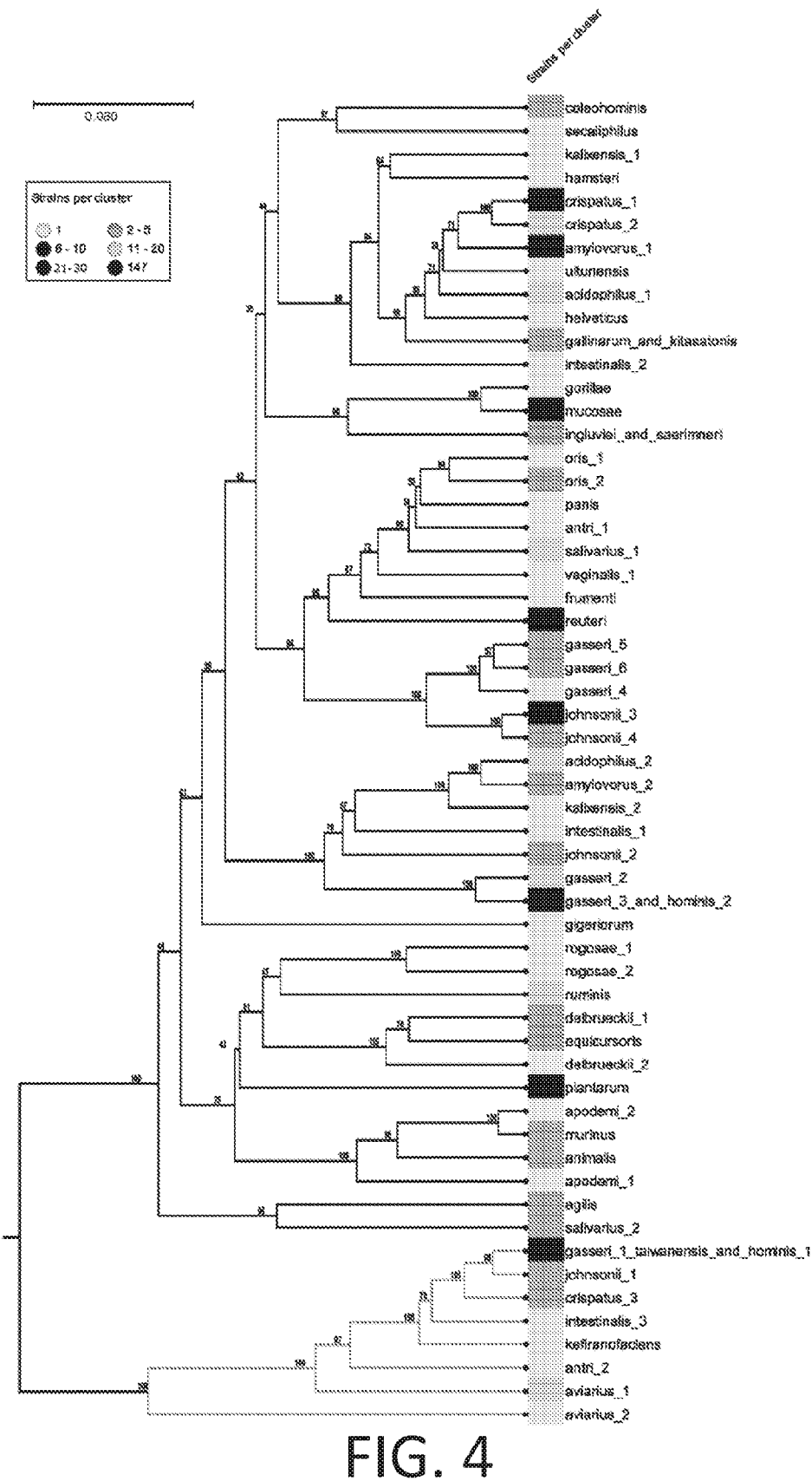

FIG. 4: Sampling of bsh diversity and characterization. Phylogenetic tree of lactobacilli BSHs from 57 CD-HIT clusters, concentrated from 490 BSHs with a 95% identity threshold. The two major clades are shown in black and green. Multiple BSHs can be encoded by a single strain, and some species encode multiple BSHs that belong to several clusters. *L. acidophilus* strains encode 2 BSHs belonging to different clusters (O'Flaherty et al. 2018.

Figures 5A, 5B, 5C:
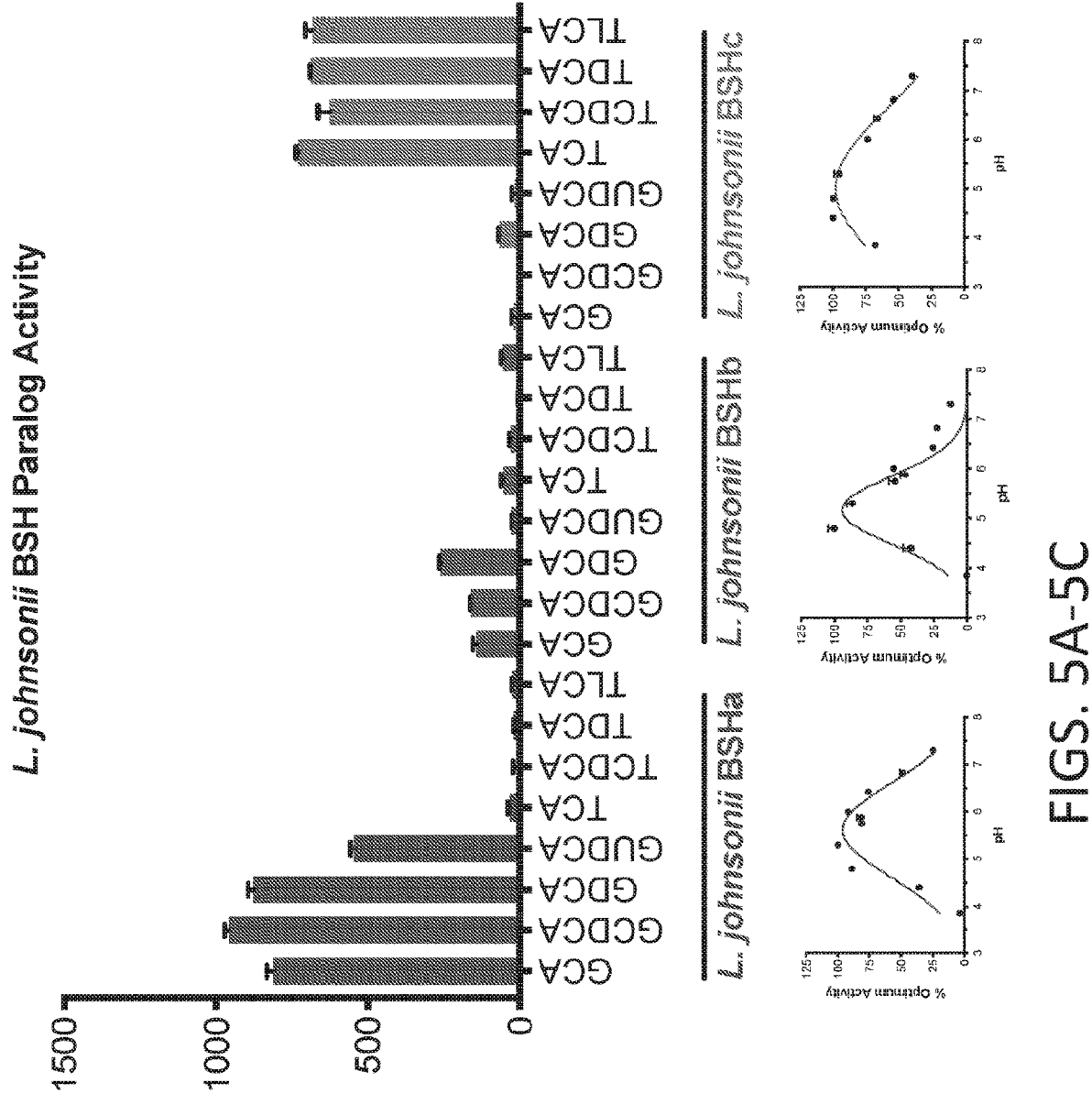
Figures 5A, 5B, 5C:
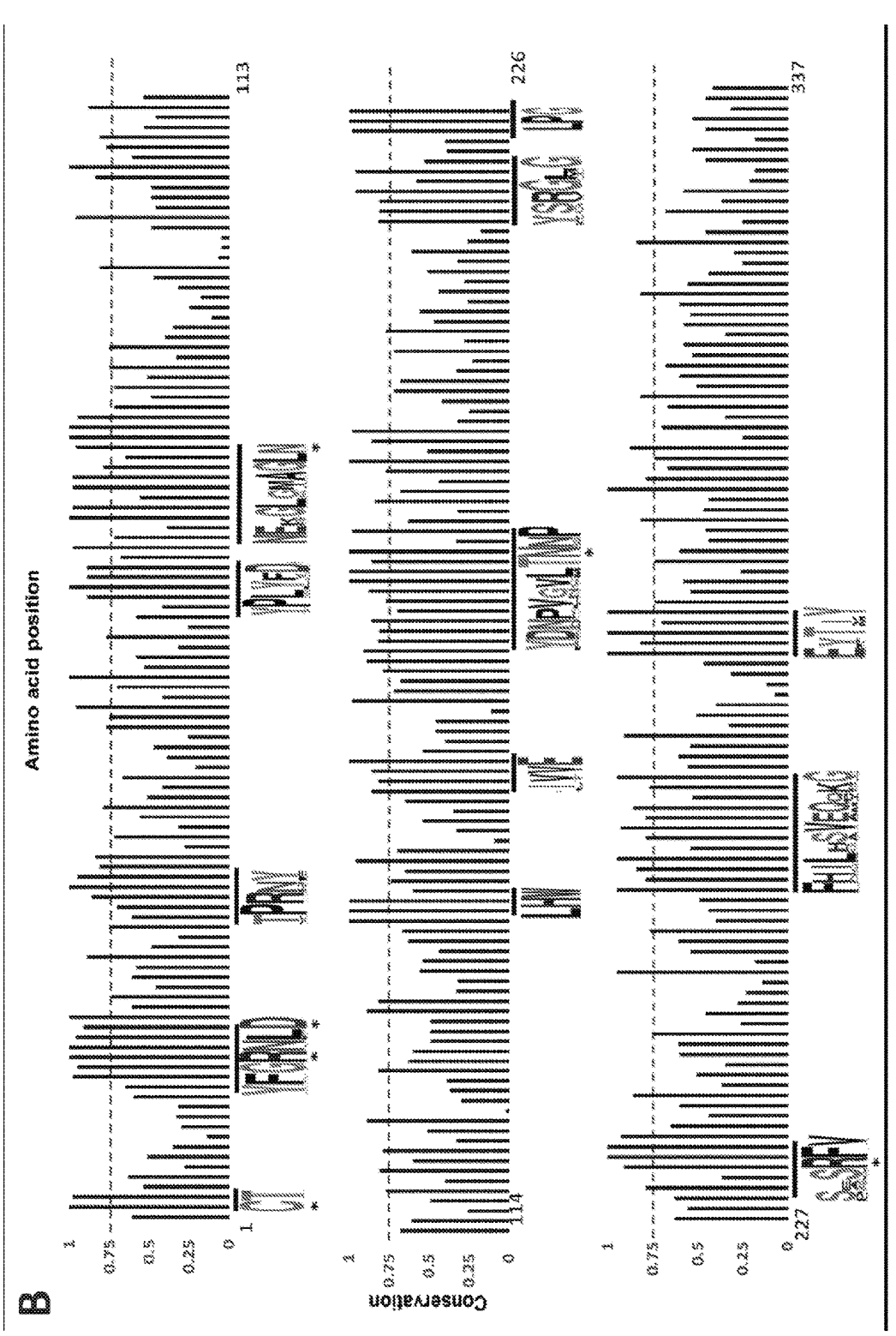
Figures 5A, 5B, 5C:
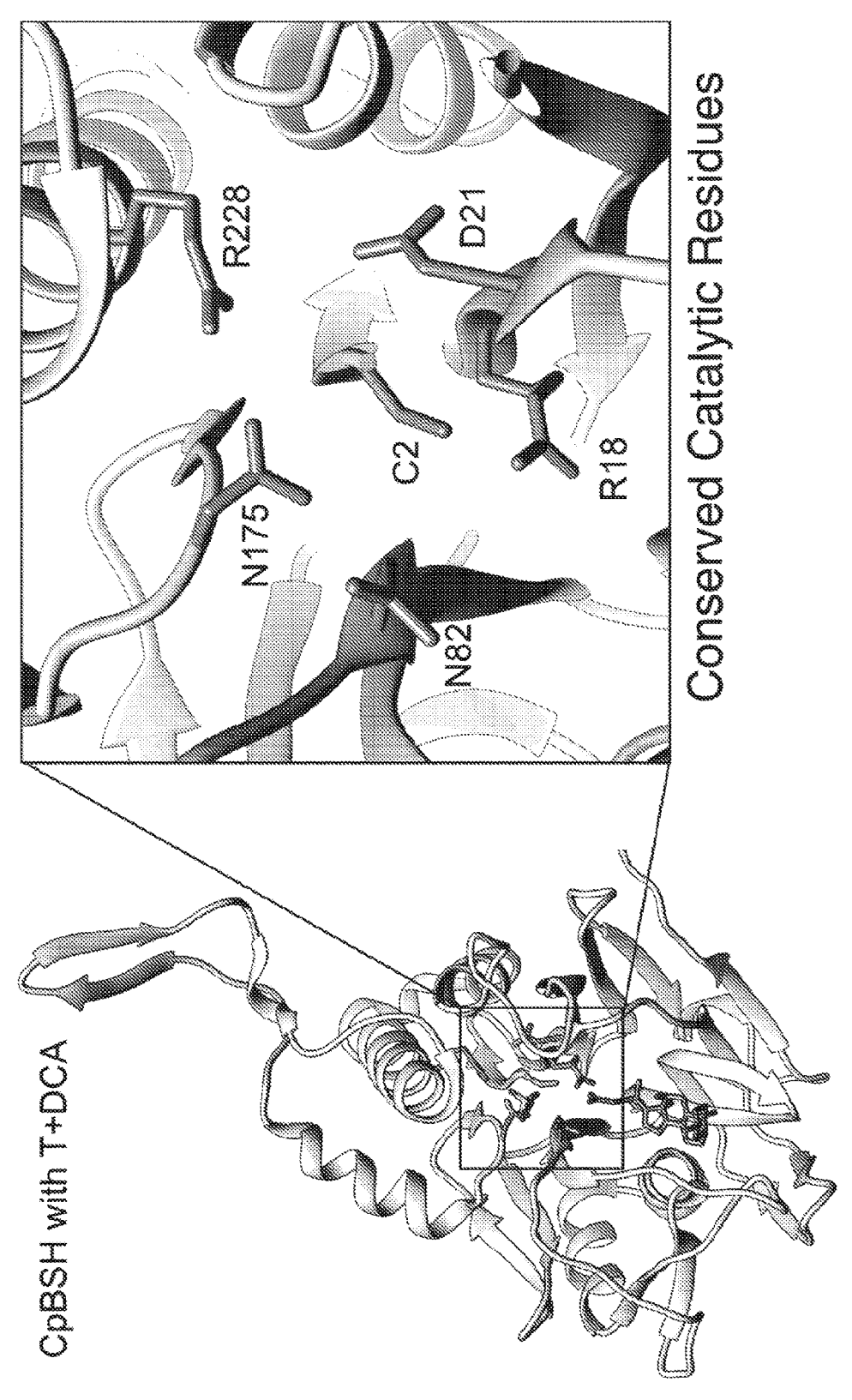

FIGS. 5A-5C: Lactobacilli BSHs display varied preferences for conjugated bile acids. (A) To evaluate BSH activity from model Lactobacilli strain, *L. johnsonii* bshA, bshB and bshC (LjBSHa, LjBSHb, and LjBSHc respectively) were purified and their specific activities and pH optima were determined by the Ninhydrin assay. Enzymes tested displayed different preferences for glyco-conjugated and tauro-conjugated bile acids and acidic conditions. (B) Conservation analysis of the BSH amino acid sequence. The alignment of the representative BSH proteins from the 57 clusters from the clustered data set was analyzed for conserved amino acid motifs. A conservation score of 0.75 or higher is indicated by a dashed line. Motifs and conserved amino acids are indicated by the WebLogo. An asterisk indicates the previously described conserved active-site residues, from O'Flaherty et al., 2018, (C) A close up structural view of the CpBSH active site with hydrolyzed TDCA. Conserved catalytically important residues are highlighted to show their location within the active site pocket.

Figure 6:
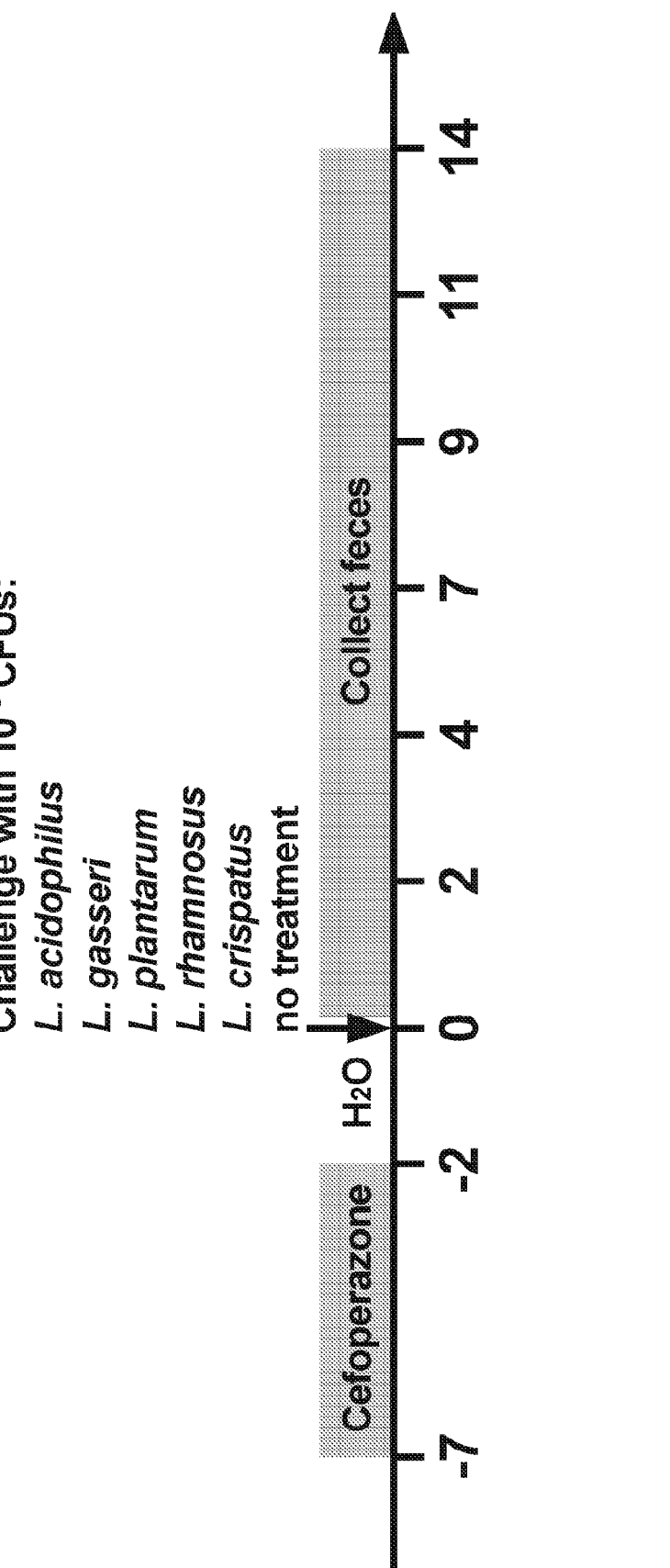
Figures 7A, 7B, 7C, 7D, 7E, 7F:
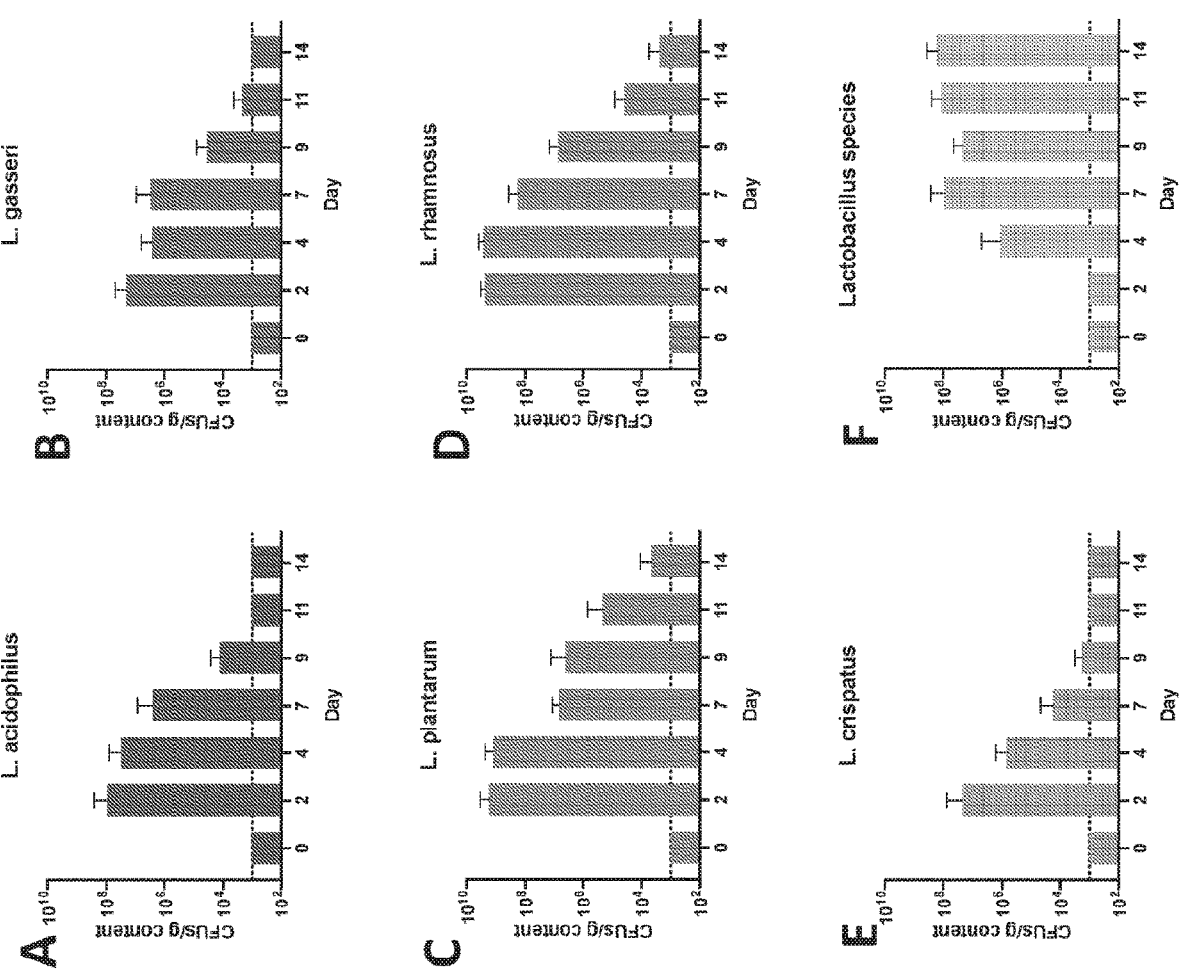

FIG. 6: *Lactobacillus* colonization in the cefoperazone-treated mouse model of CDI. An overview of the experimental timeline. Briefly, mice were treated for 5 days with cefoperazone in their drinking water. Following a 2 day wash out, mice (n=16) were gavaged with $10^9$ CFUs of rifampicin-resistant *Lactobacillus*. Colonization was monitored by plating feces on LBS agar supplemented with 100 μg/mL of rifampicin on the noted days.

FIGS. 7A-7F: *Lactobacillus* bacterial load in an antibiotic treated mouse model. Colonization levels of *Lactobacillus* species over time are displayed by CFUs/g of feces. The dashed line denotes the limit of detection. Indigenous *Lactobacillus* was enumerated on LBS agar lacking rifampicin.

Figures 8A, 8B:
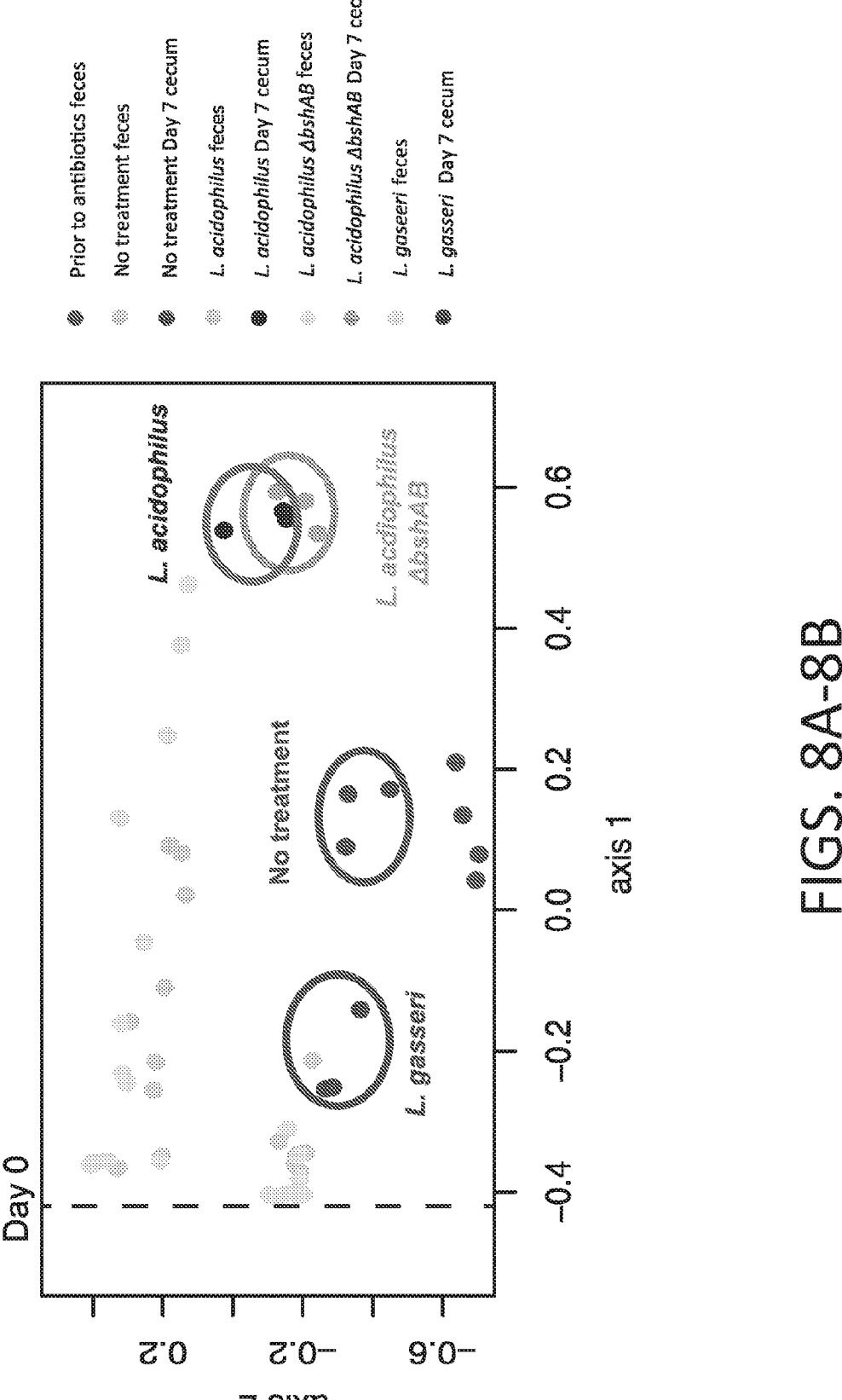
Figures 8A, 8B:
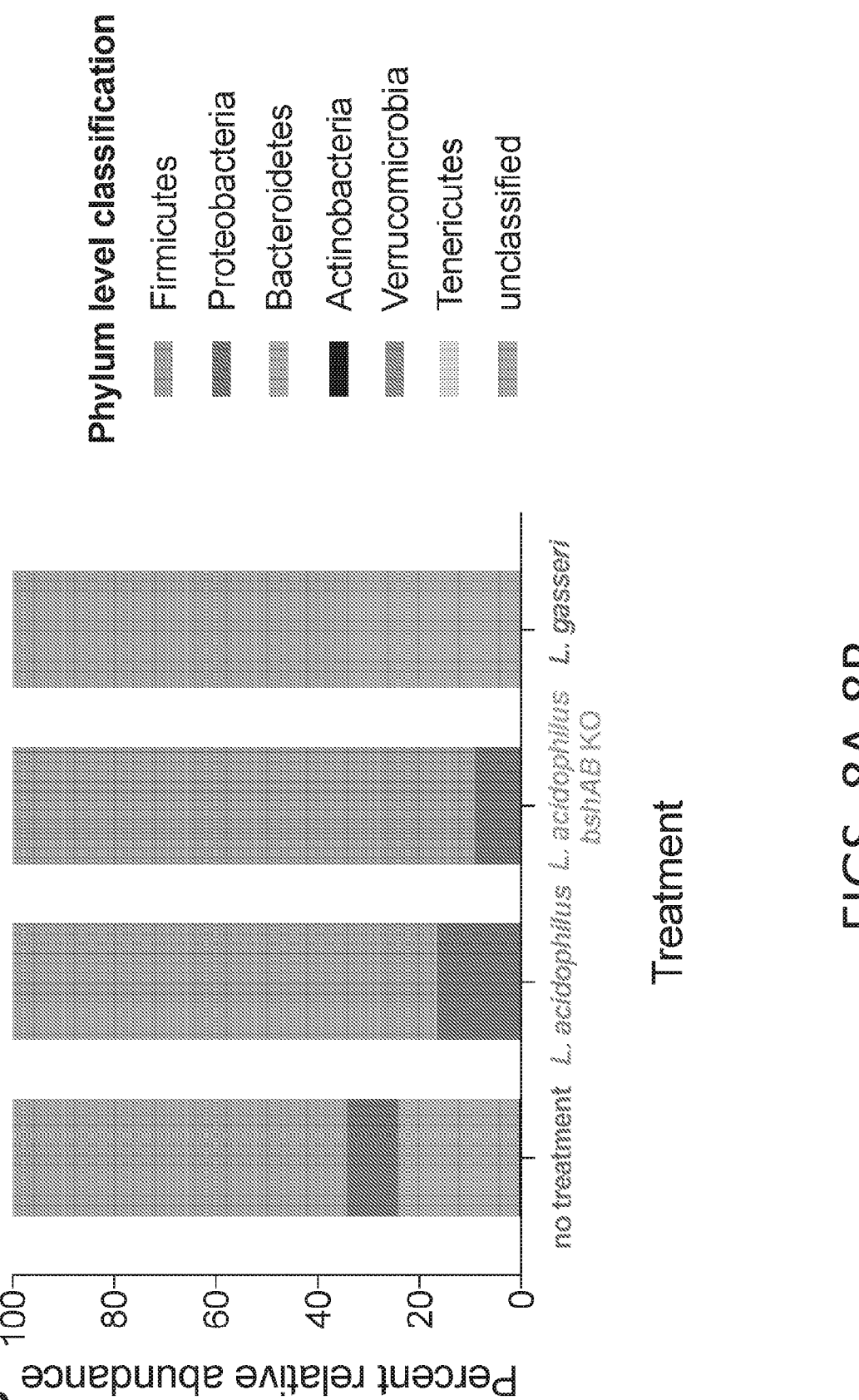

FIGS. 8A-8B: Administration of different *Lactobacillus* strains result in distinct structures of the gut microbiota after 7 days. (A) Sequencing the V4 region of the 16S rRNA gene was used to characterize taxonomic diversity within stool and cecal samples of LAB colonized mice. Nonmetric Multidimensional Scaling ordination based on Bray-Curtis distances was used to visualize β-diversity of the microbiota of LAB treatment groups as the murine microbiota recovers from cefoperazone treatment. Differences in the day 7 cecal communities suggest that LAB colonization alters the assembly of the gut microbiota after antibiotic perturbation. (B) The differences in community structure among LAB-colonized mice were further described by assessing the relative abundance of bacterial phyla in day 7 cecal samples. The Firmicutes, Bacteroidetes, and Proteobacteria dominated the microbiota of mice without LAB treatment. However, *L. acidophilus* colonization suppressed the return of the Bacteroidetes while *L. gasseri* suppressed the return of Proteobacteria.

Figures 9A, 9B, 9C:
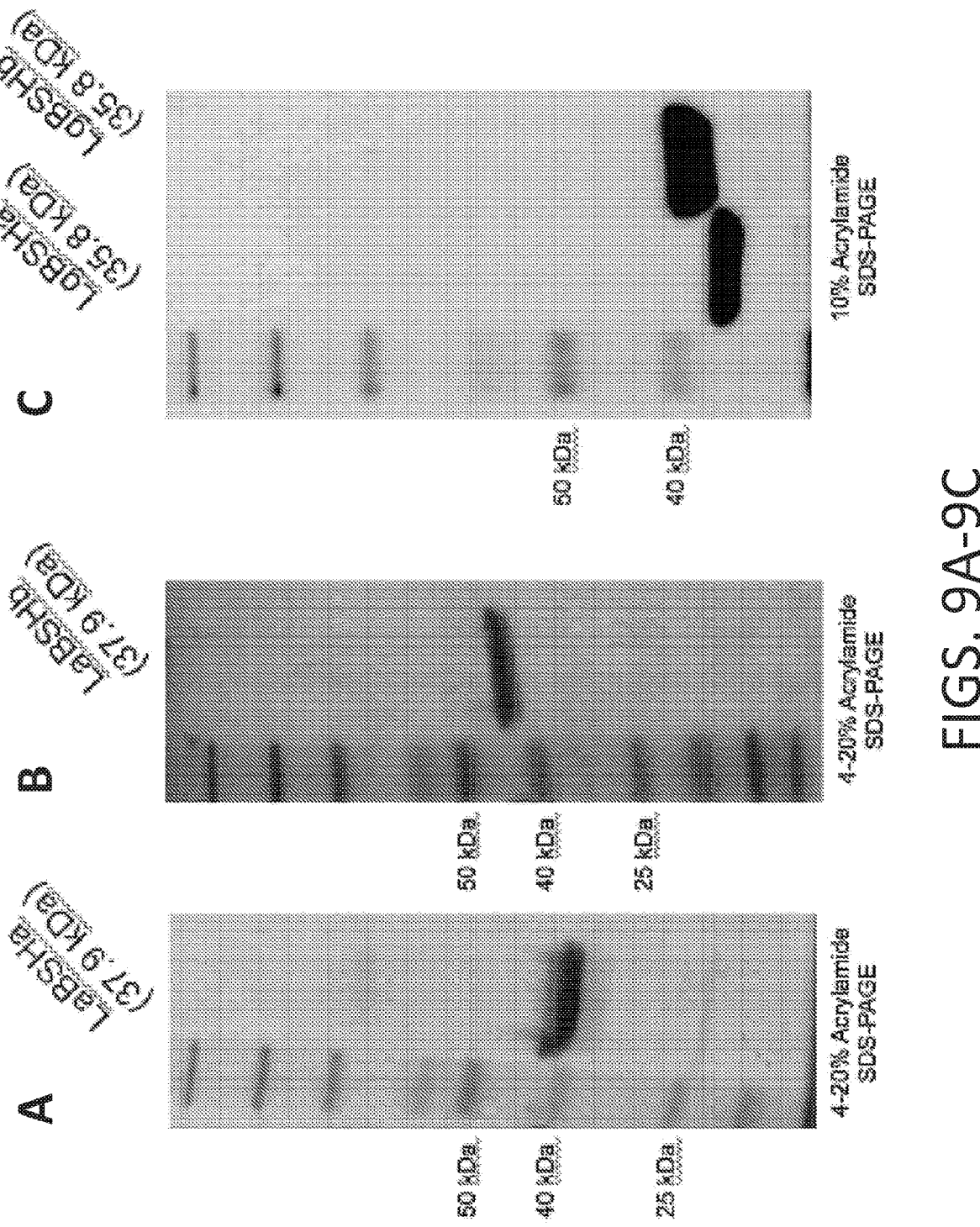
Figures 10A, 10B, 10C, 10D:
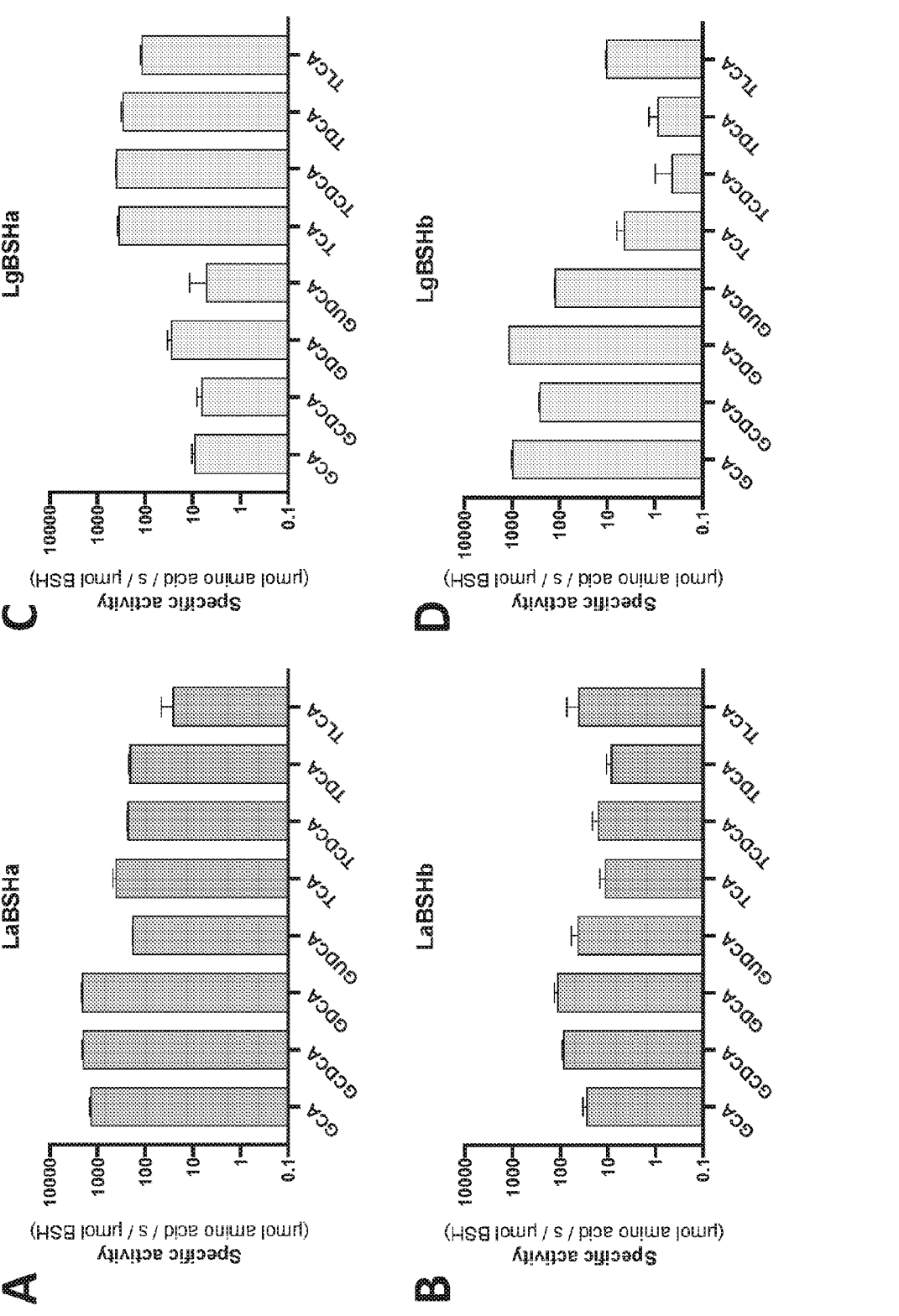

FIGS. 9A-9C: Overexpression and purification of recombinant BSHs from *E. coli*. To further evaluate BSH activity from strains (A, B) *L. acidophilus* NCFM (LaBSHa and LaBSHb) and (C) *L. gasseri* ATCC 33323 BSHs (LgBSHa and LgBSHb) were expressed recombinantly in *Escherichia*

6

*coli* strain BL21 (λDE3) and purified using a C terminal His-tag purification with a Cobalt column. Purified BSH proteins are visualized on SDS-PAGE with protein molecular masses, protein ladder standards, and gel.

FIGS. 10A-10D: *Lactobacillus* BSHs display variable preferences for bile acid conjugation. Average specific activities from recombinantly expressed and purified (A) LaBSHa, (B) LaBSHb, (C) LgBSHa, and (D) LgBSHb were determined by the ninhydrin assay on a panel of conjugated bile acids. Error bars represent s.d. from n=3 independent experiments.

FIGS. 11A-11D: Purified BSHs and their pH optima. (A) LaBSHa, (B) LaBSHb, (C) LgBSHa, and (D) LgBSHb specific activities across a range of pH conditions with respective preferred substrates.

Figure 12:
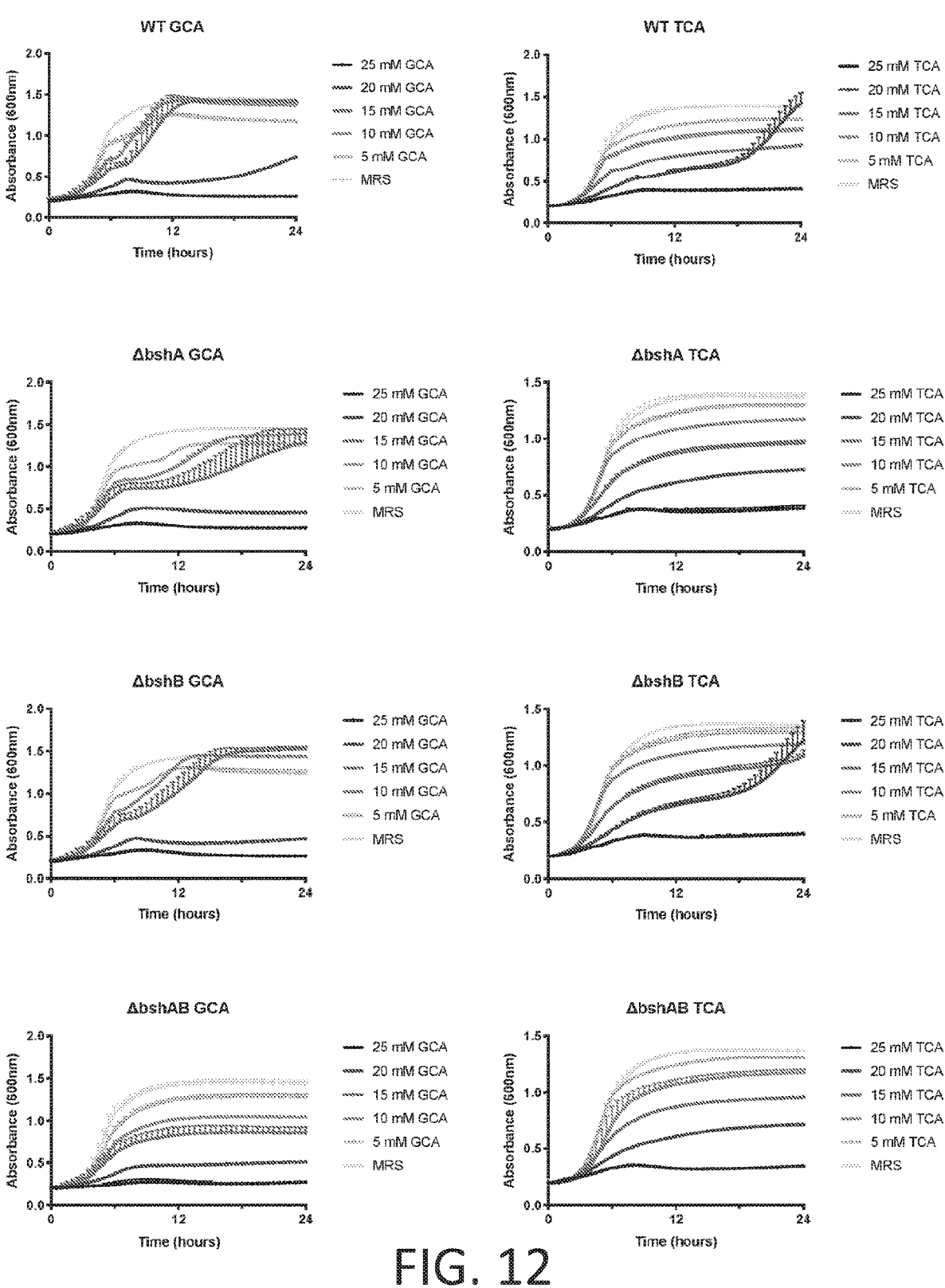
Figure 12:
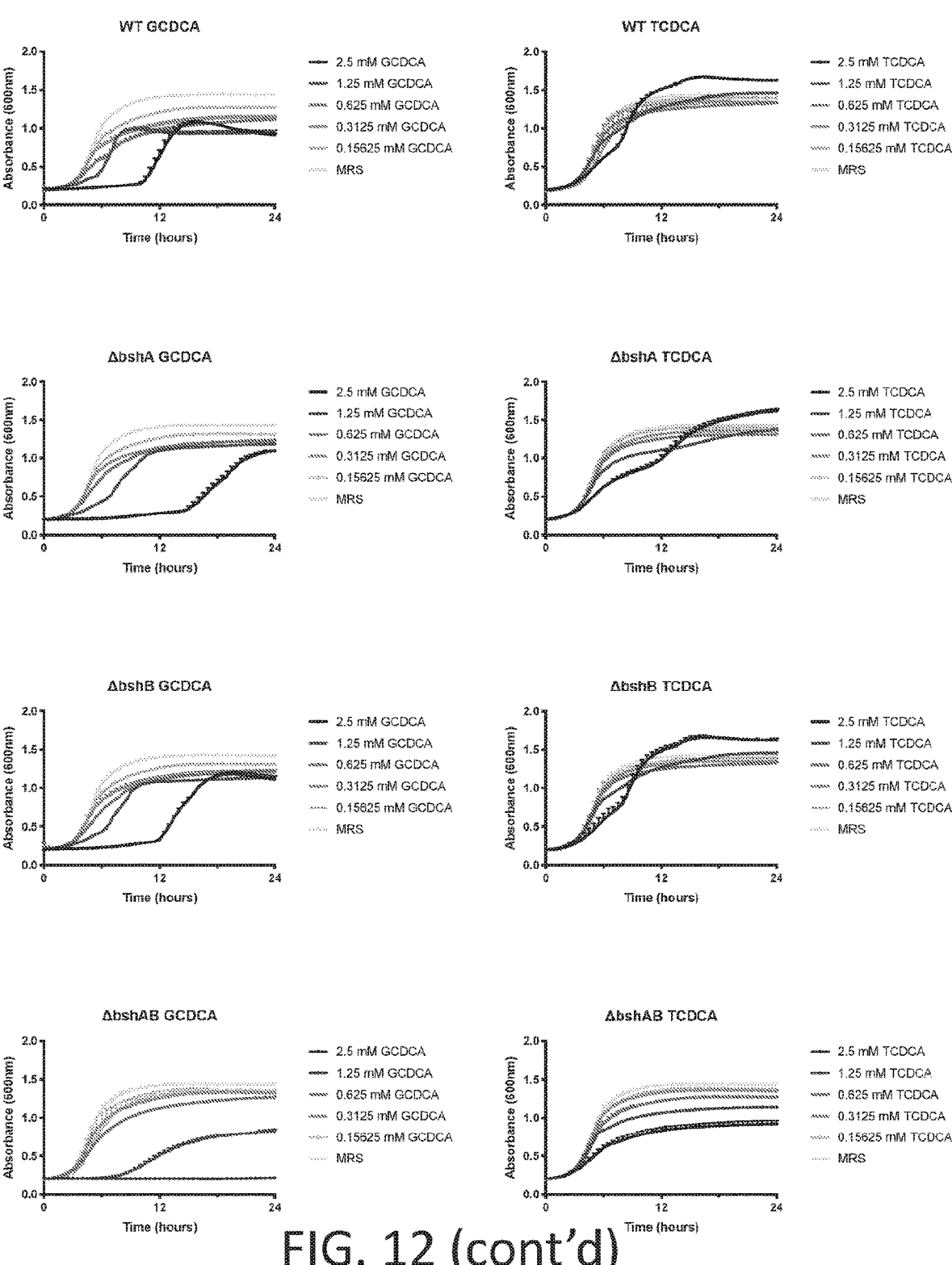
Figure 12:
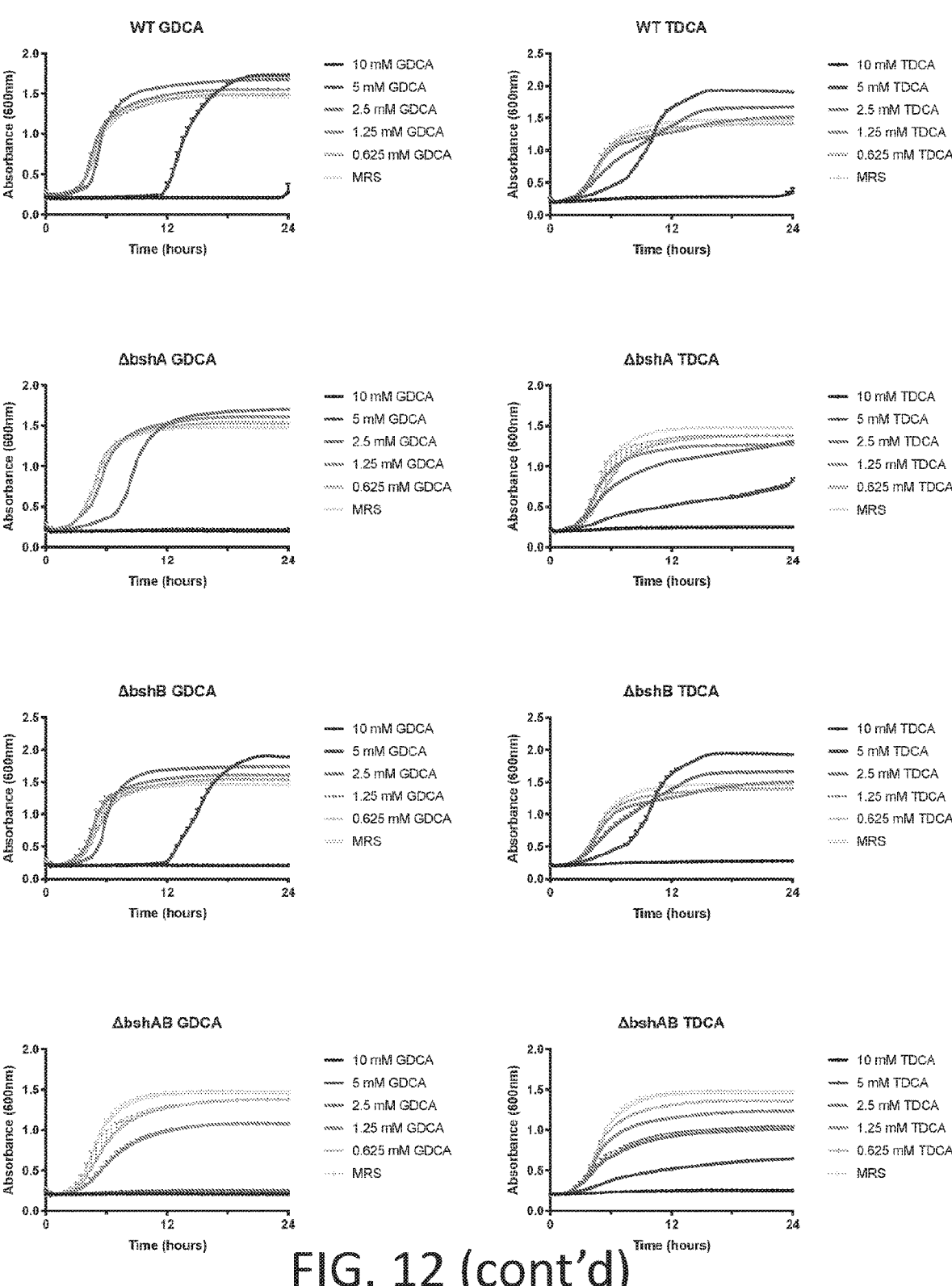

FIG. 12: *L. acidophilus* bshA and bshB contribute to bile acid detoxification in a substrate dependent manner. Growth of BSH mutants in the presence of bile acids. To evaluate the role of BSH activity during *L. acidophilus* growth, single and double BSH mutants were grown in MRS media supplemented with bile acids and growth was measured by OD600 nm.

FIGS. 13A-13G: *L. acidophilus* bshA and bshB contribute to bile acid detoxification in a substrate and concentration dependent manner. Growth of *L. acidophilus* bsh mutants in the presence of bile acids was evaluated by measuring OD600 nm in (A) MRS media alone and supplemented with bile acids (B) GCA, (C) TCA, (D) GCDCA, (E) TCDCA, (F) GDCA, and (G) TDCA. Endpoint CFUs for each growth are displayed in FIG. 17A.

Figure 14:
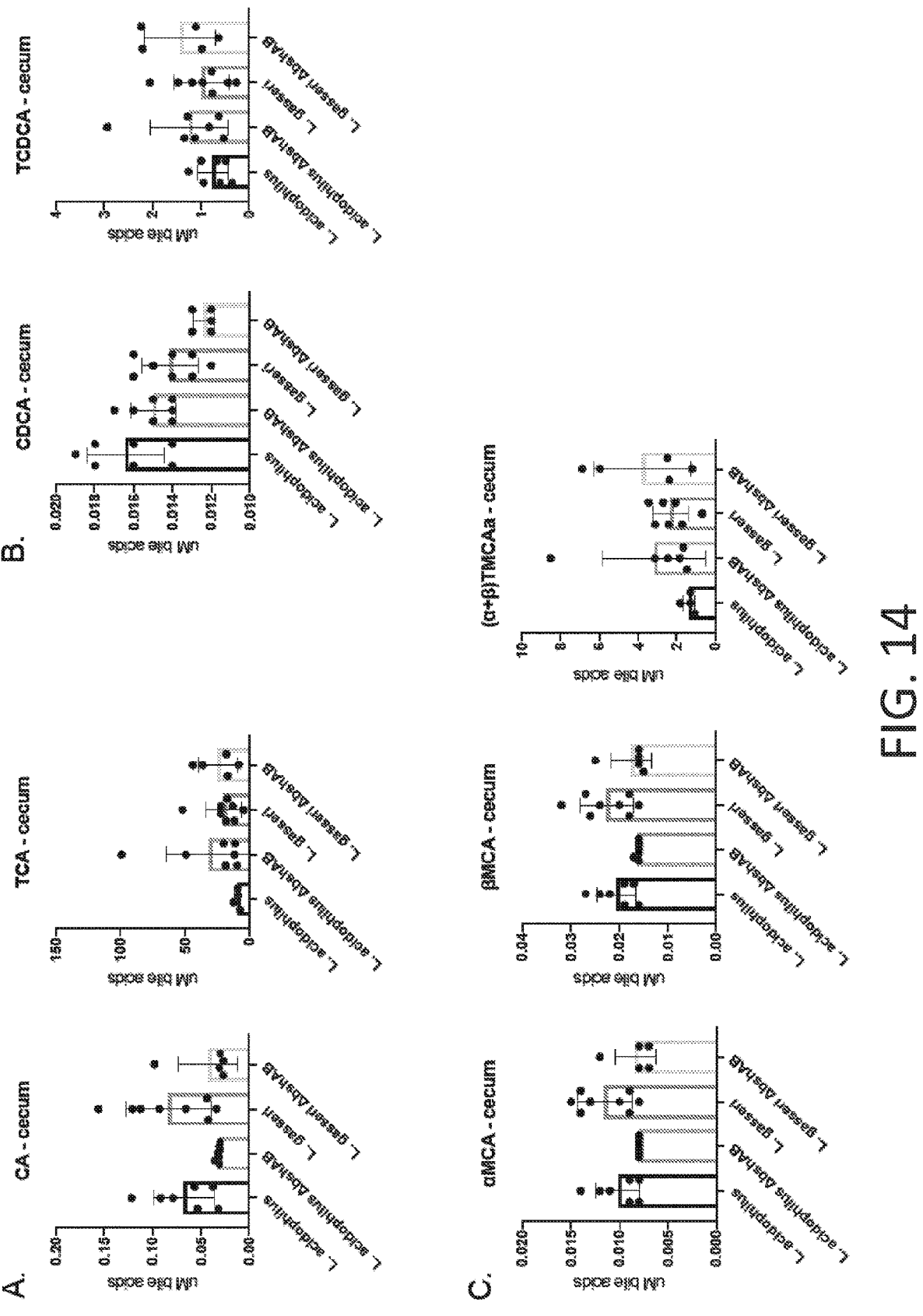

FIG. 14: *L. acidophilus* and *L. gasseri* germ free C57BL/6 mouse colonization marginally increases cecal deconjugated bile acids. The primary bile acids (A) CA, (B) CDCA, and (C) α/βMCA were quantified by targeted metabolomics performed on cecal samples.

Figures 15A, 15B, 15C:
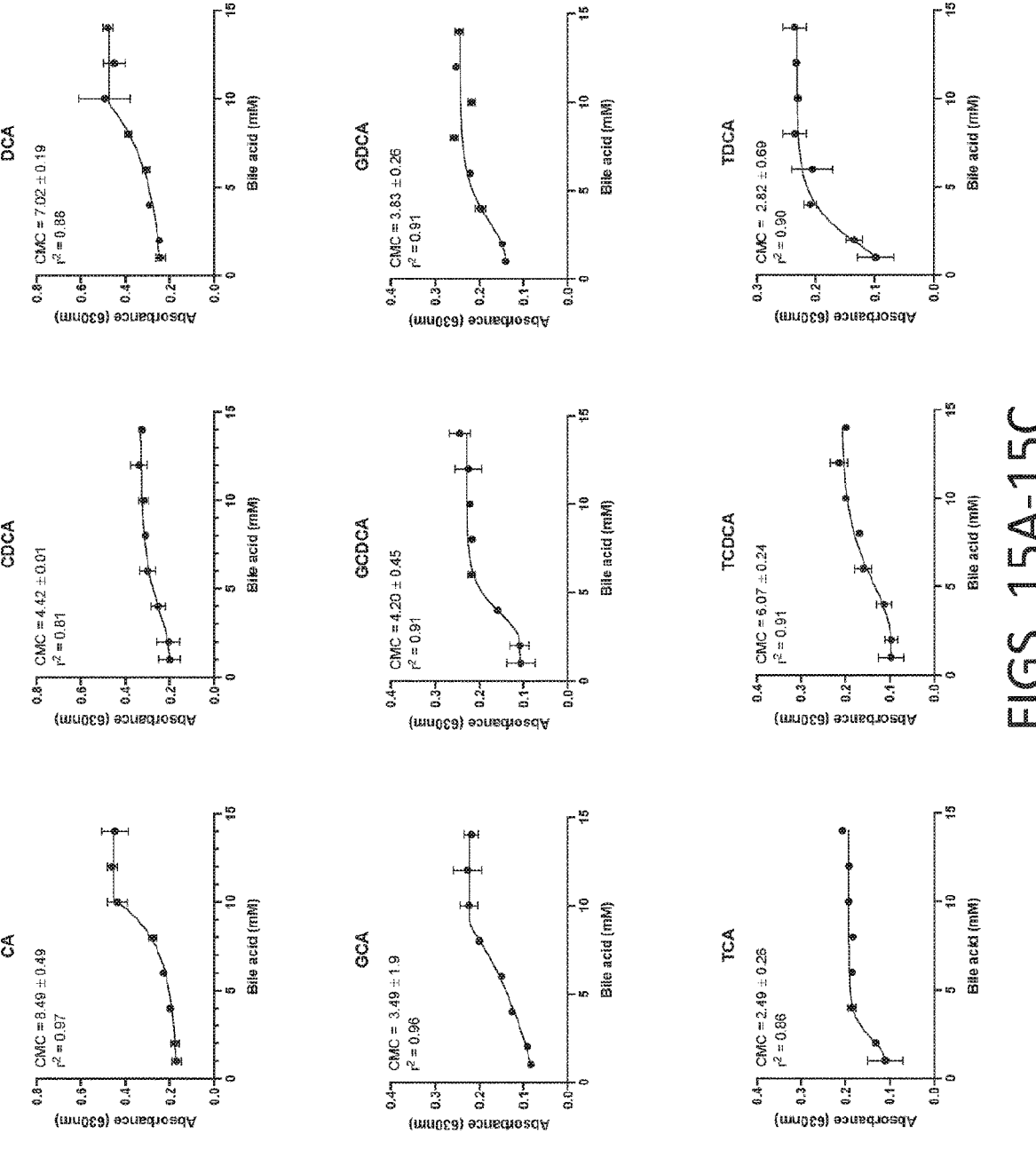

FIGS. 15A-15C: Bile acid structures and their critical micelle concentrations (CMCs). (A) Bile acid structures and abbreviations used in the present disclosure. (B) Bile acid critical micelle concentrations (CMC) experimentally determined herein. Bars represent mean CMC±s.e.m from n=2 independent experiments. (C) CMCs were determined using Optimizer-BlueBALLS. Absorbance data from two independent experiments was plotted against bile acid concentrations for each molecule. A standard five-parameter logistic curve fit was performed using Graphpad Prism, and the CMC was determined by calculating the inflection point of each curve represented by the $Log_{10}$ EC50. Inflection point values represent mean±s.e.m.

Figures 16A, 16B:
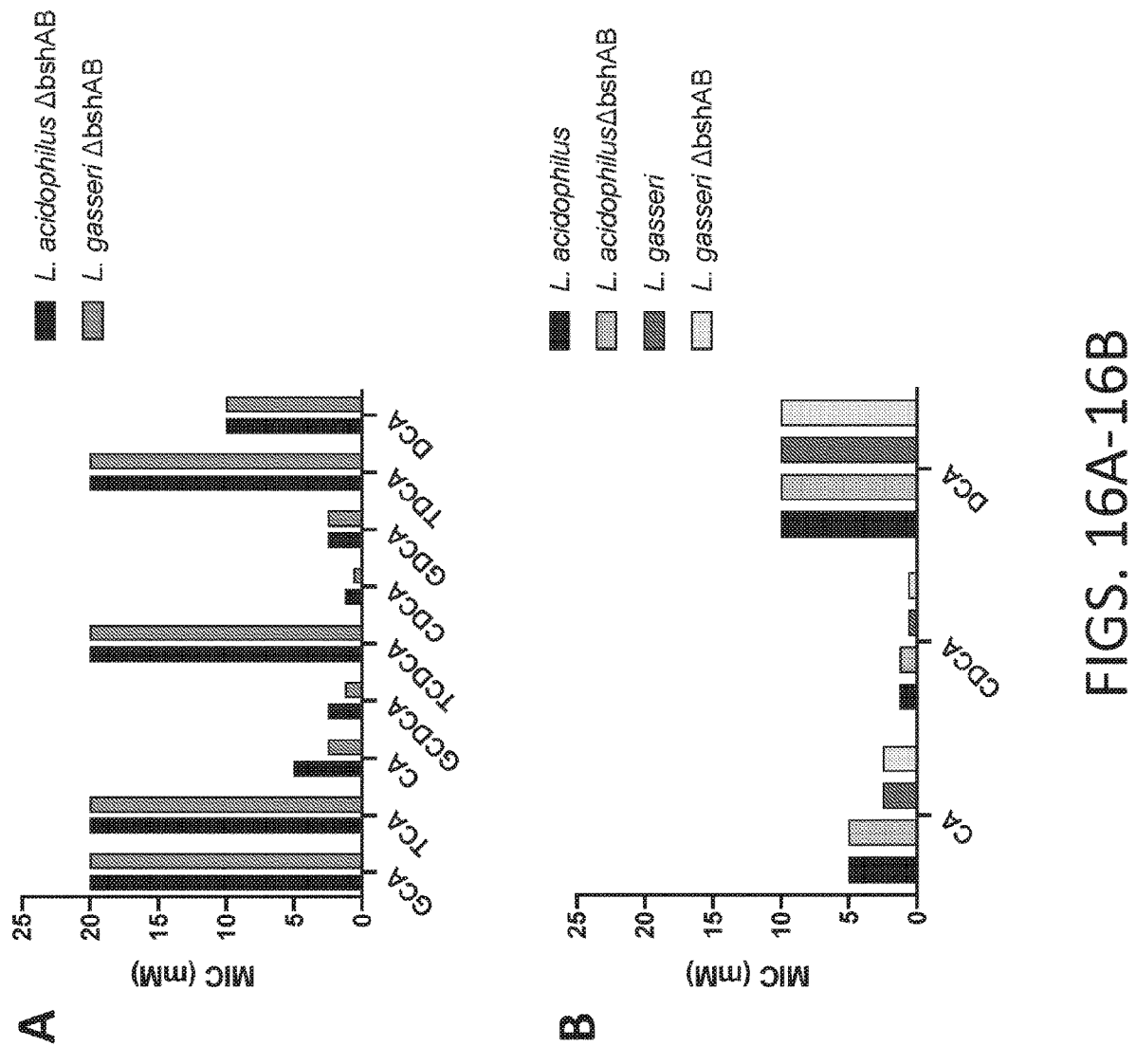

FIGS. 16A-16B: Wild type and ΔbshAB deconjugated bile acid minimum inhibitory concentrations (MICs). (A) BSH null *L. acidophilus* and *L. gasseri* (ΔbshAB) strains were used to determine conjugated and deconjugated bile acid MICs. (B) Wild type and ΔbshAB MICs of deconjugated bile acids only. Bars represent mean MICs from n=3 independent experiments.

Figures 17A, 17B:
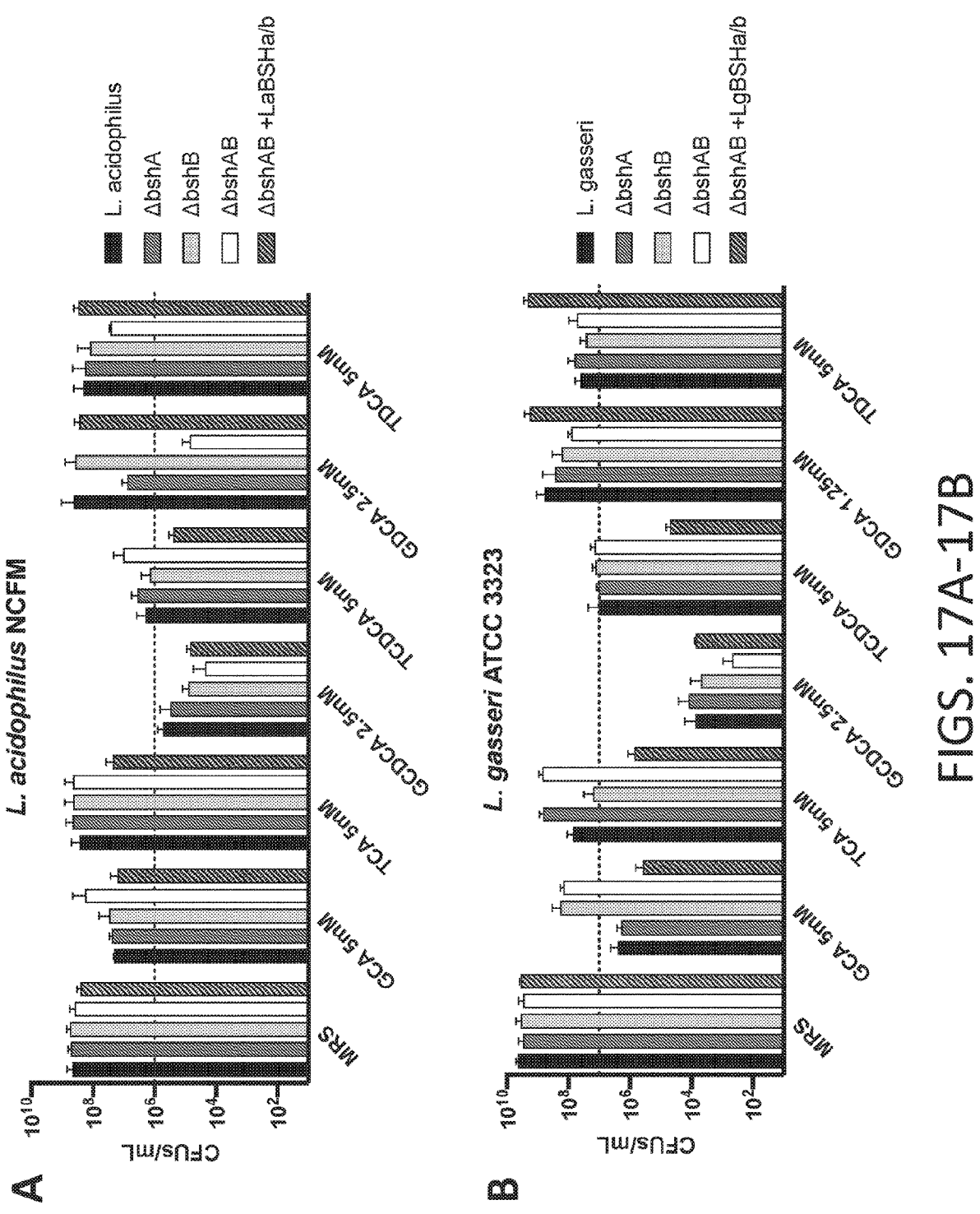

FIGS. 17A-17B: BSHs impact *Lactobacillus* fitness in a BSH and bile acid specific-manner. (A) *L. acidophilus* and (B) *L. gasseri* BSH mutants grown for 24 h in MRS, GCA, TCA, GCDCA, TCDCA, GDCA, of TDCA. Error bars represent standard deviation (s.d.) from n=4 independent experiments. Dashed lined denotes the approximate starting CFUs/mL at 0 h. Exogenous recombinant LaBSHa and LaBSHb (LaBSHab) or LgBSHa and LgBSHb (LgBSHab) were supplemented to cultures in equimolar amounts to (A) *L. acidophilus* ΔbshAB or (B) *L. gasseri* ΔbshAB growths to functionally complement ΔbshAB strains.

FIGS. 18A-18D: BSH activity alters membrane integrity and competitive dynamics in a bile acid specific manner. (A, B) Propidium iodide (PI) staining to assess membrane integrity of mid-log grown *Lactobacillus* exposed to various bile acids or heat killed (HK). Normalized fluorescence was calculated by subtracting background PI fluorescence and normalizing to the starting OD600 at bile acid exposure. Bars represent average fluorescence from n=3 independent experiments and error bars represent s.d. (C, D) Competitive indexes for *Lactobacillus* co-cultures anaerobically for 24 h in the presence of various bile acids. Competitive indexes (CI) were calculated as follows: $CI=Final[Log_{10}(\Delta bshAB\ CFUs)/Log_{10}(wild\ type\ CFUs)]/Initial[Log_{10}(\Delta bshAB\ CFUs)/Log_{10}(wild\ type\ CFUs)]$. Equimolar LaBSHa and LaBSHb (LaBSHab) or LgBSHa and LgBSHb (LgBSHab) were added to cultures at 0 h. Dashed lines denotes a CI=0.

Figures 19A, 19B, 19C:
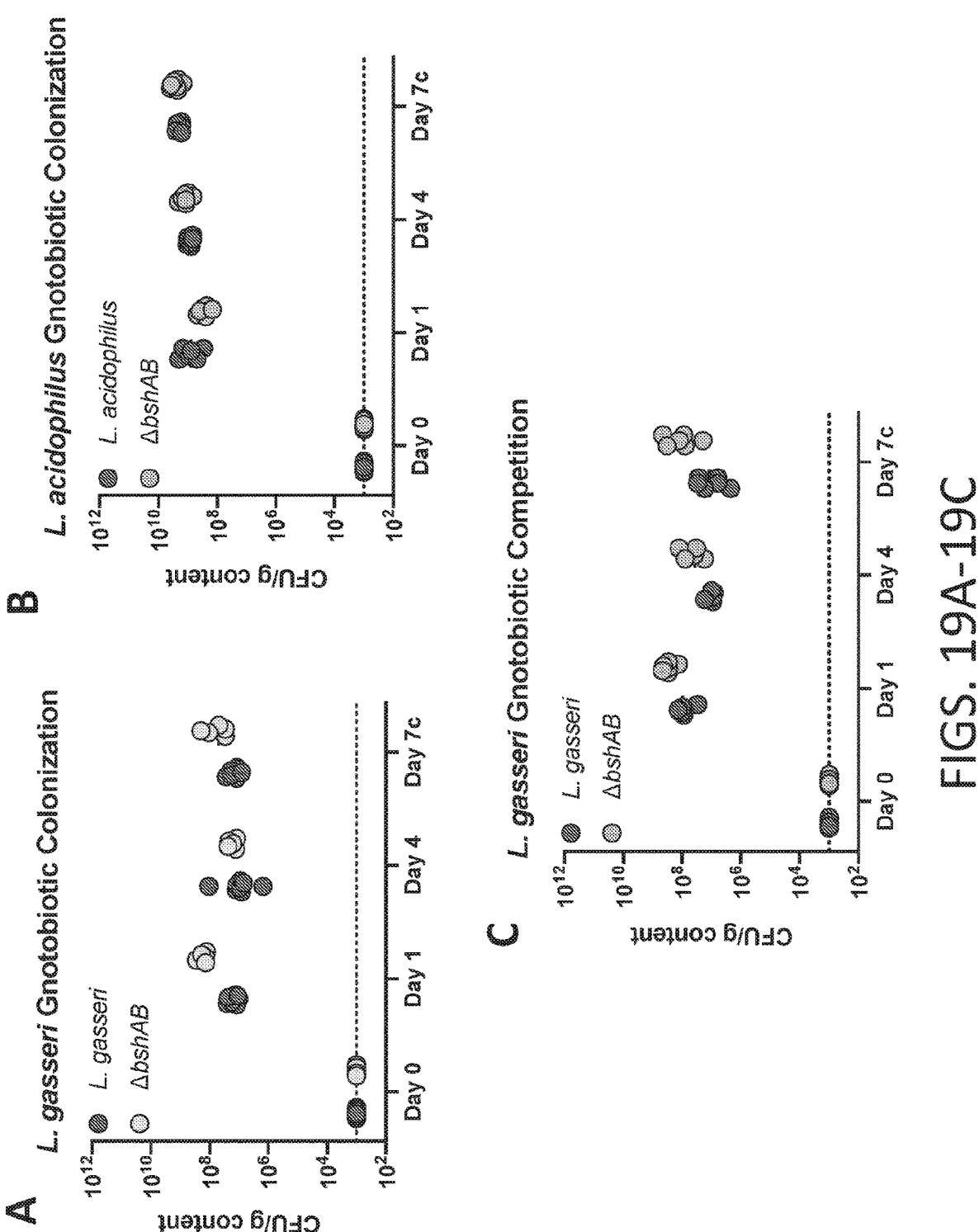

FIGS. 19A-19C: Gnotobiotic mouse colonization is altered by BSH activity in a strain-dependent manner. (A) *L. acidophilus* and (B) *L. gasseri* mono-colonization of germfree 5-8 week old C57BL/6 mice. Feces were collected at days 0, 1 and 4 and mice were sacrificed at day 7 and their ceca were plated (day 7c). (C) *L. gasseri* co-colonization using wild-type (RifR) and ΔbshAB (StrR) strains. Dashed lined denotes the limit of detection.

FIGS. 20A-20B: BSH specificity displays an evolutionary relationship. (A) Recombinantly expressed and purified LAB BSHs were assayed for deconjugation against a panel of glycine and taurine conjugated bile acids. Specific activities for each BSH were determined by quantifying the rate of amino acid release by Ninhydrin assay. A phylogenetic tree based on the primary amino acid sequence of each BSH was constructed using the neighbor joining method. Some BSH clades exhibit similar substrate specificity profiles which can be used to predict the activity of a BSH and understand which residues contribute to substrate specificity. (B) Corresponding SEQ ID NOs for each BSH (percent amino acid identity for each is >95%).

Figures 21A, 21B, 21C:

FIGS. 21A-21C: (A) CLUSTALW sequence alignment was performed on BSH_1-21. Identities are shaded dark grey and similarities are outlined in black boxes. Regions that putatively interact with the conjugated amino acid are outlined in black boxes. (B) Predicted structure of LgBSHa with GCA in the active site (in dark grey spheres). Putative substrate-binding loops with 3 amino acids are highlighted in dark grey. (C) Three chimeric mutants of LgBSHa in putative substrate-binding loops and their relative activity on GCA and TCA.

Figures 22A, 22B, 22C:
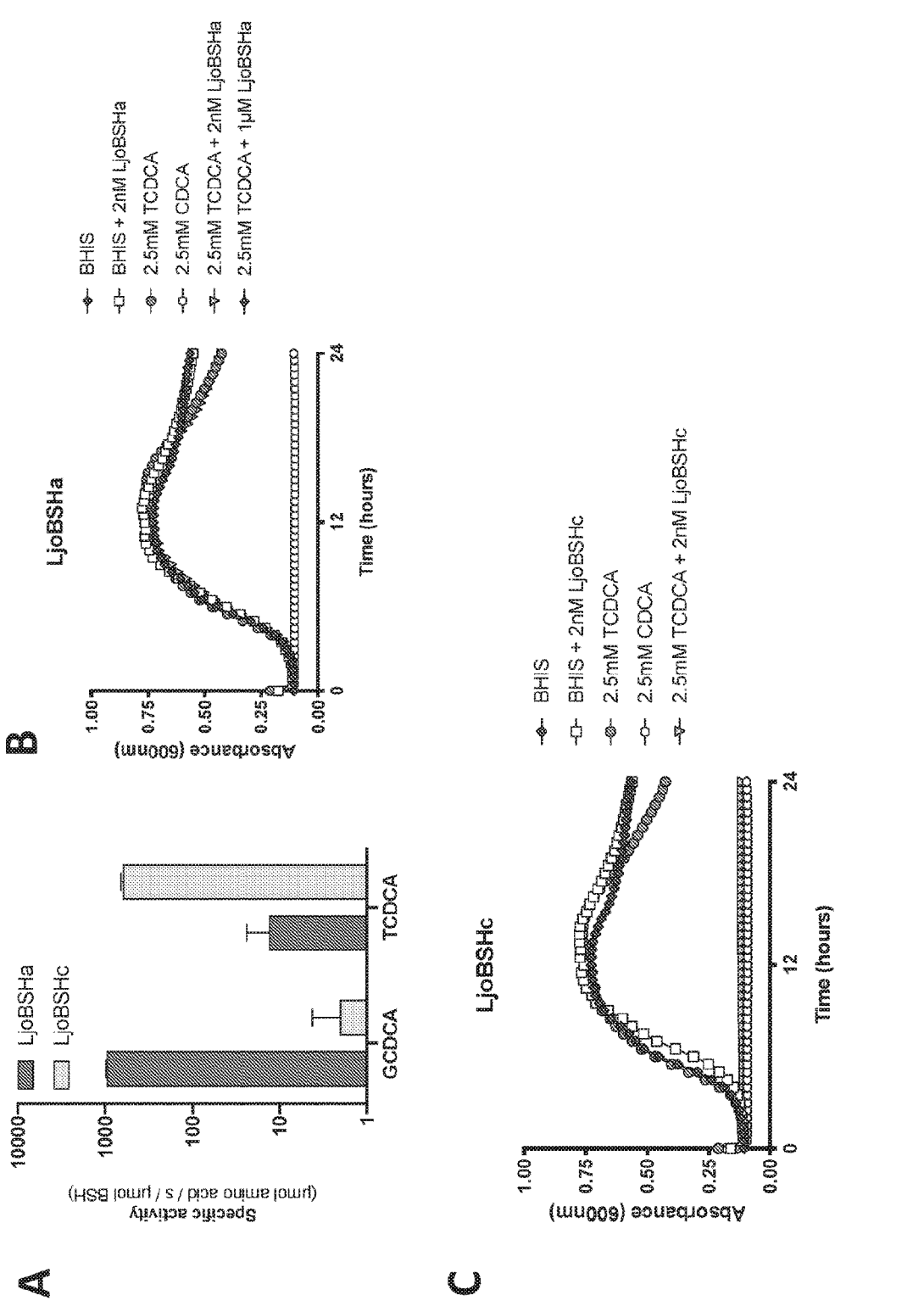

FIGS. 22A-22C: BSH specificity can leveraged to inhibit *Clostridioides difficile* in a conjugated bile acid substrate-dependent manner. (A) Recombinantly expressed and purified *L. johnsonii* BSHs were assayed for deconjugation with GCDCA and TCDCA. Specific activities for each BSH were determined by quantifying the rate of amino acid release by Ninhydrin assay. (B, C) Growth of *C. difficile* anaerobically in BHIS medium supplemented with GCDCA, TCDCA, or CDCA in combination with purified LjoBSHa or LjoBSHc.

Figure 23:
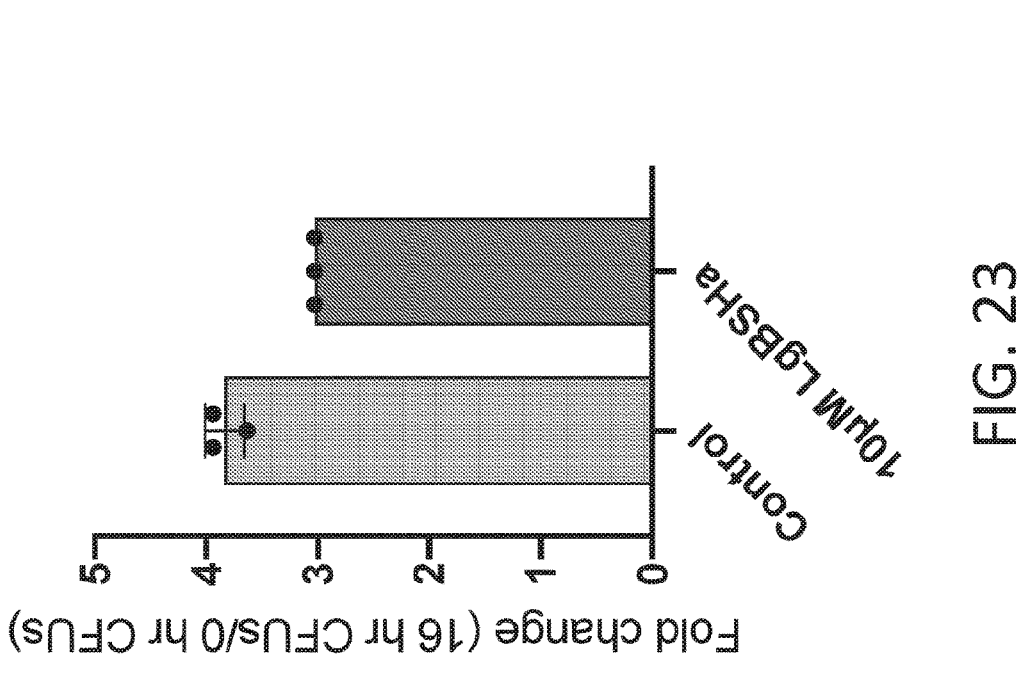

FIG. 23: Cefoperazone-treated mouse cecum ex vivo *C. difficile* growth. BSH activity generated inhibitory deconjugated bile acids in mouse cecal content that inhibited *C. difficile* growth.

DETAILED DESCRIPTION

Embodiments of the present disclosure provide compositions and methods related to modulating the gastrointestinal tract. In particular, the present disclosure provides a novel therapeutic strategy for selective modulation of the gut microbiota bile acid pool using bile acid hydrolases (BSHs) for the prevention and treatment of diseases such as obesity, diabetes, Inflammatory bowel disease (IBD), liver and colon cancer, and *Clostridioides difficile* infections, among others. Embodiments of the present disclosure facilitate the identification of the genetic and functional features of important bile salt hydrolases that can modulate bile composition in vivo. In some embodiments, *Lactobacillus*-derived beneficial BSHs are engineered and delivered to other intestinal microbes to promote health and fend off infections.

The indigenous gastrointestinal tract (GIT) microbiota is important for human health. Alterations to this microbial community influence bile acid metabolism, and are associated with the development of obesity, diabetes, inflammatory bowel disease (IBD), liver and colon cancer, and other GI diseases including *Clostridioides difficile* infection (CDI). The burden of these diseases on the U.S. healthcare system is astronomical, with obesity alone surpassing $237 billion dollars in 2017. New therapeutics that can selectively tailor the gut microbiota-bile acid pool represent a novel strategy for prevention and treatment of the above described diseases.

Figures 1A, 1B, 1C:
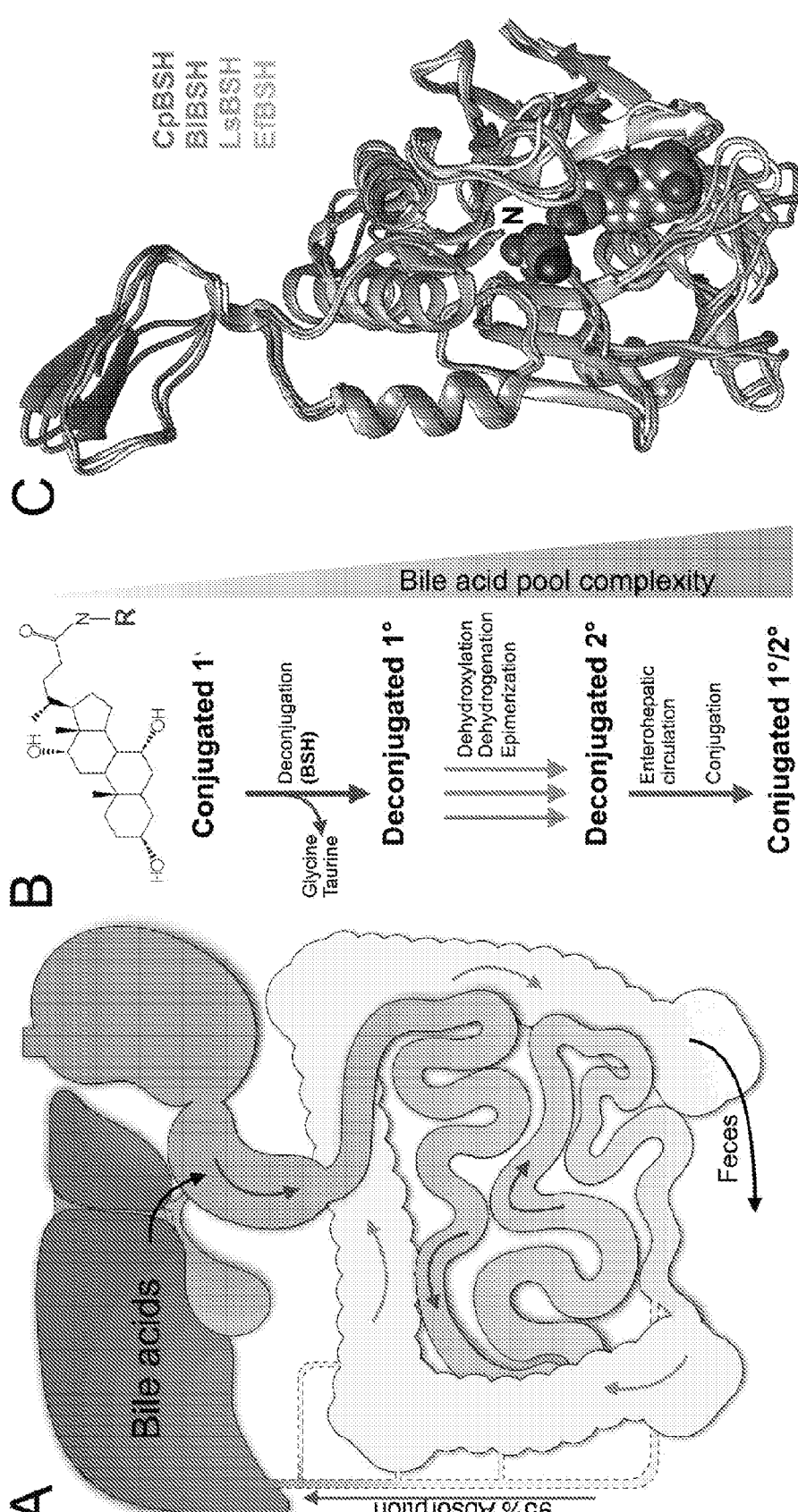
FIGS. 1A-1C: Bile salt hydrolases act on circulating conjugated bile acids in the gut-liver axis. (A) Bile acids (BAs) synthesized in the liver and stored in the gall bladder enter the small intestine through the duodenum where they reach millimolar concentrations. The majority of BAs (95%) are reabsorbed in the ileum and recirculate to the liver through the portal vein. The remaining population transit to the colon as they continue to be reabsorbed, and a small (<5%) amount exit through the feces. Recirculating BAs access host tissues outside the intestines to impart systemic effects on host physiology. (B) BSHs cleave the amide bond in conjugated BAs to open up the bile acid pool and increase complexity. The gut microbiota performs additional chemistry on deconjugated BAs to generate the secondary BA pool, which can undergo enterohepatic circulation and be reconjugated in the liver. (C) Monomeric BSH overlay from *B. longum, E. faecalis, L. salivarius*, and *C. perfringens*. Hydrolyzed taurodeoxycholate (TDCA) in the CpBSH active site is coordinated by several loops that contain the most variation in the peptide backbone compared to the other structures (Foley, et al. 2019).

Bile acids are synthesized by the liver from cholesterol and are essential for lipoprotein, glucose, drug, and energy metabolism. Bile acids can directly shape host physiology in a variety of ways including acting as signaling molecules to the nuclear receptor farnesoid X receptor (FXR) and the G-protein-coupled receptor TGR5. The gut microbiota can regulate both metabolism and synthesis of bile acids through FXR. Primary bile acids mainly cholate (CA) and chendeoxycholate (CDCA) are made by the host, and can be conjugated with a glycine or taurine. As they make their way through the small intestine, 95% of bile acids are absorbed in the terminal ileum through the enterohepatic system, a majority being conjugated bile acids (FIG. 1A). The remaining bile acids that reach the large intestine are further biotransformed by members of the gut microbiota via dehydroxylation into secondary bile acids, including deoxycholate (DCA) and lithocholate (LCA). Members of the gut microbiota play an essential role in bile acid metabolism throughout the GIT.

Secondary bile acids can be reabsorbed and conjugated with glycine or taurine (ex. GDCA, TDCA, etc.), which further increases the complexity of the bile acid pool. The most predominant conjugated bile acids in the GIT include taurocholate (TCA), glycocholate (GCA), taurochendeoxycholate (TCDCA), glycochendeoxycholate (GCDCA), taurodeoxycholate (TDCA) and glycodeoxycholate (GDCA). Gut microbes that encode bile salt hydrolase (bsh) genes are able to deconjugate or cleave the glycine and taurine from conjugated bile acids to yield unconjugated bile acids (ex. taurocholate→taurine and cholate). This is a critical first step in microbial bile acid metabolism that leads to all subsequent biotransformations (FIG. 1B). Conjugated bile acids have amphipathic characteristics and are more efficient as detergents, which can further shape the gut microbiota by promoting growth of bile acid metabolizing bacteria, and decreasing growth of bile sensitive bacteria. Therefore, these enzymes can be leveraged to rationally design the bile acid pool, altering the gut microbiota and host metabolism, and ultimately shaping host health. Few studies have investigated how bile acid altering enzymes are able to alter both the gut microbiota and the host in the context of disease.

Lactobacilli are used extensively in probiotic formulations and are often taken in concert with antibiotics to restore the normal indigenous gut microbiota; however, the mechanisms for how they improve host health, and shape the gut microbiota are not well understood. Recent research has shown that some probiotics could be detrimental, and prolong the recovery of the gut microbiota after antibiotic treatment. This continues to be controversial and more studies are needed to investigate the underlying mechanism. Some *Lactobacillus* strains carry multiple bsh genes which encode for BSH enzymes that deconjugate primary and secondary conjugated bile acids. The molecular basis by which these enzymes recognize and act on bile acids, and how this activity impacts *Lactobacillus* fitness and the GIT environment, is currently unclear.

Many gut bacteria including lactobacilli, *Bifidobacterium, Clostridium*, and *Bacteroides* encode BSHs, and more than thirty-three enzymes have been biochemically characterized. However, these studies fail to provide key structural and biochemical information underlying BSH enzymology and substrate specificity and recognition. This is further illustrated by the fact that there are only four solved crystal structures from *Lactobacillus salivarius, Bifidobacterium longum, Enterococcus faecalis*, and *Clostridium perfringens*, which is the only enzyme with substrate TDCA (FIG. 1C). Some *Lactobacillus* bsh mutant strains have growth defects in the presence of conjugated bile acids, suggesting they are important for bile tolerance and colonization of the GIT. Yet, bile tolerance studies with lactobacilli are usually done in vitro in the presence of Oxgall, which does not mimic the bile acid composition or complexity present in the GIT. Additionally, previous studies have highlighted the importance of gut lactobacilli BSH activity in regulating host weight gain, lipid metabolism, and bile tolerance, but failed to look at how this altered the gut microbiota, which is known to be a variable that shapes its composition.

As provided herein, the current status quo is to ingest over the counter probiotic dietary supplements or yogurt containing live cultures after antibiotic treatment to restore host GI health, although mechanistic studies defining how this improves host health are lacking. On the other hand, there are multiple probiotic formulations in different stages of pre-clinical and clinical trials for the prevention and treatment of variety of diseases: *Lactobacillus plantarum* from OptiBiotix Health for obesity, *Lactococcus lactis* from Intrexon for IBD, and a cocktail of three *Lactobacillus* strains from BioK Plus to treat patients with *C. difficile* infection (CDI).

As the microbiome field moves forward there is hope that defined bacterial cocktails or engineered probiotic strains could be used to treat metabolic diseases including obesity and diabetes and other GI diseases like CDI. However, before this can become a therapeutic reality, basic mechanistic studies need to be carried out in robust well-characterized systems to validate probiotic effects. The compositions and methods of the present disclosure contrast with currently available approaches by using a novel platform to robustly engineer microbial BSHs for enhanced enzyme activity against physiologically relevant conjugated bile acids. These novel synthetic constructs were tested in a well-characterized system, both in vitro and in vivo. Results described further herein indicate that this approach can be effective for altering the bile acid composition in the gut, and as a consequence, provide the therapeutic basis for modulating GI and metabolic diseases.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

As used herein, the term "animal" refers to any animal (e.g., a mammal), including, but not limited to, humans, non-human primates, pigs, rodents (e.g., mice, rats, etc.), flies, and the like.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

The term "transgene" as used herein refers to a foreign, heterologous, or autologous gene and/or fragment thereof that is placed into an organism (e.g., by introducing the gene into newly fertilized eggs or early embryos). The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "transgenic animal" refers to any animal containing a transgene.

As used herein, the term "microorganism" refers to an organism or microbe of microscopic, submicroscopic, or ultramicroscopic size that typically consists of a single cell. Examples of microorganisms include bacteria, yeast, viruses, parasites, fungi, certain algae, and protozoa. In some aspects, the microorganism is engineered ("engineered microorganism") to produce one or more therapeutic molecules or proteins of interest. In certain aspects, the microorganism is engineered to take up and catabolize certain metabolites or other compounds from its environment. In certain aspects, the microorganism is engineered to synthesize certain beneficial metabolites or other compounds (synthetic or naturally occurring) and release them into its environment. In certain embodiments, the engineered microorganism is an engineered bacterium. In certain embodiments, the engineered microorganism is an engineered virus.

As used herein, "non-pathogenic bacteria" refer to bacteria that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria do not contain lipopolysaccharides (LPS). In some embodiments, non-pathogenic bacteria are commensal bacteria, which are present in the indigenous microbiota of the gut. Examples of non-pathogenic bacteria include, but are not limited to certain strains belonging to the genus *Bacillus, Bacteroides, Bifidobacterium, Brevibacteria, Clostridium, Enterococcus, Escherichia coli, Lactobacillus, Lactococcus, Saccharomyces, Streptococcus* and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Escherichia coli* Nissle, *Lactobacillus acidophilus, Lactobacillus bulgaricus, Lactobacillus casei, Lactobacillus crispatus, Lactobacillus gasseri, Lactobacillus johnsonii, Lactobacillus paracasei, Lactobacillus plantarum, Lactobacillus reuteri, Lactobacillus rhamnosus, Lactobacillus salivarius Lactobacillus fermentum, Lactobacillus delbrueckii, Lactococcus lactis*, and *Saccharomyces boulardii*. Naturally pathogenic bacteria may be genetically engineered to provide reduce or eliminate pathogenicity.

As used herein, the term "probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. In some embodiments, the probiotic bacteria are Gram-negative bacteria. In some embodiments, the probiotic bacteria are Gram positive bacteria. Some species, strains, and/or subtypes of non-pathogenic bacteria are currently recognized as probiotic bacteria. Examples of probiotic bacteria include, but are not limited to certain strains belonging to the genus Bifidobacteria, *Escherichia, Lactobacillus, Streptococcus* and *Saccharomyces*, e.g., *Bifidobacterium bifidum, Enterococcus faecium, Escherichia coli, Escherichia coli* strain Nissle, *Lactobacillus acidophilus, Lactobacillus crispatus, Lactobacillus gasseri, Lactobacillus bulgaricus, Lactobacillus paracasei, Lactobacillus plantarum, Lactobacillus reuteri, Lactobacillus rhamnosus, Lactobacillus salivarius, Lactobacillus fermentum, Lactobacillus delbrueckii* and *Saccharomyces boulardii*. In some embodiments, examples of strains include, but are not limited to, *L. acidophilus* NCFM, *L. acidophilus* La-14, *L. casei* Lc11, *L. crispatus* NCK 1350, *L. crispatus* NCK 1351, *L. crispatus* DNH-429, *L. gasseri* ATCC 33323, *L. gasseri* NCK 1338, *L. gasseri* NCK 1340, *L. gasseri* NCK 1341, *L. gasseri* NCK 1342, *L. gasseri* NCK 1343, *L. gasseri* Lg-36, *L. gasseri* NCK2140, *L. gasseri* NCK2141, *L. gasseri* JV V03, *L. plantarum* Lp-115, *L. johnsonii* NCK948, *L. johnsonii* NCK957, *L. johnsonii* NCK964, *L. johnsonii* NCK979, *L. johnsonii* NCK1370, *L. johnsonii* NCK2677, *L. johnsonii* NCC 533 *L. plantarum* Lpc-37, *L. plantarum* Lp115, *L. rhamnosus* HN001, *L. rhamnosus* GG, *L. rhamnosus* Lr-32, *L. reuteri* 1E1, *L. salivarius* Ls-33, *L. salivarius* NCK1352, *L. salivarius* NCK1355, *B. lactis*

BL-04, *B. lactis* Bb-02, *B. lactis* Bl-04, *B. lactis* Bi-07, *B. breve* Bb-03, *B. bifidum* Bb-06, *B. longum* Bl-05, *B. longum* sp *infantis* Bi-26, or any combination thereof.

The probiotic may be a variant or a mutant strain of bacterium. Nonpathogenic bacteria may be genetically engineered to enhance or improve desired biological properties, e.g., survivability. Non-pathogenic bacteria may be genetically engineered to provide probiotic properties. Probiotic bacteria may be genetically engineered or programmed to enhance or improve probiotic properties.

As used herein, the term "recombinant bacterial cell" or "recombinant bacteria" refers to a bacterial cell or bacteria that have been genetically modified from their native state. For instance, a recombinant bacterial cell may have nucleotide insertions, nucleotide deletions, nucleotide rearrangements, and nucleotide modifications introduced into their DNA. These genetic modifications may be present in the chromosome of the bacteria or bacterial cell, or on a plasmid in the bacteria or bacterial cell. Recombinant bacterial cells disclosed herein may comprise exogenous nucleotide sequences on plasmids. Alternatively, recombinant bacterial cells may comprise exogenous nucleotide sequences stably incorporated into their chromosome.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full-length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence. The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. The non-native nucleic acid sequence may be present on a plasmid or chromosome. In addition, multiple copies of any regulatory region, promoter, gene, and/or gene cassette may be present in the bacterium, wherein one or more copies of the regulatory region, promoter, gene, and/or gene cassette may be mutated or otherwise altered as described herein. In some embodiments, the genetically engineered bacteria are engineered to comprise multiple copies of the same regulatory region, promoter, gene, and/or gene cassette in order to enhance copy number or to comprise multiple different components of a gene cassette performing multiple different functions. In some embodiments, the genetically engineered bacteria of the invention comprise a gene encoding a bile salt hydrolase enzyme that is operably linked to a directly or indirectly inducible promoter that is not associated with said gene in nature, e.g., an FNR promoter operably linked to a gene encoding a bile salt hydrolase.

As used herein, "operably linked" refers a nucleic acid sequence, e.g., a gene encoding a bile salt hydrolase enzyme, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

As used herein, "promoter" refers to a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Prokaryotic promoters are typically classified into two classes: inducible and constitutive.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human). In some embodiments, the subject may be a human or a non-human. In one embodiment, the subject is a human. The subject or patient may be undergoing various forms of treatment.

As used herein, the term "treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a treatment to a subject that is not at the time of administration afflicted with the disease. "Preventing" also refers to preventing the recurrence of a disease or of one or more symptoms associated with such disease.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. COMPOSITIONS AND METHODS

Embodiments of the present disclosure include genetically engineered microorganisms, pharmaceutical compositions thereof, and methods of treating disorders associated with bile salts and/or bile acids. Specifically, the recombinant bacteria disclosed herein have been engineered to modulate the microbiota of a subject. These recombinant bacteria are safe and well tolerated and augment the innate activities of a subject's microbiome to achieve a therapeutic effect.

Embodiments of the present disclosure also include BSH enzymes, both naturally occurring and non-naturally occurring enzymes. Non-naturally occurring BSH enzymes include, but are not limited to, recombinants, mutants, chimeras, fusion proteins, tagged peptides/polypeptides, and the like, and any combinations thereof. For example, non-naturally occurring BSH enzymes of the present disclosure can include polypeptides having an amino acid sequence of any of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, and 113, and at least one amino acid substitution. Non-naturally occurring BSH enzymes of the present disclosure can also include chimeric polypeptides or fusion proteins having an amino acid sequence of any of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, and 113, and at least one additional peptide or polypeptide fragment. In some embodiments, recombinant BSH enzymes contain specific mutations in select amino acids within an active site, or INDELS, as well as peptide or polypeptide fragments of various sections of different BSHs fused together.

As disclosed further herein, recombinant BSH enzymes can be included in a pharmaceutical composition. For example, recombinant BSH enzymes can be included within a strain of bacteria (e.g., *Lactobacillus*) as a plasmid or genomic integration, and/or included with a strain of bacteria as an exogenous peptide, polypeptide, or polynucleotide, which together comprise the pharmaceutical composition. In accordance with these embodiments, the present disclosure provides methods of treating disorders associated with bile salts and/or acids using these pharmaceutical compositions.

In some embodiments, a bacterial cell as provided herein has been genetically engineered to comprise a heterologous gene encoding a bile salt hydrolase (BSH) enzyme. In some embodiments, a bacterial cell disclosed herein has been genetically engineered to comprise at least one heterologous gene encoding a bile salt hydrolase (BSH) enzyme (e.g., SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, and 114) and/or a second gene that is not a BSH enzyme. In some embodiments, the engineered bacteria are capable of modulating levels of bile salts and/or bile acids. In some embodiments, the engineered bacteria are capable of processing and reducing levels of bile salts and/or bile acids in low-oxygen environments (e.g., the gut). Thus, the genetically engineered bacterial cells and pharmaceutical compositions comprising the bacterial cells disclosed herein may be used to convert excess bile salts into non-toxic molecules in order to treat and/or prevent disorders associated with bile salts, such as (but not limited to) cardiovascular disease, metabolic disease, liver disease, cirrhosis, cancer, obesity, diabetes, Inflammatory Bowel Disease (IBD), antibiotic associated diarrhea, Nonalcoholic fatty liver disease (NAFLD), Nonalcoholic steatohepatitis (NASH), and *Clostridioides difficile* infections. In some embodiments, the genetically engineered bacterial cells and pharmaceutical compositions comprising the bacterial cells disclosed herein may be used to convert excess bile acids into non-toxic molecules in order to treat and/or prevent disorders associated with bile salts and bile salt metabolites (e.g., bile acids), such as cardiovascular disease, metabolic disease, liver disease, cirrhosis, cancer, obesity, diabetes, Inflammatory Bowel Disease (IBD), antibiotic associated diarrhea, Nonalcoholic fatty liver disease (NAFLD), Nonalcoholic steatohepatitis (NASH), and *Clostridioides difficile* infections.

The genetically engineered microorganisms, or programmed microorganisms, such as genetically engineered bacteria of the disclosure are capable of producing one or more bile salt hydrolase enzymes. In some embodiments, the genetically engineered bacteria are obligate anaerobic bacteria. In some embodiments, the genetically engineered bacteria are facultative anaerobic bacteria. In some embodiments, the genetically engineered bacteria are aerobic bacteria. In some embodiments, the genetically engineered bacteria are Gram positive-bacteria and lack LPS. In some embodiments, the genetically engineered bacteria are Gram-negative bacteria. In some embodiments, the genetically engineered bacteria are Gram-positive and obligate anaerobic bacteria. In some embodiments, the genetically engineered bacteria are Gram-positive and facultative anaerobic bacteria. In some embodiments, the genetically engineered bacteria are non-pathogenic bacteria. In some embodiments, the genetically engineered bacteria are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. Exemplary bacteria include, but are not limited to, *Bacillus, Bacteroides, Bifidobacterium, Brevibacteria, Caulobacter, Clostridium, Enterococcus, Escherichia coli, Lactobacillus, Lactococcus, Listeria, Mycobacterium, Saccharomyces, Salmonella, Staphylococcus, Streptococcus, Vibrio, Bacillus coagulans, Bacillus subtilis, Bacteroides fragilis, Bacteroides subtilis, Bacteroides thetaiotaomicron, Bifidobacterium adolescentis, Bifidobacterium bifidum, Bifidobacterium breve* UCC2003, *Bifidobacterium infantis, Bifidobacterium lactis, Bifidobacterium longum, Clostridium acetobutylicum, Clostridium butyricum, Clostridium butyricum* M-55, *Clostridium cochlearum, Clostridium felsineum, Clostridium histolyticum, Clostridium multifermentans, Clostridium novyi*-NT, *Clostridium paraputrificum, Clostridium pasteureanum, Clostridium pectinovorum, Clostridium perfringens, Clostridium roseum, Clostridium sporogenes, Clostridium tertium, Clostridium tetani, Clostridium tyrobutyricum, Corynebacterium parvum, Escherichia coli* MG1655, *Escherichia coli* Nissle 1917, *Listeria monocytogenes, Mycobacterium bovis, Salmonella choleraesuis, Salmonella typhimurium*, and *Vibrio cholera*. In certain embodiments, the genetically engineered bacteria are selected from the group consisting of *Enterococcus faecium, Lactobacillus acidophilus, Lactobacillus gasseri, Lactobacillus crispatus Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis, Streptococcus thermophilus* and *Saccharomyces boulardii*. In certain embodiments, the genetically engineered bacteria are selected from the group consisting of *Enterococcus faecium, Lactobacillus acidophilus, Lactobacillus gasseri, Lactobacillus crispatus Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactobacillus salivarius, Lactobacillus fermentum, Lactobacillus delbrueckii Lactococcus lactis, Streptococcus thermophilus* and *Saccharomyces boulardii*. In certain embodiments, the genetically engineered bacteria are selected from the group consisting of *Bacteroides fragilis, Bacteroides thetaiotaomicron, Bacteroides subtilis, Bifidobacterium bifidum, Bifidobacterium infantis, Bifidobacterium lactis, Clostridium butyricum, Escherichia coli* Nissle, *Lactobacillus acidophilus, Lactobacillus plantarum, Lactobacillus reuteri, Lactobacillus salivarius, Lactobacillus fermentum, Lactobacillus delbrueckii*, and *Lactococcus lactis*. In one embodiment, the bacterial cell is a Gram positive bacterial cell.

In another embodiment, the bacterial cell is a Gram negative bacterial cell. In certain embodiments, the cell is selected from one of the following strains: *L. acidophilus*

NCFM, *L. acidophilus* La-14, *L. casei* Lc11, *L. crispatus* NCK 1350, *L. crispatus* NCK 1351, *L. crispatus* DNH-429, *L. gasseri* ATCC 33323, *L. gasseri* NCK 1338, *L. gasseri* NCK 1340, *L. gasseri* NCK 1341, *L. gasseri* NCK 1342, *L. gasseri* NCK 1343, *L. gasseri* Lg-36, *L. gasseri* NCK2140, *L. gasseri* NCK2141, *L. gasseri* JV V03, *L. plantarum* Lp-115, *L. johnsonii* NCK948, *L. johnsonii* NCK957, *L. johnsonii* NCK964, *L. johnsonii* NCK979, *L. johnsonii* NCK1370, *L. johnsonii* NCK2677, *L. johnsonii* NCC 533 *L. plantarum* Lpc-37, *L. plantarum* Lp115, *L. rhamnosus* HN001, *L. rhamnosus* GG, *L. rhamnosus* Lr-32, *L. reuteri* 1E1, *L. salivarius* Ls-33, *L. salivarius* NCK1352, *L. salivarius* NCK1355, *B. lactis* BL-04, *B. lactis* Bb-02, *B. lactis* Bl-04, *B. lactis* Bi-07, *B. breve* Bb-03, *B. bifidum* Bb-06, *B. longum* Bl-05, *B. longum* sp *infantis* Bi-26, or any combination thereof.

In some embodiments of the above described genetically engineered bacteria, the bacteria comprise gene sequence encoding one or more bile salt hydrolase enzymes. In some embodiments of the above described genetically engineered bacteria, the bacteria comprise gene sequence encoding one or more bile salt hydrolase enzymes and one or more other exogenous genes. In some embodiments, the gene encoding a bile salt hydrolase is present on a plasmid in the bacterium. In some embodiments, the gene encoding a bile salt hydrolase is present on a plasmid in the bacterium and operatively linked on the plasmid to a non-native promoter. In other embodiments, the gene encoding a bile salt hydrolase is present in the bacterial chromosome. In other embodiments, the gene encoding a bile salt hydrolase is present in the bacterial chromosome and is operatively linked in the chromosome to the promoter.

As used herein, the term "bile salt hydrolase" enzyme refers to an enzyme involved in the cleavage of the amino acid sidechain of glycol- or tauro-conjugated bile acids to generate unconjugated bile acids (FIG. 1). Bile salt hydrolase (BSH) enzymes are well known to those of skill in the art. For example, bile salt hydrolase activity has been detected in *Lactobacillus* spp., *Bifidobacterium* spp., *Enterococcus* spp., *Clostridium* spp., *Bacteroides* spp., *Methanobrevibacter* spp., and *Listeria* spp. The bacterial cells described herein comprise a heterologous gene sequence encoding a bile salt hydrolase enzyme. In some embodiments, the bacterial cells described herein comprise gene sequence encoding a bile salt hydrolase enzyme and are capable of deconjugating bile salts into unconjugated bile acids. In some embodiments, the bacterial cells described herein are capable of modulating (increasing or decreasing) the levels of bile salts in a subject or cell. In some embodiments, the bacterial cells described herein are capable of increasing the levels of bile acids in a subject or cell. In some embodiments, the bacterial cells described herein are capable of decreasing the level of TCA in a subject or cell.

In some embodiments, the bacterial cells described herein are capable of decreasing the level of GCDCA, GCA, TCA, TCDCA, TLCA, TDCA, TUDCA, GLCA, GDCA, GUDCA, FCA, FCDCA, FLCA, FDCA, FUDCA, LCA, LCDCA, LLCA, LDCA, LUDCA, YCA, YCDCA, YLCA, YDCA, YUDCA, and/or combinations thereof. In some embodiments, the bacterial cells described herein are capable of increasing the levels of primary bile acids in a subject or cell. In some embodiments, the bacterial cells described herein are capable of increasing the level of CA in a subject or cell. In some embodiments, the bacterial cells described herein are capable of increasing the level of CDCA in a subject or cell. In some embodiments, the bacterial cells described herein are capable of increasing the levels of CA and CDCA in a subject or cell. In one embodiment, the bile salt hydrolase enzyme increases the rate of bile salt catabolism in the cell. In one embodiment, the bile salt hydrolase enzyme decreases the level of bile salts in the cell or in the subject. In one embodiment, the bile salt hydrolase enzyme decreases the level of taurocholic acid (TCA) in the cell or in the subject. In one embodiment, the bile salt hydrolase enzyme decreases the level of glycochenodeoxycholic acid (GCDCA) in the cell or in the subject. Methods for measuring the rate of bile salt catabolism and the level of bile salts and bile acids are well known to one of ordinary skill in the art. For example, bile salts and acids may be extracted from a sample, and standard LC/MS methods may be used to determine the rate of bile salt catabolism and/or level of bile salts and bile acids.

In another embodiment, the bile salt hydrolase enzyme increases the level of bile acids in the cell or in the subject as compared to the level of bile salts in the cell or in the subject. In another embodiment, the bile salt hydrolase enzyme increases the level of cholic acid (CA) in the cell. In another embodiment, the bile salt hydrolase enzyme increases the level of chenodeoxycholic acid (CDCA) in the cell.

In some embodiments, the recombinant bacteria comprise gene sequence encoding one or more bile salt hydrolase enzyme(s), wherein the bacteria produce CDCA. In some embodiments, the recombinant bacteria comprise gene sequence encoding one or more bile salt hydrolase enzyme(s), wherein the bacteria produce CDCA and reduce intestinal inflammation the recombinant bacteria comprise gene sequence encoding one or more bile salt hydrolase enzyme(s), wherein the bacteria produce CDCA and reduce atherosclerosis the recombinant bacteria comprise gene sequence encoding one or more bile salt hydrolase enzyme(s), wherein the bacteria produce CDCA and reduce inflammation and/or autoimmune disease in the CNS. In some embodiments, the recombinant bacteria comprise gene sequence encoding one or more bile salt hydrolase enzyme(s), wherein the bacteria produce CDCA and reduce liver fat and fibrosis. In some embodiments, the recombinant bacteria comprise gene sequence encoding one or more bile salt hydrolase enzyme(s), wherein the bacteria produce CDCA and increase glucose and insulin tolerance. In some embodiments, the recombinant bacteria comprise gene sequence encoding one or more bile salt hydrolase enzyme(s), wherein the bacteria produce CDCA and decrease steatohepatitis. the recombinant bacteria comprise gene sequence encoding one or more bile salt hydrolase enzyme(s), wherein the bacteria produce CDCA and decrease the hepatic expression of genes involved in fatty acid synthesis and/or reduce TNF-α and/or reduce elevated peroxisome-proliferator activated receptor alpha expression, thereby improving NASH phenotype. In some embodiments, the recombinant bacteria comprise gene sequence encoding one or more bile salt hydrolase enzyme(s), wherein the bacteria produce CDCA and prevent fibrosis progression, and/or decrease fibrosis and/or decrease cirrhosis development and/or reduce portal hypertension.

Embodiments of the present disclosure also include nucleic acids comprising gene sequence encoding one or more bile salt hydrolase enzyme(s) (e.g., SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, and 114). In some embodiments, the nucleic acid comprises gene sequence encoding one or more bile salt hydrolase enzyme(s) that comprise amino acids in its sequence that are substantially the same as an amino acid sequence described herein. Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T. Similarly contemplated is replacing a basic amino acid with another basic amino acid (e.g., replacement among Lys, Arg, His), replacing an acidic amino acid with another acidic amino acid (e.g., replacement among Asp and Glu), replacing a neutral amino acid with another neutral amino acid (e.g., replacement among Ala, Gly, Ser, Met, Thr, Leu, He, Asn, Gin, Phe, Cys, Pro, Trp, Tyr, Val).

In some embodiments, the gene encoding a BSH enzyme is mutagenized; mutants exhibiting increased activity are selected; and the mutagenized gene encoding the BSH enzyme is isolated and inserted into the bacterial cell of the present disclosure. The gene comprising the modifications described herein may be present on a plasmid or chromosome. In some embodiments, the disclosure provides a nucleic acid comprising gene sequence encoding one or more BSH enzymes, wherein the BSH enzyme is mutagenized and synthesized into its corresponding peptide or polypeptide. In some embodiments, the BSH enzyme is a chimeric protein comprising different peptide motifs conferring substrate specificity to one more different bile acids, as described further herein. In one embodiment, the BSH enzyme includes at least one amino acid substitution that is present in one of the following peptide motifs: GQD, IPA, and/or AMI.

In some embodiments, the mutagenized BSH enzyme is administered to a subject independent of any bacterial cell, and as part of a pharmaceutical composition. The pharmaceutical composition can include one or more mutagenized BHS enzymes, as described further herein. In accordance with these embodiments, the present disclosure provides methods of treating disorders associated with bile salts and/or acids using these pharmaceutical compositions.

In some embodiments, the nucleic acid comprising gene sequence encoding one or more bile salt hydrolase enzymes, may comprise gene sequence encoding bile salt hydrolase from various different species of bacteria. For example, in one embodiment, the gene encoding the bile salt hydrolase enzyme is from *Lactobacillus* spp. In one embodiment, the *Lactobacillus* spp. is *Lactobacillus plantarum* WCFS1, *Lactobacillus plantarum* 80, *Lactobacillus johnsonii* NCC533, *Lactobacillus johnsonii* 100-100, *Lactobacillus acidophilus* NCFM ATCC700396, *Lactobacillus brevis* ATCC 367, or *Lactobacillus* gasseri ATCC 33323. In another embodiment, the gene encoding the bile salt hydrolase enzyme is from a *Bifidobacterium* spp. In one embodiment, the *Bifidobacterium* spp. is *Bifidobacterium longum* NCC2705, *Bifidobacterium longum* DJO10A, *Bifidobacterium longum* BB536, *Bifidobacterium longum* SBT2928, *Bifidobacterium bifidum* ATCC 11863, or *Bifidobacterium adolescentis*. In another embodiment, the gene encoding the bile salt hydrolase enzyme is from *Bacteroides* spp. In one embodiment, the *Bacteroides* spp. is *Bacteroides fragilis* or *Bacteroides vulgatus*. In another embodiment, the gene encoding the bile salt hydrolase enzyme is from *Clostridium* spp. In one embodiment, the *Clostridium* spp. is *Clostridium perfringens* MCV 185 or *Clostridium perfringens* 13. In another embodiment, the gene encoding the bile salt hydrolase enzyme is from *Listeria* spp. In one embodiment, the *Listeria* spp. is *Listeria monocytogenes*. In one embodiment, the gene encoding the bile salt hydrolase enzyme is from *Methanobrevibacter* spp. In one embodiment, the *Methanobrevibacter* spp. is *Methanobrevibacter smithii*. Other genes encoding bile salt hydrolase enzymes are well-known to one of ordinary skill in the art.

In some embodiments, the polynucleotide comprises a sequence encoding one or more bile salt hydrolase enzymes selected from any of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, and 113, or any variants, mutants, chimeras, or fusions thereof. In one embodiment, the bile salt hydrolase has at least about 80% identity with the sequence of any of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, and 113. In another embodiment, the bile salt hydrolase has at least about 85% identity with any of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, and 113. In one embodiment, the bile salt hydrolase has at least about 90% identity with any of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, and 113. In one embodiment, the bile salt hydrolase has at least about 95% identity with any of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, and 113. In another embodiment, the bile salt hydrolase has at least about 96%, 97%, 98%, or 99% identity with any of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, and 113. Accordingly, in one embodiment, the bile salt hydrolase gene has at least about 80%, 81%, 82%, 83%, 84%, 85%, 86%, 87%, 88%, 89%, 90%, 91%, 92%, 93%, 94%, 95%, 96%, 97%, 98%, or 99% identity with any of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, and 114.

Further disclosed herein are methods of treating a disease or disorder associated with bile salts. In some embodiments, disclosed herein are methods for reducing, ameliorating, or eliminating one or more symptom(s) associated with these diseases or disorders. In some embodiments, the disease or disorder associated with bile salts is cardiovascular disease, metabolic disease, liver disease, such as cirrhosis or NASH, inflammatory and autoimmune diseases, such as multiple sclerosis and experimental autoimmune encephalomyelitis (EAE), gastrointestinal cancer, and/or *C. difficile* infection.

In some embodiments, the disease or condition is selected from the group consisting of cardiovascular disease, metabolic disease, liver disease, cirrhosis, cancer, obesity, diabetes, Inflammatory Bowel Disease (IBD), antibiotic associated diarrhea, Nonalcoholic fatty liver disease (NAFLD), Nonalcoholic steatohepatitis (NASH) and *Clostridioides difficile* infections.

In some embodiments, the disclosure provides methods for reducing, ameliorating, or eliminating one or more symptom(s) associated with these diseases, including but not limited to chest pain, heart failure, or weight gain. In some embodiments, the disease is secondary to other conditions, e.g., cardiovascular disease or liver disease. In certain embodiments, the bacterial cells are capable of deconjugating bile salts in a subject in order to treat a disorder associated with bile salts. In these embodiments, a patient suffering from a disorder associated with bile salts, e.g., obesity, may be able to resume a substantially normal diet, or a diet that is less restrictive.

In certain embodiments, the bacterial cells are capable of metabolizing primary bile acids into secondary bile acids in a subject in order to treat or prevent a disorder associated with bile salts and/or bile acids, such as *C. difficile* infection. In these embodiments, a subject at risk of suffering from *C. difficile* infection will have enhanced resistance to infection, and a subject having *C. difficile* infection will have enhanced resistance and recover more quickly. For example, a hospital patient receiving treatment will be less likely to become infected with *C. difficile*.

The method may comprise preparing a pharmaceutical composition with at least one genetically engineered species, strain, or subtype of bacteria described herein, and administering the pharmaceutical composition to a subject in a therapeutically effective amount. In some embodiments, the method may comprise preparing a pharmaceutical composition with at least one genetically engineered species, strain, or subtype of bacteria described herein, along with a recombinant polynucleotide or polypeptide comprising a sequence of a BSH enzyme, and administering the pharmaceutical composition to a subject in a therapeutically effective amount. In some embodiments, the genetically engineered bacteria and/or recombinant BSH enzyme disclosed herein are administered orally, e.g., in a liquid suspension. In some embodiments, the genetically engineered bacteria and/or recombinant BSH enzyme are lyophilized in a gel cap and administered orally. In some embodiments, the genetically engineered bacteria and/or recombinant BSH enzyme are administered via a feeding tube or gastric shunt. In some embodiments, the genetically engineered bacteria and/or recombinant BSH enzyme are administered rectally, e.g., by enema. In some embodiments, the genetically engineered bacteria and/or recombinant BSH enzyme are administered topically, intraintestinally, intrajejunally, intraduodenally, intraileally, and/or intracolically.

The method may comprise preparing a pharmaceutical composition with at least one genetically engineered species, strain, or subtype of bacteria described herein, and/or at least one recombinant BSH enzyme, and administering the pharmaceutical composition to a subject in a therapeutically effective amount. The genetically engineered microorganisms and/or recombinant BSH enzymes may be administered locally, e.g., injected directly into a tissue or supplying vessel, or systemically, e.g., intravenously by infusion or injection. In some embodiments, the genetically engineered bacteria and/or recombinant BSH enzyme are administered intravenously, intra-arterially, intramuscularly, intraperitoneally, orally, or topically. In some embodiments, the genetically engineered microorganisms and/or recombinant BSH enzyme are administered intravenously, i.e., systemically.

Pharmaceutical compositions comprising the genetically engineered bacteria and/or recombinant BSH enzyme of the invention may be used to treat, manage, ameliorate, and/or prevent a diseases associated with bile salts or symptom(s) associated with diseases or disorders associated with bile salts. Pharmaceutical compositions of the also include one or more genetically engineered bacteria, and/or one or more recombinant BSH enzymes, alone or in combination with prophylactic agents, therapeutic agents, and/or and pharmaceutically acceptable carriers.

In certain embodiments, the pharmaceutical composition comprises one species, strain, or subtype of bacteria that are engineered to comprise the genetic modifications described herein, e.g., to express a bile salt hydrolase enzyme. In alternate embodiments, the pharmaceutical composition comprises two or more species, strains, and/or subtypes of bacteria that are each engineered to comprise the genetic modifications described herein, e.g., to express a bile salt hydrolase enzyme.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, PA). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered bacteria and/or recombinant BSH enzymes described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). Suitable dosage amounts for the genetically engineered bacteria may range from about $10^5$ to $10^{12}$ bacteria, e.g., approximately $10^5$ bacteria, approximately $10^6$ bacteria, approximately $10^7$ bacteria, approximately $10^8$ bacteria, approximately $10^9$ bacteria, approximately $10^{10}$ bacteria, approximately $10^{11}$ bacteria, or approximately $10^{12}$ bacteria, or more. The compositions, which may comprise any combinations of the genetically engineered bacteria and/or recombinant enzymes described herein, can be administered once or more daily, weekly, or monthly. These compositions may be administered before, during, or following a meal. In some embodiments, these pharmaceutical compositions can be administered before the subject eats a meal. In some embodiments, these pharmaceutical compositions can be administered currently with a meal. In some embodiments, these pharmaceutical compositions can be administered after the subject eats a meal.

The genetically engineered bacteria and/or recombinant BSH enzymes may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered bacteria and/or recombinant BSH enzymes disclosed herein may be administered topically and formulated in the form of an ointment, cream, transdermal patch, lotion, gel, shampoo, spray, aerosol, solution, emulsion, or other form well-known to one of skill in the art. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The genetically engineered bacteria and/or recombinant BSH enzymes disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG).

Disintegrating agents may also be added, such as cross-linked polyvinylpyrrolidone, agar, alginic acid or a salt thereof such as sodium alginate.

3. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Figures 2A, 2B, 2C:
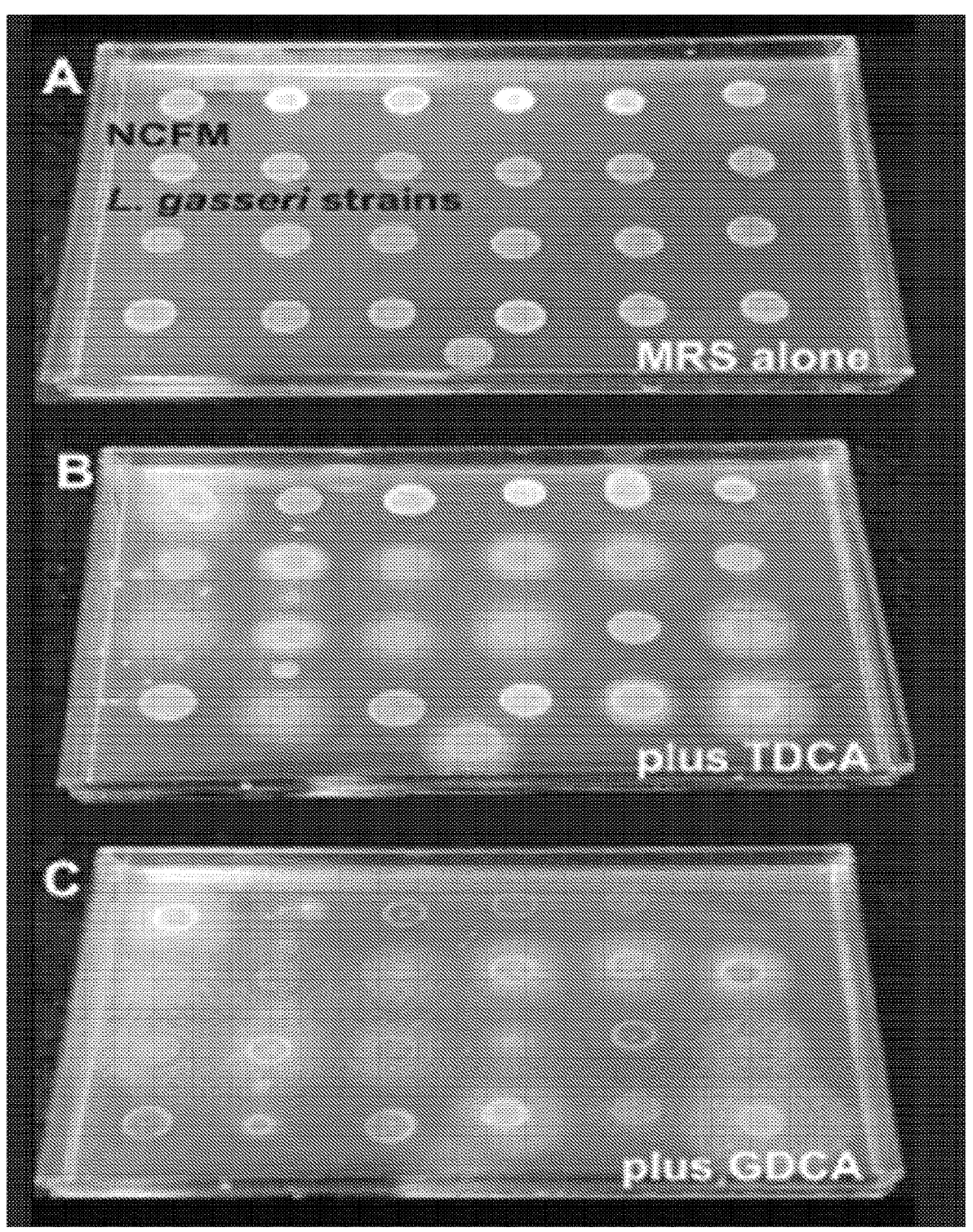
FIGS. 2A-2C: High throughput screening of *Lactobacillus* strains in the presence of conjugated bile acids. *Lactobacillus* strains were used in a BSH plate precipitation assay and plated on (A) MRS media, (B) plus 0.2% TDCA, and (C) plus 0.2% GDCA. Halos represent lactobacilli with active BSHs. Starting from the top left corner of each plate, strain details are as follows, *L. acidophilus* NCFM, *L. casei* ATCC 334, *L. pentosus* DSM 20314, *L. rhamnosus* LGG, *L. bucherni* CD034, *L. jenseni* DSM 20557, *L. gasseri* NCK99, *L. gasseri* ATCC 33323, *L. gasseri* NCK335, *L. gasseri* NCK1338, *L. gasseri* NCK1339, *L. gasseri* NCK1340, *L. gasseri* NCK1341, *L. gasseri* NCK1342 *L. gasseri* NCK1343, *L. gasseri* NCK1344, *L. gasseri* NCK1345, *L. gasseri* NCK1346, *L. gasseri* NCK1347, *L. gasseri* NCK1348, *L. gasseri* NCK1349, *L. gasseri* NCK1557, *L. gasseri* NCK2140, *L. gasseri* NCK2141 and *L. gasseri* JV V03.

*L. acidophilus* NCFM strains, *L. gasseri* strains, and other strains were grown overnight and spotted onto MRS plates, and MRS supplemented with TDCA, and GDCA (conjugated bile acids present in the GIT, FIGS. 2A-2C). The plate precipitation assay was used to first determine whether lactobacilli strains had active BSHs. Briefly, bile salts are supplemented onto agar medium and BSH-positive strains are identified by halos of precipitated free bile acids surrounding the colonies due to hydrolysis and acidification of the medium. *Lactobacillus* strains displayed no halos on MRS media alone, as expected, and differential halos were produced when the medium was supplemented with TDCA and GDCA. These data demonstrate that these *Lactobacillus* strains have BSH activity and suggests differences in substrate specificity.

Strains that can be used in conjunction with the embodiments provided herein include, but are not limited to, *L. acidophilus* NCFM, *L. casei* ATCC 334, *L. pentosus* DSM 20314, *L. rhamnosus* LGG, *L. bucherni* CD034, *L. jenseni* DSM 20557, *L. gasseri* NCK99, *L. gasseri* ATCC 33323, *L. gasseri* NCK335, *L. gasseri* NCK1338, *L. gasseri* NCK1339, *L. gasseri* NCK1340, *L. gasseri* NCK1341, *L. gasseri* NCK1342 *L. gasseri* NCK1343, *L. gasseri* NCK1344, *L. gasseri* NCK1345, *L. gasseri* NCK1346, *L. gasseri* NCK1347, *L. gasseri* NCK1348, *L. gasseri* NCK1349, *L. gasseri* NCK1557, *L. gasseri* NCK2140, *L. gasseri* NCK2141 and *L. gasseri* JV V03.

To further evaluate BSH activity from strains in FIG. 2, *L. acidophilus* NCFM bshA and bshB (LaBSHa, and LaBSHb, respectively), and *L. gasseri* ATCC 33323 bshA and bshB (LgBSHa, and LgBSHb, respectively) were expressed recombinantly in *Escherichia coli* strain BL21 (λDE3), purified (FIG. 9), and tested against a panel of relevant conjugated bile acids in an enzymatic assay (FIG. 10). LaBSHa, LaBSHb, and LgBSHb were more active against glyco-conjugated bile acids compared to the tauro-conjugates. LgBSHa displayed high activity against tauro-conjugated bile acids tested. BSH specific activities were determined by Ninhydrin assay. The amount of liberated amino acid was calculated using a standard curve of known concentrations of glycine and taurine. These data demonstrate that recombinant *Lactobacillus* BSHs overexpressed in *E. coli* have different specific activities against conjugated bile acids.

The BSH enzyme catalyzes the hydrolysis of glycine and/or taurine conjugated bile salts into the amino acid residue and the unconjugated bile acid. *Lactobacillus* strains that were isolated from the human GIT and encode an active BSH (cholylglycine hydrolase) enzyme were characterized (see, e.g., FIGS. 3-4). *L. acidophilus* NCFM and *L. gasseri* ATCC 33323 strains were selected based on a specific set of criteria. Both strains have fully sequenced genomes, available genetic tools, active and annotated BSHs, and they are associated with positive health effects in human studies. Previous studies have detailed the bsh loci in both strains which share 33% and 65% identity at the protein level. To date, *L. acidophilus* NCFM BSH enzymes have only been characterized with a plate precipitation assay and gene knockouts in both bsh genes (bshA and bshB) have been constructed. Even though, *L. gasseri* ATCC 33323 encodes two different bsh genes, they have not been fully characterized, nor have other clinically relevant *L. gasseri* strains and their BSHs.

*Lactobacillus* strains that can grow in the presence of conjugated bile acids and display a halo or precipitation on the plate assay, were subjected to a BSH enzyme assay. Briefly, *Lactobacillus* strains are cultured anaerobically at 37° C. overnight in 15 ml reduced MRS broth. BSH activity is determined through a modified two-step process, as previously described. In the first step, 100 μl of whole cell extract, 90 μl of reaction buffer (0.1M sodium phosphate, pH 6.0), and 10 μl of specific conjugated bile acids (100 mM) are gently mixed and incubated at 37° C. for 30 min. The reaction is stopped by adding 50 μl of 15% trichloroacetic acid to a 50 μl aliquot of the reaction mixture. This mixture is centrifuged at room temperature for 5 min at 12,000×g to remove any precipitate. In the second step 50 μl of the resulting supernatant from the previous step is added to 950 μl of ninhydrin reagent. The reaction mixture is incubated for 14 min in a boiling water bath and cooled on ice for 3 min. Absorbance at 570 nm (A570) is measured. A standard curve using taurine or glycine is generated for each assay to determine the molecular extinction coefficient. All assays are carried out in triplicate with two biological replicates. BSH activity is stated as μmol of taurine or glycine released from the substrate per min per mg of crude extract.

BSHs belong to the choloylglycine hydrolase family and there are many members of the gut microbiota that encode the bsh gene, although their function remains unclear. Although they share a conserved amino acid active site (Cys2, Arg18, Asp21, Asn175, and Arg228), BSHs differ in enzyme kinetic properties, substrate specificity, optimal pH, and regulation. The Cys2 is required for nucleophilic attack of the N-acyl amide bond, which is conserved in all active BSHs. While the active site amino acids are conserved, the residues that make up the substrate-binding pocket are not. Studies detailing the enzyme kinetic properties of *Lactobacillus* BSHs are lacking. To better understand BSH enzyme kinetics lactobacilli bsh genes were cloned into expression vector pET-21b and transformed into *E. coli* BL21 (λDE3) cells, which has isopropyl-β-D-thiogalactopyranoside (IPTG) inducible expression of T7-RNA polymerase encoded on the chromosome. Large-scale protein expression and purification of recombinant *Lactobacillus* BSHs were be done via his-tag affinity chromatography with a nickel column. All fractions were be visualized on 12.5% SDS-polyacrylamide gels, and enzyme assays were be performed throughout each purification step.

Example 2

Figure 3:
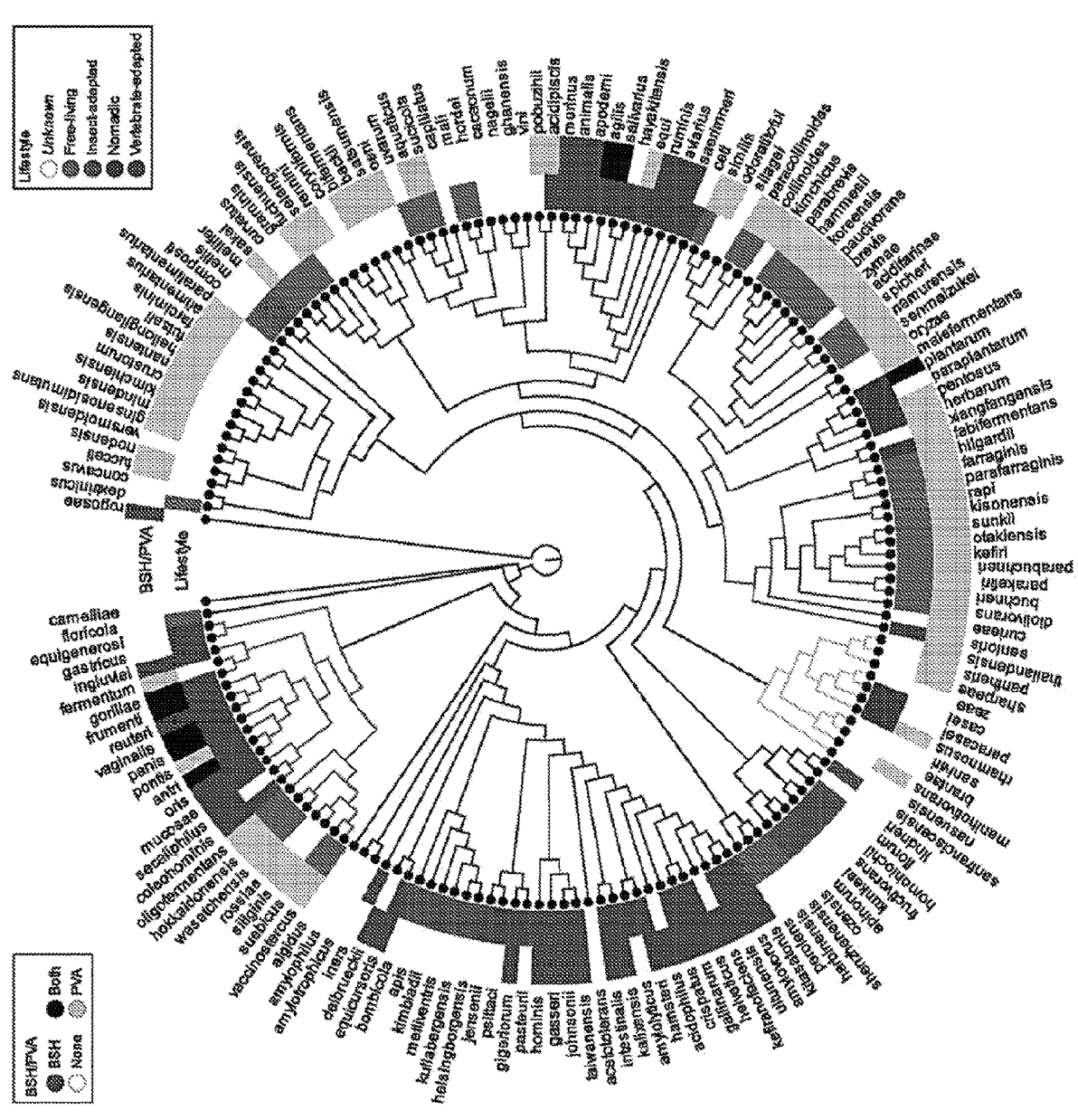

A phylogenetic tree was created for the 170 species of lactobacilli on the basis of the pyruvate kinase enzyme sequence (FIG. 3) using the method recently described by Brandt and Barrangou. A metadata layer of unknown, free-living, insect-adapted, nomadic, or vertebrate-adapted lifestyles was added as recently described by Duar et al. The presence and absence of BSH proteins was mapped to the 170 *Lactobacillus* species (FIG. 3). The majority (84.62%) of species encoding BSH proteins mapped to the vertebrate-adapted lifestyle (with a minority mapping to unknown [12.82%] and nomadic [2.56%] lifestyles). No BSH-containing species mapped to the insect-adapted lifestyle. This distribution pattern likely reflects evolutionary pressure on vertebrate-associated species to preferentially encode BSH proteins.

As shown in FIGS. 5A-5C, Lactobacilli BSHs display varied preferences for conjugated bile acids. To evaluate BSH activity from model Lactobacilli strain, *L. johnsonii* bshA, bshB and bshC (LjBSHa, LjBSHb, and LjBSHc respectively) were purified and their specific activities and pH optima were determined by the Ninhydrin assay. Enzymes tested displayed different preferences for glyco-conjugated and tauro-conjugated bile acids and acidic conditions (FIG. 5A). Conservation analysis of the BSH amino acid sequence was also performed (FIG. 5C). The alignment of the representative BSH proteins from the 57 clusters from the clustered data set was analyzed for conserved amino acid motifs. A conservation score of 0.75 or higher is indicated by a dashed line. Motifs and conserved amino acids are indicated by the WebLogo. An asterisk indicates the previously described conserved active-site residues, from O'Flaherty et al., 2018 (FIG. 5C).

Example 3

The germ free mouse lacks a gut microbiota or bacteria able to deconjugate taurine conjugated bile acids into unconjugated bile acids. Targeted bile acid metabolomics of the GF mouse revealed that the GIT (ileum, cecum, and colon) is solely made up of taurine conjugated primary bile acids, TαMCA, TβMCA, TCA, TCDCA, and THDCA/TUDCA (FIG. 15). The GF mouse represents a robust model system due to its lack of a gut microbiota and the presence of taurine conjugated primary bile acids in the GIT. In preliminary studies, GF mice were mono-colonized with $10^9$ CFUs of *L. acidophilus* of *L. gasseri* WT or a strain lacking both BSHs (ΔbshAB) on Day 0. Feces was collected throughout a one-week period, cecal content on Day 7, and plated for bacterial enumeration.

By day 7, the WT *L. gasseri* strain had significantly less CFUs than the double mutant, suggesting that some BSHs can be detrimental for fitness in the mouse GIT (FIG. 19A). Over the same timeframe, *L. acidophilus* colonization was not impacted by the ΔbshAB deletion (FIG. 19B).

Previous studies have defined the microbiome of the ileum and cecum after various antibiotic treatments including, cefoperazone, clindamycin, vancomycin, metronidazole, and kanamycin. To examine the relationship between members of the gut microbiota and bile acids, the Spearman's rank correlation coefficient was calculated for all Operational Taxonomic Units (OTUs) bile acid pairs using data across all mouse treatment groups from both ileum and cecum (FIG. 7). To visualize these correlations, unsupervised clustering of OTUs and bile acids from all treatment groups was performed, which revealed three distinct OTU clusters (O1-O3) and two bile acid clusters (B1-B2). The organization of the correlation revealed distinctive relationships between OTUs and bile acids in the different groups. OTUs in the first OTU cluster (O1) were positively correlated with bile acids in the first bile acid cluster B1, which was made up of taurine conjugated bile acids (aqua), and negatively correlated with most of the bile acids in cluster B2. The OTUs in cluster O1 include many members from the Proteobacteria and Firmicutes phyla, more specifically from the Enterobacteriaceae and Lactobacillaceae families. Cluster O1 has the opposite relationship with cluster B2, which contains all of the secondary bile (black). This is in contrast to the relationship between cluster O2 and B2, which has a positive correlation. O2 is made up of members from the Firmicutes phylum; specifically, these Lachnospiraceae and Ruminococcaceae family members are positively correlated with all secondary bile acids. Cluster O3 is made up of members from the Bacteroidetes phylum, from the Porphyromonadaceae family, and is positively correlated with all bile acids from clusters B1 and B2. In some cases, as would be recognized by one of ordinary skill in the art based on the present disclosure, use of qRT-PCR experiments can be conducted to define expression of FXR-signaling related genes in paired tissue samples from FIG. 7 and in GF mice seen in FIG. 6.

*C. difficile* colonization and pathogenesis in the GIT is exquisitely sensitive to the changes in the gut microbiota and alterations in the bile acid pool. Previous studies developed a mouse model that approximates CDI in humans. After antibiotic treatment, mice are susceptible to CDI, and their gut is made up of host associated primary bile acids, specifically TCDCA and TCA. TCDCA alone does not affect *C. difficile*; however the deconjugated CDCA inhibits *C. difficile* spore germination, and kills vegetative cells. In patients with recurrent CDI, increased levels of TCDCA have been observed in the feces prior to their FMT. It has also been reported that there is a significant decrease in TCDCA in stool samples post FMT when compared to pre-FMT samples. These data in humans and mice make TCDCA an effective target for the BSH enzymes in a CDI mouse model.

Example 4

As shown in FIGS. 9-11, recombinant BHSs were over-expressed and purified to homogeneity, and experiments were conducted to evaluate their activity. Two recombinant BSH enzymes were used for this assay. LjoBSHc, a BSH specific for taurine conjugated bile acids (TCDCA), was chosen due to *C. difficile*'s sensitivity to the CDCA that is released. LjoBSHa is specific for glycine conjugated bile acids (GCDCA). TCDCA was chosen as a conjugated bile acid to be used in the growth assays due to *C. difficile*'s sensitivity to the CDCA that is released from BSH activity. *C. difficile* grown in BHIS media supplemented with TCDCA shows no inhibition of growth, whereas with CDCA there is complete inhibition (FIG. 9). When *C. difficile* is cultured with LjoBSHa, there is growth presumably because it cannot efficiently cleave TCDCA (it is most active on GDCA). A high dosage of LjoBSHa is needed to overcome its catalytic deficiency (FIG. 9). These data also show that only when *C. difficile* is supplemented with TCDCA and LjoBSHc that there is efficient inhibition of growth due to the cleavage of TCDCA into CDCA.

As shown in FIG. 10, average specific activities from recombinantly expressed and purified (A) LaBSHa, (B) LaBSHb, (C) LgBSHa, and (D) LgBSHb were determined by the ninhydrin assay on a panel of conjugated bile acids. Error bars represent s.d. from n=3 independent experiments. These are enzymatic activities on a variety of conjugated bile acids from the BSHs encoded by the strains in the previous figure. *Lactobacillus acidophilus*/gasseri BSHs display variable preferences for bile acid conjugation.

Figures 11A, 11B, 11C, 11D:
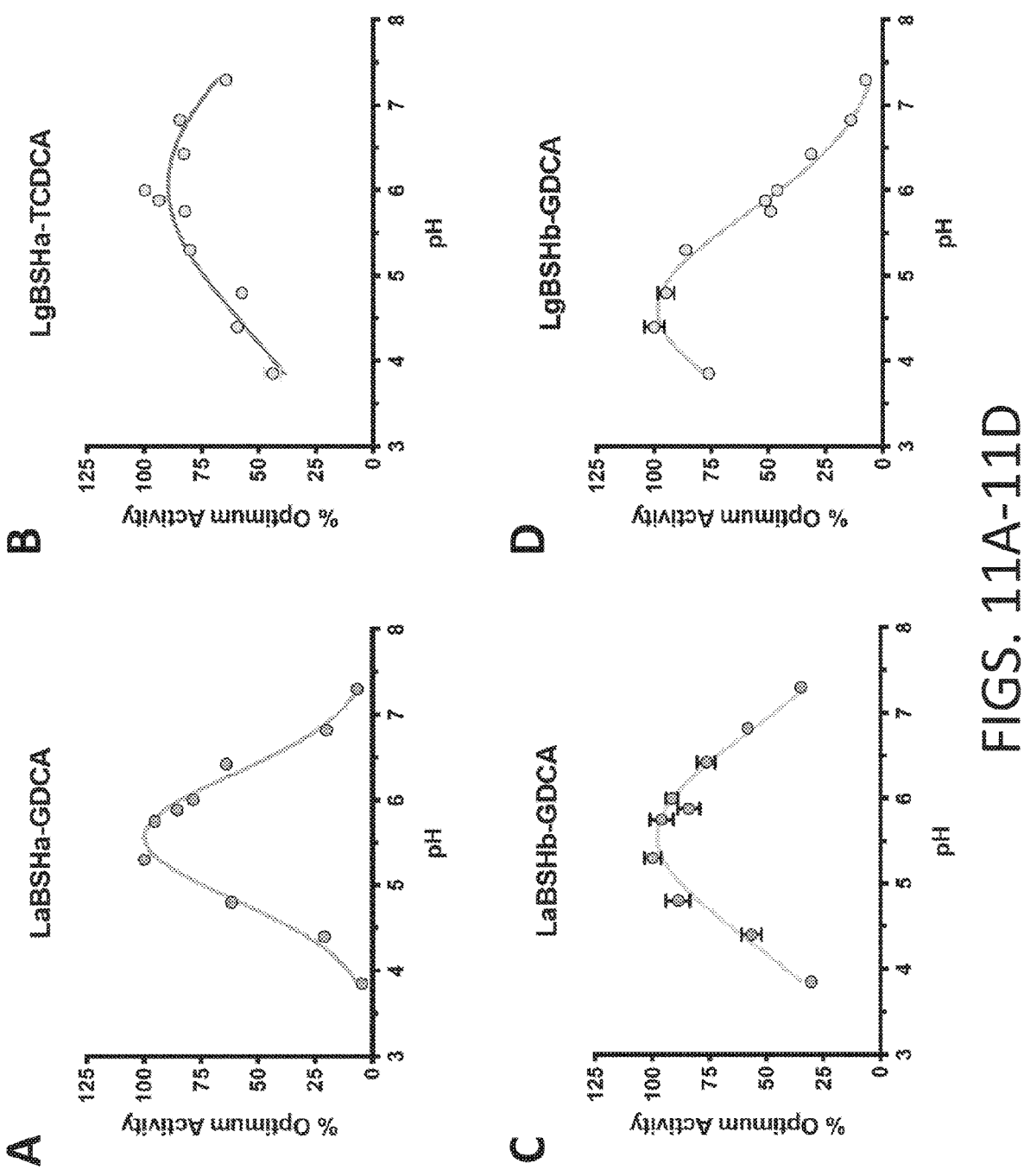

Additionally, the results provided in FIG. 11 demonstrate that purified recombinant BSHs exhibit optimum activity over a range of different pH values. The relative specific activities are provided across the range of pH values shown for LaBSHa (FIG. 11A), LaBSHb (FIG. 11B), LgBSHa (FIG. 11C), and LgBSHb (FIG. 11D) with their respective preferred substrates.

Example 5

Figures 18A, 18B, 18C, 18D:
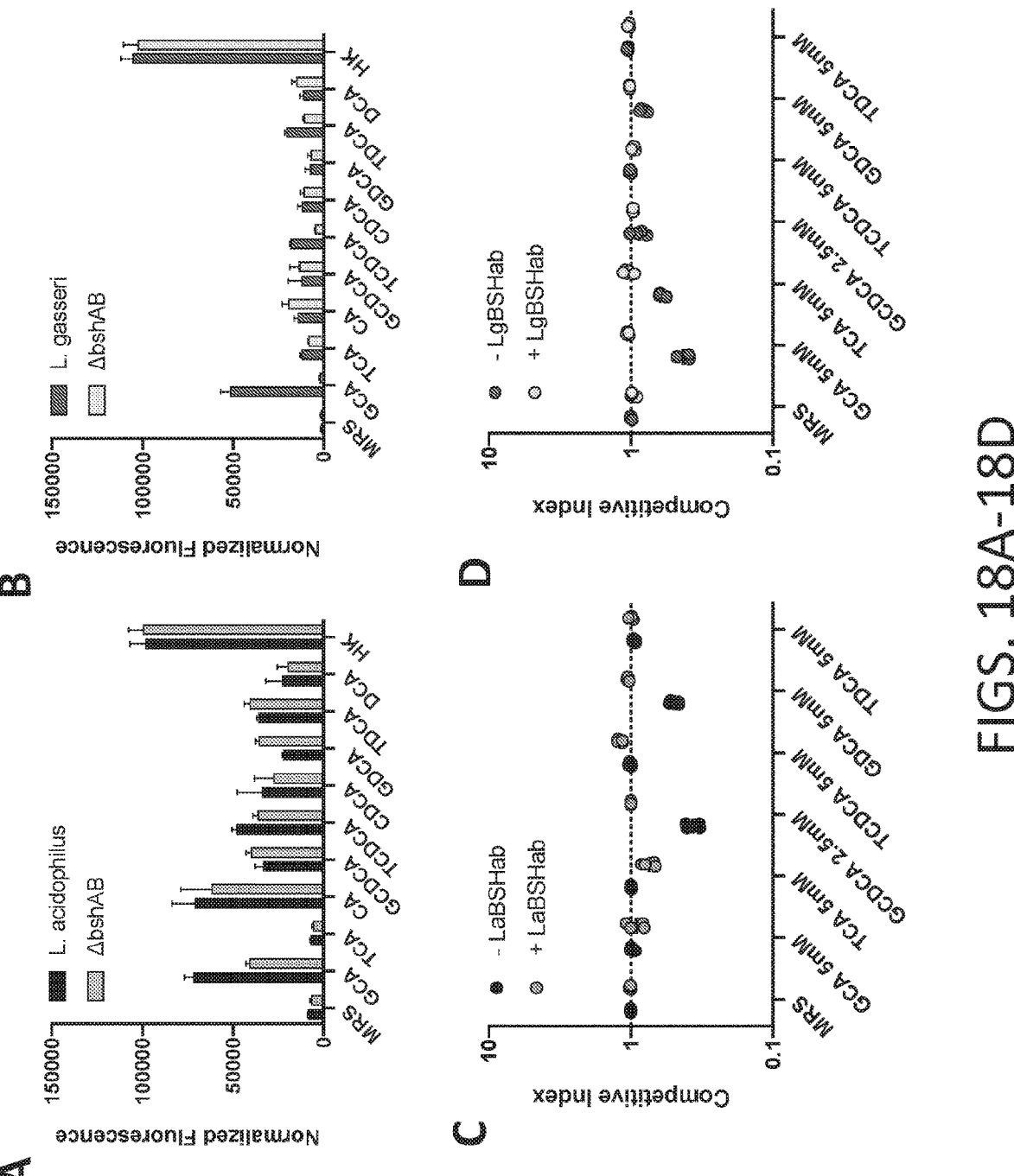

FIGS. 12-14 include representative results of experiments conducted to evaluate the role of BSH activity during *L. acidophilus* growth. In frame clean deletions of the bshA and bshB genes from *L. acidophilus* were constructed resulting in strains that do not harbor a plasmid in the chromosome and therefore do not require antibiotics in the growth medium. The *L. acidophilus* strains with deletion in bshA, bshB, and bshAB were tested in plate assays and growth curves were determined. The ΔbshA, ΔbshB, and ΔbshAB *L. acidophilus* and *L. gasseri* strains were grown in the presence of conjugated bile acids to test BSH contributions to bile acid detoxification. FIG. 12 provides growth curves of *L. acidophilus* mutants grown in a variety of bile acid concentrations. As shown, single and double BSH mutants (ΔbshA and ΔbshB) were grown in MRS media supplemented with bile acids. The results demonstrate that growth curve phenotypes are dependent on both the type and concentration of bile acid present. The double deletion *L. acidophilus* mutant ΔbshAB was significantly inhibited by 2.5 mM GCDCA, 2.5 mM GDCA, and 5 mM TDCA. However, this strain's growth was less inhibited by 5 mM GCA and 5 mM TCDCA. The double deletion *L. gasseri* mutant ΔbshAB was significantly inhibited by 2.5 mM GCDCA and 1.25 mM GDCA. However, this strain's growth was significantly less inhibited by 5 mM GCA and 5 mM TCA (FIG. 18B). These data underscore a potential role for manipulating BSH activity to impact lactobacilli fitness in the dynamic GIT.

Figures 13A, 13B, 13C, 13D, 13E, 13F, 13G:
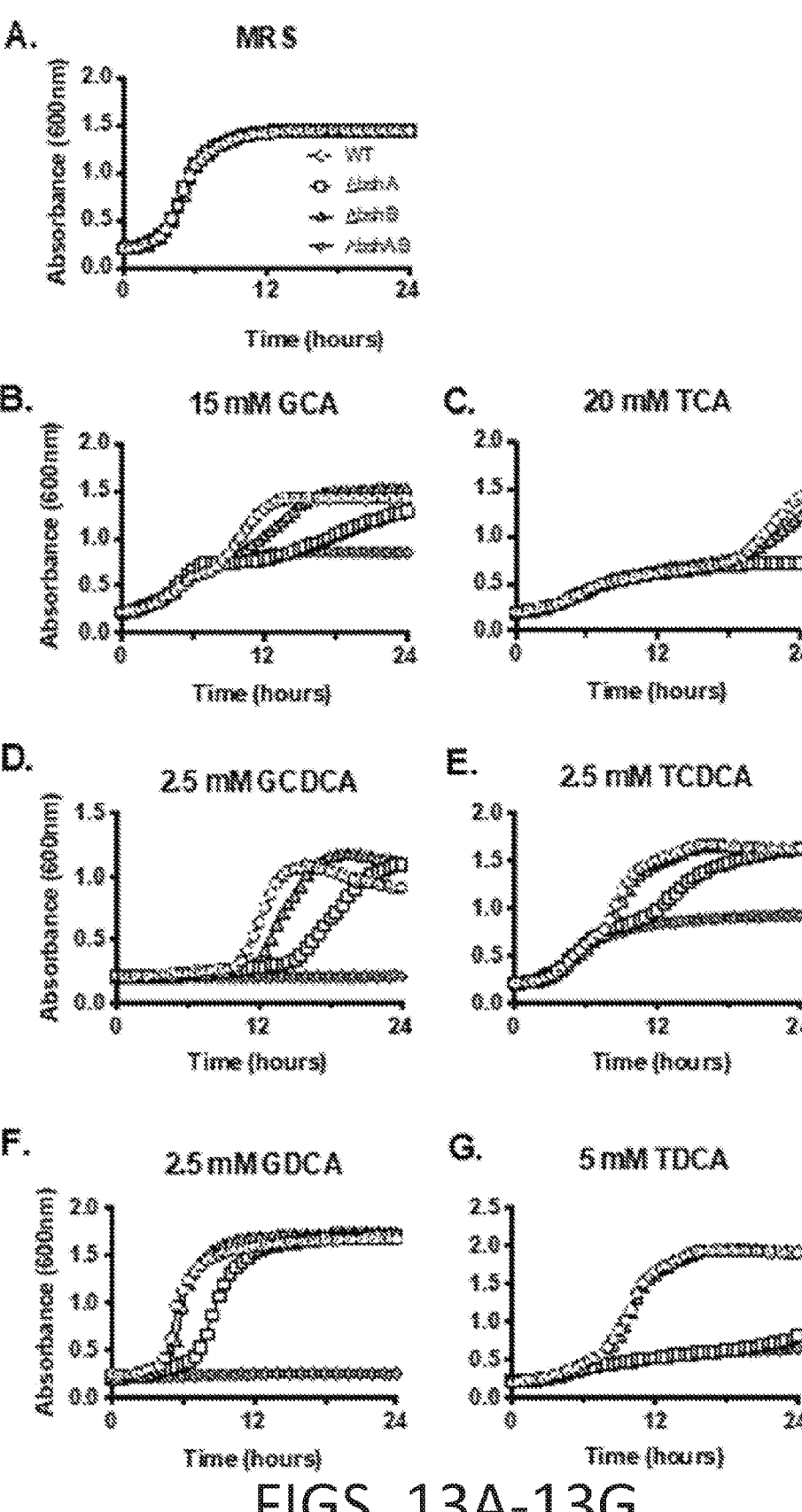

Additionally, representative results provided in FIG. 13 demonstrates that *L. acidophilus* bshA and bshB contribute to bile acid detoxification in a substrate dependent manner. Growth curves of BSH mutants in the presence of various bile acids at a single concentration are provided. To evaluate the role of BSH activity during *L. acidophilus* growth, single and double BSH mutants were grown in MRS media alone (FIG. 13A) or MRS media supplemented with bile acids GCA (FIG. 13B), TCA (FIG. 13C), GCDCA (FIG. 13D), TCDCA (FIG. 13E), GDCA (FIG. 13F), and TDCA (FIG. 13G). Growth was determined after 24 hours by OD600. The results are consistent with those of FIG. 12, which demonstrate that growth curve phenotypes are dependent on both the type and concentration of bile acid present.

Experiments were also conducted to evaluate the effects of recombinant BSHs in vivo by investigating targeted metabolomics of conjugated primary bile acids from germfree mice mono-colonized with either wild type or ΔbshAB *L. acidophilus*. Targeted metabolomics of *L. acidophilus* monocolonized mice was performed to assess the concentrations of the prominent conjugated primary murine bile acids (TCA, TCDCA, and TMCA) in the serum, ileum, or cecum, encompassing full enterohepatic recirculation.

Wild-type *L. acidophilus* did not induce any significant changes in the tested bile acid levels relative to the ΔbshAB mutant, indicating that colonizing mice with *L. acidophilus* encoding BSHs did not result in high levels of deconjugation. Thus, although BSHs can be effectively administered in vivo, various probiotic strains and/or delivered BSHs may need to be altered and optimized for efficient deconjugation in vivo.

Example 6

Experiments were conducted to evaluate the critical micelle concentrations (CMC) of the various bile acids described herein, which can be an indicator of the capacity of a detergent to induce membrane damage. FIG. 15 includes representative bile acid structures (FIG. 15A) and their critical micelle concentrations (CMCs) (FIGS. 15B-15C) determined experimentally. Bars represent mean CMC±s.e.m from n=2 independent experiments. CMCs were determined using Optimizer-BlueBALLS. Absorbance data from two independent experiments was plotted against bile acid concentrations for each molecule. A standard five-parameter logistic curve fit was performed using Graphpad Prism, and the CMC was determined by calculating the inflection point of each curve represented by the $Log_{10}$ EC50. Inflection point values represent mean±s.e.m.

Experiments were also conducted to evaluate the minimum inhibitory concentrations (MICs) of various bile acids against wild type and mutant strains of *L. acidophilus* and *L. gasseri*. As shown in FIGS. 16A-16B, BSH null *L. acidophilus* and *L. gasseri* (ΔbshAB) strains were used to determine conjugated and deconjugated bile acid MICs. Wild type and ΔbshAB MICs of deconjugated bile acids only are shown in FIG. 16B. Bars represent mean MICs from n=3 independent experiments. These data demonstrate the unexpected finding that bile acid deconjugation does not necessarily exert positive effects on BSH-encoding *Lactobacillus* in all cases; thus, modulation of the bile acid pool, especially in the context of a disease or condition, is more complex than previously realized.

Additionally, representative results in FIG. 17 demonstrate that BSHs impact *Lactobacillus* fitness in a BSH and bile acid specific-manner. *L. acidophilus* (FIG. 17A) and *L. gasseri* (FIG. 17B) BSH mutants were grown for 24 h in MRS, GCA, TCA, GCDCA, TCDCA, GDCA, of TDCA. Error bars represent s.d. from n=4 independent experiments. Dashed lined denotes the approximate starting CFUs/mL at 0 h. Exogenous recombinant LaBSHa and LaBSHb (LaBSHab) or LgBSHa and LgBSHb (LgBSHab) were supplemented to cultures in equimolar amounts to *L. acidophilus* ΔbshAB or *L. gasseri* ΔbshAB growths to functionally complement ΔbshAB strains. These data represent a comprehensive summary of growth phenotypes on various bile acids and across various bsh mutant strains. As demonstrated, in some cases, BSHs assist *Lactobacillus* in adapting to bile acid stress, and in other cases, BSHs exacerbate bile acid toxicity and growth inhibition. Additionally, purified recombinant BSHs were added to the ΔbshAB mutants to show that BSHs can function exogenously outside the cell as well, and functionally complement the mutant.

Example 7

As shown in FIG. 18, experiments were conducted to evaluate how BSH activity can alter membrane integrity and competitive dynamics in a bile acid specific manner. Propidium iodide (PI) staining was used to assess membrane integrity of mid-log grown *Lactobacillus* exposed to various bile acids or heat killed (HK). Normalized fluorescence was calculated by subtracting background PI fluorescence and normalizing to the starting OD600 at bile acid exposure (FIGS. 18A-18B). Bars represent average fluorescence from n=3 independent experiments and error bars represent standard deviation (s.d.). Competitive indexes for *Lactobacillus* co-cultures anaerobically for 24 h in the presence of various bile acids (FIGS. 18C-18D). Competitive indexes (CI) were calculated as follows: CI=Final[Log$_{10}$($\Delta$bshAB CFUs)/Log$_{10}$(wild type CFUs)]/Initial[Log$_{10}$($\Delta$bshAB CFUs)/Log$_{10}$(wild type CFUs)]. Equimolar LaBSHa and LaBSHb (LaBSHab) or LgBSHa and LgBSHb (LgBSHab) were added to cultures at 0 h. Dashed lines denotes a CI=0.

These data demonstrate the basis of a mechanism for BSH-related growth phenotypes. Unexpectedly, BSH activity may exert beneficial or detrimental effects in a bacterium by protecting it from or exposing it to toxic bile acids (FIGS. 18A-18B). Additionally, these data demonstrate unpredictable nature of the effects that BSHs have on bacterial competition during co-culture (FIGS. 18C-18D).

Example 8

The activity of the various BSHs used herein were then evaluated from an evolutionary perspective. As shown in FIG. 20, BSH specificity was shown to exhibit an evolutionary relationship. Recombinantly expressed and purified LAB BSHs were assayed for deconjugation against a panel of glycine and taurine conjugated bile acids. Specific activities for each BSH were determined by quantifying the rate of amino acid release by Ninhydrin assay. A phylogenetic tree based on the primary amino acid sequence of each BSH was constructed using the neighbor joining method (FIG. 20A). Some BSH Glades exhibit similar substrate specificity profiles which can be used to predict the activity of a BSH and understand which residues contribute to substrate specificity. Corresponding SEQ ID NOs for each BSH (percent amino acid identity for each is >95%) are provided in FIG. 20B.

Overall, these analyses provide a summary of the enzymatic activities of the BSHs tested herein as well as their evolutionary distances based on amino acid sequence. All BSHs showed a preference for either glycine or taurine-conjugated bile acids.

Example 9

Figures 21A, 21B, 21C:
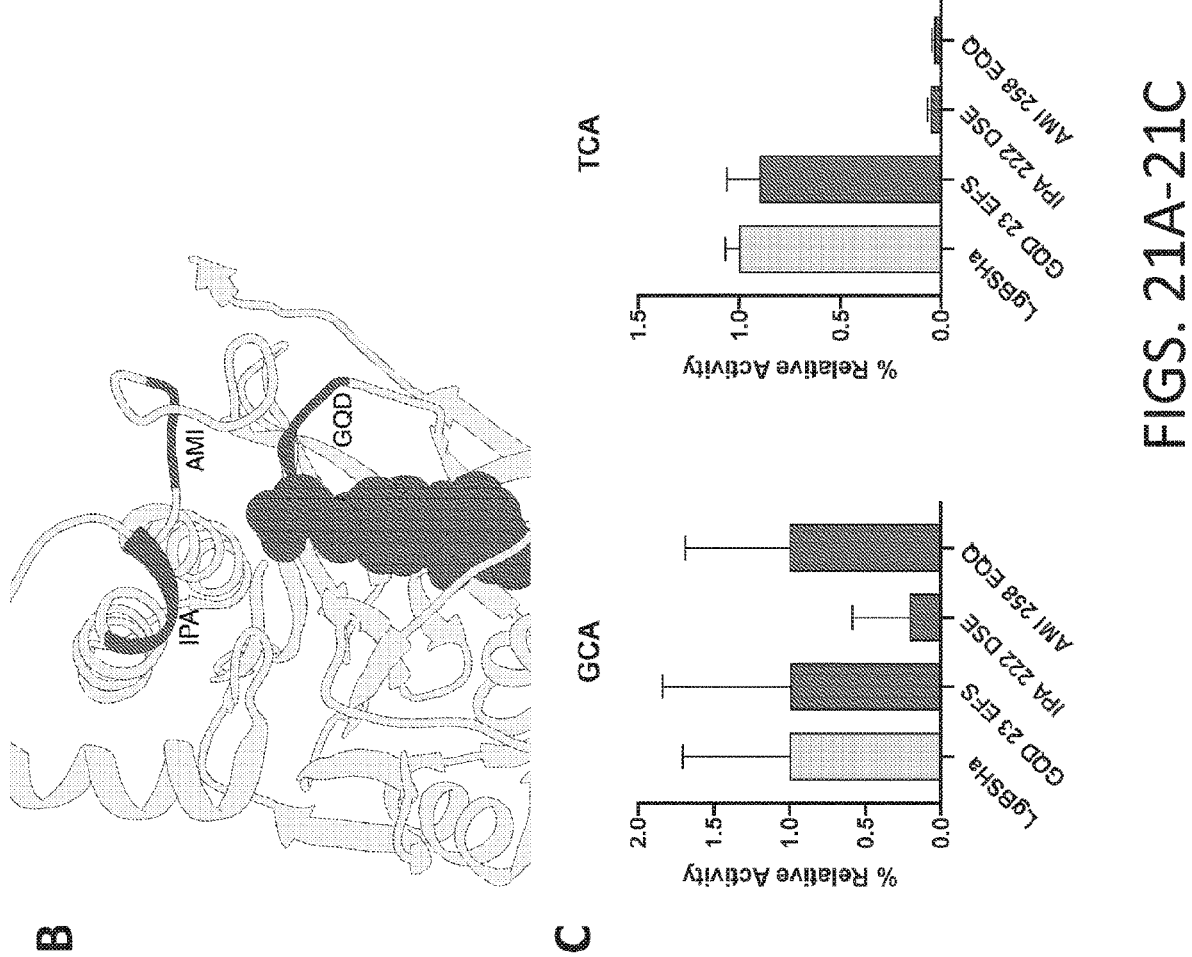

Sequence alignments and structural prediction (FIG. 21) facilitated the identification of putative regions of the BSH active site that determine substrate specificity. Three chimeric mutants were made to test the effect on substrate specificity. In particular, three regions of LgBSHa (GQD, IPA, and AMI) were predicted to play a role in coordinating the conjugated glycine in GCA into the active site based on the *L. salivarius* BSH highlighted in FIG. 21B. To understand the importance of each region in determining substrate preference, chimeric mutants were generated by replacing those motifs from LgBSHa (that prefers taurine conjugated bile acids) with analogous motifs from homologous BSHs that prefer glycine conjugated bile acids. As shown in FIG. 21C, chimeric mutants were then assayed for BSH activity on the substrates GCA and TCA. The GQD 23 EFS mutation did not have any impact on substrate preference, but the IPA 222 DSE mutation significantly diminished activity on both substrates. Additionally, the AMI 258 EQQ mutation significantly decreased activity on TCA but not GCA, suggesting that this motif is important for coordinating taurine conjugated bile acids. The chimera AMI mutant was determined to be novel because it generated a mutated BSH with new substrate specificity.

As shown in FIG. 22, two recombinant BSH enzymes were used for this assay. LjoBSHc, a BSH specific for taurine conjugated bile acids (TCDCA in FIG. 22A), was chosen due to *C. difficile*'s sensitivity to the CDCA that is released. LjoBSHa is specific for glycine conjugated bile acids (GCDCA in FIG. 22A). TCDCA was chosen as a conjugated bile acid to be used in this growth (FIGS. 22B-22C) assay due to *C. difficile*'s sensitivity to the CDCA that is released from BSH activity. *C. difficile* grown in BHIS media supplemented with TCDCA shows no inhibition of growth, whereas with CDCA there is complete inhibition. When *C. difficile* is cultured with LjoBSHa in FIG. 22B, there is growth presumably because it cannot efficiently cleave TCDCA (it is most active on GDCA). A high dosage of LjoBSHa is needed to overcome its catalytic deficiency. In FIG. 22C, data demonstrate that only when *C. difficile* is supplemented with TCDCA and LjoBSHc is there efficient inhibition of growth due to the cleavage of TCDCA into CDCA. Thus, these data demonstrate that two BSHs with different bile acid preferences can be used to inhibit *C. diff* growth based on the presence of their preferred substrates, and that the specificity of the BSH enzyme is important for inhibition of *C. difficile*.

As shown in FIG. 23, *C. difficile* vegetative cells were diluted in both control cecal content and cecal content pre-incubated with 10 μM of LgBSHa. While both conditions were able to support *C. difficile* growth, the addition of LgBSHa significantly limited *C. difficile* replication. This suggests that the BSH, which is specific to taurine conjugated bile acids such as TCDCA, was active in cecal content and generated deconjugated bile acids that inhibited *C. difficile*. These data demonstrate that BSH activity can generate inhibitory deconjugated bile acids in mouse cecal content that inhibits *C. diff* growth.

Sequences. The various embodiments of the present disclosure described herein may include one or more of the sequences referenced below, which can be found in the corresponding sequence listing.

WP_003546965.1 choloylglycine hydrolase family protein [*Lactobacillus acidophilus*] (SEQ ID NO: 1).

NC_006814.3 869317-870294 (−) *Lactobacillus acidophilus* NCFM chromosome, complete genome (SEQ ID NO: 2).

WP_003547395.1 choloylglycine hydrolase family protein [*Lactobacillus acidophilus*] (SEQ ID NO: 3).

NC_006814.3 1058279-1059256 (+) *Lactobacillus acidophilus* NCFM chromosome, complete genome (SEQ ID NO: 4).

WP_056976419.1 choloylglycine hydrolase family protein [*Lactobacillus agilis*] (SEQ ID NO: 5).

NZ_AYYP01000019.1 39634-40608 (−) *Lactobacillus agilis* DSM 20509, whole genome shotgun sequence (SEQ ID NO: 6).

WP_056939313.1 choloylglycine hydrolase family protein [*Lactobacillus amylovorus*] (SEQ ID NO: 7).

NZ_CP017706.1 1987830-1988807 (−) *Lactobacillus amylovorus* DSM 20531, complete genome (SEQ ID NO: 8).

WP_013641959.1 choloylglycine hydrolase family protein [*Lactobacillus amylovorus*] (SEQ ID NO: 9).

NC_015214.1 1143487-1144464 (+) *Lactobacillus amylovorus* strain 30SC, complete genome (SEQ ID NO: 10).

WP_010690294.1 choloylglycine hydrolase family protein [*Lactobacillus animalis*] (SEQ ID NO: 11).

NZ_JMHU01000001.1 90494–91468 (+) *Lactobacillus animalis* strain 381-IL-28, whole genome shotgun sequence (SEQ ID NO: 12).

WP_007123019.1 choloylglycine hydrolase family protein [*Lactobacillus antri*] (SEQ ID NO: 13).

NZ_AZDK01000017.1 3962-4939 (+) *Lactobacillus antri* DSM 16041, whole genome shotgun sequence (SEQ ID NO: 14).

KRK55307.1 choloylglycine hydrolase [*Lactobacillus antri* DSM 16041] (SEQ ID NO: 15).

AZDK01000040.1 10995-11966 (–) *Lactobacillus antri* DSM 16041, whole genome shotgun sequence (SEQ ID NO: 16).

WP_025087276.1 choloylglycine hydrolase family protein [*Lactobacillus apodemi*] (SEQ ID NO: 17).

NZ_AZFT01000006.1 27647-28621 (+) *Lactobacillus apodemi* DSM 16634, whole genome shotgun sequence (SEQ ID NO: 18).

WP_025087062.1 choloylglycine hydrolase family protein [*Lactobacillus apodemi*] (SEQ ID NO: 19).

NZ_AZFT01000053.1 337991-338968 (+) *Lactobacillus apodemi* DSM 16634=JCM 16172, whole genome shotgun sequence (SEQ ID NO: 20).

KRM52756.1 choloylglycine hydrolase [*Lactobacillus aviarius* subsp. *araffinosus* DSM 20653] (SEQ ID NO: 21).

AYYZ01000015.1 32728-33693 (–) *Lactobacillus aviarius* subsp. *araffinosus* DSM 20653, whole genome shotgun sequence (SEQ ID NO: 22).

KRM51566.1 choloylglycine hydrolase [*Lactobacillus aviarius* subsp. *araffinosus* DSM 20653] (SEQ ID NO: 23).

AYYZ01000030.1 84720-85673 (+) *Lactobacillus aviarius* subsp. *araffinosus* DSM 20653, whole genome shotgun sequence (SEQ ID NO: 24).

WP_006917586.1 choloylglycine hydrolase family protein [*Lactobacillus coleohominis*] (SEQ ID NO: 25).

NZ_GG698807.1 84982-85968 (–) *Lactobacillus coleohominis* 101-4-CHN, whole genome shotgun sequence (SEQ ID NO: 26).

WP_005718943.1 choloylglycine hydrolase family protein [*Lactobacillus crispatus*] (SEQ ID NO: 27).

NZ_GG669816.1 298652-299629 (–) *Lactobacillus crispatus* JV-V01, whole genome shotgun sequence (SEQ ID NO: 28).

WP_023488404.1 choloylglycine hydrolase family protein [*Lactobacillus crispatus*] (SEQ ID NO: 29).

NZ_AXLM01000021.1 27967-28944 (–) *Lactobacillus crispatus* EM-LC1, whole genome shotgun sequence (SEQ ID NO: 30).

WP_068813776.1 linear amide C—N hydrolase [*Lactobacillus crispatus*] (SEQ ID NO: 31).

NZ_PKIW01000023.1 17541-18491 (+) *Lactobacillus crispatus* strain UMB0085, whole genome shotgun sequence (SEQ ID NO: 32).

WP_013439461.1 choloylglycine hydrolase family protein [*Lactobacillus delbrueckii*] (SEQ ID NO: 33).

NC_014727.1 878842-879816 (–) *Lactobacillus delbrueckii* subsp. *bulgaricus* ND02, complete genome (SEQ ID NO: 34).

WP_008460025.1 choloylglycine hydrolase family protein [*Lactobacillus equicursoris*] (SEQ ID NO: 35).

NZ_CALZ01000132.1 4316-5290 (+) *Lactobacillus equicursoris* 66c, whole genome shotgun sequence (SEQ ID NO: 36).

WP_057750462.1 choloylglycine hydrolase family protein [*Lactobacillus frumenti*] (SEQ ID NO: 37).

NZ_AZER01000016.1 90337-91314 (+) *Lactobacillus frumenti* DSM 13145, whole genome shotgun sequence (SEQ ID NO: 38).

WP_056945645.1 choloylglycine hydrolase family protein [*Lactobacillus gallinarum*] (SEQ ID NO: 39).

NZ_AZEL01000083.1 23986-24963 (–) *Lactobacillus gallinarum* DSM 10532=JCM 2011 strain DSM 10532 NODE 173, whole genome shotgun sequence (SEQ ID NO:40).

WP_003648098.1 linear amide C—N hydrolase [*Lactobacillus gasseri*] (SEQ ID NO: 41).

NC_008530.1 69430-70380 (–) *Lactobacillus gasseri* ATCC 33323, complete genome (SEQ ID NO: 42).

WP_003647335.1 choloylglycine hydrolase family protein [*Lactobacillus gasseri*] (SEQ ID NO: 43).

NC_008530.1 960746-961723 (+) *Lactobacillus gasseri* ATCC 33323, complete genome (SEQ ID NO: 44).

WP_003649005.1 choloylglycine hydrolase family protein [*Lactobacillus paragasseri*] (SEQ ID NO: 45).

NZ_CP040500.1 823547-824527 (+) *Lactobacillus paragasseri* JV-V03, whole genome shotgun sequence (SEQ ID NO: 46).

WP_048686801.1 choloylglycine hydrolase family protein [*Lactobacillus gasseri*] (SEQ ID NO: 47).

NZ_MUJA01000002.1 362407-363387 (+) *Lactobacillus gasseri* strain AL5, whole genome shotgun sequence (SEQ ID NO: 48).

WP_049159599.1 choloylglycine hydrolase family protein [*Lactobacillus gasseri*] (SEQ ID NO: 49).

NZ_MTZT01000001.1 791430-792410 (–) *Lactobacillus gasseri* strain AL3, whole genome shotgun sequence (SEQ ID NO: 50).

WP_008474271.1 choloylglycine hydrolase family protein [*Lactobacillus gigeriorum*] (SEQ ID NO: 51).

NZ_CAKC01000094.1 5388-6368 (+) *Lactobacillus gigeriorum* CRBIP 24.85, whole genome shotgun sequence (SEQ ID NO: 52).

WP_093625227.1 choloylglycine hydrolase family protein [*Lactobacillus gorillae*] (SEQ ID NO: 53).

NZ_BCAH01000018.1 62312-63292 (–) *Lactobacillus gorillae* strain KZ01, whole genome shotgun sequence (SEQ ID NO: 54).

WP_025081289.1 bile salt hydrolase [*Lactobacillus hamsteri*] (SEQ ID NO: 55).

NZ_AZGI01000062.1 8492-9469 (–) *Lactobacillus hamsteri* DSM 5661=JCM 6256 strain DSM 5661 NODE 93, whole genome shotgun sequence (SEQ ID NO: 56).

KRO15311.1 hypothetical protein IV62 GL000337 [*Lactobacillus helveticus*] (SEQ ID NO: 57).

JQCJ01000014.1 7605-8582 (–) *Lactobacillus helveticus* strain LMG 22464, whole genome shotgun sequence (SEQ ID NO: 58).

WP_008470790.1 choloylglycine hydrolase family protein [*Lactobacillus hominis*] (SEQ ID NO: 59).

NZ_CAKE01000010.1 103437-104414 (+) *Lactobacillus hominis* CRBIP 24.179 whole genome shotgun sequence (SEQ ID NO: 60).

WP_056955493.1 choloylglycine hydrolase protein family [*Lactobacillus ingluviei*] (SEQ ID NO: 61).

NZ_AZFK01000085.1 846-1829 (–) *Lactobacillus ingluviei* DSM 15946, whole genome shotgun sequence (SEQ ID NO: 62).

WP_057810467.1 choloylglycine hydrolase protein family [*Lactobacillus intestinalis*] (SEQ ID NO: 63).

NZ_AZGN01000044.1 42134-43111 (−) *Lactobacillus intestinalis* DSM 6629, whole genome shotgun sequence (SEQ ID NO: 64).

WP_057810964.1 choloylglycine hydrolase family protein [*Lactobacillus intestinalis*] (SEQ ID NO: 65).

NZ_AZGN01000048.1 20014-20994 (−) *Lactobacillus intestinalis* DSM 6629, whole genome shotgun sequence (SEQ ID NO:66).

WP_057811657.1 conjugated bile salt hydrolase [*Lactobacillus intestinalis*] (SEQ ID NO: 67).

NZ_AZGN01000055.1 59158-60108 (+) *Lactobacillus intestinalis* DSM 6629, whole genome shotgun sequence (SEQ ID NO: 68).

WP_004898444.1 conjugated bile salt hydrolase [*Lactobacillus johnsonii*] (SEQ ID NO: 69).

NC_005362.1 77465-78415 (−) *Lactobacillus johnsonii* NCC 533, complete genome (SEQ ID NO: 70).

WP_011161986.1 choloylglycine hydrolase family protein [*Lactobacillus johnsonii*] (SEQ ID NO: 71).

NC_005362.1 1065946-1066923 (+) *Lactobacillus johnsonii* NCC 533, complete genome (SEQ ID NO: 72).

WP_011162170.1 choloylglycine hydrolase family protein [*Lactobacillus johnsonii*] (SEQ ID NO: 73).

NC_005362.1 1286673-1287653 (−) *Lactobacillus johnsonii* NCC 533, complete genome (SEQ ID NO: 74).

WP_004897162.1 choloylglycine hydrolase family protein [*Lactobacillus johnsonii*] (SEQ ID NO: 75).

AFQJ01000004.1 720-1700 (+) *Lactobacillus johnsonii* pf01, whole genome shotgun sequence (SEQ ID NO: 76).

WP_057797848.1 choloylglycine hydrolase family protein [*Lactobacillus kalixensis*] (SEQ ID NO: 77).

NZ_AZFM01000007.1 62-1039 (−) *Lactobacillus kalixensis* DSM 16043, whole genome shotgun sequence (SEQ ID NO: 78).

WP_057798736.1 choloylglycine hydrolase family protein [*Lactobacillus kalixensis*] (SEQ ID NO: 79).

NZ_AZFM01000016.1 8000-8977 (+) *Lactobacillus kalixensis* DSM 16043, whole genome shotgun sequence (SEQ ID NO: 80).

WP_056941310.1 choloylglycine hydrolase family protein [*Lactobacillus kefiranofaciens*] (SEQ ID NO: 81).

AZEM01000127.1 117315-118265 (+) *Lactobacillus kefiranofaciens* subsp. *kefirgranum* DSM 10550=JCM 8572, whole genome shotgun sequence (SEQ ID NO: 82).

WP_006499363.1 choloylglycine hydrolase family protein [*Lactobacillus mucosae*] (SEQ ID NO: 83).

NZ_AZEQ01000014.1 64201-65181 (−) *Lactobacillus mucosae* DSM 13345, whole genome shotgun sequence (SEQ ID NO: 84).

WP_056959219.1 choloylglycine hydrolase family protein [*Lactobacillus murinus*] (SEQ ID NO: 85).

NZ_BCVJ01000114.1 203-1180 (+) *Lactobacillus murinus* DSM 20452=NBRC 14221, whole genome shotgun sequence (SEQ ID NO: 86).

WP_003711849.1 choloylglycine hydrolase family protein [*Lactobacillus oris*] (SEQ ID NO: 87).

NZ_AEKL01000025.1 102912-103889 (−) *Lactobacillus oris* PB013-T2-3, whole genome shotgun sequence (SEQ ID NO: 88).

WP_003715241.1 choloylglycine hydrolase family protein [*Lactobacillus oris*] (SEQ ID NO: 89).

NZ_AZGE01000001.1 271904-272881 (−) *Lactobacillus oris* DSM 4864, whole genome shotgun sequence (SEQ ID NO: 90).

KRM25060.1 choloylglycine hydrolase [*Lactobacillus panis*] (SEQ ID NO: 91).

NZ_AZGM01000138.1 91-1068 (−) *Lactobacillus panis* DSM 6035, whole genome shotgun sequence (SEQ ID NO: 92).

WP_003642898.1 choloylglycine hydrolase family protein [*Lactobacillus plantarum*] (SEQ ID NO: 93).

NZ_AZEJ01000005.1 141793-142767 (−) *Lactobacillus plantarum* subsp. *plantarum* ATCC 14917=JCM 1149=CGMCC 1.2437, whole genome shotgun sequence (SEQ ID NO: 94).

SFE54619.1 choloylglycine hydrolase [*Lactobacillus rogosae*] (SEQ ID NO: 95).

FONU01000010.1 85472-86449 (−) *Lactobacillus rogosae* strain ATCC 27753, whole genome shotgun sequence (SEQ ID NO: 96).

SFE73109.1 choloylglycine hydrolase [*Lactobacillus rogosae*] (SEQ ID NO: 97).

FONU01000017.1 2131-3120 (−) *Lactobacillus rogosae* strain ATCC 27753, whole genome shotgun sequence (SEQ ID NO: 98).

WP_003697845.1 choloylglycine hydrolase family protein [*Lactobacillus ruminis*] (SEQ ID NO: 99).

NZ_AFYE01000056.1 37484-38458 (+) *Lactobacillus ruminis* ATCC 25644, whole genome shotgun sequence (SEQ ID NO: 100).

WP_034983830.1 choloylglycine hydrolase family protein [*Lactobacillus salivarius*] (SEQ ID NO: 101).

NZ_CP007646.1 789241-790218 (+) *Lactobacillus salivarius* strain JCM1046, complete genome (SEQ ID NO: 102).

WP_003706767.1 choloylglycine hydrolase family protein [*Lactobacillus salivarius*] (SEQ ID NO: 103).

NZ_AFMN01000003.1 7914-8888 (+) *Lactobacillus salivarius* NIAS840, whole genome shotgun sequence (SEQ ID NO: 104).

WP_057742369.1 choloylglycine hydrolase family protein [*Lactobacillus secaliphilus*] (SEQ ID NO: 105).

NZ_JQBW01000010.1 627328-628302 (−) *Lactobacillus secaliphilus* strain DSM 17896, whole genome shotgun sequence (SEQ ID NO: 106).

WP_007125470.1 choloylglycine hydrolase family protein [*Lactobacillus ultunensis*] (SEQ ID NO: 107).

NZ_GG693253.1 508807-509784 (−) *Lactobacillus ultunensis* DSM 16047, whole genome shotgun sequence (SEQ ID NO: 108).

WP_076461871.1 choloylglycine hydrolase family protein [*Lactobacillus* sp. Marseille-P3519] (SEQ ID NO: 109).

NZ_FTOY01000011.1 692188-693165 (−) *Lactobacillus* sp. Marseille-P3519, whole genome shotgun sequence (SEQ ID NO: 110).

WP_056974571.1 choloylglycine hydrolase family protein [*Lactobacillus vaginalis*] (SEQ ID NO: 111).

NZ_AZGL01000010.1 39469-40446 (−) *Lactobacillus vaginalis* DSM 5837 ATCC 49540 strain DSM 5837, whole genome shotgun sequence (SEQ ID NO: 112).

WP_003668136.1 choloylglycine hydrolase family protein [*Lactobacillus reuteri*] (SEQ ID NO: 113).

NC_009513.1 799117-800094 (+) *Lactobacillus reuteri* DSM 20016, complete genome (SEQ ID NO: 114).

What is claimed is:

1. An engineered bacterial cell comprising a heterologous gene encoding a functional bile salt hydrolase polypeptide from *Lactobacillus gasseri*, wherein the heterologous gene encoding the bile salt hydrolase polypeptide comprises at least one mutation that produces at least one amino acid substitution in an alanine-methionine-isoleucine (AMI) motif at amino acid positions 259-261 of SEQ ID NO: 41, wherein the at least one amino acid substitution decreases bile acid substrate specificity.

2. The engineered cell of claim 1, wherein the at least one amino acid substitution comprises a glutamate residue and/ or a glutamine residue.

3. The engineered cell of claim 1, wherein the bile acid substrate is TCA.

4. The engineered cell of claim 1, wherein a polypeptide encoded by the heterologous bile salt hydrolase gene comprises at least 90% identity to a wild type bile salt hydrolase polypeptide of SEQ ID NO: 41.

5. The engineered cell of claim 1, wherein a polypeptide encoded by the heterologous bile salt hydrolase gene comprises at least 99% identity to a wild type bile salt hydrolase polypeptide of SEQ ID NO: 41.

6. The engineered cell of claim 1, wherein the cell is selected from one of the following genera: *Bacillus, Bacteroides, Bifidobacterium, Brevibacteria, Clostridium, Enterococcus, Escherichia, Lactobacillus, Lactococcus, Saccharomyces, Staphylococcus* and *Streptococcus*.

7. The engineered cell of claim 1, wherein the cell is selected from one of the following species: *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Escherichia coli* Nissle, *Lactobacillus acidophilus, Lactobacillus bulgaricus, Lactobacillus casei, Lactobacillus crispatus, Lactobacillus gasseri, Lactobacillus johnsonii, Lactobacillus paracasei, Lactobacillus plantarum, Lactobacillus reuteri, Lactobacillus rhamnosus, Lactobacillus salivarius, Lactobacillus fermentum, Lactobacillus delbrueckii, Lactococcus lactis*, and *Saccharomyces boulardii*.

8. The engineered cell of claim 1, wherein the cell improves at least one physiological parameter associated with a disease or condition when administered to a subject in need thereof as part of a therapeutic composition.

9. The engineered cell of claim 8, wherein the disease or condition is associated with bile acid dysregulation.

10. The engineered cell of claim 8, wherein the disease or condition is associated with a *Clostridioides difficile* infection, and wherein administering the therapeutic composition treats the *Clostridioides difficile* infection.

11. A pharmaceutical composition comprising:

the engineered bacterial cell of claim 1; and a pharmaceutically acceptable carrier or excipient;

wherein administration of the composition improves at least one physiological parameter associated with a disease or condition in a subject.

12. The composition of claim 11, wherein the disease or condition is associated with bile acid dysregulation.

13. The composition of claim 11, wherein the disease or condition is associated with a *Clostridioides difficile* infection, and wherein administering the composition treats the *Clostridioides difficile* infection.

14. A method of modulating at least one bile acid in a subject in need thereof, the method comprising administering to said subject the pharmaceutical composition of claim 11.

* * * * *